(12) United States Patent
White et al.

(10) Patent No.: US 9,770,711 B2
(45) Date of Patent: Sep. 26, 2017

(54) GENERAL CATALYST FOR C-H FUNCTIONALIZATION

(71) Applicant: The Board of Trustees of the University of Illinois, Urbana, IL (US)

(72) Inventors: M. Christina White, Champaign, IL (US); Shauna M. Paradine, Cambridge, MA (US); Jennifer R. Griffin, Champaign, IL (US); Jinpeng Zhao, Champaign, IL (US); Aaron L. Petronico, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/076,434

(22) Filed: Mar. 21, 2016

(65) Prior Publication Data

US 2016/0272662 A1  Sep. 22, 2016

Related U.S. Application Data

(60) Provisional application No. 62/136,229, filed on Mar. 20, 2015.

(51) Int. Cl.
| | | |
|---|---|---|
| *C07D 291/06* | (2006.01) | |
| *B01J 31/18* | (2006.01) | |
| *C07D 515/06* | (2006.01) | |
| *C07J 71/00* | (2006.01) | |
| *C07J 41/00* | (2006.01) | |
| *C07J 63/00* | (2006.01) | |
| *C07F 13/00* | (2006.01) | |

(52) U.S. Cl.
CPC .......... *B01J 31/183* (2013.01); *C07D 291/06* (2013.01); *C07D 515/06* (2013.01); *C07F 13/005* (2013.01); *C07J 41/005* (2013.01); *C07J 41/0055* (2013.01); *C07J 63/008* (2013.01); *C07J 71/0094* (2013.01); *B01J 2231/44* (2013.01); *B01J 2531/72* (2013.01)

(58) Field of Classification Search
None
See application file for complete search history.

(56) References Cited

U.S. PATENT DOCUMENTS

| 7,829,342 B2 | 11/2010 | White et al. |
| 2004/0087820 A1 | 5/2004 | Fuchs et al. |
| 2009/0093638 A1 | 4/2009 | Doyle et al. |
| 2009/0221083 A1 | 9/2009 | White et al. |
| 2011/0015397 A1 | 1/2011 | White et al. |
| 2012/0190635 A1 | 7/2012 | Li et al. |
| 2013/0184494 A1 | 7/2013 | Kurosawa et al. |

FOREIGN PATENT DOCUMENTS

WO  2007059015 A1  5/2007

OTHER PUBLICATIONS

Knecht et al., Journal of Porphyrins and Phthalocyanines (1999), 3(4), 292-298.*
Dolotova et al., Zhurnal Obshchei Khimii (1992), 62(9), 2064-75 Coden: ZOKHA4; ISSN: 0044-460X.*
Dolotova et al.,Zhurnal Obshchei Khimii (1988), 58(9), 2173 Coden: ZOKHA4; ISSN: 0044-460X.*
Gormisky, Paul E. et al., "Catalyst-Controlled Aliphatic C-H Oxidations With a Predictive Model for Site Selectivity," Journal of the American Chemical Society, 2013, 135, 14052-14055.
Gustafson, Jeffrey L. et al., "Linear Free Energy Relationship Analysis of a Catalytic Desymmetrization Reaction of a Diarylmethane-Bis(Phenol)," Original Letters, Jun. 18, 2010; 12(12); 2794-2797.
Harper, Kaid C. et al., "Three-Dimensional Correlation of Steric and Electronic Free Energy Relationships Guides Asymmetric Propargylation," Science, 333, 1875-1878 (2011).
Paradine, Shauna M. et al., "A Manganese Catalyst for Highly Reactive Yet Chemoselective Intramolecular C(sp3)-H Amination," Nature Chemistry, Dec. 2015, vol. 7, pp. 987-994.

* cited by examiner

*Primary Examiner* — Paul V Ward
(74) *Attorney, Agent, or Firm* — Haukaas Fortius LLP; Michael H. Haukaas

(57) ABSTRACT

The invention provides novel manganese catalysts such as [Mn(ᵗBuPc)], which are general for the amination of all types of C(sp³)-H bonds (aliphatic, allylic, propargylic, benzylic, ethereal), including strong 1° aliphatic C—H bonds, while achieving excellent chemoselectivity, stereospecificity, and high functional group tolerance. We demonstrate the late-stage diversification of bioactive complex molecules that encompass the range of C(sp³)-H bond types, such as selective 1° C—H aminations of betulinic acid and pleuromutilin derivatives. The catalysts' unprecedented balance of reactivity and selectivity is in part attributed to its mechanism of C—H amination that lies between stepwise and concerted.

20 Claims, 4 Drawing Sheets

GENERAL CATALYST FOR C-H FUNCTIONALIZATION

RELATED APPLICATIONS

This application claims priority under 35 U.S.C. §119(e) to U.S. Provisional Patent Application No. 62/136,229, filed Mar. 20, 2015, which is incorporated herein by reference.

GOVERNMENT SUPPORT

This invention was made with government support under Grant No. 1R01 GM112492A awarded by the National Institutes of Health. The government has certain rights in the invention.

BACKGROUND OF THE INVENTION

A single catalyst that can site- and chemoselectively functionalize all $C(sp^3)$-H bond types stands to revolutionize the synthesis and diversification of organic molecules. An inherent challenge exists in developing small molecule catalysts that can functionalize inert $C(sp^3)$-H bonds while tolerating more reactive π-functionality.

The direct functionalization of C—H bonds by transition metal catalysts is shifting the synthetic paradigm for the construction and diversification of organic molecules. However, a profound challenge lies in the development of catalysts that are reactive enough to cleave inert C—H bonds while remaining tolerant of more readily oxidizable functional groups. In particular, small molecule catalysts have demonstrated the ability to support high valent metalheteroatom species (i.e. oxos and nitrenes) that are capable of preparative, site-selective, and stereospecific oxidation of inert C—H bonds, but suffer from poor chemoselectivity (see P. E. Gormisky, M. C. White, *J. Am. Chem. Soc.* 135, 14052-14055 (2013)). Certain enzymes, such as cytochrome P450s, form highly reactive metal oxos contained within elaborate active sites that enable exquisite control over chemoselectivity. However, the substrate-specificity often associated with enzymes precludes their use as a general synthetic method. A small molecule catalyst capable of chemoselectively oxidizing all types of $C(sp^3)$-H bonds in preparative yields would revolutionize the synthesis and diversification of bioactive compounds.

Given the ubiquity of nitrogen functionality in bioactive compounds, its selective yet general introduction via C—H amination represents a particularly powerful synthetic strategy (J. L. Jeffrey, R. Sarpong, *Chem. Sci.* 4, 4092-4106 (2013)). Metallonitrene-based C—H amination is capable of functionalizing a broad range of $C(sp^3)$-H bond types, but no single noble or base metal catalyst has yet successfully achieved a balance between reactivity and chemoselectivity. The extensively explored noble metal dirhodium carboxylate platform has resulted in catalysts that efficiently and stereospecifically functionalize robust 3° and 2° aliphatic C—H bonds via a concerted asynchronous C—H insertion mechanism (Roizen et al., *Acc. Chem. Res.* 45, 911-922 (2012)). However, these catalysts lack chemoselectivity, as direct oxidation of π-bonds competes with that of $sp^3$ C—H bonds in olefin- and alkyne-containing substrates. Alternatively, small molecule iron catalysts access mechanistically distinct single electron pathways for nitrene transfer, affording orthogonal reactivity to rhodium catalysis (S. M. Paradine, M. C. White, *J. Am. Chem. Soc.* 134, 2036-2039 (2012)). As a result, these catalysts aminate allylic C—H bonds with high chemoselectivity over competing aziridination, but are only moderately reactive toward stronger aliphatic C—H bonds. This is a consequence of the allylic radicals accessed during C—H amination being energetically favored over aliphatic radicals that would be generated in aziridination or aliphatic C—H amination pathways. Additionally, there are no known metallonitrene-based catalysts capable of effectively aminating propargylic C—H bonds or very strong 1° aliphatic C—H bonds.

What is needed is a catalyst with high reactivity and high selectivity for C—H bonds, for example, to aminate benzylic, ethereal, 3°, 2°, and 1° aliphatic C—H bonds. Also needed are new catalysts and methods for preparing the synthetically important 1,3 amino alcohol motif.

SUMMARY

The invention provides a compound of Formula I:

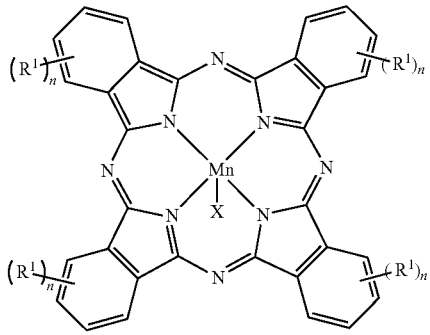

(I)

wherein
X is anion capable of forming a bond with manganese;
each $R^1$ is independently $(C_1-C_{16})$alkyl, $(C_1-C_{16})$cycloalkyl, or $(C_1-C_8)$alkyl$(C_1-C_{16})$cycloalkyl; and
each n is independently 1, 2, 3, or 4.

Values for X include halo or $SbF_6$, or other suitable Mn counterions.

A specific value for X is chloro. Another specific value for X is bromo.

In one embodiment, $R^1$ is $(C_3-C_5)$alkyl.
In another embodiment, $R^1$ is tert-butyl.
In another embodiment, $R^1$ is $(C_3-C_{10})$cycloalkyl.
In another embodiment, $R^1$ is adamantyl.
In some embodiments, each $R^1$ is the same.
In some embodiments, at least one $R^1$ is different than another $R^1$.

A specific value for n is 1. Another specific value for n is 2. Another specific value for n is 3. Another specific value for n is 4. The variables "n" can each be different or they can each be the same.

In one specific embodiment, the compound is compound 3:

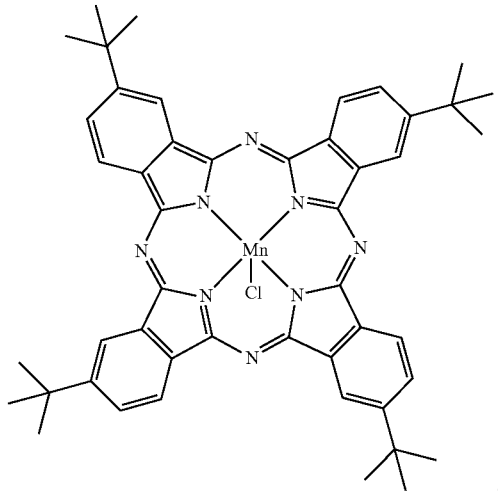

3

The invention also provides a method to carry out a C—H amination comprising contacting a substrate and an effective amount of a compound of claim 1 in a suitable solvent system;

wherein the substrate comprises at least three carbon atoms, a sulfonamide (—S(O)$_2$NH$_2$) moiety, and at least one sp$^3$ C—H bond;

thereby effecting C—H amination of the substrate.

The contacting can be carried out in the presence of an oxidant.

The oxidant can be PhI(OPiv)$_2$.

The contacting can be carried out in the presence of a drying agent such as 4 Å molecular sieves.

The contacting can be carried out at approximately room temperature, or at about 20° C. to about 30° C.

The contacting can be carried out in the presence of AgSbF$_6$.

The substrate can comprise benzylic, ethereal, 3°, 2°, or 1° aliphatic C—H bonds, or a combination thereof.

The amination can form a six-membered ring, or in other embodiments, a five-membered ring.

The amination can form a 1,3 amino alcohol motif.

The C—H amination can occur at a strong 1° sp$^3$ C—H bond in the presence of weaker 2° and/or 3° C—H bonds.

The substrate comprises one or more alkene or alkyne moieties.

The invention provides novel compounds of the formulas described herein, intermediates for the synthesis of compounds and formulas described herein, as well as methods of preparing and using the compounds and catalysts. The invention also provides compounds that are useful as intermediates for the synthesis of other useful compounds and catalysts.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
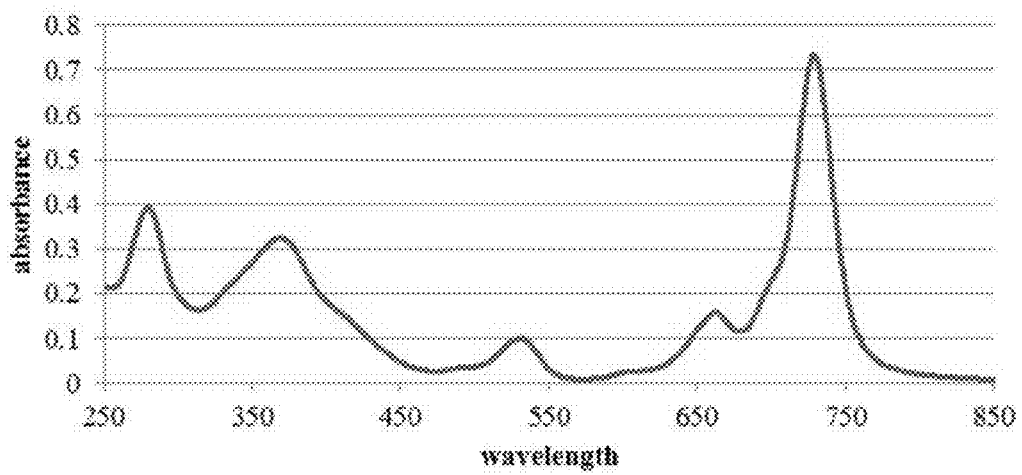
FIG. 1. UV-Vis Spectral Studies. [Mn$^{III}$($^t$BuPc)] (4.2 mg; 0.005 mmol) was taken up in CHCl$_3$ to 5 mL solution (1.0 mM). 100 µL of this solution was diluted to 10 mL (10.0 µM). UV-Vis was taken from 850-250 nm in a quartz cuvette (path length=1 cm).

Herein we describe small molecule C—H amination catalysts such as [Mn($^t$BuPc)] (3), that achieve an unprecedented balance between reactivity and selectivity. Catalyst 3 is general for the preparative amination of all sp$^3$ C—H bond types including allylic, benzylic, propargylic, ethereal, 3°, 2°, and 1° aliphatic C—H bonds. The catalysts can provide remarkably high chemoselectivity (generally >20:1) for allylic and propargylic C—H amination while maintaining stereospecificity, site-selectivity, and high functional group tolerance.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount of a catalyst necessary to form products in a reaction mixture under certain reaction conditions. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "complex" means a molecular entity including a central metal atom, to which is associated a surrounding array of other groups of atoms, referred to as "ligands." The catalysts described herein can be referred to as complexes.

The term "group" means a linked collection of atoms or a single atom within a molecular entity, where a molecular entity is any constitutionally or isotopically distinct atom, molecule, ion, ion pair, radical, radical ion, complex, conformer, etc., identifiable as a separately distinguishable entity. The description of a group as being "formed by" a particular chemical transformation does not imply that this chemical transformation is involved in making the molecular entity that includes the group.

The term "alkyl group" means a group formed by removing a hydrogen from a carbon of an alkane, where an alkane is an acyclic or cyclic compound consisting entirely of hydrogen atoms and saturated carbon atoms. An alkyl group may also be substituted with one or more substituent groups. Of course, when an alkyl group or a group described below is disubstituted, two hydrogen atoms are removed from an atom or two separate atoms of the group (e.g., resulting in an alkylene group). The term "alkyl" therefore refers to a straight- or branched-chain alkyl group having from 1 to about 20 carbon atoms in the chain. For example, the alkyl group can be a $(C_1-C_{20})$alkyl, $(C_1-C_{16})$alkyl, $(C_1-C_{12})$alkyl, $(C_1-C_8)$alkyl, $(C_1-C_6)$alkyl, $(C_1-C_4)$alkyl, or a $(C_3-C_5)$alkyl. Examples of alkyl groups include methyl (Me), ethyl (Et), n-propyl, isopropyl, butyl, isobutyl, sec-butyl, tert-butyl (t-Bu), pentyl, isopentyl, tert-pentyl, hexyl, isohexyl, and groups that in light of the ordinary skill in the art and the teachings provided herein would be considered equivalent to any one of the foregoing examples. Alkyl groups can be optionally substituted or unsubstituted, and optionally partially unsaturated, such as in an alkenyl group.

The term "cycloalkyl" refers to cyclic alkyl groups of, for example, from 3 to about 16 carbon atoms, or about 3 to about 10 carbon atoms, having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, pinenyl, substituted derivatives thereof, and the like. The cycloalkyl group can be monovalent or divalent, and can be optionally substituted, for example, by one or more alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "alkyl(cycloalkyl)" refers to an alkyl group, including a substituent on an aromatic group, that is further substituted with a cycloalkyl group. Examples include ethyl (cyclohexyl) ($-CH_2CH_2-C_6H_{11}$). In various embodiments, the alkyl(cycloalkyl) group can be a $(C_1-C_8)$alkyl $(C_1-C_{16})$cycloalkyl.

The term "substituent group" means a group that replaces one or more hydrogen atoms in a molecular entity. Examples of substituent groups include halide groups, alkyl groups, heteroalkyl groups, aryl groups, heteroaryl groups, and nitro groups. The $(C_1-C_{16})$alkyl, $(C_1-C_{16})$cycloalkyl, or $(C_1-C_8)$alkyl$(C_1-C_{16})$cycloalkyl groups described herein can be optionally substituted.

The term "halide group" or "halo" refers to —F, —Cl, —Br or —I.

The term "sp³ C—H bond" means a C—H bond in which the carbon atom is bonded to three other atoms through individual single bonds. A 2° C—H bond is one where the carbon is attached to two other carbon atoms; a 3° C—H bond is one where the carbon is attached to three other carbon atoms A General Manganese Catalyst for Intramolecular C(sp³)-H Amination Herein we describe a small molecule C—H amination catalyst, [Mn(ᵗBuPc)] (3), that achieves an unprecedented balance between reactivity and selectivity. Catalyst 3 is general for the preparative amination (>50% yield) of all sp³ C—H bond types: benzylic, ethereal, 3°, 2°, and even 1° aliphatic C—H bonds. Remarkably, despite this high reactivity, [Mn(ᵗBuPc)] (3) shows high chemoselectivity (generally >20:1) for allylic and propargylic C—H amination while maintaining stereospecificity, site-selectivity, and high functional group tolerance.

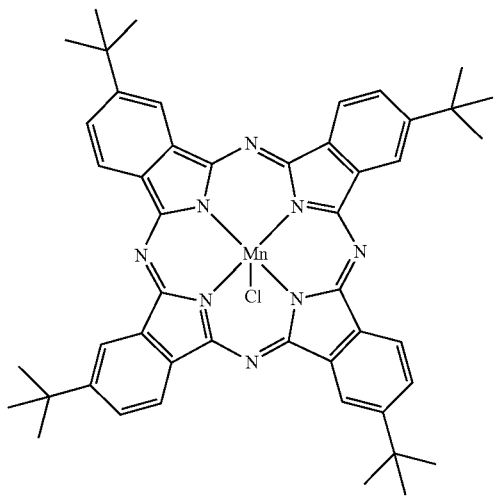

3

We hypothesized that a metal catalyst capable of transferring bound nitrenes to sp³ C—H bonds via a mechanism that lies on the continuum between a concerted C—H insertion, observed with rhodium, and a stepwise radical C—H abstraction/rebound, observed with iron, would achieve high reactivity while maintaining high chemoselectivity. Although nature rarely uses manganese metal centers to mediate oxidations, early studies using synthetic metalloporphryins as models for cytochrome P450 demonstrated that manganese and iron oxos react via mechanistically analogous one electron pathways, with manganese exhibiting significantly higher C—H hydroxylation reactivity (Groves et al., *J. Am. Chem. Soc.* 102, 6375-6377 (1980)). Importantly, the manganese catalysts were found to have smaller kinetic isotope effects (KIE) than their iron counterparts, suggestive of attenuated radical behavior (Cook et al., *J. Am. Chem. Soc.* 108, 7281-7286 (1986)). Moreover, well-characterized nitridomanganese(V) porphyrin complexes have been shown to stoichiometrically transfer nitrenes when the nitrogen is rendered electron deficient, much like with iron. Based on this, we compared a series of manganese complexes to their iron counterparts for the C—H amination of challenging 3° aliphatic substrate 4 (BDE~96 kcal/mol). We observed improved yields of aminated product 5 with the manganese complexes across all ligand classes evaluated (Scheme 1, entries 1-8).

Scheme 1. Mn-Catalyzed Intramolecular C—H Amination. Reactivity studies for 3° aliphatic C—H amination of 4 with Fe and Mn-based catalysts across ligand classes and [Mn^{III}Pc] reaction optimization.

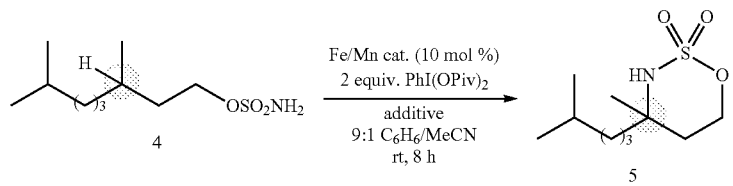

| entry | catalyst | additive | % yield (% rsm) |
|---|---|---|---|
| 1 | [FePc]Cl (1) + AgSbF₆ | — | 29 (32) |
| 2 | [MnPc]Cl (2) + AgSbF₆ | — | 43 (27) |
| 3 | Fe(TPP)Cl + AgSbF₆ | — | 4 (85) |
| 4 | Mn(TPP)Cl + AgSbF₆ | — | 18 (62) |
| 5 | Fe(R,R-salen)Cl + AgSbF₆ | — | <1 (85) |
| 6 | Mn(R,R-salen)Cl + AgSbF₆ | — | 4 (78) |
| 7 | Fe(R,R-PDP)(SbF₆)₂ | — | <1 (91) |
| 8 | Mn(R,R-PDP)(SbF₆)₂ | — | 7 (82) |
| 9 | [MnPc]Cl (2) + AgSbF₆ | 4Å MS | 60 (11) |
| 10 | [MnPc]Cl (2) + AgSbF₆ | 4Å MS | 58 (20)* |
| 11 | [Mn(ᵗBuPc)]Cl (3) + AgSbF₆ | 4Å MS | 75 (<5) |
| 12 | [Fe(ᵗBuPc)]Cl + AgSbF₆ | 4Å MS | 29 (34) |
| 13 | [Mn(ᵗBuPc)]Cl (3) + AgSbF₆ | 4Å MS | 72 (14)* |

Scheme 1. Mn-Catalyzed Intramolecular C—H Amination. Reactivity studies for 3° aliphatic C—H amination of 4 with Fe and Mn-based catalysts across ligand classes and [Mn$^{III}$Pc] reaction optimization.

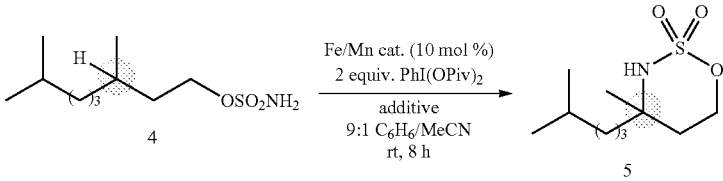

| entry | catalyst | additive | % yield (% rsm) |
|---|---|---|---|
| 14 | [Mn($^t$BuPc)]Cl (3) + AgSbF$_6$ | 4Å MS | 71 (13)† |
| 15 | [Mn($^t$BuPc)]Cl (3) + AgSbF$_6$ | 4Å MS | 68 (16)*,‡ |

Pc = phthalocyanine; TPP = tetraphenylporphyrin; salen = N,N'-bis(3,5-di-tert-butylsalicylidene)-1,2-cyclohexanediamine; PDP = [N,N'-Bis(2-pyridylmethyl)]-2,2'-bipyrrolidine.
Isolated yields are average of three runs. *Used 5 mol % each Mn catalyst and AgSbF$_6$.
†Used 2.5 mol % each Mn catalyst and AgSbF6. ‡Used 1.2 equiv PhI(OPiv)$_2$.

The phthalocyanine ligand was the most effective, and so catalyst 2 was employed for further optimization. Addition of molecular sieves significantly improved reactivity, affording 60% of 5 (entry 9). Catalyst 3, in which tert-butyl groups were introduced into the periphery of the phthalocyanine ligand, further improved the yield to 75% (entry 11). Interestingly, this modification was not similarly beneficial for the corresponding iron complex (29% yield, entry 12). The enhanced productivity of 3 enables the catalyst loading to be reduced to 5 mol % (72%, entry 13) and in some cases to 2.5 mol % (71%, entry 14) with a negligible reduction in reactivity. The oxidant loading can also be reduced from 2 equivalents to 1.2 equivalents while still maintaining high reactivity with 5 mol % 3 (68%, entry 15).

We first examined this new catalytic method with all other major sp$^3$ C—H bond types (benzylic, allylic, 2° and 1° aliphatic) using unsubstituted linear sulfamate esters, one of the most difficult substrate classes for intramolecular C—H amination (Scheme 2A). In all cases, a significant improvement in yield is observed in switching from the iron to the manganese phthalocyanine catalyst, with the benzylic and allylic substrates affording synthetically useful yields of aminated products 6 and 7. Remarkably, catalyst 3 exhibited good reactivity across all bond types; even 2° (8, BDE~98 kcal/mol) and 1° (9, BDE~101 kcal/mol) C—H bonds were efficiently aminated. Moreover, despite the high reactivity of 3, excellent chemoselectivity (>20:1 ins./azir.) was maintained for allylic C—H amination.

Scheme 2. Substrate scope of [Mn($^t$BuPc)]-catalyzed C—H amination. For specific experimental details, see the examples section below.

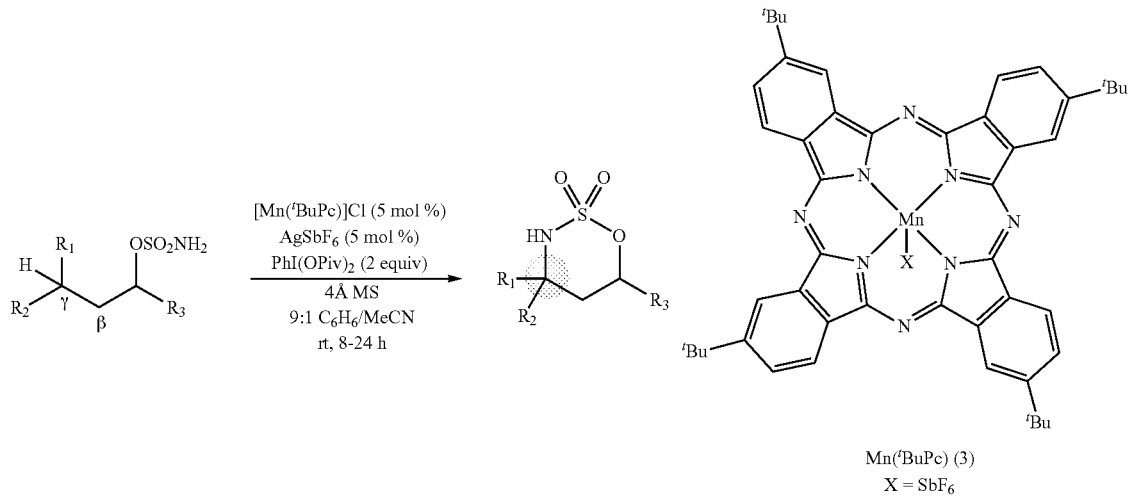

Mn($^t$BuPc) (3)
X = SbF$_6$

-continued
A.
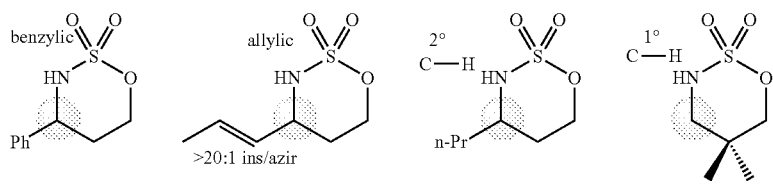
| catalyst | 6 | 7 | 8 | 9 |
|---|---|---|---|---|
| [FePc]* | 22% | 10% | 5%† | 3%† |
| [MnPc] | 71% | 61% | 39%† | 37%† |
| [Mn(tBuPc)] | 74% | 61% | 57%† | 64%† |
B. Aliphatic C—H
tertiary
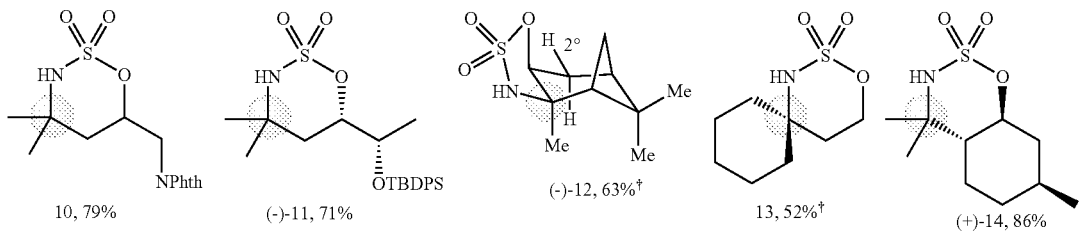
secondary                                                                                     primary
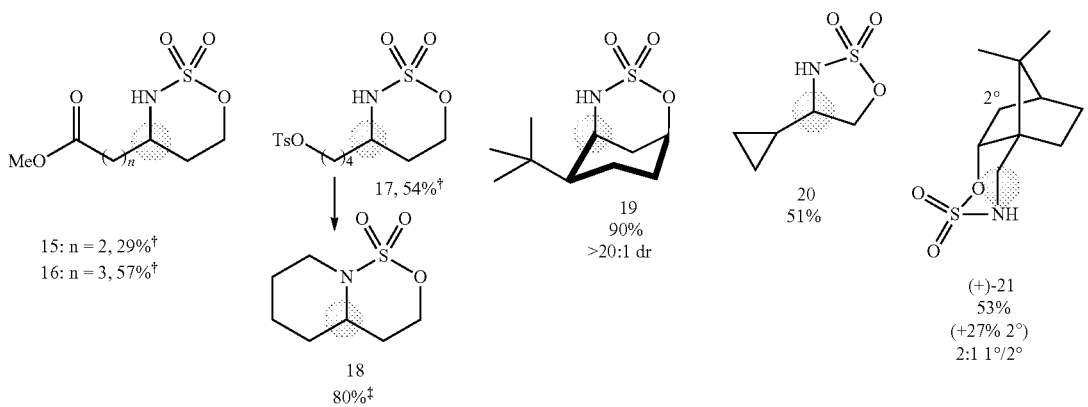
Allylic C—H
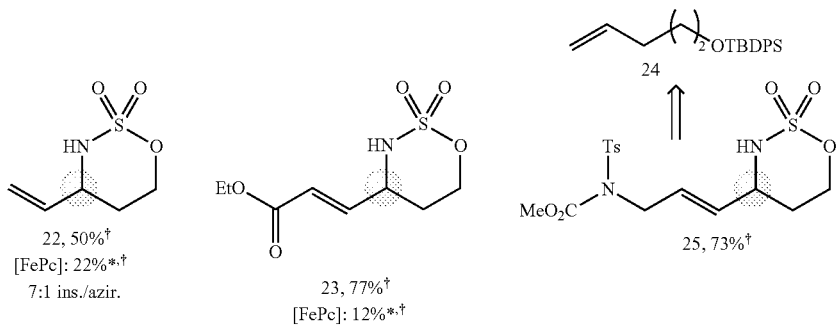

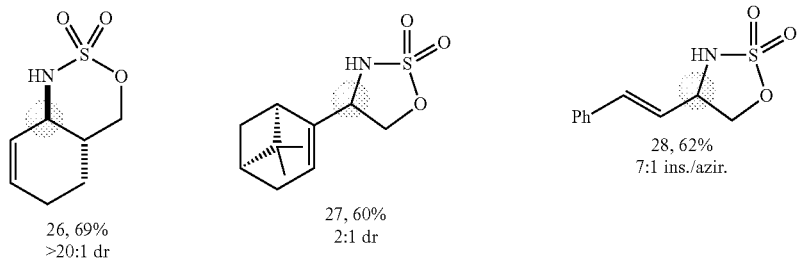
26, 69%
>20:1 dr
27, 60%
2:1 dr
28, 62%
7:1 ins./azir.
Benzylic C—H
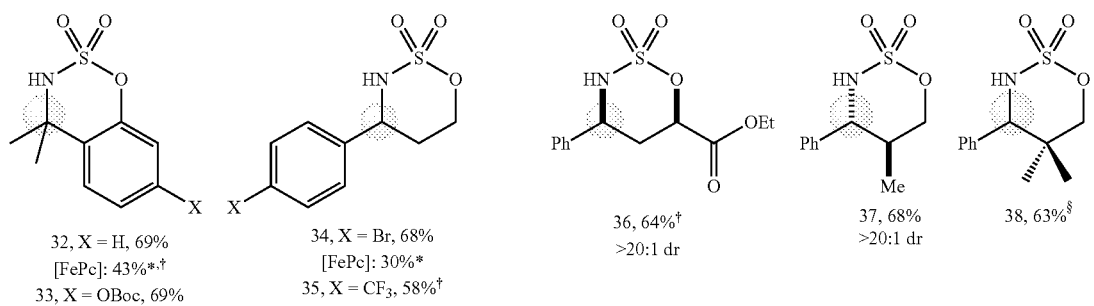
32, X = H, 69%
[FePc]: 43%*,†
33, X = OBoc, 69%
34, X = Br, 68%
[FePc]: 30%*
35, X = CF₃, 58%†
36, 64%†
>20:1 dr
37, 68%
>20:1 dr
38, 63%§
Other C—H
propargylic
ethereal
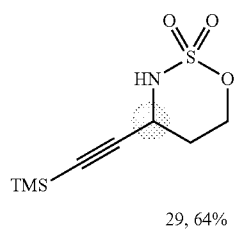
29, 64%
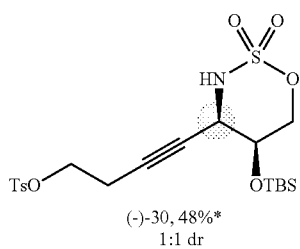
(−)-30, 48%*
1:1 dr
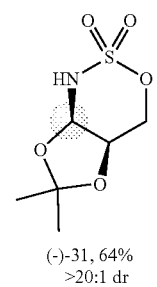
(−)-31, 64%
>20:1 dr heterocycles

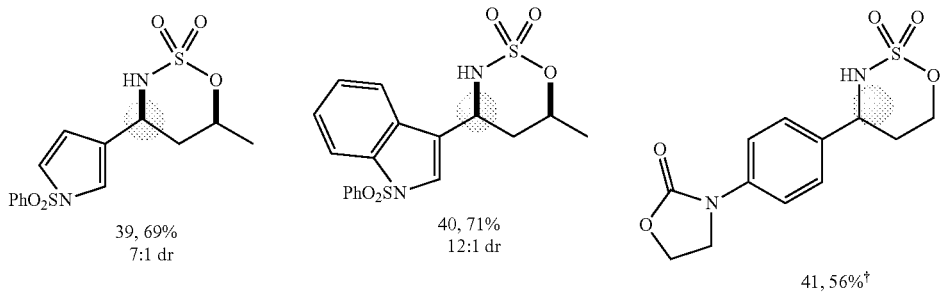

39, 69%
7:1 dr 40, 71%
12:1 dr 41, 56%†

42, 63%†

43, 63%
oxaprozin derivative (A) Comparison of reactivity of [Fe^III Pc] 1, [Mn^III Pc] 2, and [Mn^III(^tBuPc)] 3 across different sp³ C—H bond types with unsubstituted linear substrates. (B) Evaluation of reactivity and selectivity of 3-catalyzed aminations in simple substrates having 3°, 2°, and 1° aliphatic, allylic, benzylic, P propargylic, and ethereal C—H bonds. Standard reaction procedure: sulfamate ester substrate (1 equiv.), 3 (5 mol %), AgSbF₆ (5 mol %), 4Å mol. sieves, and PhI(OPiv)₂ (2 equiv.) were stirred in 9:1 C₆H₆/MeCN (0.5M) under argon at rt for 8-24 h. Increased catalyst loadings of 3 (10 mol %) and AgSbF₆ (10 mol %) were used when specified.
* Conditions: 5 mol % [FePc]Cl, 5 mol % AgSbF₆, 2 equiv. PhI(OPiv)₂, 4:1 PhMe/MeCN (0.5M), rt, 8 h.
† Used 10 mol % catalyst.
‡ Conditions: 1.5 equiv K₂CO₃, 10 mol % TBAI, DMF, rt, 15 h.
§ 10% of 1° C—H amination also isolated.
Isolated yields are average of three runs.

Catalyst 3 is capable of efficiently functionalizing a broad range of 3°, 2°, and 1° aliphatic C—H bonds with good functional group tolerance and site-selectivity (Scheme 2B). Adjacent functionality such as protected nitrogen (10, 79%) and silyl ethers (11, 71%) is well tolerated. Catalyst 3 is able to discriminate among different C—H bonds in a molecule, functionalizing at the 3° C—H bond of an isopinocampheol derivative in the presence of an alternative 2° C—H bond (12, 63%). Amination of 3° C—H bonds is also efficient for the formation of azaspirocycles (13, 52%) and fused bicycles (14, 86%). For strong 2° aliphatic C—H bonds, catalyst 3 exhibits sensitivity to substrate electronics (15, 29%), with reactivity restored as an ester group on a linear substrate is made more remote (16, 57%). A tosylate group is tolerated under the reaction conditions to afford 17 in 54% yield, and is subsequently displaced to generate heterobicycle 18 in 80% yield. In addition, 2° C—H amination in cyclohexanes can occur across the ring in a 1,3-fashion, functionalizing adjacent to a bulky tert-butyl group in a cis relationship (19, 90%), which would be challenging to accomplish through traditional synthetic methods. A cyclopropane-containing substrate aminates exclusively at the stereoelectronically activated β 2° C—H bond (BDE~95 kcal/mol) to form five-membered oxathiazole 20 (51%) as opposed to the six-membered oxathiazinane, which would require abstraction of a very strong 3° cyclopropane C—H bond (BDE~106 kcal/mol). However, in the functionalization of a borneol derivative, amination selectively occurs at the stronger γ 1° C—H bond of the adjacent methyl group in preference to a β 2° C—H bond (21, 53% of 1°; 1°/2°=2:1). Although a preference for formation of the six-membered oxathiazinane versus five-membered sulfamidate has been previously demonstrated with dirhodium carboxylate catalysts, such amination reactivity at 1° methyl groups with metallonitrenes is rare (E. T. Hennessy, T. A. Betley, Science 340, 591-595 (2013)); the only reported example under rhodium catalysis is low yielding (K. Huard, H. Lebel, Chem. Eur. J. 14, 6222-6230 (2008)).

Catalyst 3 successfully aminates at the allylic position in a variety of molecules, in all cases maintaining the excellent chemoselectivity previously observed with [Fe^III Pc] for olefin-containing substrates (Scheme 2B). For example, with a challenging linear terminal olefin substrate, iron catalyst 1 demonstrates good levels of selectivity favoring C—H insertion over aziridination (7:1 ins./azir.) but sacrifices reactivity (22%). In contrast, catalyst 3 affords C—H amination product 22 in 50% yield and in 7:1 excess over the aziridine. The higher reactivity of this catalyst is also underscored by insensitivity to electronic effects with this weaker sp³ bond type. Catalyst 3 readily functionalizes C—H bonds proximal to electron-withdrawing groups like α,β-unsaturated esters (23, 77%), while other chemoselective catalysts such as 1 and [Ru₂(hp)₄] are poorly reactive for these substrates (12% and 25%, respectively). The electronic insensitivity of 3-catalyzed amination with allylic C—H bonds is further highlighted by the tolerance of electron-withdrawing nitrogen functionality (25, 73%), which was installed by palladium bis-sulfoxide-catalyzed linear C—H amination of alkenol 24 (Reed et al., *J. Am. Chem. Soc.* 131, 11701-11706 (2009)). Additionally, a cyclohexene derivative readily cyclizes to form bicycle 26 in 69% yield with excellent diastereoselectivity (>20:1 anti/syn). Notably, despite the strong preference for formation of six-membered oxathiazinanes previously noted, five-membered heterocycle formation is facile with no observed aziridination, as demonstrated with homoallylic sulfamate derivative of terpene (−)-nopol (27, 60%). The bias of 3 toward allylic C—H amination versus aziridination persists even in acyclic styrenyl substrates (28, 69%, 7:1 ins./azir.). In contrast, under rhodium catalysis, six-membered bicyclic aziridine products are strongly favored (D. N. Zalatan, J. Du Bois, *J. Am. Chem. Soc.* 130, 9220-9221 (2008)).

A general method for chemoselective propargylic C—H amination via sulfamate ester metal nitrene catalysis has not been reported, as the alkyne typically undergoes alternate oxidation pathways (A. R. Thornton, S. B. Blakey, *J. Am. Chem. Soc.* 130, 5020-5021 (2008)). Instead, two-step sequences have been developed that involve amination of activated ethereal C—H bonds to furnish N,O-acetals followed by Lewis acid-promoted alkylations to generate propargylic amines. Further underscoring the remarkable balance of selectivity and reactivity achieved with manganese catalysis, a TMS-protected terminal alkyne sulfamate ester readily undergoes exclusive propargylic C—H amination (29, 64%). α-Substituted alkyne 30 functionalizes in moderate yields and serves as a viable intermediate for a streamlined synthesis of saxitoxin. Alternatively, ethereal C—H amination can be performed in good yield and diastereoselectivity (64%; >20:1 d.r.) with catalyst 3 to furnish the sensitive oxathiazinane N,O-acetal 31, a known precursor to alkyne 30.

Catalyst 3 effectively functionalizes benzylic C—H bonds in a variety of aromatic and heterocyclic compounds, further highlighting the generality of this method (Scheme 2B). Phenolic sulfamate esters cyclize with iron catalyst 1 in low yields (32, 43%) due to deleterious substrate decomposition, but these substrates are readily functionalized with manganese catalyst 3 (32, 69% and 33, 69%). Catalyst 3 promotes benzylic C—H amination on unbiased substrates with varying degrees of electronic deactivation, such as para-Br- and para-CF$_3$-substituted benzylic substrates (34, 68%; 35, 58%, respectively). Both α- and β-branched sulfamates readily undergo benzylic C—H amination with excellent diastereoselectivity (>20:1) favoring the syn and anti oxathiazinane, respectively (36, 64%; 37, 68%). Despite the steric bulk of catalyst 3, benzylic substrates with quaternary centers adjacent to the site of functionalization aminate in good yields (38, 63%). Given the prevalence of heterocycles in medicinally relevant compounds, we evaluated the tolerance of this method to aromatics with varying degrees of heteroatom incorporation. Pyrrole and indole substrates both afforded good yields and diastereoselectivities of the desired C—H amination products (39, 69%, 7:1 d.r. and 40, 71%, 12:1 d.r., respectively). N-aryloxazolidinones and oxadiazoles, which contain both nitrogen and oxygen heteroatoms, proceeded smoothly under the reaction conditions (41, 56% and 42, 63%, respectively). Exemplifying the ability of this method to rapidly diversify pharmaceuticals, an oxazole-based substrate was derived in two steps from the commercial NSAID oxaprozin and furnished oxathiazinane 43 in 63% yield.

We next investigated our hypothesis that the unprecedented generality of catalyst 3 can be attributed to its intermediate position along the continuum between the stepwise mechanism of iron and the concerted mechanism of rhodium (Scheme 3). Intramolecular competition experiments were conducted to probe the C—H amination steps of the catalytic cycle independently from the reaction kinetics (Scheme 3A). The electronic nature of the transition state for C—H cleavage was assessed by way of Hammett analysis with a series of sulfamate ester substrates having two electronically dissimilar benzylic sites (Scheme 3B) (see also, Example 5 below).

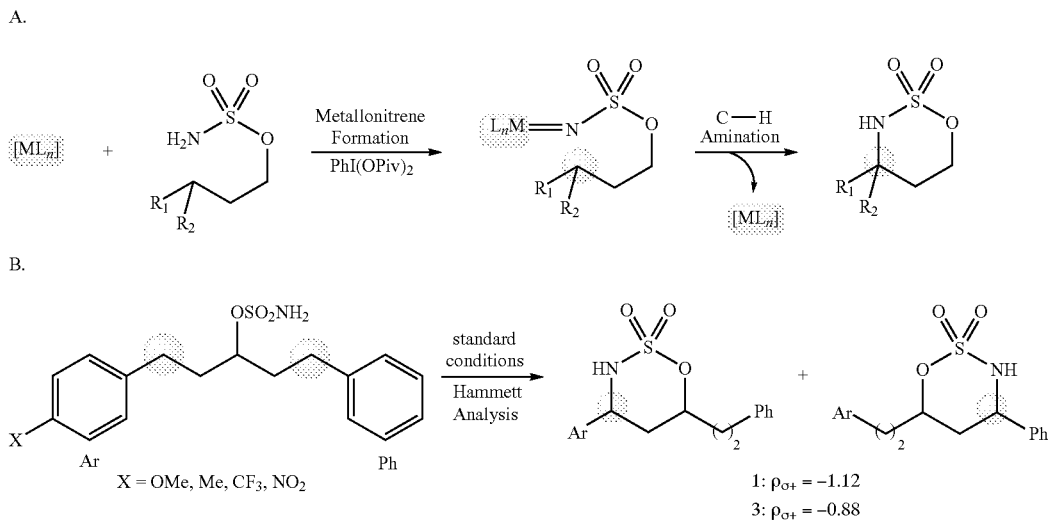

Scheme 3. Mechanistic studies of Mn and Fe C—H amination catalysts.

C.

allylic

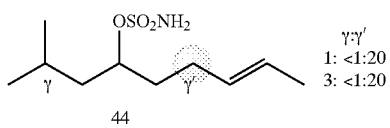

44 benzylic

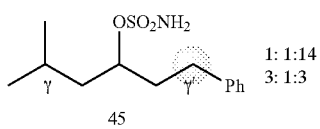

45 propargylic

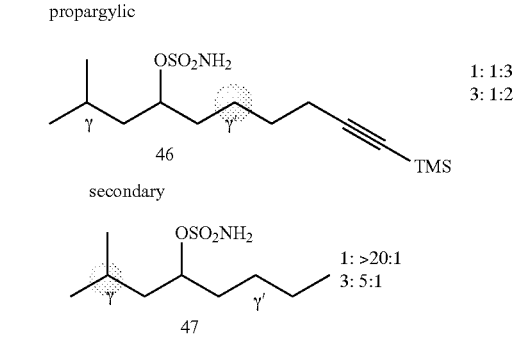

46 secondary

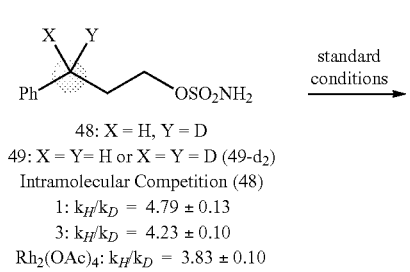

47

D.

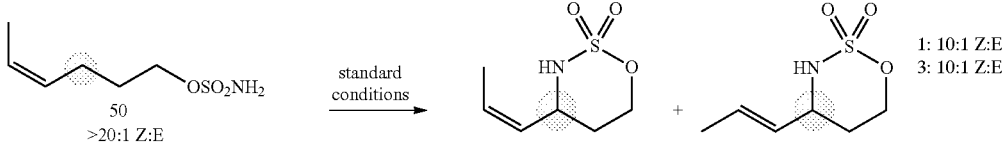

48: X = H, Y = D
49: X = Y = H or X = Y = D (49-d$_2$)
Intramolecular Competition (48)
1: k$_H$/k$_D$ = 4.79 ± 0.13
3: k$_H$/k$_D$ = 4.23 ± 0.10
Rh$_2$(OAc)$_4$: k$_H$/k$_D$ = 3.83 ± 0.10

Parallel Reactions (49 or 49-d$_2$)
3: k$_H$/k$_D$ = 1.7 ± 0.1
Intermolecular Competition (49 or 49-d$_2$)
3: k$_H$/k$_D$ = 1.6 ± 0.1

E.

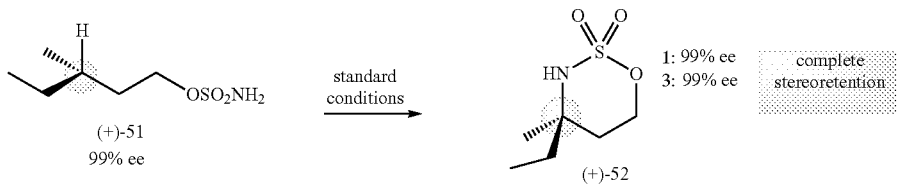

F.

(A) General reaction mechanism. (B) Intramolecular Hammett analysis (σ$^+$); X = NO$_2$, CF$_3$, Me, OMe. (C) C—H bond reactivity trends. (D) KIE studies; KIE values for the intramolecular and intermolecular competition experiments were established by quantitative $^{13}$C NMR analysis of column-purified oxathiazinane. KIE value for parallel reactions was established by measurement of separate initial rates for 49 and 49-d$_2$. (E) Olefin isomerization studies. (F) Stereoretention in the amination of enantiomerically enriched 3° aliphatic substrate (+)-51; enantiopurity was established by chiral GC analysis of column-purified oxathiazinane (+)-52.

Plotting log(k$_{Ar}$/k$_H$) against substituent parameter σ$^+$ furnished linear correlations, with manganese showing less sensitivity to the electronics of the C—H bond relative to iron (ρ=–0.88 for 3, –1.12 for 1), but significantly more than that reported for rhodium dicarboxylate catalysts (ρ=–0.55) (see, Roizen et al., Acc. Chem. Res. 45, 911-922 (2012); Harvey et al., J. Am. Chem. Soc. 133, 17207-17216 (2011)). This data suggests a transition structure in which C—H cleavage for manganese is more pronounced than for rhodium but less than for iron. We also systematically compared the C—H bond reactivity trends for 3° aliphatic C—H bonds (γ) relative to other bond types (γ') (44-47, Scheme 3C). The reactivity trends correlate with the homolytic C—H BDEs for both manganese and iron, but manganese generally shows less discrimination between the different bond types, consistent with attenuated electrophilic radical character in the C—H cleavage transition state. Additionally, benzylic amination of monodeuterated substrate 48 provides an intramolecular KIE for manganese catalyst 3 (4.23) that lies between iron catalyst 1 (4.79) and Rh$_2$(OAc)$_4$ catalyst (3.83) (Scheme 3D). Taken together, these data support our hypothesis that catalyst 3 proceeds through a stepwise mechanism with a transition structure in which the extent of C—H bond breakage is somewhere between that of iron and rhodium. Notably, catalyst 3 behaved comparably to its unsubstituted manganese analogue 2 in all cases, with the exception that a slightly smaller intramolecular KIE was observed with 3 (4.23) relative to 2 (4.46), suggesting that this ligand modification results in further attenuation of radical character (see Example 7 below).

We next sought to evaluate the recombination step for manganese catalyst 3. In the allylic C—H amination of Z-olefin substrate 50 (>20:1 Z/E), olefin isomerization was observed with catalyst 3 to the same degree as with iron catalyst 1, affording a 10:1 Z/E mixture of 7 (Scheme 3E). In contrast, rhodium catalysis with an analogous substrate has been reported to proceed with no isomerization (S. M. Paradine, M. C. White, *J. Am. Chem. Soc.* 134, 2036-2039 (2012)). Importantly, C—H amination at a defined aliphatic stereocenter in 51 proceeds with complete stereoretention for manganese catalysts 2 and 3 as well as for iron catalyst 1 (52, 99% ee, Scheme 3F). These data further support a stepwise mechanism for manganese that proceeds through H-atom abstraction followed by rapid radical rebound from the base metal catalyst. In contrast to aminations that proceed via free radical intermediates, this mechanistic feature of metallonitrene chemistry enables C—H amination reactions to harness the powerful features of such stepwise processes while proceeding stereospecifically and with high functional group tolerance.

In order to gain further mechanistic insight, we investigated the influence of the manganese catalyst 3 on reaction kinetics. The reaction profile for a 2° aliphatic substrate suggested an overall reaction rate enhancement with 3 relative to both 1 and 2, resulting in significantly higher product yields with 3 (see Example 10 below). Initial rate measurements for 2° and benzylic C—H amination with 3 quantitatively support catalyst involvement in the rate-determining step of the reaction, as changes in catalyst concentration (5 mol % to 10 mol %) result in proportional changes in the initial rate (see Example 10 below). This is in sharp contrast to rhodium catalysis where there is no rate dependence on catalyst concentration and iminoiodinane formation is hypothesized to be rate-determining. Moreover, measuring initial rates on parallel reactions with benzylic substrate 49 and 49-d$_2$ revealed a primary KIE of 1.7, suggesting that the manganese nitrene-mediated C—H cleavage step influences the rate of these reactions (Scheme 3D). Consistent with this, an intermolecular competition experiment with one equivalent of each 49 and 49-d$_2$ gave a KIE of 1.6 from isolated product ratios (Scheme 3D). These two KIE experiments with catalyst 3 provide values that are larger than would be expected for a rate-determining step that did not involve C—H cleavage ($k_H/k_D$~1), but smaller than if C—H cleavage was solely rate-determining ($k_H/k_D$~3.5-6). Collectively, these data suggest that the C—H cleavage step contributes significantly to the overall reactivity and selectivity observed with catalyst 3.

Remarkably, the reactivity and selectivity trends observed with catalyst 3 on relatively simple molecules are maintained in more topologically and functionally complex natural product settings (Scheme 4A). A functionally dense picrotoxinin derivative, containing an unprotected 3° alcohol, reacted smoothly under standard reaction conditions at a 3° C—H bond to produce fused bicycle 53 in 57% yield. Allylic C—H amination of sulfamate ester derived steroids pregnenolone and stigmasterol furnished five-membered heterocycles 54 and 55 in 55% and 66% yields, respectively, as single diastereomers. A leelamine-derived phenolic sulfamate ester with a remote imide moiety gave 70% yield of the 3° benzylic C—H amination product 56. Isosteviol derivative 57 is functionalized at the equatorial γ 2° aliphatic C—H bond to furnish 58 in 92% yield as a single syn diastereomer, reflecting the stereochemical preference of simpler substrates. Importantly, this reaction is high yielding with reduced catalyst (2.5 mol % 3) and oxidant (1.5 equiv) loadings (75%), and scales readily with no loss of efficiency. The versatile oxathiazinane moiety can also be readily diversified. For example, reaction of N-CBz-protected oxathiazinane 58 with NaN$_3$ or KOAc affords 1,3-diamines (59, 56%) or amino alcohol (60, 76%) precursors. These results establish that alcohols and phenols, which are present in a wide range of readily available natural products, can serve as valuable handles to install nitrogen into a broad range of sp$^3$ C—H bonds in predictable 1,3- or 1,2-relationships.

The lack of reactivity of electrophilic metal nitrenes and oxos with 1° methyl C—H bonds is attributed to their high BDEs and low basicity. However, given the choice between a γ 1° C—H bond and a β 2° C—H bond, catalyst 3 preferentially aminates at the 1° C—H bond in synthetically useful yields (21, vide supra). Studies were therefore undertaken to explore this exciting new reactivity and selectivity in complex molecule settings (Scheme 4B). Betulinic acid is a readily available pentacyclic triterpenoid with demonstrated mitochondrial-targeted antitumor activity. Betulinic acid-derived sulfamate ester 61 was functionalized by catalyst 3 with complete site- and diastereoselectivity, aminating the 1° C—H bond of the equatorial C23 methyl group to form oxathiazinane 62 in 76% yield. This provides a functional handle for a range of further modifications (vide supra) that may attenuate betulinic acid's high lipophilicity that has thus far limited its bioavailability.

Scheme 4. Late-stage diversification of complex molecules via [Mn($^t$BuPc)]-catalyzed C—H amination.

A.

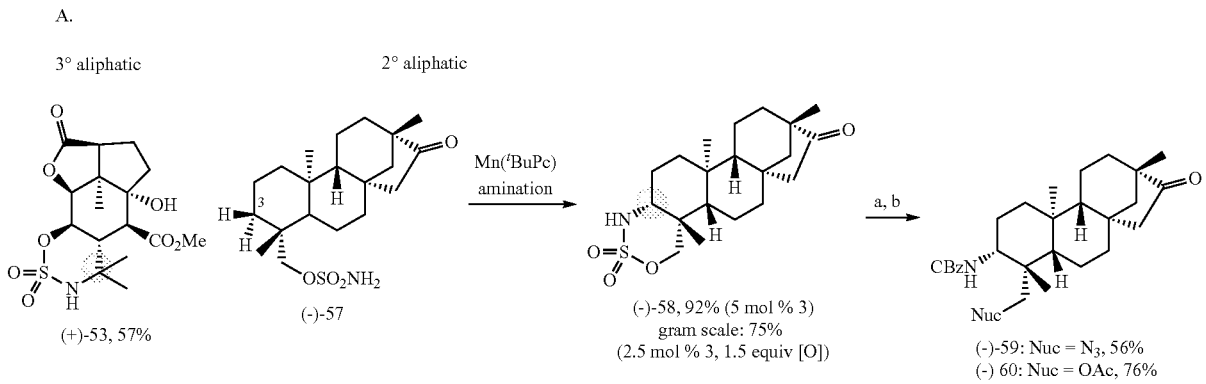

allylic

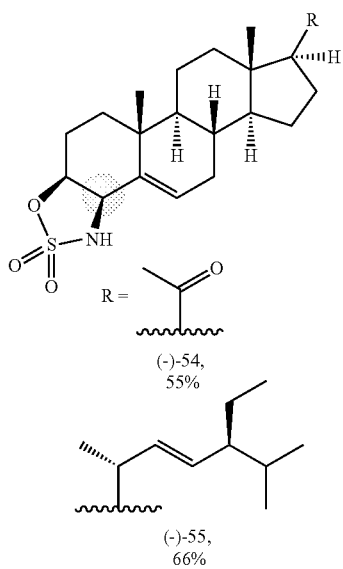

-continued benzylic

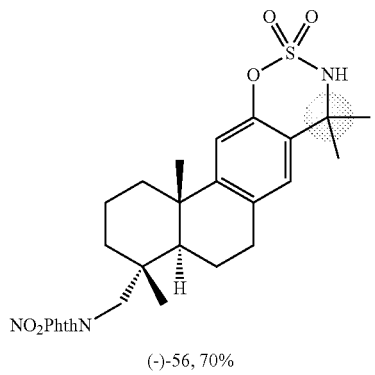

B.

1° aliphatic

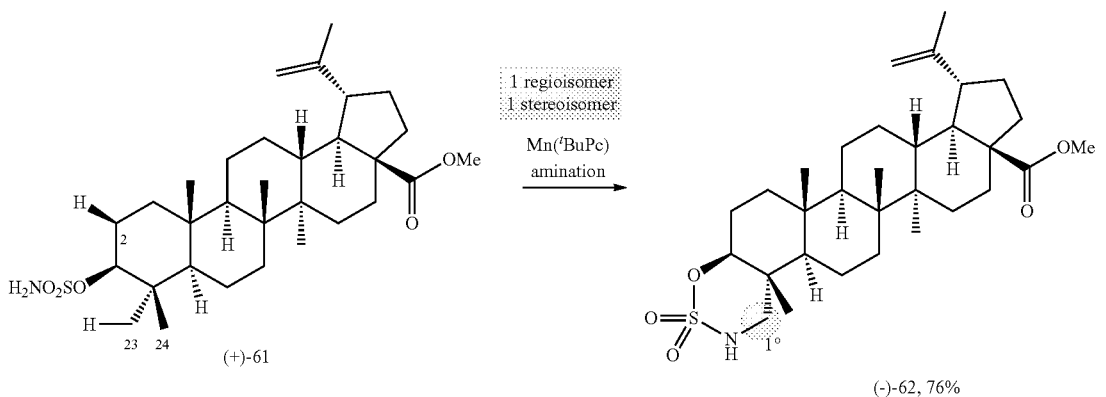

Sequential 2° C—H Hydroxylation/1° C—H Amination

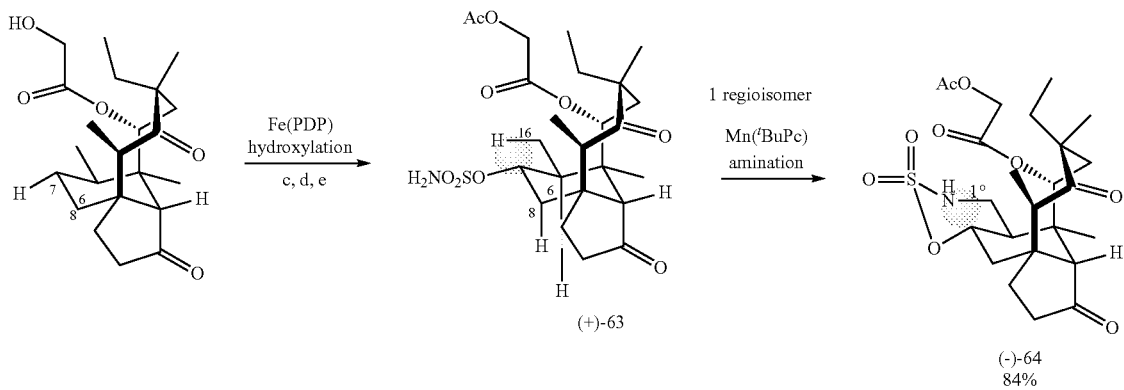

(A.) Derivatization of alcohol and phenol-containing complex molecules. Standard reaction procedure: sulfamate ester substrate (1 equiv.), 3 (10 mol %), AgSbF$_6$ (10 mol %), 4Å mol. sieves, and PhI(OPiv)$_2$ (2 equiv.) were stirred in 9:1 C$_6$H$_6$/MeCN (0.5M) under argon at rt for 8-24 h. Lower loadings of catalyst 3 (5 mol %) and AgSbF$_6$ (5 mol %) were used when specified. Gram-scale C—H amination of isosteviol derivative (-)-57 was conducted using 2.5 mol % 3 and 1.5 equiv PhI(OPiv)$_2$. Reaction conditions for elaboration of oxathiazinane (-)-58: a) CbzCl, Et$_3$N, DMAP, THF, rt, 2 h, 83%. b) NaN$_3$, DMF, 40° C., 48 h, 56% or KOAc, DMF, 80° C., 72 h, 76%.
(B.) Selective 1° aliphatic C—H amination of complex molecules and sequential C—H functionalization strategy. Reaction conditions for preparation of dihydropleuromutilone-derived sulfamate ester 63: c) Fe(PDP), AcOH, H$_2$O$_2$, MeCN, rt, 30 min, 42%. d) AcCl, pyr., 0° C., 72%. e) Et$_3$N, ClSO$_2$NH$_2$, CH$_2$Cl$_2$, 0° C to rt 48%.

Dihydropleuromutilone sulfamate ester 63, rapidly generated via Fe(PDP)-catalyzed C—H hydroxylation and subsequent sulfamoylation at C7 (M. S. Chen, M. C. White, *Science* 327, 566-571 (2010)), presented the opportunity for additional investigation of site-selectivity in a complex molecule setting. For 63, C—H amination can feasibly occur at three sites: the γ1° C—H bond (C16), the equatorial β 2° C—H bond (C8) or the β 3° C—H bond (C6). Remarkably, 3-catalyzed C—H amination again resulted in exclusive formation of 1° C—H amination oxathiazinane product 64 in 84% yield. To the best of our knowledge, 3 represents the first example of a metallonitrene catalyst capable of highly selective 1° aliphatic C—H bond amination. Additionally, the demonstrated sequence of aliphatic C—H oxidation followed by sulfamate ester installation and C—H amination enables rapid access to amino alcohol motifs that would be difficult to achieve via traditional synthetic or enzymatic methods.

We have therefore reported a novel manganese C—H amination catalyst, readily synthesized in one step from commercial materials (Example 1 below), that is non-toxic and ten million times more abundant that its noble metal predecessor. In addition to these practical advances, [Mn($^t$BuPc)] is unprecedented in its capacity to preparatively functionalize all types of C(sp$^3$)-H bonds, including 1° aliphatic and propargylic, while maintaining stereospecificity and broad functional group tolerance in complex molecule settings. The general features of this sustainable C—H amination catalyst render it highly enabling for the rapid preparation and diversification of nitrogen-containing compounds.

The following Example is intended to illustrate the above invention and should not be construed as to narrow its scope. One skilled in the art will readily recognize that the reactions, methods, and examples suggest many other ways in which the invention could be practiced. It should be understood that numerous variations and modifications may be made while remaining within the scope of the invention.

EXAMPLES

Example 1. Compound 3, a General Manganese Catalyst for C(Sp$^3$)-H Amination

The following commercially obtained reagents were used as received: iron(III) phthalocyanine chloride ([FePc]Cl, Sigma-Aldrich), manganese(III) phthalocyanine chloride ([MnPc]Cl, Sigma-Aldrich), 5,10,15,20-Tetraphenyl-21H,23H-porphine iron(III) chloride (Fe(TPP)Cl, Strem), 5,10,15,20-Tetraphenyl-21H,23H-porphine manganese(III) chloride (Mn(TPP)Cl, Strem), Mn(R,R-salen)Cl (Sigma-Aldrich), silver hexafluoroantimonate (AgSbF$_6$, Strem), and bis (tert-butylcarbonyloxy)iodobenzene (PhI(OPiv)$_2$, Sigma-Aldrich) (alternatively, this reagent can be prepared using the following procedure: Fiori, K. W.; Du Bois, J. *J. Am. Chem. Soc.* 2007, 129, 562). All reactions were run in flame- or oven-dried glassware under an atmosphere of N$_2$ or Ar gas with dry solvents unless otherwise stated. All products were filtered through a glass wool plug prior to obtaining a final weight. Solid reagents were stored in a desiccators or glovebox, and anhydrous solvents were purified by passage through a bed of activated alumina immediately prior to use (Glass Countour, Laguna Beach, Calif.). Chloroform-d was stored over 3 Å molecular sieves in a secondary container with drierite. Fe(R,R-PDP)(SbF$_6$)$_2$,$^5$ Mn(R,R-PDP)(SbF$_6$)$_2$, and Fe(R,R-salen)Cl were prepared according to methods described in the literature and stored at 4° C. See "Preparation of Fe(R,R-salen)Cl": Salomão et al., *Cat. Commun.* 2007, 8, 69. No characterization data is reported in the literature, but successful preparation of the catalyst was confirmed via low-resolution field desorption (LR-FD) mass spectrometry: m/z=600.4 (C$_{36}$H$_{52}$N$_2$O$_2$Fe, 5%), 635.3 (C$_{36}$H$_{52}$N$_2$O$_2$ClFe, 100%).

Chlorosulfonyl isocyanate (ClSO$_2$NCO, Sigma-Aldrich or TCI America) was transferred to a Schlenk-type flask and stored at 4° C. under an inert atmosphere. Caution: ClSO$_2$NCO reacts violently with water so the transfer should be done under an inert atmosphere, preferably in a glovebox. Because of its propensity for freezing glass stopcocks, ClSO$_2$NCO should be stored in a flask with a Teflon stopcock. 4 Å MS beads were crushed with a mortar and pestle until fine, then activated in a 180° C. oven for at least 48 h and stored in a desiccator or glovebox. Thin-layer chromatography (TLC) was conducted with E. Merck silica gel 60 F254 pre-coated plates (0.25 mm) and visualized with UV and ethanolic anisaldehyde or potassium permanganate stains. Flash chromatography was performed as described by Still (Still, W. C.; Kahn, M.; Mitra, A. *J. Org. Chem.* 1978, 43, 2923) using American International ZEOprep 60 ECO silica gel (230-400 mesh). Achiral gas chromatographic (GC) analysis was performed on an Agilent 6890N Series instrument equipped with FID detectors using a HP-5 (5%-Phenyl)-methylpolysiloxane column (30 m, 0.32 mm, 0.25 mm), and chiral GC analysis using a CycloSil-B column (30 m, 0.25 mm, 0.25 mm).

$^1$H-NMR spectra were recorded on a Varian Inova-500 (500 MHz) or Varian Unity-500 (500 MHz) spectrometer and are reported in ppm using solvent as an internal standard (CDCl$_3$ at 7.26 ppm). Data reported as: s=singlet, d=doublet, t=triplet, q=quartet, p=pentet, sxt=sextet, spt=septet, m=multiplet, br=broad, app=apparent; coupling constant(s) in Hz; integration. Proton-decoupled $^{13}$C-NMR spectra were recorded on a Varian Unity-500 (125 MHz) spectrometer and are reported in ppm using solvent as an internal standard (CDCl$_3$ at 77.16 ppm). Kinetic isotope effect analyses were recorded on a Varian Inova-600 (600 MHz) spectrometer. IR spectra were recorded as thin films on NaCl plates or by ATR on a Perkin Elmer Frontier FTIR and are reported in frequency of absorption (cm$^{-1}$). Optical rotations were measured using a 1 mL cell with a 50 mm path length on a Jasco P-1020 polarimeter. Optical rotations were obtained with a sodium lamp and are reported as follows: [α]$_λ$T°C (c=g/100 mL, solvent). High-resolution mass spectra were obtained at the University of Illinois Mass Spectrometry Laboratory. Electrospray ionization (ESI) spectra were performed on a Waters Q-Tof Ultima spectrometer, and electron ionization (EI) and field desorption (FD) spectra were performed on a Micromass 70-VSE spectrometer. Elemental analysis was performed by Robertson Microlit Laboratories.

Preparation of [Mn$^{III}$($^t$BuPc)]

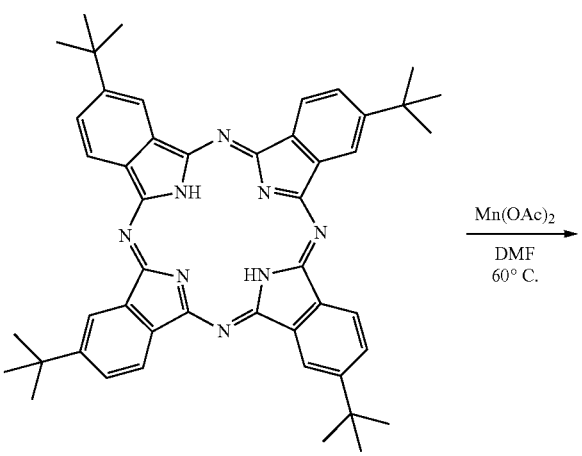

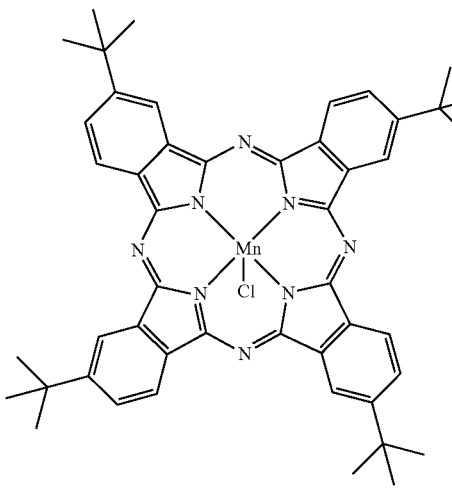

(3)

[Mn(<sup>t</sup>BuPc)]Cl from Ligand

The following procedure was adapted from a literature preparation (Liu et al., *Eur. J. Inorg. Chem.* 2004, 286). 2,9,16,23-Tetra-tert-butyl-29H,31H-phthalocyanine (250 mg, 0.338 mmol, 1.0 equiv, Sigma-Aldrich) was taken up in degassed DMF (16 mL) in a 50 mL round-bottom flask equipped with stir bar and septum (the flask and stir bar should be free of trace metal impurities). Mn(OAc)$_2$ (58.5 mg, 0.338 mmol, 1.0 equiv, Sigma-Aldrich) was added under a stream of N$_2$, then reaction was warmed to 60° C. and stirred for 12 h. Upon completion, the reaction cooled to rt, then was diluted with water (10 mL), transferred to a separatory funnel, and the aqueous layer was washed with hexanes (20 mL) to remove unreacted ligand. Brine (15 mL) was added, and then complex was extracted with chloroform (3×30 mL). The combined organic layers were dried over Na$_2$SO$_4$ and filtered. Neutral alumina (15 mL) was added to the solution of crude complex and concentrated to dryness. The adsorbed catalyst-alumina powder was then applied to a flash column with dry neutral alumina (45 mm column, 100 mm Al$_2$O$_3$). Remaining uncomplexed ligand, which is a bright turquoise color, was eluted with 9:1 hex/EtOAc (~1.5 L). Once the ligand fully eluted, 3, which is a dark evergreen color, was eluted with neat EtOAc (~1 L). Pure product was isolated as a flaky dark green solid in 89% yield.

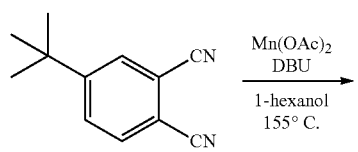

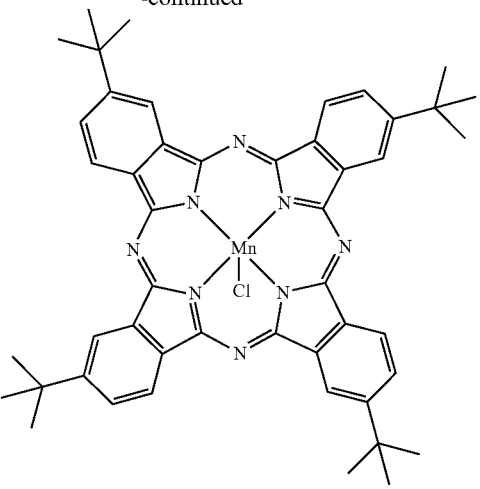

3

[Mn(<sup>t</sup>BuPc)]Cl from Phthalonitrile

A flame dried 100 mL round-bottom flask equipped with a stir bar and reflux condenser (the flask and stir bar should be free of trace metal impurities) was sequentially charged with 4-tert-butyl-phthalonitrile (2.211 g, 12.0 mmol, 4.0 equiv, TCI America), 1-hexanol (24 mL, freshly distilled over MgSO$_4$ and degassed), Mn(OAc)$_2$ (519 mg, 3.00 mmol, 1.0 equiv, Sigma-Aldrich) and DBU (3.59 mL, 24.0 mmol, 8.0 equiv, Sigma-Aldrich). Reaction flask was evacuated under vacuum and refilled with N$_2$ three times, then heated to 155° C. The reaction mixture changed from colorless to turquoise green over 10 min. After stirring at 155° C. overnight (12-15 h), the heat was ceased and the condenser was removed. Brine (15 mL) was cautiously added into the reaction dropwise via a pasteur pipette while the reaction temperature was maintained over 100° C., then the reaction was stirred open to air while cooling to room temp for 1 h. Brine and chloroform were added to the flask and the mixture was extracted with chloroform 3 times. The combined organic layer was dried over Na$_2$SO$_4$, filtered, and concentrated by rotatory evaporation. The remaining solution was transferred to a round-bottom flask equipped with stir bar and short path distillation head, placed under high vac, and then heated to ~60-80° C. until crude material was a sticky solid (~2-3 days). The crude catalyst was taken up in CH$_2$Cl$_2$ with 50 mL neutral alumina (Brockmann Type I, Alfa Aesar), then concentrated to dryness and applied to a plug of 200 mL neutral Al$_2$O$_3$ (50 mm fritted glass column) pre-wetted with 5% EtOAc/hexanes. Nonpolar impurities were eluted with 10% EtOAc/hexanes→20% EtOAc/hexanes (~2 L) until eluting solution turned green. [Mn(<sup>t</sup>BuPc)]Cl was eluted as a separate dark green fraction by flushing with EtOAc (~2-4 L). The solution was concentrated by rotatory evaporation and was dried under high vac overnight to afford 971 mg (1.17 mmol) of 3 as a dark green powder (39% yield). Catalyst obtained by this method contains a minor unknown impurity (visible in IR at 1711 cm$^{-1}$), which has no observable impact on reactivity or reaction rate for any of the substrate classes examined. Due to the convenience and economy of this procedure, this was the standard method for preparing the catalyst used in this report. [Mn(<sup>t</sup>BuPc)]Cl prepared in this way can be made analytically pure by column chromatography on silica using a gradient of 10%→20%→30%→50%→100% EtOAc/hexanes.

UV-Vis (CHCl$_3$, $\lambda_{max}$=nm, $\epsilon$=M$^{-1}$ cm$^{-1}$): 729 ($\epsilon$=73400), 662 ($\epsilon$=15900), 531 ($\epsilon$=10100), 369 ($\epsilon$=32400), 280 ($\epsilon$=39200); IR (ATR, cm$^{-1}$) 2955, 2865, 1612, 1506, 1482, 1459, 1394, 1363, 1328, 1280, 1255, 1199, 1147, 1075, 932, 893, 828, 763, 746; HRMS (ESI) m/z calculated for C$_{48}$H$_{48}$MnN$_8$ [M-Cl]$^+$: 791.3382, found 791.3380. LRMS (FD) m/z 792.9 (Mn($^t$BuPc)+H), 827.8 (M$^+$). Anal. calculated for C$_{48}$H$_{48}$ClMnN$_8$ (FW=827.36), C, 69.68, H, 5.85, N, 13.54, Mn, 6.64, found C, 70.07, H, 6.05, N, 13.21, Mn, 6.62.

UV-Vis Studies:

4.2 mg (0.005 mmol) of [Mn$^{III}$($^t$BuPc)] was taken up in CHCl$_3$ to 5 mL solution (1.0 mM). 100 μL of this solution was diluted to 10 mL (10.0 μM). UV-Vis was taken from 850-250 nm in a quartz cuvette (path length=1 cm) (see FIG. 1).

Example 2. Preparation of Sulfamate Ester Starting Materials

General Procedure for Preparation of Sulfamate Ester Substrates (see also Espino et al., *J. Am. Chem. Soc.* 2001, 123, 6935).

Method A.

Preparation of ClSO$_2$NH$_2$ Solution (2M in MeCN)

A round-bottom flask equipped with stir bar and rubber septum was charged with ClSO$_2$NCO (1.5 equiv) and MeCN (2M relative to isocyanate). The flask was cooled to 0° C., and then neat formic acid (1.5 equiv) was added dropwise. The reaction stirred vigorously at 0° C. (1 h) then room temp (~20° C.) overnight.

Sulfamate Ester Formation

A 50 mL round-bottom flask equipped with stir bar and rubber septum was charged with 95% NaH (1.1 equiv) and 5 mL DMF (1M relative to starting material) and cooled to 0° C. The alcohol starting material (1.0 equiv) in DMF was slowly added. The reaction was stirred at room temp for 1 h, after which it was cooled again to 0° C. The freshly prepared 2M MeCN solution of ClSO$_2$NH$_2$ (vide supra) was then added dropwise via syringe, and the reaction stirred at room temp. for 2-4 h. Upon complete consumption of starting material as monitored by TLC, the reaction was quenched with H$_2$O until the mixture turned clear (~8 mL). The reaction mixture was partitioned between H$_2$O (15 mL) and Et$_2$O (60 mL) and separated. The aqueous layer was then extracted with Et$_2$O (2×30 mL). The organic layers were combined, dried over MgSO$_4$, filtered, and concentrated under reduced pressure. Although the sulfamate esters were generally pure by NMR after a single column, as a precaution they were subjected to a second column to remove minor NMR-silent impurities that have been shown to inhibit the amination reaction. Following purification, sulfamate esters were thrice dissolved in benzene and concentrated under reduced pressure to remove trace H$_2$O, then stored in a desiccator until use.

Method B.

A round-bottom flask equipped with stir bar and rubber septum was charged with ClSO$_2$NCO (2.0 equiv) and CH$_2$Cl$_2$ (2M relative to isocyanate). The flask was cooled to 0° C., and then neat formic acid (2.0 equiv) was added dropwise. The reaction stirred vigorously at 0° C. (1 h) then room temp (~20° C.) overnight. After cooling the reaction flask back to 0° C., the alcohol starting material (1.0 equiv) with Et$_3$N (2.0 equiv) in CH$_2$Cl$_2$ (0.75M relative to starting material) was slowly added via syringe. After complete addition, the reaction warmed back to room temp. and stirred for 4-6 h. If conversion is low after 3-4 h, additional Et$_3$N (1-2 equiv) can be added. Upon complete consumption of starting material as monitored by TLC, the reaction was quenched with H$_2$O until the mixture turned clear (~8 mL). The reaction mixture was partitioned between H$_2$O (15 mL) and CH$_2$Cl$_2$ (30 mL) and separated. The aqueous layer was then extracted with CH$_2$Cl$_2$ (2×30 mL). The organic layers were combined, dried over MgSO$_4$, filtered, and concentrated under reduced pressure. Although the sulfamate esters were generally pure by NMR after a single column, as a precaution they were subjected to a second column to remove minor NMR-silent impurities that have been shown to inhibit the amination reaction. Following purification, sulfamate esters were thrice dissolved in benzene and concentrated under reduced pressure to remove trace H$_2$O, then stored in a desiccator until use.

Method C.

A round-bottom flask equipped with stir bar and rubber septum was charged with ClSO$_2$NCO (1.5 equiv). The flask was cooled to 0° C., and then neat formic acid (1.5 equiv) was added dropwise. After vigorously stirring for 5 min at 0° C., MeCN (2M relative to isocyanate) was added, and the reaction stirred vigorously at 0° C. (1 h) then room temp (~20° C.) overnight. After cooling the reaction flask back to 0° C., the phenol (1.0 equiv) in N,N-dimethylacetamide (DMA, 1.6M) was slowly added via syringe. After complete addition, the reaction warmed back to room temp and stirred for 4-6 h. Upon complete consumption of starting material as monitored by TLC, the reaction was quenched with H$_2$O (~5 mL). The reaction mixture was partitioned between H$_2$O (15 mL) and Et$_2$O (30 mL) and separated. The aqueous layer was then extracted with Et$_2$O (2×30 mL). The organic layers were combined, dried over MgSO$_4$, filtered, and concentrated under reduced pressure. Following purification of the crude product via flash column chromatography, the pure product was dissolved in CH$_2$Cl$_2$ and filtered through a short silica plug, then twice dissolved in benzene and concentrated under reduced pressure to remove trace H$_2$O, then stored in a desiccator until use.

NOTE: Some sulfamate esters exhibited suboptimal reactivity after storing for more than a month (although some are bench stable for much longer); repurification usually restored reactivity in these cases.

(±)-3,7-dimethyloctyl sulfamate [4]

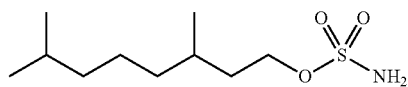

Prepared according to method A. 4.75 g (30.0 mmol) of (±)-3,7-dimethyloctanol were used, along with NaH (834 mg, 33.0 mmol, 1.1 equiv), DMF (30+15 mL), ClSO$_2$NCO (3.92 mL, 45.0 mmol, 1.5 equiv), formic acid (1.70 mL, 45.0 mmol, 1.5 equiv) and MeCN (23 mL). Flash column chromatography on silica (45 mm fritted glass column, 200 mm SiO$_2$) using 4:1 hexanes/EtOAc as eluent gave 5.835 g (24.6 mmol) of pure product as a colorless oil (82% yield).

$^1$H-NMR (500 MHz, CDCl$_3$) δ 4.71 (br. s, 2H), 4.29-4.22 (m, 2H), 1.82-1.76 (m, 1H), 1.64-1.48 (m, 3H), 1.34-1.22 (m, 3H), 1.20-1.10 (m, 3H), 0.92 (d, J=6.5 Hz, 3H), 0.87 (d, J=6.5 Hz, 6H); $^{13}$C-NMR (125 MHz, CDCl$_3$) δ 70.3, 39.3, 37.1, 35.8, 29.5, 28.1, 24.7, 22.8, 22.7, 19.4; IR (film, cm$^{-1}$) 3392, 3294, 2953, 2870, 1556, 1468, 1367, 1180, 1034, 953, 766; HRMS (ESI) m/z calculated for C$_{10}$H$_{23}$NO$_3$SNa [M+Na]$^+$: 260.1296, found 260.1297.

(±)-3-phenylpropan-1-yl sulfamate [49]

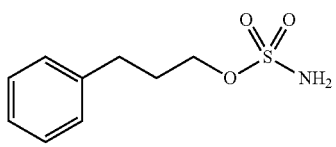 [SMILES: NS(=O)(=O)OCCCc1ccccc1]

Prepared according to method A. 1.634 g (12.0 mmol) of 3-phenyl-1-propanol were used, along with NaH (333 mg, 13.2 mmol, 1.1 equiv), DMF (12 mL+9 mL), ClSO$_2$NCO (1.57 mL, 18.0 mmol, 1.5 equiv), formic acid (679 μL, 18.0 mmol, 1.5 equiv) and MeCN (9 mL). Flash column chromatography on silica (100 mL SiO$_2$) using 2:1 hexanes/EtOAc as eluent gave 1.592 g (7.40 mmol) of pure product as a white solid (62% yield).

$^1$H-NMR (500 MHz, CDCl$_3$) δ 7.30 (t, J=7.5 Hz, 2H), 7.23-7.19 (m, 3H), 4.75 (br s, 2H), 4.22 (t, J=6.5 Hz, 2H), 2.76 (dd, J=7.5 Hz, 2H), 2.08 (dt, J=7.5, 7.0 Hz, 2H). This compound has been prepared, reported, and fully characterized previously by our group.[10]

(E)-hex-4-en-1-yl sulfamate [S1]

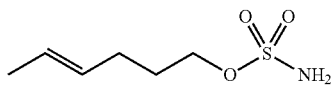

Prepared according to method A. 500 mg (5.00 mmol) of (E)-hex-4-en-1-ol were used, along with NaH (138 mg, 5.50 mmol, 1.1 equiv), DMF (8.9 mL), ClSO$_2$NCO (651 μL, 7.50 mmol, 1.5 equiv), formic acid (283 μL, 7.50 mmol, 1.5 equiv) and MeCN (3.8 mL). Flash column chromatography on silica (100 mL SiO$_2$) using 4:1 hexanes/EtOAc→3:1 hexanes/EtOAc as eluent gave 613 mg (3.40 mmol) of pure product as a colorless oil (68% yield).

$^1$H-NMR (500 MHz, CDCl$_3$) δ 5.52-5.45 (m, 1H), 5.42-5.35 (m, 1H), 4.73 (s, 2H), 4.21 (t, J=6.5 Hz, 2H), 2.13-2.08 (m, 2H), 1.80 (tt, J=7.3, 6.6 Hz, 2H), 1.65 (ddd, J=6.3, 2.3, 1.2 Hz, 3H); $^{13}$C-NMR (125 MHz, CDCl$_3$) δ 129.3, 126.7, 71.1, 28.7, 28.4, 18.0. These data are in agreement with that previously reported in the literature (Fiori et al., *Tetrahedron* 2009, 65, 3042).

Hexyl Sulfamate [S2]

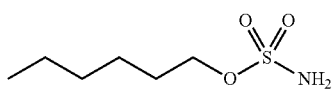

Prepared according to method A. 1.88 mL (15.0 mmol) of 1-hexanol were used, along with NaH (417 mg, 16.5 mmol, 1.1 equiv), DMF (15+12 mL), ClSO$_2$NCO (1.96 mL, 22.5 mmol, 1.5 equiv), formic acid (849 μL, 22.5 mmol, 1.5 equiv) and MeCN (11 mL). Flash column chromatography on silica (45 mm fritted glass column, 170 mm SiO$_2$) using 2:1 hexanes/EtOAc as eluent gave 2.533 g (14.0 mmol) of pure product as a white solid (93% yield).

$^1$H-NMR (500 MHz, CDCl$_3$) δ 4.81 (br. s, 2H), 4.21 (t, J=6.5 Hz, 2H), 1.74 (app. p, J=7.0 Hz, 2H), 1.43-1.37 (m, 2H), 1.34-1.28 (m, 4H), 0.89 (t, J=7.0 Hz, 3H); $^{13}$C-NMR (125 MHz, CDCl$_3$) δ 71.8, 31.4, 28.9, 25.3, 22.6, 14.1; IR (ATR, cm$^{-1}$) 3263, 2963, 2936, 2875, 1421, 1359, 1234, 1188, 1137, 1088, 1029, 996, 941, 861, 782; HRMS (ESI) m/z calculated for C$_6$H$_{15}$NO$_3$SNa [M+Na]$^+$: 204.0670, found 204.0671.

Neopentyl Sulfamate [S3]

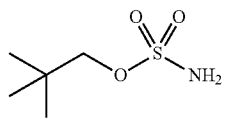

Prepared according to method B. 2,2-dimethylpropan-1-ol (440 mg, 5.00 mmol) was used, along with ClSO$_2$NCO (653 μL, 7.50 mmol, 1.5 equiv), formic acid (283 μL, 7.50 mmol, 1.5 equiv), Et$_3$N (1.05 mL, 7.50 mmol, 1.5 equiv) and CH$_2$Cl$_2$ (3.8 mL+7.0 mL). Flash column chromatography on silica (35 mm fritted column, 150 mL SiO$_2$) using 15% EtOAc/hexanes→40% EtOAc/hexanes as eluent gave 728 mg (4.35 mmol) of pure product as a white solid (87% yield).

$^1$H-NMR (500 MHz, CDCl$_3$) δ 4.69 (br, s, 2H), 3.88 (s, 2H), 1.00 (s, 9H); $^{13}$C-NMR (125 MHz, CDCl$_3$) δ 80.5, 31.7, 26.2; IR (ATR, cm$^{-1}$) 3364, 3274, 2958, 2872, 1552, 1477, 1465, 1355, 1191, 1170, 979, 919, 832; HRMS (ESI) m/z calculated for C$_5$H$_{13}$NaNO$_3$S [M+Na]$^+$: 190.0514, found 190.0510.

(±)-1-(1,3-dioxoisoindolin-2-yl)-4-methylpentan-2-yl sulfamate [S4]

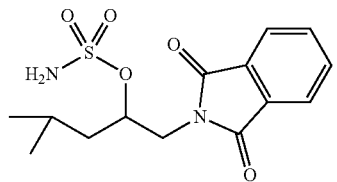 [SMILES: CC(C)CC(CN1C(=O)c2ccccc2C1=O)OS(N)(=O)=O]

Prepared according to method B. 1.446 g (5.85 mmol) of (±)-2-(2-hydroxy-4-methylpentyl)isoindoline-1,3-dione were used, along with Et$_3$N (1.63 mL, 11.7 mmol, 2.0 equiv), ClSO$_2$NCO (1.02 mL, 11.7 mmol, 2.0 equiv), formic acid (2441 μL, 11.7 mmol, 2.0 equiv) and CH$_2$Cl$_2$ (6 mL+8 mL). Flash column chromatography on silica (35 mm fritted glass column, 150 mm SiO$_2$) using 2:1 hexanes/EtOAc→1:1 hexanes/EtOAc as eluent gave 976 mg (2.99 mmol) of pure product as a white solid (51% yield).

$^1$H-NMR (500 MHz, CDCl$_3$) δ 7.89-7.85 (m, 2H), 7.77-7.73 (m, 2H), 5.03 (br. s, 2H), 4.92-4.88 (m, 1H), 4.08 (dd,

J=15.0, 3.0 Hz, 1H), 3.91 (dd, J=15.0, 5.0 Hz, 1H), 1.89-1.81 (m, 1H), 1.68 (ddd, J=14.5, 9.5, 5.0 Hz, 1H), 1.47 (ddd, J=13.5, 8.5, 4.5 Hz, 1H), 0.98 (d, J=6.5 Hz, 3H), 0.97 (d, J=7.0 Hz, 3H); $^{13}$C-NMR (125 MHz, CDCl$_3$) δ 168.8, 134.4, 132.0, 123.7, 79.8, 41.7, 41.5, 24.3, 23.1, 21.9; IR (ATR, cm$^{-1}$) 3381, 3279, 2964, 2936, 2877, 1770, 1705, 1552, 1466, 1428, 1402, 1360, 1314, 1180, 1070, 987, 976, 866, 796, 770, 747, 722, 713, 694; HRMS (ESI) m/z calculated for C$_{14}$H$_{19}$N$_2$O$_5$S [M+H]$^+$: 327.1015, found 327.1014.

(−)-(2S,3R)-2-((tert-butyldiphenylsilyl)oxy)-5-methylhexan-3-yl sulfamate [S5]

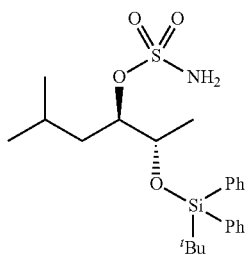 [SMILES: CC(C)C[C@@H](OS(N)(=O)=O)[C@H](C)O[Si](c1ccccc1)(c1ccccc1)C(C)(C)C]

Prepared according to method B. 518 mg (1.40 mmol) of (2S,3R)-2-((tert-butyldiphenylsilyl)oxy)-5-methylhexan-3-ol were used, along with Et$_3$N (391 μL, 2.80 mmol, 2.0 equiv), ClSO$_2$NCO (244 μL, 2.80 mmol, 2.0 equiv), formic acid (106 μL, 2.80 mmol, 2.0 equiv) and CH$_2$Cl$_2$ (1.4 mL+2.8 mL). Flash column chromatography on silica (35 mm fritted glass column, 130 mm SiO$_2$) using 9:1 hexanes/EtOAc→4:1 hexanes/EtOAc as eluent gave 204 mg (0.454 mmol) of pure product as a white solid (32% yield).

$^1$H-NMR (500 MHz, CDCl$_3$) δ 7.73-7.66 (m, 4H), 7.48-7.39 (m, 6H), 4.53 (dt, J=9.0, 4.0 Hz, 1H), 4.17 (dq, J=6.5, 4.0 Hz, 1H), 4.09 (br. s, 2H), 1.79-1.71 (m, 1H), 1.66-1.56 (m, 2H), 1.15 (d, J=6.5 Hz, 3H), 1.07 (s, 9H), 0.95 (d, J=6.5 Hz, 3H), 0.91 (d, J=6.0 Hz, 3H); $^{13}$C-NMR (125 MHz, CDCl$_3$) δ 136.2, 136.0, 133.8 (2 peaks), 130.2, 130.0, 128.0, 127.8, 83.6, 68.6, 36.6, 27.1, 23.9 (d, J$_{C-Si}$=10.9 Hz), 21.7, 19.3, 16.9; IR (ATR, cm$^{-1}$) 3289, 2959, 2859, 1472, 1428, 1367, 1187, 1112, 1078, 923, 822, 740, 702; [α]$^{25}_D$=−19.3° (c=1.1, CHCl$_3$); HRMS (ESI) m/z calculated for C$_{23}$H$_{35}$NO$_4$SSiNa [M+Na]$^+$: 472.1954, found 472.1956.

(−)-(1S,2S,3S,5R)-isopinocamphenyl sulfamate [S6]

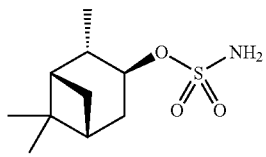

Prepared according to method B. 1.543 g (10.0 mmol) of (+)-isopinocampheol were used, along with Et$_3$N (2.79 mL, 20.0 mmol, 2.0 equiv), ClSO$_2$NCO (1.74 mL, 20.0 mmol, 2.0 equiv), formic acid (755 μL, 20.0 mmol, 2.0 equiv) and CH$_2$Cl$_2$ (10+10 mL). Flash column chromatography on silica (45 mm fritted glass column, 170 mm SiO$_2$) using 4:1 hexanes/EtOAc as eluent gave 580 mg (2.49 mmol) of pure product as a white solid (25% yield).

$^1$H-NMR (500 MHz, CDCl$_3$) δ 4.90 (ddd, J=9.5, 5.5, 4.5 Hz, 1H), 4.72 (s, 2H), 2.68-2.62 (m, 1H), 2.40 (dtd, J=10.0, 6.0, 2.5 Hz, 1H), 2.28 (qdd, J=7.5, 5.5, 2.0 Hz, 1H), 2.11 (ddd, J=14.5, 4.5, 3.0 Hz, 1H), 1.98 (tt, J=6.0, 3.0 Hz, 1H), 1.85 (td, J=6.0, 2.0 Hz, 1H), 1.23 (s, 3H), 1.18 (d, J=7.5 Hz, 3H), 1.08 (d, J=10.0 Hz, 1H), 0.94 (s, 3H); $^{13}$C-NMR (125 MHz, CDCl$_3$) δ 84.3, 47.6, 44.2, 44.1, 38.4, 36.2, 33.8, 27.4, 24.1, 20.2; IR (ATR, cm$^{-1}$); [α]$^{26}_D$=−24.1° (c=0.5, CHCl$_3$); HRMS (EI) m/z cal'd for C$_{10}$H$_{19}$NO$_3$S [M]$^+$: 233.1086, found 233.1087.

2-cyclohexylethyl sulfamate [S7]

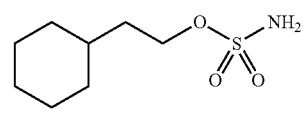

Prepared according to method A. 1.145 g (8.93 mmol) of cyclohexylethanol were used, along with NaH (248 mg, 9.82 mmol, 1.1 equiv), DMF (9+7 mL), ClSO$_2$NCO (1.17 mL, 13.4 mmol, 1.5 equiv), formic acid (505 μL, 13.4 mmol, 1.5 equiv) and MeCN (7 mL). Flash column chromatography on silica (35 mm fritted glass column, 150 mm SiO$_2$) using 3:1 hexanes/EtOAc as eluent gave 1.702 g (8.21 mmol) of pure product as a colorless oil (91% yield).

$^1$H-NMR (500 MHz, CDCl$_3$) δ 4.88 (br. s, 2H), 4.25 (t, J=6.5 Hz, 2H), 1.74-1.66 (m, 5H), 1.64 (app. q, J=7.0 Hz, 2H), 1.48-1.39 (m, 1H), 1.29-1.10 (m, 3H), 0.93 (app. dq, J=12.0, 3.0 Hz, 2H); $^{13}$C-NMR (125 MHz, CDCl$_3$) δ 69.9, 36.1, 34.0, 33.1, 26.5, 26.2; IR (ATR, cm$^{-1}$) 3369, 3289, 2916, 2844, 1539, 1450, 1376, 1353, 1189, 1097, 1028, 999, 966, 917, 888, 849, 787, 746; HRMS (ESI) m/z calculated for C$_8$H$_{17}$NO$_3$SNa [M+Na]$^+$: 230.0827, found 230.0835.

(−)-(1R,2S,5R)-menthyl sulfamate [S8]

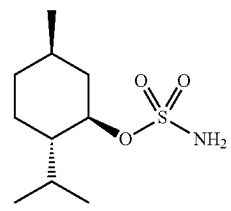

Prepared according to method A. 1.563 g (10.0 mmol) of (−)-menthol were used, along with NaH (278 mg, 11.0 mmol, 1.1 equiv), DMF (10 mL+8 mL), ClSO$_2$NCO (1.31 mL, 15.0 mmol, 1.5 equiv), formic acid (566 μL, 15.0 mmol, 1.5 equiv) and MeCN (7.5 mL). Flash column chromatography on silica (35 mm fritted glass column, 150 mm SiO$_2$) using 4:1 hexanes/EtOAc as eluent, followed by recrystallization from CH$_2$Cl$_2$ layered with hexanes, gave 1.821 g (7.70 mmol) of pure product as a crystalline white solid (77% yield).

$^1$H-NMR (500 MHz, CDCl$_3$) δ 4.71 (br. s, 2H), 4.43 (dt, J=11.0, 4.5 Hz, 1H), 2.38-2.34 (m, 1H), 2.12 (ddt, J=14.0, 7.0, 2.0 Hz, 1H), 1.74-1.66 (m, 2H), 1.51-1.38 (m, 2H), 1.26 (app. q, J=11.8 Hz, 1H), 1.04 (dq, J=13.0, 3.5 Hz, 1H), 0.94 (d, J=7.0 Hz, 3H), 0.92 (d, J=7.5 Hz, 3H), 0.89-0.86 (m, 1H), 0.83 (d, J=7.0 Hz, 3H); $^{13}$C-NMR (125 MHz, CDCl$_3$) δ 84.9, 47.7, 41.6, 33.9, 31.8, 25.7, 23.2, 22.1, 21.0, 15.9; IR

Methyl 6-(sulfamoyloxy)hexanoate [S9]

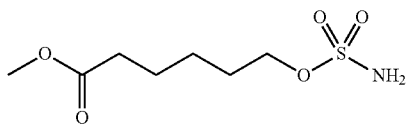

Prepared according to method B. 1.385 g (9.47 mmol) of methyl 6-hydroxyhexanoate (Choi, S. E.; Pflum, M. K. H. *Bioorg. Med. Chem. Lett.* 2012, 22, 7084) were used, along with Et$_3$N (2.64 mL, 18.9 mmol, 2.0 equiv), ClSO$_2$NCO (1.65 mL, 18.9 mmol, 2.0 equiv), formic acid (713 μL, 18.9 mmol, 2.0 equiv) and CH$_2$Cl$_2$ (9 mL+10 mL). Flash column chromatography on silica (35 mm fritted glass column, 150 mm SiO$_2$) using 3:2 hexanes/EtOAc as eluent gave 1.520 g (6.75 mmol) of pure product as a white solid (71% yield).

$^1$H-NMR (500 MHz, CDCl$_3$) δ 4.84 (br. s, 2H), 4.22 (t, J=6.5 Hz, 2H), 3.67 (s, 3H), 2.34 (t, J=7.0 Hz, 2H), 1.77 (dt, J=13.5, 7.0 Hz, 2H), 1.70-1.64 (m, 2H), 1.49-1.43 (m, 2H); $^{13}$C-NMR (125 MHz, CDCl$_3$) δ 174.4, 71.0, 51.8, 33.8, 28.4, 25.0, 24.2; IR (ATR, cm$^{-1}$) 3352, 3328, 3268, 3226, 2955, 2875, 1735, 1712, 1547, 1475, 1435, 1414, 1399, 1359, 1305, 1242, 1108, 1040, 970, 924, 820, 735; HRMS (ESI) m/z calculated for C$_7$H$_{16}$NO$_5$S [M+H]$^+$: 226.0749, found 226.0748.

Methyl 7-(sulfamoyloxy)heptanoate [S10]

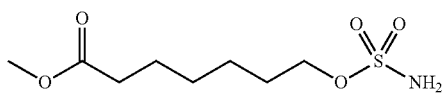

Prepared according to method B. 1.556 g (9.71 mmol) of methyl 7-hydroxyheptanoate (Kai et al., *Tetrahedron* 2008, 64, 6760) were used, along with Et$_3$N (2.71 mL, 19.4 mmol, 2.0 equiv), ClSO$_2$NCO (1.69 mL, 19.4 mmol, 2.0 equiv), formic acid (732 μL, 19.4 mmol, 2.0 equiv) and CH$_2$Cl$_2$ (10 mL+10 mL). Flash column chromatography on silica (35 mm fritted glass column, 150 mm SiO$_2$) using 3:2 hexanes/EtOAc as eluent gave 1.655 g (6.91 mmol) of pure product as a colorless oil (71% yield).

$^1$H-NMR (500 MHz, CDCl$_3$) δ 4.96 (br. s, 2H), 4.21 (t, J=6.5 Hz, 2H), 3.67 (s, 3H), 2.32 (t, J=7.3 Hz, 2H), 1.75 (dt, J=15.0, 5.5 Hz, 2H), 1.64 (dt, J=17.0, 5.5 Hz, 2H), 1.47-1.33 (m, 4H); $^{13}$C-NMR (125 MHz, CDCl$_3$) δ 174.5, 71.3, 51.7, 33.9, 28.6, 28.5, 25.2, 24.7; IR (ATR, cm$^{-1}$) 3363, 3283, 2950, 2865, 1738, 1698, 1549, 1472, 1430, 1376, 1339, 1304, 1235, 1099, 1011, 986, 961, 915, 882, 845, 792, 742, 722; HRMS (ESI) m/z calculated for C$_8$H$_{18}$NO$_5$S [M+H]$^+$: 240.0906, found 240.0905.

(film, cm$^{-1}$) 3361, 3253, 2945, 2872, 1560, 1454, 1358, 1186, 1169, 916; [α]$^{25}$$_D$=−82.1° (c=1.0, CHCl$_3$); HRMS (ESI) m/z calculated for C$_{10}$H$_{21}$NO$_3$SNa [M+Na]$^+$: 258.1140, found 258.1139.

7-(tosyloxy)heptyl sulfamate [S11]

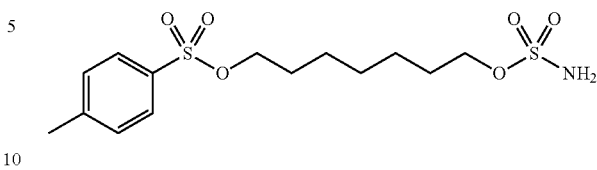

Prepared according to method B. 1.989 g (6.94 mmol) of 7-(tosyloxy)heptan-1-ol were used, along with Et$_3$N (1.94 mL, 13.9 mmol, 2.0 equiv), ClSO$_2$NCO (1.21 mL, 13.9 mmol, 2.0 equiv), formic acid (524 μL, 13.9 mmol, 2.0 equiv) and CH$_2$Cl$_2$ (7 mL+8 mL). Flash column chromatography on silica (45 mm fritted glass column, 170 mm SiO$_2$) using 3:2 hexanes/EtOAc→1:1 hexanes/EtOAc as eluent gave 1.491 g (4.08 mmol) of pure product as a colorless oil (59% yield).

$^1$H-NMR (500 MHz, CDCl$_3$) δ 7.78 (d, J=6.5 Hz, 2H), 7.35 (d, J=8.0 Hz, 2H), 4.83 (br. s, 2H), 4.19 (t, J=6.5 Hz, 2H), 4.02 (t, J=6.3 Hz, 2H), 2.45 (s, 3H), 1.74-1.69 (m, 2H), 1.67-1.62 (m, 2H), 1.41-1.27 (m, 6H); $^{13}$C-NMR (125 MHz, CDCl$_3$) δ 144.9, 133.1, 130.0, 128.0, 71.3, 70.7, 28.7, 28.6, 28.2, 25.3, 25.2, 21.8; IR (ATR, cm$^{-1}$) 3376, 3285, 2937, 2861, 1598, 1561, 1465, 1349, 1097, 916, 814, 769, 662; HRMS (ESI) m/z calculated for C$_{14}$H$_{24}$NO$_6$S$_2$ [M+H]$^+$: 366.1045, found 366.1037.

(±)-cis-4-(tert-butyl)cyclohexyl sulfamate [S12]

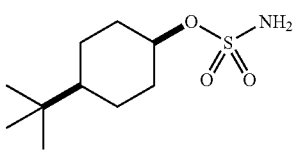

Prepared according to method A. 1.563 g (10.0 mmol) of cis-4-(tert-butyl)cyclohexanol were used, along with NaH (278 mg, 11.0 mmol, 1.1 equiv), DMF (10+8 mL), ClSO$_2$NCO (1.31 mL, 15.0 mmol, 1.5 equiv), formic acid (566 μL, 15.0 mmol, 1.5 equiv) and MeCN (7.5 mL). Flash column chromatography on silica (35 mm fritted glass column, 150 mm SiO$_2$) using 4:1 hexanes/EtOAc as eluent, followed by recrystallization from CH$_2$Cl$_2$ layered with hexanes, gave 1.821 g (7.70 mmol) of pure product as a crystalline white solid (77% yield).

$^1$H-NMR (500 MHz, CDCl$_3$) δ 4.89-4.88 (m, 1H), 4.67 (br. s, 2H), 2.21-2.18 (m, 2H), 1.64-1.61 (m, 2H), 1.57-1.51 (m, 2H), 1.37 (app. dq, J=13.0, 3.5 Hz, 2H), 1.03 (tt, J=12.0, 3.0 Hz, 1H), 0.86 (s, 9H); $^{13}$C-NMR (125 MHz, CDCl$_3$) δ 84.3, 43.3, 34.3, 26.9, 23.0, 22.7, 22.5, 14.1; IR (ATR, cm$^{-1}$) 3386, 3293, 2952, 2868, 1560, 1440, 1373, 1358, 1347, 1305, 1237, 1193, 1176, 1161, 1106, 1031, 875, 808, 756; HRMS (ESI) m/z calculated for C$_{10}$H$_{21}$NO$_3$SNa [M+Na]$^+$: 258.1140, found 258.1143.

2-cyclopropylethyl sulfamate [S13]

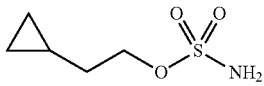

Prepared according to method B. 431 mg (5.00 mmol) of 2-cyclopropylethan-1-ol were used, along with ClSO$_2$NCO (653 µL, 7.50 mmol, 1.5 equiv), formic acid (283 µL, 7.50 mmol, 1.5 equiv), Et$_3$N (1.05 mL, 7.50 mmol, 1.5 equiv) and CH$_2$Cl$_2$ (3.8 mL+7 mL). Flash column chromatography on silica (35 mm fritted glass column, 150 mL SiO$_2$) using 20%→25% EtOAc/hexanes as eluent gave 478 mg (2.89 mmol) of pure product as a colorless oil (58% yield).

$^1$H-NMR (500 MHz, CDCl$_3$) δ 4.71 (br. s, 2H), 4.28 (td, J=6.7, 1.4 Hz, 2H), 1.73-1.61 (app. q, 2H), 0.82-0.74 (m, 1H), 0.52-0.49 (m, 2H), 0.13-0.10 (m, 2H); $^{13}$C-NMR (125 MHz, CDCl$_3$) δ 71.7, 33.9, 7.3, 4.3; IR (ATR, cm$^{-1}$): 3384, 3283, 3082, 3004, 1557, 1467, 1428, 1352, 1172, 1079, 1050, 1018, 916, 802, 765; HRMS (ESI) m/z calculated for C$_5$H$_{11}$NO$_3$SNa [M+Na]$^+$: 188.0357, found 188.0357.

(−)-(1S,2R,4S)-borneyl sulfamate [S14]

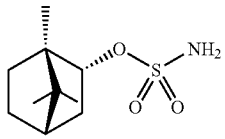

Prepared according to method A. 1.543 g (10.0 mmol) of (−)-borneol were used, along with NaH (278 mg, 11.0 mmol, 1.1 equiv), DMF (10+8 mL), ClSO$_2$NCO (1.31 mL, 15.0 mmol, 1.5 equiv), formic acid (566 µL, 15.0 mmol, 1.5 equiv) and MeCN (7.5 mL). Flash column chromatography on silica (35 mm fritted glass column, 150 mm SiO$_2$) using 3:1 hexanes/EtOAc as eluent, followed by recrystallization from Et$_2$O layered with hexanes, gave 1.353 g (5.80 mmol) of pure product as a crystalline white solid (58% yield).

$^1$H-NMR (500 MHz, CDCl$_3$) δ 4.73 (ddd, J=10.0, 3.4, 2.1 Hz, 1H), 4.64 (br. s, 2H), 2.37 (ddt, J=14.0, 10.1, 4.0 Hz, 1H), 1.91 (ddd, J=14.6, 9.9, 4.4 Hz, 1H), 1.80-1.72 (m, 2H), 1.55 (s, 1H), 1.40 (dd, J=14.0, 3.5 Hz, 1H), 1.36-1.25 (m, 2H), 0.93 (s, 3H), 0.89 (s, 6H); $^{13}$C-NMR (125 MHz, CDCl$_3$) δ 89.1, 76.9, 49.7, 47.9, 44.8, 36.3, 28.0, 26.7, 19.8, 18.9, 13.3; IR (ATR, cm$^{-1}$) 3344, 3274, 2961, 2887, 1562, 1459, 1394, 1350, 1326, 1184, 1141, 1113, 1007, 989, 974, 956, 941, 906, 871, 838, 809, 784, 744; [α]$^{26}_D$=−27.9° (c=1.0, CHCl$_3$); HRMS (ESI) m/z calculated for C$_{10}$H$_{19}$NO$_3$SNa [M+Na]$^+$: 256.0983, found 256.0992.

Pent-4-en-1-yl sulfamate [S15]

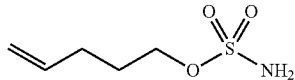

Prepared according to method A. 1.03 g (12.0 mmol) of 4-penten-1-ol were used, along with NaH (333 mg, 13.2 mmol, 1.1 equiv), DMF (21.4 mL), ClSO$_2$NCO (2.2 mL, 25.5 mmol, 1.5 equiv), formic acid (959 µL, 25.5 mmol, 1.5 equiv) and MeCN (12.8 mL). Flash column chromatography on silica (45 mm fritted glass column, 170 mm SiO$_2$) using 3:1 hexanes/EtOAc as eluent gave 1.60 g (9.70 mmol) of pure product as a colorless oil (81% yield).

$^1$H-NMR (500 MHz, CDCl$_3$) δ 5.79 (ddt, J=17.0, 10.2, 6.7 Hz, 1H), 5.07 (dd, J=17.2, 1.7 Hz, 1H), 5.03 (dd, J=10.2, 1.3 Hz, 1H), 4.81 (s, 2H), 4.23 (t, J=6.5 Hz, 2H), 2.23-2.14 (m, 2H), 1.86 (tt, J=7.4, 6.5 Hz, 2H); $^{13}$C-NMR (125 MHz, CDCl$_3$) δ 137.0, 116.2, 71.0, 29.7, 28.1. These data are in agreement with that previously reported in the literature (Harvey et al., *J. Am. Chem. Soc.* 2011, 133, 17207).

Ethyl (E)-6-(sulfamoyloxy)hex-2-enoate [S16]

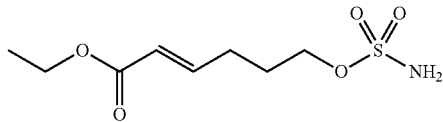

Prepared according to method B. 949 mg (6.00 mmol) of ethyl (E)-6-hydroxyhex-2-enoate were used, along with Et$_3$N (1.74 mL, 9.00 mmol, 1.5 equiv), ClSO$_2$NCO (783 µL, 9.00 mmol, 1.5 equiv), formic acid (340 µL, 9.00 mmol, 1.5 equiv) and CH$_2$Cl$_2$ (4.5+8.6 mL). Flash column chromatography on silica (45 mm fritted glass column, 200 mm SiO$_2$) using 25% acetone/hexanes→30% acetone/hexanes as eluent gave 968 mg (4.08 mmol) of pure product as a colorless oil (68% yield).

$^1$H-NMR (500 MHz, CDCl$_3$) δ6.93 (dt, J=15.6, 7.0 Hz, 1H), 5.87 (dt, J=15.7, 1.6 Hz, 1H), 4.93 (br. s, 2H), 4.23 (t, J=6.2 Hz, 2H), 4.19 (q, J=7.1 Hz, 2H), 2.36 (qd, J=7.2, 1.6 Hz, 2H), 1.93 (tt, J=7.5, 6.2 Hz, 2H), 1.29 (t, J=7.1 Hz, 3H); $^{13}$C-NMR (125 MHz, CDCl$_3$) δ 166.7, 147.0, 122.7, 70.3, 60.6, 28.2, 27.3, 14.4. These data are in agreement with that previously reported in the literature (Harvey et al., *J. Am. Chem. Soc.* 2011, 133, 17207).

(E)-6-((N-(methoxycarbonyl)-4-methylphenyl)sulfonamido)hex-4-en-1-yl sulfamate [S17]

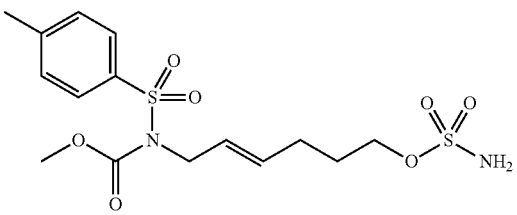 [SMILES: COC(=O)N(C/C=C/CCCOS(N)(=O)=O)S(=O)(=O)c1ccc(C)cc1]

Prepared according to method B. 1.15 g (3.50 mmol) of methyl (E)-(6-hydroxyhex-2-en-1-yl)(tosyl)carbamate were used, along with Et$_3$N (731 µL, 5.3 mmol, 1.5 equiv), ClSO$_2$NCO (461 µL, 5.3 mmol, 1.5 equiv), formic acid (198 µL, 5.3 mmol, 1.5 equiv) and CH$_2$Cl$_2$ (5+2.6 mL). Flash column chromatography on silica (45 mm fritted glass column, 150 mm SiO$_2$) using 4:1 hexanes/acetone as eluent gave 810 mg (1.99 mmol) of pure product as a white solid (57% yield).

$^1$H-NMR (500 MHz, CDCl$_3$) δ 7.81 (d, J=8.3 Hz, 2H), 7.32 (d, J=8.5 Hz, 2H), 5.77 (dt, J=15.2, 7.0 Hz, 1H), 5.67-5.61 (m, 1H), 4.82 (s, 2H), 4.41 (d, J=6.1 Hz, 2H), 4.21 (t, J=6.3 Hz, 2H), 3.70 (s, 3H), 2.44 (s, 3H), 2.23 (dd, J=13.6, 7.0 Hz, 2H), 1.88 (p, J=6.6 Hz, 3H); $^{13}$C-NMR (125 MHz, CDCl$_3$) δ152.7, 144.9, 136.1, 133.3, 129.4, 128.3, 126.1, 70.0, 54.0, 48.6, 27.9, 27.7, 21.6; IR (film, cm$^{-1}$) 3378, 3283, 2959, 1736, 1596, 1559, 1495, 1447, 1359, 1244, 1127, 974, 928, 816, 768, 737, 677, 578, 547; HRMS (ESI) m/z calculated for C$_{15}$H$_{23}$N$_2$O$_7$S$_2$ [M+H]$^+$: 407.0947, found 407.0941.

(±)-cyclohex-3-en-1-ylmethyl sulfamate [S18]

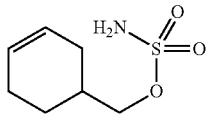

Prepared according to method A. 841 mg (875 µL, 7.50 mmol) of 3-cyclohexene-1-methanol were used, along with Et$_3$N (1.57 mL, 11.3 mmol, 1.5 equiv), ClSO$_2$NCO (984 µL, 11.3 mmol, 1.5 equiv), formic acid (426 µL, 11.3 mmol, 1.5 equiv) and CH$_2$Cl$_2$ (5.7+10.7 mL). Flash column chromatography on silica (45 mm fritted glass column, 200 mm SiO$_2$) using 4:1 hexanes/EtOAc→3:1 hexanes/EtOAc as eluent gave 1.07 g (5.60 mmol) of pure product as a colorless oil (75% yield).

$^1$H-NMR (500 MHz, CDCl$_3$) δ 5.71-5.64 (m, 2H), 4.80 (br. s, 2H), 4.11 (d, J=6.6 Hz, 2H), 2.19-2.03 (m, 1H), 2.11-2.04 (m, 3H), 1.86-1.78 (m, 2H), 1.37 (dddd, J=12.9, 10.8, 8.8, 7.0 Hz, 1H); $^{13}$C-NMR (125 MHz, CDCl$_3$) δ 127.2, 125.1, 75.4, 33.2, 27.7, 24.9, 24.2. These data are in agreement with that previously reported in the literature (Harvey et al., *J. Am. Chem. Soc.* 2011, 133, 17207).

(−)-2-((1R,5S)-6,6-dimethylbicyclo[3.1.1]hept-2-en-2-yl)ethyl sulfamate [S19]

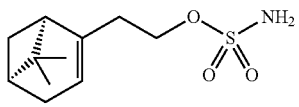 [SMILES: CC1(C)[C@H]2CC=C(CCOS(N)(=O)=O)[C@@H]1C2]

Prepared according to method A. 1.25 g (1.3 mL, 7.50 mmol) of (−)-(1R)-nopol were used, along with NaH (208 mg, 8.30 mmol, 1.1 equiv), DMF (13.4 mL), ClSO$_2$NCO (984 µL, 11.3 mmol, 1.5 equiv), formic acid (426 µL, 11.3 mmol, 1.5 equiv) and MeCN (5.6 mL). Flash column chromatography on silica (35 mm fritted glass column, 170 mm SiO$_2$) using 4:1 hexanes/EtOAc as eluent gave 1.30 g (5.30 mmol) of pure product as a white solid (71% yield).

$^1$H-NMR (500 MHz, CDCl$_3$) δ 5.36 (app tt, J=3.0, 1.5 Hz, 1H), 4.71 (br. s, 2H), 4.21 (td, J=7.2, 1.9 Hz, 2H), 2.54-2.36 (m, 3H), 2.29-2.17 (m, 2H), 2.10 (app tdt, J=6.9, 4.0, 1.9 Hz, 1H), 2.04 (td, J=5.6, 1.5 Hz, 1H), 1.28 (s, 3H), 1.15 (d, J=8.6 Hz, 1H), 0.83 (s, 3H); $^{13}$C-NMR (125 MHz, CDCl$_3$) δ 142.8, 119.9, 69.7, 45.7, 40.7, 38.2, 36.1, 31.7, 31.5, 26.3, 21.3; IR (film, cm$^{-1}$) 3371, 3288, 2989, 2928, 2875, 1542, 1467, 1443, 1341, 1190, 1067, 1056, 969, 955, 912, 837, 769, 698; [α]$_D^{25}$=−25.0° (c=1.0, CHCl$_3$); HRMS (ESI) m/z calculated for C$_{11}$H$_{19}$NO$_3$SNa [M+Na]$^+$: 268.0983, found 268.0987.

(E)-4-phenylbut-3-en-1-yl sulfamate [S20]

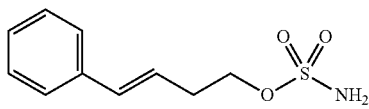 [SMILES: NS(=O)(=O)OCC/C=C/c1ccccc1]

Prepared according to method B. 727 mg (4.90 mmol) of (E)-4-phenylbut-3-en-1-ol were used, along with Et$_3$N (1.03 mL, 7.36 mmol, 1.5 equiv), ClSO$_2$NCO (639 µL, 7.36 mmol, 1.5 equiv), formic acid (278 µL, 7.36 mmol, 1.5 equiv) and CH$_2$Cl$_2$ (3.7+7.0 mL). Flash column chromatography on silica (150 mL SiO$_2$) using 3:1 hexanes/EtOAc as eluent gave 830 mg (3.65 mmol) of pure product as a white solid (75% yield).

$^1$H-NMR (500 MHz, CDCl$_3$) δ 7.37-7.28 (m, 4H), 7.26-7.21 (m, 1H), 6.52 (d, J=16.0 Hz, 1H), 6.17 (dt, J=15.8, 7.0 Hz, 1H), 4.71 (br. s, 2H), 4.32 (t, J=6.7 Hz, 2H), 2.67 (qd, J=6.7, 1.5 Hz, 2H); $^{13}$C-NMR (125 MHz, CDCl$_3$) δ 137.0, 133.5, 128.7, 127.7, 126.3, 124.1, 70.6, 32.5. These data are in agreement with that previously reported in the literature (Guthikonda, K.; Wehn, P. M; Du Bois, J.; *Tetrahedron*, 2006, 62, 11331-11342).

(±)-5-(trimethylsilyl)pent-4-yn-1-yl sulfamate [S21]

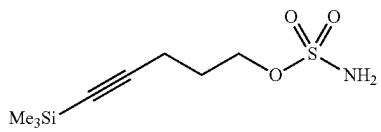 [SMILES: C[Si](C)(C)C#CCCCOS(N)(=O)=O]

Prepared according to method B. 782 mg (5.00 mmol) of 5-(trimethylsilyl)pent-4-yn-1-ol were used, along with Et$_3$N (1.05 mL, 7.50 mmol, 1.5 equiv), ClSO$_2$NCO (653 µL, 7.50 mmol, 1.5 equiv), formic acid (283 µL, 7.50 mmol, 1.5 equiv) and CH$_2$Cl$_2$ (3.8+7.1 mL). Flash column chromatography on silica (45 mm fritted glass column, 150 mm SiO$_2$) using 5% Et$_2$O/hexanes→10% Et$_2$O/hexanes→15% Et$_2$O/hexanes as eluent gave 605 mg (2.57 mmol) of pure product as a clear oil (51% yield).

$^1$H-NMR (500 MHz, CDCl$_3$) δ 4.82 (br. s, 2H), 4.34 (t, J=6.1 Hz, 2H), 2.39 (t, J=6.9 Hz, 2H), 1.95 (p, J=6.4 Hz, 2H), 0.15 (s, 9H); $^{13}$C-NMR (125 MHz, CDCl$_3$) δ 105.0, 86.4, 69.9, 27.8, 16.3, 0.2; IR (film, cm$^{-1}$) 3383, 3284, 2960, 2175, 1557, 1359, 1249, 1177, 1070, 1017, 979, 929, 759, 698; HRMS (ESI) m/z calculated for C$_8$H$_{18}$O$_3$SSi [M+H]$^+$: 236.0777, found 236.0779.

(+)-(S)-2-((tert-butyldimethylsilyl)oxy)-7-(tosyloxy)hept-4-yn-1-yl sulfamate [S22]

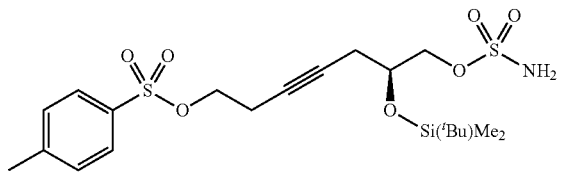

Prepared according to method B. 940 mg (2.30 mmol) of (S)-6-((tert-butyldimethylsilyl)oxy)-7-hydroxyhept-3-yn-1-yl 4-methylbenzene sulfonate were used, along with Et$_3$N (488 µL, 3.50 mmol, 1.5 equiv), ClSO$_2$NCO (304 µL, 3.50 mmol, 1.5 equiv), formic acid (132 µL, 3.50 mmol, 1.5 equiv) and CH$_2$Cl$_2$ (1.75+3.3 mL). Flash column chromatography on silica (35 mm fritted glass column, 150 mm SiO$_2$) using 3:1 hexanes/EtOAc→2:1 hexanes/EtOAc as eluent gave 688 mg (1.40 mmol) of pure product as a pale yellow oil (61% yield).

$^1$H-NMR (500 MHz, CDCl$_3$) δ 7.80 (d, J=8.3 Hz, 2H), 7.36 (d, J=7.9 Hz, 2H), 5.03 (s, 2H), 4.33 (dd, J=10.2, 3.7

Hz, 1H), 4.15 (dd, J=10.2, 5.9 Hz, 1H), 4.08-4.01 (m, 3H), 2.51 (tt, J=6.5, 2.4 Hz, 2H), 2.46 (s, 3H), 2.38 (dt, J=6.6, 2.4 Hz, 2H), 0.88 (s, 9H), 0.11 (s, 3H), 0.09 (s, 3H); $^{13}$C-NMR (125 MHz, CDCl$_3$) δ 145.3, 132.7, 130.1, 128.1, 78.1, 77.5, 73.3, 69.3, 68.4, 25.8, 24.5, 21.8, 20.0, 18.2, −4.6, −4.8; IR (film, cm$^{-1}$) 3378, 3288, 2929, 2857, 1598, 1558, 1463, 1358, 1255, 1120, 1096, 971, 903, 808, 775, 663; [α]$_D^{25}$=+ 8.21° (c=0.56, CHCl$_3$); HRMS (ESI) m/z calculated for C$_{20}$H$_{34}$NO$_7$S$_2$Si [M+H]$^+$: 492.1546, found 492.1542.

(−)-(S)-(2,2-dimethyl-1,3-dioxolan-4-yl)methyl sulfamate [S23]

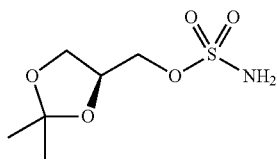

Prepared according to method B. 661 mg (622 μL, 5.00 mmol) of (R)-glycerol acetonide were used, along with Et$_3$N (1.05 mL, 7.50 mmol, 1.5 equiv), ClSO$_2$NCO (651 μL, 7.50 mmol, 1.5 equiv), formic acid (282.9 μL, 7.5 mmol, 1.5 equiv) and CH$_2$Cl$_2$ (3.8+7.1 mL). Flash column chromatography on silica (150 mL SiO$_2$) using 2:1 hexanes/EtOAc as eluent gave 704 mg (3.30 mmol) of pure product as a clear oil (67% yield).

$^1$H-NMR (500 MHz, CDCl$_3$) δ 5.20 (s, 2H), 4.41 (p, J=5.7 Hz, 1H), 4.23 (dd, J=10.7, 6.1 Hz, 1H), 4.18 (dd, J=10.7, 4.8 Hz, 1H), 4.11 (dd, J=8.8, 6.5 Hz, 1H), 3.83 (dd, J=8.8, 5.4 Hz, 1H), 1.45 (s, 3H), 1.37 (s, 3H); $^{13}$C-NMR (125 MHz, CDCl$_3$) δ 110.4, 73.2, 70.6, 65.7, 26.6, 25.2. These data are in agreement with that previously reported in the literature (Fleming et al., *J. Am. Chem. Soc.* 2007, 129, 9964).

2-isopropylphenyl sulfamate [S24]

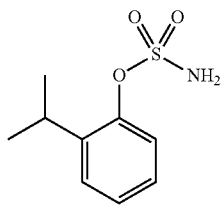

Prepared according to method C. 681 mg (5.00 mmol) of 2-isopropylphenol were used, along with ClSO$_2$NCO (653 μL, 7.50 mmol, 1.5 equiv), formic acid (283 μL, 7.50 mmol, 1.5 equiv), MeCN (3.8 mL, 2M), DMA (3.0 mL). Flash column chromatography on silica (35 mm fritted glass column, 150 mm SiO$_2$) using 3:1 hexanes/EtOAc as eluent gave 877 mg (4.07 mmol) of pure product as a white solid (81% yield).

$^1$H-NMR (500 MHz, CDCl$_3$) δ 7.37 (dd, J=7.9, 1.4 Hz, 2H), 7.30-7.26 (m, 1H), 7.23-7.19 (m, 1H), 5.14 (br. s, 2H), 3.39 (hept, J=6.9 Hz, 1H), 1.24 (d, J=6.9 Hz, 6H); $^{13}$C-NMR (125 MHz, CDCl$_3$) δ 147.7, 141.7, 127.6, 127.5, 127.0, 121.7, 27.0, 23.4; IR (ATR, cm$^{-1}$): 3374, 3279, 2986, 2928, 1540, 1488, 1445, 1379, 1359, 1201, 1182, 1151, 1077, 1033, 945, 928, 900, 873, 860; HRMS (ESI) m/z calculated for C$_9$H$_{13}$NNaO$_3$S [M+Na]$^+$: 238.0514, found 238.0512.

5-((tert-butoxycarbonyl)oxy)-2-isopropylphenyl sulfamate [S25]

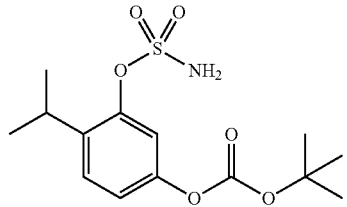 [SMILES: CC(C)c1ccc(OC(=O)OC(C)(C)C)cc1OS(N)(=O)=O]

Prepared according to method C. 1.030 g (4.08 mmol) of tert-butyl (3-hydroxy-4-isopropylphenyl) carbonate was used, along with ClSO$_2$NCO (533 μL, 6.12 mmol, 1.5 equiv), formic acid (231 μL, 6.12 mmol, 1.5 equiv), 3.1 mL MeCN and 6 mL DMA. Flash column chromatography on silica (35 mm fritted glass column, 150 mL SiO$_2$) using 15% EtOAc/hexanes→30% EtOAc/hexanes as eluent gave 1.113 g (3.36 mmol) of pure product as a yellowish oil (82% yield).

$^1$H-NMR (500 MHz, CDCl$_3$) δ 7.35 (d, J=8.6 Hz, 1H), 7.28 (d, J=2.4 Hz, 1H), 7.11 (dd, J=8.6, 2.4 Hz, 1H), 4.97 (br. s, 2H), 3.36 (hept, J=7.0 Hz, 1H), 1.56 (s, 9H), 1.23 (d, J=6.9 Hz, 6H); $^{13}$C-NMR (125 MHz, CDCl$_3$) δ 151.9, 149.0, 147.3, 139.4, 127.8, 120.4, 115.2, 84.4, 27.8, 26.8, 23.3; IR (ATR, cm$^{-1}$): 3389, 3242, 3081, 2970, 1725, 1589, 1562, 1498, 1417, 1399, 1370, 1294, 1264, 1244, 1184, 1154, 1131, 1084, 964, 887, 870, 813, 778; HRMS (ESI) m/z calculated for C$_{14}$H$_{21}$NO$_6$SNa [M+Na]: 354.0987, found 354.0992.

3-(4-bromophenyl)propyl sulfamate [S26]

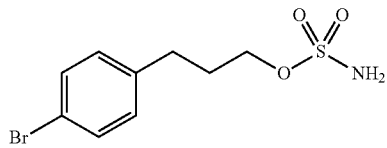 [SMILES: NS(=O)(=O)OCCCc1ccc(Br)cc1]

Prepared according to method B. 1.617 g (7.52 mmol) of 3-(4-bromophenyl)propan-1-ol were used, along with ClSO$_2$NCO (982 μL, 11.28 mmol, 1.5 equiv), formic acid (425 μL, 11.28 mmol, 1.5 equiv), Et$_3$N (1.57 mL, 11.28 mmol, 1.5 equiv) and CH$_2$Cl$_2$ (5.7 mL+10.5 mL). Flash column chromatography on silica (35 mm fritted glass column, 150 mL SiO$_2$) using 25% EtOAc/hexanes→30% EtOAc/hexanes as eluent gave 1.493 g (5.08 mmol) of pure product as a white solid (68% yield).

$^1$H-NMR (500 MHz, CDCl$_3$) δ 7.42 (d, J=8.3 Hz, 2H), 7.07 (d, J=8.3 Hz, 1H), 4.67 (br. s, 2H), 4.21 (t, J=6.2 Hz, 1H), 2.72 (t, J=7.6 Hz, 2H), 2.12-2.00 (m, 2H); $^{13}$C-NMR (125 MHz, CDCl$_3$) δ 139.5, 131.7, 130.4, 120.2, 70.4, 31.1, 30.3; IR (ATR, cm$^{-1}$): 3357, 3270, 2977, 1548, 1487, 1471, 1350, 1183, 1164, 1072, 1010, 967, 917, 829, 790; HRMS (ESI) m/z calculated for C$_9$H$_{11}$NO$_3$SBr [M−H]$^-$: 291.9643, found 291.9644.

3-(4-(trifluoromethyl)phenyl)propyl sulfamate [S27]

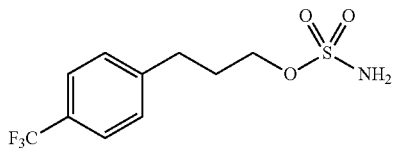 [SMILES: NS(=O)(=O)OCCCc1ccc(C(F)(F)F)cc1]

Prepared according to method B. 1.865 g (9.13 mmol) of 3-(4-trifluoromethyl)propan-1-ol were used, along with ClSO$_2$NCO (1.19 mL, 13.70 mmol, 1.5 equiv), formic acid (517 µL, 13.70 mmol, 1.5 equiv), Et$_3$N (1.92 mL, 13.70 mmol, 1.5 equiv) and CH$_2$Cl$_2$ (6.9 mL+12.8 mL). Flash column chromatography on silica (50 mm fritted glass column, 300 mL SiO$_2$) using 25% EtOAc/hexanes→45% EtOAc/hexanes as eluent gave 1.989 g (7.02 mmol) of pure product as a white solid (77% yield).

$^1$H-NMR (500 MHz, Acetonitrile-d$_3$) δ 7.61 (d, J=7.9 Hz, 2H), 7.42 (d, J=7.9 Hz, 2H), 5.66 (br. s, 2H), 4.12 (t, J=6.3 Hz, 2H), 2.80 (t, J=7.7 Hz, 2H), 2.06-2.01 (m, 2H); $^{13}$C-NMR (125 MHz, Acetonitrile-d$_3$) δ 146.9, 130.1, 128.6 (q, J=32.0 Hz), 126.1 (q, J=3.9 Hz), 125.5 (q, J=270.1 Hz), 70.2, 32.0, 30.8; $^{19}$F-NMR (470 MHz, Acetonitrile-d$_3$) δ −62.45; IR (ATR, cm$^{-1}$): 3370, 3270, 1619, 1544, 1357, 1324, 1162, 1111, 1068, 1009, 931, 846, 833, 816; HRMS (EI) m/z calculated for C$_{10}$H$_{12}$NO$_3$SF$_3$ [M$^+$]: 283.0490, found 283.0497.

(±)-ethyl 4-phenyl-2-(sulfamoyloxy)butanoate [S28]

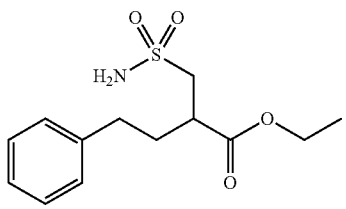 [SMILES: CCOC(=O)C(CCc1ccccc1)CS(N)(=O)=O]

Prepared according to method B. 1.553 g (7.46 mmol) of (1)-ethyl 4-phenyl-2-(hydroxy)butanoate were used, along with Et$_3$N (1.56 mL, 11.2 mmol, 1.5 equiv), ClSO$_2$NCO (973 µL, 11.2 mmol, 1.5 equiv), formic acid (422 µL, 11.2 mmol, 1.5 equiv) and CH$_2$Cl$_2$ (6 mL+7 mL). Flash column chromatography on silica (35 mm fritted glass column, 150 mm SiO$_2$) using 4:1 hexanes/EtOAc→2:1 hexanes/EtOAc as eluent gave 611 mg (2.16 mmol) of pure product as a white solid (29% yield).

$^1$H-NMR (500 MHz, CDCl$_3$) δ 7.31 (t, J=7.3 Hz, 2H), 7.24-7.20 (m, 3H), 5.13 (br. s, 2H), 4.95 (dd, J=8.0, 4.0 Hz, 1H), 4.22 (q, J=7.0 Hz, 2H), 2.79 (t, J=7.8 Hz, 2H), 2.30-2.17 (m, 2H), 1.30 (t, J=7.3 Hz, 3H); $^{13}$C-NMR (125 MHz, CDCl$_3$) δ 170.5, 139.9, 128.8, 128.7, 126.6, 79.2, 62.5, 33.5, 31.0, 14.2. These data are in agreement with that previously reported in the literature (Espino et al., *J. Am. Chem. Soc.* 2001, 123, 6935).

(±)-2-methyl-3-phenylpropyl sulfamate [S29]

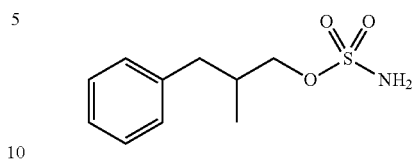

Prepared according to method A. 719 mg (4.79 mmol) of (±)-2-methyl-3-phenylpropan-1-ol were used, along with NaH (133 mg, 5.27 mmol, 1.1 equiv), DMF (5.0+4.0 mL), ClSO$_2$NCO (625 µL, 7.19 mmol, 1.5 equiv), formic acid (271 µL, 7.19 mmol, 1.5 equiv) and MeCN (3.6 mL). Flash column chromatography on silica (50 mm fritted glass column, 300 mL SiO$_2$) using 3:2 hexanes/EtOAc as eluent gave 954 mg (4.16 mmol) of pure product as a colorless oil (87% yield).

$^1$H-NMR (500 MHz, CDCl$_3$) δ 7.35-7.28 (m, 2H), 7.27-7.21 (m, 1H), 7.20-7.16 (m, 2H), 5.20 (br. s, 2H), 4.06 (qd, J=9.4, 5.8 Hz, 2H), 2.79 (dd, J=13.6, 6.4 Hz, 1H), 2.51 (dd, J=13.6, 8.0 Hz, 1H), 2.25-2.15 (m, 1H), 0.99 (d, J=6.8 Hz, 3H); $^{13}$C-NMR (125 MHz, CDCl$_3$) δ 139.4, 129.2, 128.5, 126.3, 75.1, 39.1, 34.7, 16.3; IR (ATR, cm$^{-1}$): 3360, 3275, 2920, 1544, 1497, 1453, 1391, 1330, 1260, 1177, 971, 951, 924, 887, 820, 805; HRMS (ESI) m/z calculated for C$_{10}$H$_{16}$NO$_3$S [M+H]$^+$: 230.0851, found 230.0855.

2,2-dimethyl-3-phenylpropyl sulfamate [S30]

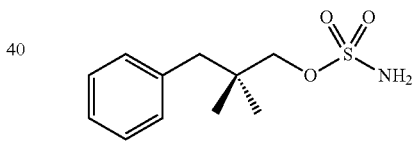

Prepared according to method A. 821 mg (5.00 mmol) of 2,2-dimethyl-3-phenylpropan-1-ol (Klamo et al., *Organometallics*, 2007, 26, 3018) were used, along with NaH (139 mg, 5.50 mmol, 1.1 equiv), DMF (5.0 mL+4.0 mL), ClSO$_2$NCO (653 µL, 7.50 mmol, 1.5 equiv), formic acid (293 µL, 7.50 mmol, 1.5 equiv) and MeCN (3.8 mL). Flash column chromatography on silica (50 mm fritted glass column, 300 mL SiO$_2$) using 35% EtOAc/hexanes as eluent gave 726 mg (2.98 mmol) of pure product as a white solid (60% yield).

$^1$H-NMR (500 MHz, CDCl$_3$) δ 7.31-7.27 (m, 2H), 7.25-7.21 (m, 1H), 7.16-7.14 (m, 2H), 4.90 (br. s, 2H), 3.86 (s, 2H), 2.62 (s, 2H), 0.97 (s, 6H); $^{13}$C-NMR (125 MHz, CDCl$_3$) δ 137.5, 130.7, 128.2, 126.5, 78.2, 44.6, 35.3, 24.2; IR (ATR, cm$^{-1}$): 3327, 3238, 2975, 1602, 1561, 1494, 1452, 1471, 1395, 1353, 1194, 1161, 1007, 975, 930, 921, 906, 844, 826; HRMS (ESI) m/z calculated for C$_{11}$H$_{18}$NO$_3$S [M+H]$^+$: 244.1007, found 244.1003.

(±)-4-(1-(phenylsulfonyl)-1H-pyrrol-3-yl)butan-2-yl sulfamate [S31]

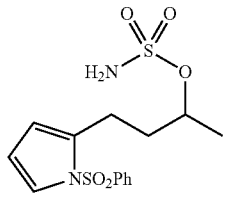

Prepared according to method B. 838 mg (3.00 mmol) 4-(1-(phenylsulfonyl)-1H-pyrrol-3-yl) butan-2-ol were used, along with Et$_3$N (455 μL, 4.50 mmol, 1.5 equiv), CH$_2$Cl$_2$ (2.25 mL+4.5 mL), ClSO$_2$NCO (391 μL, 4.50 mmol, 1.5 equiv), formic acid (170 μL, 4.50 mmol, 1.5 equiv). Flash column chromatography on silica (45 mm fritted glass column, 180 mm SiO$_2$) using 9:1 hexanes/acetone→3:2 hexanes/acetone as eluent gave 751 mg (2.10 mmol) of pure product as a white solid (70% yield).

$^1$H NMR (5 $^1$H NMR (500 MHz, CDCl$_3$) δ 7.76 (dd, J=7.5, 1.8 Hz, 2H), 7.61 (t, J=7.6 Hz, 1H), 7.52 (t, J=7.8 Hz, 2H), 7.29 (dd, J=3.5, 1.7 Hz, 1H), 6.22 (t, J=3.4 Hz, 1H), 6.04-6.03 (m, 1H), 4.87 (s, 2H), 4.77-4.70 (m, 1H), 2.80 (dd, J=9.2, 6.5 Hz, 2H), 1.97-1.92 (m, 2H), 1.41 (d, J=6.3 Hz, 3H); $^{13}$C NMR (125 MHz, CDCl$_3$) δ 139.2, 134.2, 134.1, 129.7, 126.9, 122.8, 112.8, 111.8, 80.4, 35.8, 23.0, 20.8; HRMS (ESI) m/z calculated for C$_{14}$H$_{19}$N$_2$O$_5$S$_2$ [M+H]$^+$: 359.0735, found 359.0734.

(±)-4-(1-(phenylsulfonyl)-1H-indol-3-yl)butan-2-yl sulfamate [S32]

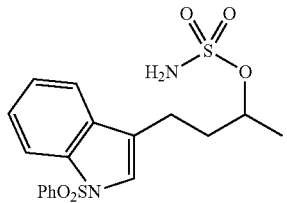

Prepared according to method B. 988 mg (3.00 mmol) 4-(1-(phenylsulfonyl)-1H-indol-3-yl)butan-2-ol were used, along with Et$_3$N (455 μL, 4.5 mmol, 1.5 equiv), CH$_2$Cl$_2$ (2.25 mL+4.5 mL), ClSO$_2$NCO (392 μL, 4.50 mmol, 1.5 equiv), formic acid (170 μL, 4.50 mmol, 1.5 equiv). Flash column chromatography on silica (45 mm fritted glass column, 200 mm SiO$_2$) using 9:1 hexanes/EtOAc→3:2 hexanes/EtOAc as eluent gave 897 mg (2.20 mmol) of pure product as an off-white solid (73% yield).

$^1$H NMR (500 MHz, CDCl$_3$) δ 7.99-7.97 (m, 1H), 7.88-7.86 (m, 2H), 7.52-7.39 (m, 5H), 7.33-7.30 (m, 1H), 7.24-7.21 (m, 1H), 4.96 (s, 2H), 4.77-4.71 (m, 1H), 2.83-2.73 (m, 2H), 2.12-2.05 (m, 1H), 1.99-1.92 (m, 1H), 1.44 (d, J=6.3 Hz, 3H); $^{13}$C NMR (125 MHz, CDCl$_3$) δ 138.2, 135.5, 133.9, 130.8, 129.4, 126.9, 125.0, 123.4, 123.1, 122.1, 119.5, 114.0, 80.6, 35.7, 20.8, 20.7; HRMS (ESI) m/z calculated for C$_{18}$H$_{20}$N$_2$O$_5$S$_2$Na [M+Na]$^+$: 431.0711, found 431.0709.

3-(4-(2-oxooxazolidin-3-yl)phenyl)propyl sulfamate [S33]

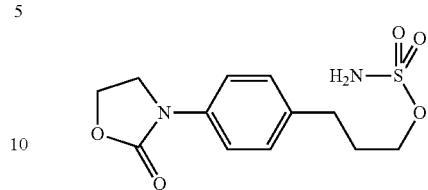

Prepared according to method B. 487 mg (2.20 mmol) 3-(4-(3-hydroxypropyl)phenyl)oxazolidin-2-one were used, along with Et$_3$N (614 μL, 4.40 mmol, 2.0 equiv), DCM (2 mL+4 ml), ClSO$_2$NCO (383 μL, 4.40 mmol, 2.0 equiv), formic acid (166 μL, 4.40 mmol, 2.0 equiv). Flash column chromatography on silica (45 mm fritted glass column, 200 mm SiO$_2$) using 10% EtOAc/hexanes→80% EtOAc/hexanes as eluent gave 390 mg (1.30 mmol) of pure product as an off white solid (59% yield).

$^1$H NMR (500 MHz, Acetone-d$_6$) δ 7.55-7.53 (m, 2H), 7.26-7.25 (m, 2H), 6.63 (s, 2H), 4.49 (dd, J=9.5, 7.0 Hz, 2H), 4.16-4.11 (m, 4H), 2.72 (dd, J=8.5, 6.7 Hz, 2H), 2.09-1.99 (m, 2H); $^{13}$C NMR (125 MHz, Acetone) δ 155.9, 138.2, 137.1, 129.7, 119.0, 69.7, 62.3, 45.9, 31.6, 31.5; HRMS (ESI) m/z calculated for C$_{12}$H$_{17}$N$_2$O$_5$S [M+H]$^+$: 301.0858, found 301.0857.

3-(4-(1,3,4-oxadiazol-2-yl)phenyl)propyl sulfamate [S34]

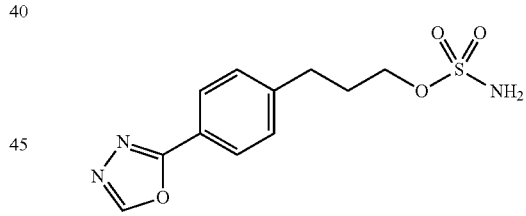

Prepared according to method A. 600 mg (2.90 mmol) of 3-(4-(1,3,4-oxadiazol-2-yl)phenyl)propan-1-ol were used, along with NaH (81 mg, 3.20 mmol, 1.1 equiv), DMF (5.8 mL), ClSO$_2$NCO (500 μL, 5.80 mmol, 2.0 equiv), formic acid (220 μL, 5.80 mmol, 2.0 equiv) and MeCN (2.9 mL). Flash column chromatography on silica (45 mm fritted glass column, 200 mm SiO$_2$) using 20% acetone/hexanes→60% acetone/hexanes as eluent gave 390 mg (1.38 mmol) of pure product as a white solid (48% yield).

$^1$H NMR (500 MHz, Acetone-d$_6$) δ 8.96 (s, 1H), 8.01 (d, J=8.5 Hz, 2H), 7.50 (d, J=8.0 Hz, 2H), 6.67 (s, 2H), 4.19 (t, J=6.3 Hz, 2H), 2.88-2.83 (m, 2H), 2.11-2.09 (m, 2H); $^{13}$C NMR (125 MHz, Acetone-d$_6$) δ 165.2, 154.5, 146.7, 130.4, 127.9, 122.8, 69.7, 32.5, 31.2; HRMS (ESI) m/z calculated for C$_{11}$H$_{14}$N$_3$O$_4$S [M+H]$^+$: 284.0705, found 284.0699.

3-(4,5-diphenyloxazol-2-yl)propyl sulfamate [S35]

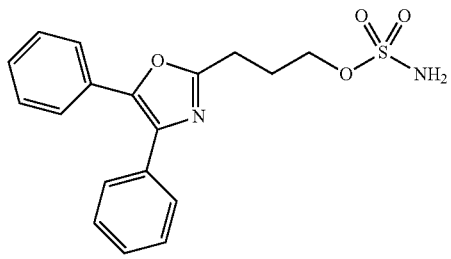 [SMILES: NS(=O)(=O)OCCCc1nc(-c2ccccc2)c(-c2ccccc2)o1]

Prepared according to method A. 1.310 g (4.70 mmol) 3-(4,5-diphenyloxazol-2-yl)propan-1-ol were used, along with NaH (130 mg, 5.12 mmol, 1.1 equiv), DCM (3.6 mL), ClSO$_2$NCO (617 μL, 7.10 mmol, 1.5 equiv), formic acid (268 μL, 7.10 mmol, 1.5 equiv) and DMF (7 mL). Flash column chromatography on silica (45 mm fritted glass column, 200 mm SiO$_2$) using 20% EtOAc/hexanes→70% EtOAc/hexanes as eluent gave 1.090 g (3.00 mmol) of pure product as a white solid (64% yield).

$^1$H NMR (500 MHz, CDCl$_3$) δ 7.62-7.60 (m, 2H), 7.57 (dt, J=6.9, 2.3 Hz, 2H), 7.40-7.32 (m, 6H), 5.16 (s, 2H), 4.40 (td, J=5.9, 0.9 Hz, 2H), 3.05 (t, J=6.9 Hz, 2H), 2.32-2.27 (m, 2H); $^{13}$C NMR (125 MHz, CDCl$_3$) δ 162.1, 145.8, 135.1, 132.2, 128.8, 128.8, 128.8, 128.4, 128.0, 126.6, 69.8, 26.3, 24.2; HRMS (ESI) m/z calculated for C$_{18}$H$_{19}$N$_2$O$_4$S [M+H]$^+$: 359.1066, found 359.1060.

Example 3. Development Mn-Catalyzed Intramolecular C—H Aminations

General Procedure for Catalyst and Optimization Studies (Entries 1-15 of Scheme 1)

Into a 10 mL round-bottom flask was added AgSbF$_6$ (13.7 mg, 0.040 mmol, 0.10 equiv), catalyst (0.040 mmol, 0.10 equiv), crushed 4 Å MS (100 mg, if using) and a stir bar in a glovebox. The flask was then sealed with a rubber septum, covered in aluminum foil (when AgSbF$_6$ was used), and taken out of the box. (±)-3,7-dimethyloctyl sulfamate 4 (94.9 mg, 0.400 mmol, 1.0 equiv) dissolved in 9:1 C$_6$H$_6$/MeCN (800 μL, 0.5M) was added via syringe, followed by PhI(OPiv)$_2$ (325 mg, 0.800 mmol, 2.0 equiv) in a single portion. The reaction stirred for 8 h at room temp (~23° C.), and then was applied directly to a silica column (35 mm fritted glass column, 150 mm SiO$_2$). The product and starting material were eluted with 5:1 hexanes/EtOAc and isolated separately.

(±)-4-methyl-4-(4-methylpentyl)-1,2,3-oxathiazinane 2,2-dioxide [5]

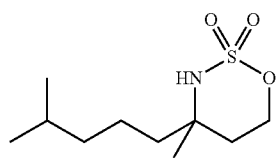

Isolated as a colorless oil. $^1$H-NMR (500 MHz, CDCl$_3$) δ 4.71-4.61 (m, 2H), 4.29 (br. s, 1H), 1.82-1.67 (m, 3H), 1.54 (app. spt, J=7.0 Hz, 1H), 1.45-1.41 (m, 2H), 1.38 (s, 3H), 1.30-1.24 (m, 1H), 1.20-1.15 (m, 2H), 0.87 (d, J=6.5 Hz, 6H); $^{13}$C-NMR (125 MHz, CDCl$_3$) δ 69.1, 59.1, 41.3, 39.1, 34.7, 27.3, 24.7, 22.7, 22.6, 20.8; IR (film, cm$^{-1}$) 3271, 2954, 2872, 1466, 1421, 1360, 1252, 1188, 1155, 1113, 1070, 1014, 987, 933, 870, 783; HRMS (ESI) m/z calculated for C$_{10}$H$_{22}$NO$_3$S [M+H]$^+$: 236.1320, found 236.1315.

Entry 1.

(±)-3,7-dimethyloctyl sulfamate (94.9 mg, 0.400 mmol, 1.0 equiv), [FePc]Cl (24 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv) and 9:1 C$_6$H$_6$/MeCN (800 μL, 0.5M) were used.

Run 1: (27.1 mg, 0.115 mmol, 29%), (12.3 mg alcohol, 0.078 mmol, 19%), (24.9 mg rsm, 0.262 mmol, 26%). Run 2: (28.0 mg, 0.119 mmol, 30%), (32.8 mg rsm, 0.138 mmol, 35%). Run 3: (26.6 mg, 0.113 mmol, 28%), (33.7 mg rsm, 0.142 mmol, 36%). Average: 29% yield±0.8, 32% rsm±4.5.

Entry 2.

(±)-3,7-dimethyloctyl sulfamate (94.9 mg, 0.400 mmol, 1.0 equiv), [MnPc]Cl (24 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv) and 9:1 C$_6$H$_6$/MeCN (800 μL, 0.5M) were used.

Run 1: (39.2 mg, 0.167 mmol, 42%), (22.3 mg rsm, 0.094 mmol, 23%). Run 2: (39.4 mg, 0.167 mmol, 42%), (27.1 mg rsm, 0.114 mmol, 29%). Run 3: (41.8 mg, 0.178 mmol, 44%), (26.7 mg rsm, 0.113 mmol, 28%). Average: 43% yield±0.9, 27% rsm±2.6.

Entry 3.

(±)-3,7-dimethyloctyl sulfamate (94.9 mg, 0.400 mmol, 1.0 equiv), Fe(TPP)Cl (28.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv) and 9:1 C$_6$H$_6$/MeCN (800 μL, 0.5M) were used.

Run 1: (4.0 mg, 0.017 mmol, 4%), (80.1 mg rsm, 0.338 mmol, 84%). Run 2: (2.9 mg, 0.012 mmol, 3%), (82.3 mg rsm, 0.347 mmol, 87%). Run 3: (3.5 mg, 0.015 mmol, 4%), (79.5 mg rsm, 0.335 mmol, 84%). Average: 4% yield±0.5, 85% rsm±1.4.

Entry 4.

(±)-3,7-dimethyloctyl sulfamate (94.9 mg, 0.400 mmol, 1.0 equiv), Mn(TPP)Cl (28.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv) and 9:1 C$_6$H$_6$/MeCN (800 μL, 0.5M) were used.

Run 1: (15.6 mg, 0.066 mmol, 17%), (51.8 mg rsm, 0.218 mmol, 55%). Run 2: (16.8 mg, 0.072 mmol, 18%), (63.1 mg rsm, 0.266 mmol, 67%). Run 3: (17.4 mg, 0.074 mmol, 18%), (61.4 mg rsm, 0.259 mmol, 65%). Average: 18% yield±0.5, 62% rsm±5.3.

Entry 5.

(±)-3,7-dimethyloctyl sulfamate (94.9 mg, 0.400 mmol, 1.0 equiv), Fe(R,R-salen)Cl (22.8 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv) and 9:1 C$_6$H$_6$/MeCN (800 μL, 0.5M) were used.

Run 1: <1% yield, (784.6 mg rsm, 0.357 mmol, 89%). Run 2: <1% yield, (77.9 mg rsm, 0.328 mmol, 82%). Run 3: <1% yield, (79.1 mg rsm, 0.333 mmol, 83%). Average: <1% yield, 85% rsm±3.1.

Entry 6.

(±)-3,7-dimethyloctyl sulfamate (94.9 mg, 0.400 mmol, 1.0 equiv), Mn(R,R-salen)Cl (22.8 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv) and 9:1 C$_6$H$_6$/MeCN (800 μL, 0.5M) were used.

Run 1: (4.0 mg, 0.016 mmol, 4%), (72.5 mg rsm, 0.306 mmol, 76%). Run 2: (4.1 mg, 0.017 mmol, 4%), (78.0 mg rsm, 0.329 mmol, 82%). Run 3: (5.1 mg, 0.022 mmol, 5%), (73.2 mg rsm, 0.309 mmol, 77%). Average: 4% yield±0.5, 78% rsm±2.6.

Entry 7.

(±)-3,7-dimethyloctyl sulfamate (94.9 mg, 0.400 mmol, 1.0 equiv), Fe(R,R-PDP)(SbF$_6$)$_2$ (33.6 mg, 0.040 mmol, 0.10 equiv), PhI(OPiv)$_2$ (325 mg, 0.800 mmol, 2.0 equiv) and 9:1 C$_6$H$_6$/MeCN (800 µL, 0.5M) were used.

Run 1: <1% yield, (87.9 mg rsm, 0.370 mmol, 93%). Run 2: <1% yield, (87.7 mg rsm, 0.370 mmol, 92%). Run 3: <1% yield, (84.7 mg rsm, 0.357 mmol, 89%). Average: <1% yield, 91% rsm±1.7.

Entry 8.

(±)-3,7-dimethyloctyl sulfamate (94.9 mg, 0.400 mmol, 1.0 equiv), Mn(R,R-PDP)(SbF$_6$)$_2$ (33.6 mg, 0.040 mmol, 0.10 equiv), PhI(OPiv)$_2$ (325 mg, 0.800 mmol, 2.0 equiv) and 9:1 C$_6$H$_6$/MeCN (800 µL, 0.5M) were used.

Run 1: (7.0 mg, 0.030 mmol, 7%), (78.3 mg rsm, 0.330 mmol, 83%). Run 2: (6.2 mg, 0.026 mmol, 7%), (73.7 mg rsm, 0.311 mmol, 78%). Run 3: (6.7 mg, 0.028 mmol, 7%), (79.4 mg rsm, 0.335 mmol, 84%). Average: 7% yield±0.0, 82% rsm±2.2.

Entry 9.

(±)-3,7-dimethyloctyl sulfamate (94.9 mg, 0.400 mmol, 1.0 equiv), [MnPc]Cl (24.0 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used.

Run 1: (56.1 mg, 0.238 mmol, 60%), (10.6 mg rsm, 0.045 mmol, 11%). Run 2: (54.3 mg, 0.231 mmol, 58%), (10.5 mg rsm, 0.044 mmol, 11%). Run 3: (58.2 mg, 0.247 mmol, 62%), (10.9 mg rsm, 0.046 mmol, 11%). Average: 60% yield±1.6, 11% rsm±0.1.

Entry 10.

(±)-3,7-dimethyloctyl sulfamate (94.9 mg, 0.400 mmol, 1.0 equiv), [MnPc]Cl (12.0 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used.

Run 1: (56.3 mg, 0.239 mmol, 60%), (21.6 mg rsm, 0.091 mmol, 23%). Run 2: (51.3 mg, 0.218 mmol, 55%), (15.0 mg rsm, 0.063 mmol, 16%). Run 3: (56.0 mg, 0.238 mmol, 59%), (20.3 mg rsm, 0.086 mmol, 21%). Average: 58% yield±2.2, 20% rsm±2.9.

Entry 11.

(±)-3,7-dimethyloctyl sulfamate (94.9 mg, 0.400 mmol, 1.0 equiv), [Mn($^t$BuPc)]Cl (33.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used.

Run 1: (71.3 mg, 0.303 mmol, 76%), <5% rsm. Run 2: (70.4 mg, 0.299 mmol, 75%), <5% rsm. Run 3: (70.1 mg, 0.298 mmol, 74%), <5% rsm. Ave: 75% yield±0.8, <5% rsm.

Entry 12.

(±)-3,7-dimethyloctyl sulfamate (94.9 mg, 0.400 mmol, 1.0 equiv), [Fe($^t$BuPc)]Cl (33.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used.

Run 1: (26.0 mg, 0.111 mmol, 28%), (26.3 mg rsm, 0.111 mmol, 28%). Run 2: (28.0 mg, 0.119 mmol, 30%), (29.2 mg rsm, 0.123 mmol, 31%). Run 3: (26.2 mg, 0.111 mmol, 28%), (41.2 mg rsm, 0.174 mmol, 43%). Average: 29% yield±0.9, 34% rsm±6.6.

Entry 13.

(±)-3,7-dimethyloctyl sulfamate (94.9 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used.

Run 1: (68.1 mg, 0.289 mmol, 72%), (12.2 mg rsm, 0.051 mmol, 12%). Run 2: (68.8 mg, 0.292 mmol, 73%), (16.6 mg rsm, 0.070 mmol, 17%). Run 3: (67.8 mg, 0.288 mmol, 72%), (13.1 mg rsm, 0.055 mmol, 14%). Average: 72% yield±0.5, 14% rsm±2.1.

Entry 14.

(±)-3,7-dimethyloctyl sulfamate (94.9 mg, 0.400 mmol, 1.0 equiv), [Mn($^t$BuPc)]Cl (8.3 mg, 0.010 mmol, 0.025 equiv), AgSbF$_6$ (3.4 mg, 0.010 mmol, 0.025 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used. Note: reactions run at these low catalyst loadings were less reproducible at 0.400 mmol scale, likely due to increased effect of balance error in weighing catalysts.

Run 1: (65.6 mg, 0.279 mmol, 70%), (16.5 mg rsm, 0.070 mmol, 17%). Run 2: (67.0 mg, 0.284 mmol, 71%), (11.8 mg rsm, 0.050 mmol, 12%). Run 3: (66.6 mg, 0.283 mmol, 71%), (10.1 mg rsm, 0.043 mmol, 11%). Average: 71% yield±0.5, 13% rsm±2.6.

Entry 15.

(±)-3,7-dimethyloctyl sulfamate (94.9 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), PhI(OPiv)$_2$ (195 mg, 0.480 mmol, 1.2 equiv), 100 mg crushed 4 Å MS, and 9:1 C$_6$H$_6$/MeCN (800 µL, 0.5M) were used.

Run 1: (64.2 mg, 0.273 mmol, 68%), (12.9 mg rsm, 0.054 mmol, 14%). Run 2: (64.1 mg, 0.272 mmol, 68%), (15.9 mg rsm, 0.067 mmol, 17%). Run 3: (63.8 mg, 0.271 mmol, 68%), (16.8 mg rsm, 0.071 mmol, 18%). Average: 68% yield±0.2, 16% rsm±1.7.

Example 4. Substrate Scope for Mn-Catalyzed Intramolecular C—H Amination

General Procedure for [MnPc] and [Mn($^t$BuPc)]-Mediated C—H Amination.

Into a 10 mL round-bottom flask was added AgSbF$_6$ (0.05 equiv or 0.10 equiv), [Mn($^t$BuPc)]Cl (0.05 equiv or 0.10 equiv), crushed 4 Å MS, and a stir bar in a glovebox. The flask was then sealed with a rubber septum, covered in aluminum foil, and taken out of the box. Sulfamate ester (1.0 equiv), 9:1 C$_6$H$_6$/MeCN (0.5M), and, lastly, PhI(OPiv)$_2$ (2.0 equiv) were then added under an inert atmosphere; if sulfamate ester was an oil, it was taken up in the solvent mixture and added to the flask via syringe. After addition of oxidant, the dark red solution gradually turned dark brown. The reaction stirred for 8 h at room temperature unless otherwise specified (~20° C.). Upon completion, the reaction mixture was applied directly to a silica column for purification. Alternatively, the reaction can be concentrated under reduced pressure, and the remaining dark brown residue suspended in Et$_2$O and filtered through a small pad of Celite. Upon removal of solvent under reduced pressure, the brown residue was taken up in minimal CH$_2$Cl$_2$ and applied to a column. Any variation of these reaction conditions is noted for individual substrates.

General Procedure for [FePc]-Mediated Intramolecular C—H Amination.

Into a 10 mL round-bottom flask was added AgSbF$_6$ (13.7 mg, 0.040 mmol, 0.10 equiv), [FePc]Cl (24.0 mg, 0.040 mmol, 0.10 equiv), and a stir bar in a glovebox. The flask was then sealed with a rubber septum, covered in aluminum foil, and taken out of the box. 4:1 PhMe/MeCN (800 µL, 0.5M), sulfamate ester (0.400 mmol, 1.0 equiv), and PhI (OPiv)$_2$ (325 mg, 0.800 mmol, 2.0 equiv) were then added sequentially; if sulfamate ester was an oil, it was taken up in the solvent mixture and added to the flask via syringe. After addition of oxidant, the deep violet solution gradually turned dark brown. The reaction stirred for 8 h at room temperature unless otherwise specified (~20° C.). Upon completion, the reaction mixture was applied directly to a silica column (35 mm fritted glass column, 150 mm SiO$_2$) for purification. Alternatively, the reaction can be concentrated under reduced pressure, and the remaining dark brown residue suspended in Et$_2$O and filtered through a small pad of Celite. Upon removal of solvent under reduced pressure, the brown residue was taken up in minimal CH$_2$Cl$_2$ and applied to a column. Any variation of these reaction conditions is noted for individual substrates.

MnPc Conditions:

3-phenylpropyl sulfamate 49 (86.5 mg, 0.400 mmol, 1.0 equiv), [MnPc]Cl (12.0 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used.

Run 1: (59.1 mg, 0.276 mmol, 69%), (<5% rsm). Run 2: (59.8 mg, 0.279 mmol, 70%), (<5% rsm). Run 3: (62.6 mg, 0.292 mmol, 73%), (<5% rsm). Ave: 71% yield±1.7, <5% rsm.

Mn($^t$BuPc) Conditions:

3-phenylpropyl sulfamate 49 (86.5 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), PhI(OPiv)$_2$ (325

TABLE 1

Catalyst comparison across C—H bond types.

| catalyst | 6 | 7 | 8 | 9 |
|---|---|---|---|---|
| [FePc]* | 22% | 10% | 5%† | 3%† |
| [MnPc] | 71% | 61% | 39%† | 37%† |
| [Mn($^t$BuPc)] | 74% | 61% | 57%† | 64%† |

Isolated yields are average of three runs. *Conditions: 5 mol % [FePc]Cl, 5 mol % AgSbF$_6$, 2 equiv. PhI(OPiv)$_2$, 4:1 PhMe/MeCN (0.5M), rt, 8 h. †Used 10 mol % catalyst.

(±)-4-phenyl-1,2,3-oxathiazinane 2,2-dioxide [6]

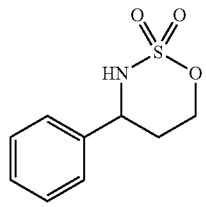 [SMILES: O=S1(=O)NC(c2ccccc2)CCO1]

In all cases, material was purified via flash column chromatography on silica (25 mm fritted glass column, 150 mm SiO$_2$) using 4:1 hexanes/EtOAc as eluent, affording oxathiazinane product and starting material separately.

FePc Conditions:

3-phenylpropyl sulfamate 49 (86.5 mg, 0.400 mmol, 1.0 equiv), [FePc]Cl (12.0 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), and 4:1 PhMe/MeCN (800 µL, 0.5M) were used.

Run 1: (18.5 mg, 0.086 mmol, 22%), (54.9 mg rsm, 0.254 mmol, 63%). Run 2: (19.0 mg, 0.089 mmol, 22%), (58.2 mg rsm, 0.269 mmol, 67%). Run 3: (17.8 mg, 0.083 mmol, 21%), (56.2 mg rsm, 0.260 mmol, 65%). Average: 22% yield±0.5, 65% rsm±1.6.

mg, 0.800 mmol, 2.0 equiv), 100 mg crushed 4 Å MS, and 9:1 C$_6$H$_6$/MeCN (800 µL, 0.5M) were used.

Run 1: (63.0 mg, 0.294 mmol, 74%), (<5% rsm). Run 2: (65.2 mg, 0.304 mmol, 76%), (<5% rsm). Run 3: (61.5 mg, 0.287 mmol, 72%), (<5% rsm). Ave: 74% yield±1.6, <5% rsm.

Pure product was isolated as a white solid. $^1$H-NMR (500 MHz, CDCl$_3$) δ 7.43-7.35 (m, 5H), 4.90-4.85 (m, 2H), 4.66 (ddd, J=11.5, 5.0, 1.5 Hz, 1H), 4.35 (br. d, J=9.0 Hz, 1H), 2.30-2.21 (m, 1H), 2.05-2.00 (m, 1H); $^{13}$C-NMR (125 MHz, CDCl$_3$) δ 137.7, 129.0, 128.7, 126.1, 71.8, 58.7, 30.0. This compound has been reported previously by our group (Paradine, S. M.; White, M. C. *J. Am. Chem. Soc.* 2012, 134, 2036).

(±)-(E)-4-(prop-1-en-1-yl)-1,2,3-oxathiazinane 2,2-dioxide [7]

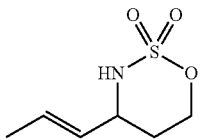

In all cases, material was purified via flash column chromatography on silica (35 mm fritted glass column, 150 mm SiO$_2$) using 3:1 hexanes/EtOAc, affording a mixture of product and starting material; yields were determined based on $^1$H NMR ratios. Pure product could be obtained by eluting with 10% hexanes/CH$_2$Cl$_2$→CH$_2$Cl$_2$→2% Et$_2$O/CH$_2$Cl$_2$. Ins./azir. ratios determined by $^1$H NMR of the crude reaction mixture. Pure product was isolated as a white solid.

FePc Conditions:

(E)-hex-4-en-1-yl sulfamate S1 (71.7 mg, 0.400 mmol, 1.0 equiv), [FePc]Cl (12.1 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), and 4:1 PhMe/MeCN (800 μL, 0.5M) were used.

Run 1: (8.2 mg, 0.046 mmol, 11%), (54.3 mg rsm, 0.303 mmol, 76%). Run 2: (7.6 mg, 0.043 mmol, 11%), (55.0 mg rsm, 0.307 mmol, 77%). Run 3: (6.7 mg, 0.038 mmol, 9%), (54.8 mg rsm, 0.306 mmol, 76%). Average: 10% yield±0.9, 76% rsm±0.5.

MnPc Conditions:

(E)-hex-4-en-1-yl sulfamate S1 (71.7 mg, 0.400 mmol, 1.0 equiv), [MnPc]Cl (12.1 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used.

Run 1: (43.1 mg, 0.243 mmol, 61%). Run 2: (43.6 mg, 0.246 mmol, 61%). Run 3: (42.7 mg, 0.241 mmol, 60%) Average: 61% yield±0.5.

Mn($^t$BuPc) Conditions:

(E)-hex-4-en-1-yl sulfamate S1 (71.7 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used.

Run 1: (45.0 mg, 0.254 mmol, 63%). Run 2: (40.9 mg, 0.231 mmol, 58%). Run 3: (44.3 mg, 0.250 mmol, 62%) Average: 61% yield±2.2.

$^1$H-NMR (500 MHz, CDCl$_3$) δ 5.78 (dqd, J=14.3, 6.5, 1.3 Hz, 1H), 5.43 (dd, J=15.4, 5.9 Hz, 1H), 4.74 (dt, J=12.0, 2.7 Hz, 1H), 4.55 (dd, J=11.6, 5.0 Hz, 1H), 4.30-4.24 (m, 1H), 4.00 (br. d, J=10.0 Hz, 1H), 1.91-1.77 (m, 2H), 1.73 (dd, J=6.5, 1.4 Hz, 3H); $^{13}$C-NMR (125 MHz, CDCl$_3$) δ 129.6, 128.1, 71.8, 56.9, 29.8, 17.9; $^{13}$C-NMR (125 MHz, CDCl$_3$) δ 129.6, 128.1, 71.8, 56.9, 29.8, 17.9. These data are in agreement with that previously reported in the literature (Fiori et al., *Tetrahedron* 2009, 65, 3042).

(±)-4-propyl-1,2,3-oxathiazinane 2,2-dioxide [8]

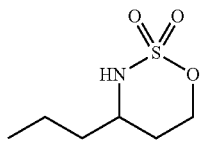

In all cases, material was purified via flash column chromatography on silica (35 mm fritted glass column, 150 mm SiO$_2$) using 3:1 hexanes/EtOAc, affording a mixture of product and starting material; yields were determined based on $^1$H NMR ratios. Pure product could be obtained by eluting with CH$_2$Cl$_2$→2% Et$_2$O/CH$_2$Cl$_2$.

FePc Conditions:

Hexyl sulfamate S2 (72.5 mg, 0.400 mmol, 1.0 equiv), [FePc]Cl (24.0 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), and 4:1 PhMe/MeCN (800 μL, 0.5M) were used.

Run 1: (3.7 mg, 0.021 mmol, 5%), (53.3 mg rsm, 0.294 mmol, 74%). Run 2: (3.3 mg, 0.018 mmol, 5%), (56.2 mg rsm, 0.310 mmol, 77%). Run 3: (2.7 mg, 0.015 mmol, 4%), (55.6 mg rsm, 0.307 mmol, 77%). Average: 5% yield±0.8, 76% rsm±1.4.

MnPc Conditions:

Hexyl sulfamate S2 (72.5 mg, 0.400 mmol, 1.0 equiv), [MnPc]Cl (24.0 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used.

Run 1: (26.1 mg, 0.146 mmol, 36%), (27.2 mg rsm, 0.150 mmol, 38%). Run 2: (29.1 mg, 0.162 mmol, 41%), (23.9 mg rsm, 0.132 mmol, 33%). Run 3: (28.1 mg, 0.157 mmol, 39%), (23.9 mg rsm, 0.132 mmol, 33%). Average: 39% yield±2.1, 35% rsm±2.4.

Mn($^t$BuPc) Conditions:

Hexyl sulfamate S2 (72.5 mg, 0.400 mmol, 1.0 equiv), [Mn($^t$BuPc)]Cl (33.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used.

Run 1: (40.8 mg, 0.228 mmol, 57%), (14.5 mg rsm, 0.080 mmol, 20%). Run 2: (42.2 mg, 0.235 mmol, 59%), (11.2 mg rsm, 0.062 mmol, 16%). Run 3: (40.1 mg, 0.224 mmol, 56%), (13.2 mg rsm, 0.073 mmol, 18%). Average: 57% yield±1.2, 18% rsm±1.6.

Product was isolated as a white solid. $^1$H-NMR (500 MHz, CDCl$_3$) δ 4.74-4.66 (m, 1H), 4.52 (dt, J=11.0, 3.3 Hz, 1H), 4.20 (br. d, J=10.5 Hz, 1H), 3.74-3.66 (m, 1H), 1.73-1.69 (m, 2H), 1.53-1.35 (m, 4H), 0.92 (t, J=7.3 Hz, 3H); $^{13}$C-NMR (125 MHz, CDCl$_3$) δ 72.2, 55.9, 37.2, 29.9, 18.4, 13.7; IR (ATR, cm$^{-1}$) 3367, 3285, 2919, 2858, 1539, 1470, 1343, 1178, 1063, 1032, 973, 922, 850, 792, 742, 717; HRMS (ESI) m/z calculated for C$_6$H$_{14}$NO$_3$S [M+H]$^+$: 180.0694, found 180.0698.

5,5-dimethyl-1,2,3-oxathiazinane 2,2-dioxide [9]

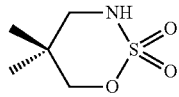

In all cases, the reaction was stirred at rt for 24 h. The crude reaction mixture was purified via flash column chromatography on silica (35 mm fritted glass column, 150 mm SiO$_2$) using 15% EtOAc/hexanes→20% EtOAc/hexanes with 0.5% AcOH as eluent.

FePc Conditions:

Neopentyl sulfamate S3 (66.9 mg, 0.400 mmol, 1.0 equiv), [FePc]Cl (24.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv) and 4:1 PhMe/MeCN (800 μL) were used. Product and recovered starting material were isolated as a mixture after column purification.

Run 1: (2.0 mg, 0.012 mmol, 3% yield), (50.2 mg, 0.300 mmol, 75% rsm). Run 2: (2.4 mg, 0.015 mmol, 4% yield), (48.0 mg, 0.287 mmol, 72% rsm). Run 3: (2.1 mg, 0.013 mmol, 3% yield), (52.2 mg, 0.312 mmol, 78% rsm). Average: 3% yield±0.6, 75% rsm±3.0.

MnPc Conditions:

Neopentyl sulfamate S3 (66.9 mg, 0.400 mmol, 1.0 equiv), [MnPc]Cl (24.2 mg, 0.040 mmol, 0.10 equiv), AgSbF$_6$ (13.7 mg, 0.040 mmol, 0.10 equiv), crushed 4 Å MS (100 mg), PhI(OPiv)$_2$ (325 mg, 0.800 mmol, 2.0 equiv) and 9:1 C$_6$H$_6$/MeCN (800 μL) were used. Product and starting material were isolated separately.

Run 1: (24.8 mg, 0.150 mmol, 38% yield), (25.9 mg, 0.155 mmol, 39% rsm). Run 2: (22.1 mg, 0.134 mmol, 33% yield), (27.0 mg, 0.161 mmol, 40% rsm). Run 3: (26.8 mg, 0.162 mmol, 41% yield), (29.5 mg, 0.176 mmol, 44% rsm). Ave: 37% yield±4.0, 41% rsm±2.6.

Mn($^t$BuPc) Conditions:

Neopentyl sulfamate S3 (66.9 mg, 0.400 mmol, 1.0 equiv), [Mn($^t$BuPc)]Cl (33.2 mg, 0.040 mmol, 0.10 equiv), AgSbF$_6$ (13.7 mg, 0.040 mmol, 0.10 equiv), crushed 4 Å MS (100 mg), PhI(OPiv)$_2$ (325 mg, 0.800 mmol, 2.0 equiv) and 9:1 C$_6$H$_6$/MeCN (800 μL) were used. Product and starting material were isolated separately.

Run 1: (42.6 mg, 0.258 mmol, 64% yield), (6.0 mg, 0.036 mmol, 9% rsm). Run 2: (41.3 mg, 0.250 mmol, 63% yield), (10.4 mg, 0.062 mmol, 16% rsm). Run 3: (42.6 mg, 0.258 mmol, 64% yield), (8.6 mg, 0.051 mmol, 13% rsm). Average: 64% yield±0.6, 13% rsm±3.5.

Product was isolated as a white solid. $^1$H-NMR (500 MHz, CDCl$_3$) δ 4.69 (br. s, 1H), 4.27 (s, 2H), 3.27 (d, J=7.5 Hz, 2H), 1.07 (s, 6H); $^{13}$C-NMR (125 MHz, CDCl$_3$) δ 81.7, 55.4, 29.1, 21.9; IR (ATR, cm$^{-1}$): 3315, 2967, 1425, 1399, 1350, 1336, 1314, 1282, 1183, 1046, 954, 930, 922, 910, 844; HRMS (ESI) m/z calculated for C$_5$H$_{12}$NO$_3$S [M+H]$^+$: 166.0538, found 166.0535.

TABLE 2

Aliphatic C—H bond substrate scope.

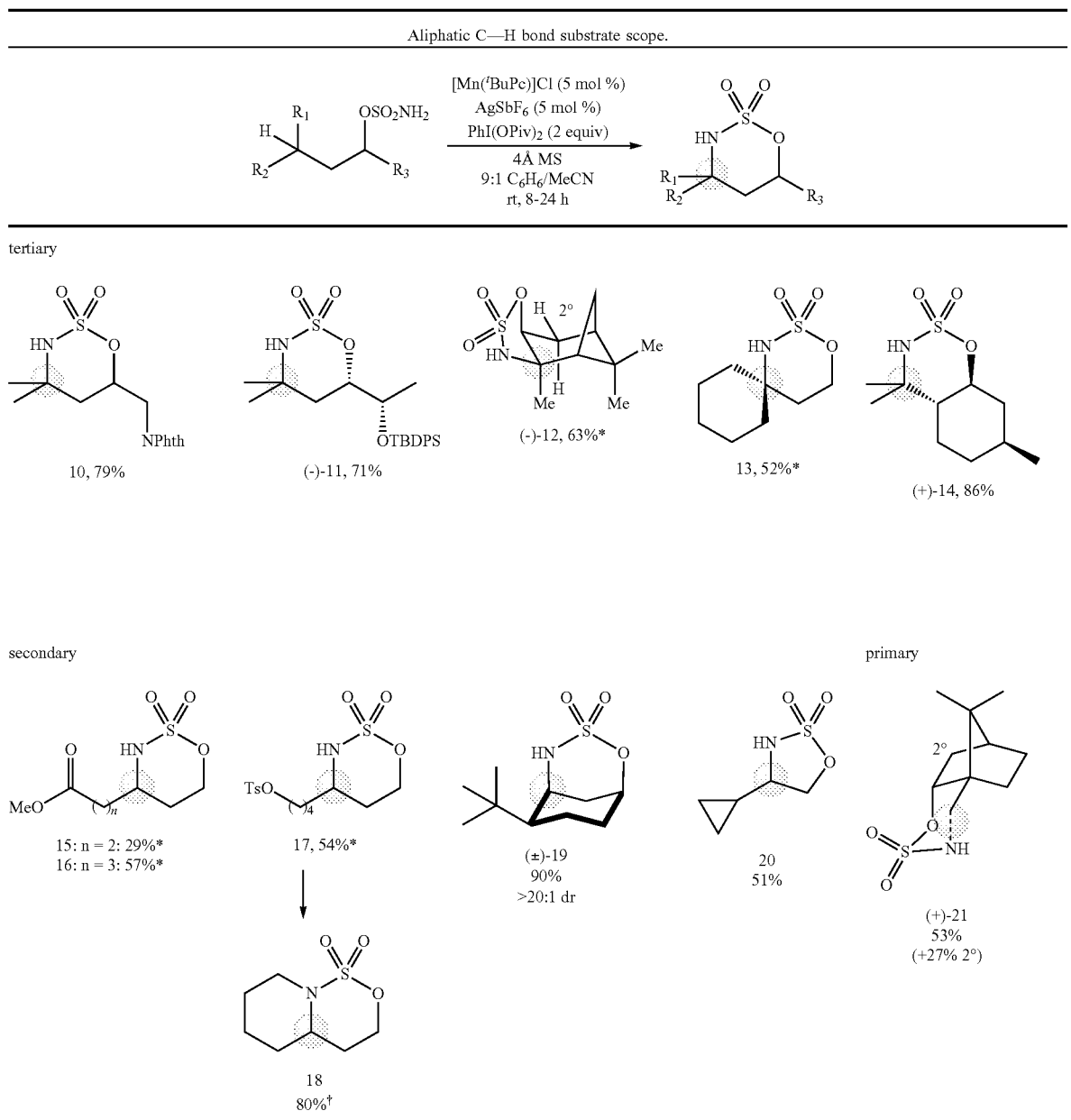

Isolated yields are average of three runs. *Used 10 mol % catalyst. †Conditions: 1.5 equiv K$_2$CO$_3$, 10 mol % TBAI, DMF, rt, 15 h.

(±)-2-((4,4-dimethyl-2,2-dioxido-1,2,3-oxathiazinan-6-yl)methyl)isoindoline-1,3-dione [10]

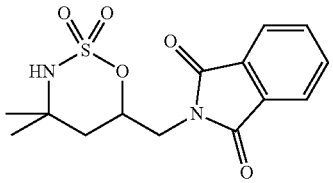 [SMILES: CC1(C)CC(CN2C(=O)c3ccccc3C2=O)OS(=O)(=O)N1]

(±)-1-(1,3-dioxoisoindolin-2-yl)-4-methylpentan-2-yl sulfamate S4 (131.0 mg, 0.400 mmol, 1.0 equiv), [Mn(tBuPc)]Cl (16.6 mg, 0.020 mmol, 0.05 equiv), AgSbF₆ (6.9 mg, 0.020 mmol, 0.05 equiv), PhI(OPiv)₂ (325 mg, 0.800 mmol, 2.0 equiv), 100 mg crushed 4 Å MS, and 9:1 C₆H₆/MeCN (800 μL, 0.5M) were used. Product was purified via flash column chromatography on silica (35 mm fritted glass column, 150 mm SiO₂) using 3:2 hexanes/EtOAc. Pure product was isolated as a white solid.

Run 1: (104.0 mg, 0.320 mmol, 80%), 0% rsm. Run 2: (100.1 mg, 0.308 mmol, 77%), 0% rsm. Run 3: (103.7 mg, 0.319 mmol, 80%), 0% rsm. Average: 79% yield±1.4, 0% rsm.

¹H-NMR (500 MHz, acetone-d₆) δ 7.91-7.86 (m, 4H), 6.01 (br. s, 1H), 5.13 (dddd, J=12.0, 7.0, 5.0, 2.0 Hz, 1H), 4.02 (dd, J=14.5, 7.0 Hz, 1H), 3.88 (dd, J=14.5, 5.0 Hz, 1H), 2.01 (dd, J=14.5, 2.0 Hz, 1H), 1.72 (dd, J=14.5, 12.0 Hz, 1H), 1.46 (s, 3H), 1.36 (s, 3H); ¹³C-NMR (125 MHz, acetone-d₆) δ 168.6, 135.4, 133.1, 124.2, 78.3, 56.5, 42.2, 39.4, 31.6, 25.6; IR (thin film, cm⁻¹) 3228, 2981, 2950, 1713, 1468, 1433, 1393, 1360, 1272, 1193, 1160, 1061, 1026, 995, 943, 869; HRMS (ESI) m/z calculated for C₁₄H₁₇N₂O₅S [M+H]⁺: 325.0858, found 325.0859.

(−)-(R)-6-((S)-1-((tert-butyldiphenylsilyl)oxy)ethyl)-4,4-dimethyl-1,2,3-oxathiazinane 2,2-dioxide [11]

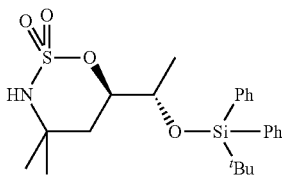 [SMILES: C[C@H](O[Si](c1ccccc1)(c1ccccc1)C(C)(C)C)[C@H]1CC(C)(C)NS(=O)(=O)O1]

(−)-(2S,3R)-2-((tert-butyldiphenylsilyl)oxy)-5-methyl-hexan-3-yl sulfamate S5 (89.9 mg, 0.200 mmol, 1.0 equiv), [Mn(tBuPc)]Cl (16.6 mg, 0.020 mmol, 0.10 equiv), AgSbF₆ (6.9 mg, 0.020 mmol, 0.10 equiv), PhI(OPiv)₂ (163 mg, 0.400 mmol, 2.0 equiv), 50 mg crushed 4 Å MS, and 9:1 C₆H₆/MeCN (400 μL, 0.5M) were used. Product was purified via flash column chromatography on silica (35 mm fritted glass column, 100 mm SiO₂) using 9:1 hexanes/EtOAc. Pure product was isolated as a white solid.

Run 1: (58.7 mg, 0.131 mmol, 66%), <10% rsm. Run 2: (66.5 mg, 0.149 mmol, 74%), <10% rsm. Run 3: (65.4 mg, 0.146 mmol, 73%), <10% rsm. Ave: 71% yield±3.6, <10% rsm.

¹H-NMR (500 MHz, CDCl₃) δ 7.68-7.65 (m, 4H), 7.47-7.43 (m, 2H), 7.41-7.38 (m, 4H), 4.68 (ddd, J=12.0, 4.5, 2.0 Hz, 1H), 3.96 (qd, J=12.5, 4.5 Hz, 1H), 3.91 (s, 1H), 1.70 (dd, J=14.5, 12.5 Hz, 1H), 1.57 (dd, J=14.0, 2.0 Hz, 1H), 1.44 (s, 3H), 1.28 (s, 3H), 1.13 (d, J=6.5 Hz, 3H), 1.07 (s, 9H); ¹³C-NMR (125 MHz, CDCl₃) δ 136.0, 133.7, 133.2, 130.2, 130.0, 127.9, 127.8, 82.8, 69.7, 55.8, 36.0, 32.3, 27.1, 25.0, 19.4, 18.3; IR (ATR, cm⁻¹) 3269, 3072, 2962, 2933, 2859, 1473, 1428, 1390, 1375, 1353, 1266, 1196, 1141, 1111, 1029, 934, 875, 822, 740, 703; [α]²⁵_D=−23.2° (c=1.1, CHCl₃); HRMS (ESI) m/z calculated for C₂₃H₃₃NO₄SSiNa [M+Na]⁺: 470.1797, found 470.1798.

(−)-(3R,4R,6R,7S)-3,5,5-trimethylhexahydro-3H-4,6-methanobenzo[d][1,2,3]oxathiazole 2,2-dioxide [12]

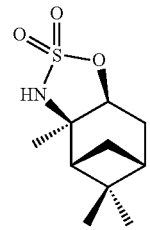

(−)-(1S,2S,3S,5R)-isopinocamphenyl sulfamate S6 (93.3 mg, 0.400 mmol, 1.0 equiv), [Mn(tBuPc)]Cl (33.2 mg, 0.040 mmol, 0.10 equiv), AgSbF₆ (6.9 mg, 0.040 mmol, 0.10 equiv), PhI(OPiv)₂ (325 mg, 0.800 mmol, 2.0 equiv), 100 mg crushed 4 Å MS, and 9:1 C₆H₆/MeCN (800 μL, 0.5M) were used. By crude ¹H NMR, ratio of 3° to other products (most likely 2° and 1° C—H amination products, but could not be isolated pure to confirm assignment) was >10:1. Product was purified via flash column chromatography on silica (35 mm fritted glass column, 150 mm SiO₂) using 7:1 hexanes/EtOAc→4:1 hexanes/EtOAc. Pure product was isolated as a white solid.

Run 1: (57.1 mg, 0.247 mmol, 62%), <5% rsm. Run 2: (59.1 mg, 0.256 mmol, 64%), <5% rsm. Run 3: (57.5 mg, 0.249 mmol, 62%), <5%. Average: 63% yield±0.9, <5% rsm.

¹H-NMR (500 MHz, CDCl₃) δ 4.67 (dd, J=8.5, 2.0 Hz, 1H), 4.24 (s 1H), 2.49-2.43 (m, 1H), 2.34 (dtd, J=11.0, 6.0, 2.0 Hz, 1H), 2.16-2.11 (m, 1H), 2.06 (dd, J=6.0, 1.5 Hz, 2H), 1.63 (s, 3H), 1.47 (d, J=11.0 Hz, 1H), 1.33 (s, 3H), 0.94 (s, 3H); ¹³C-NMR (125 MHz, CDCl₃) δ 82.1, 66.0, 51.1, 39.6, 39.0, 32.7, 28.2, 27.3, 26.1, 24.4; IR (ATR, cm⁻¹) 3244, 3005, 2985, 2959, 2941, 2926, 2912, 1479, 1450, 1393, 1381, 1318, 1281, 1181, 1131, 1085, 1062, 1029, 972, 959, 944, 893, 865, 852, 815, 753; [α]²⁶_D=−48.7° (c=1.0, CHCl₃); HRMS (ESI) m/z calculated for C₁₀H₁₇NO₃SNa [M+Na]⁺: 254.0827, found 254.0830.

3-oxa-2-thia-1-azaspiro[5.5]undecane 2,2-dioxide [13]

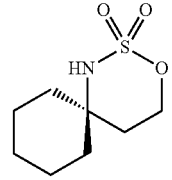

2-cyclohexylethyl sulfamate S7 (82.9 mg, 0.400 mmol, 1.0 equiv), [Mn($^t$BuPc)]Cl (33.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used. Reaction stirred for 20 h. Product was purified via flash column chromatography on silica (35 mm fritted glass column, 150 mm SiO$_2$) using CH$_2$Cl$_2$→2% Et$_2$O/CH$_2$Cl$_2$→5% Et$_2$O/CH$_2$Cl$_2$. Pure product was isolated as a white solid.

Run 1: (41.0 mg, 0.200 mmol, 50%), (13.1 mg rsm, 0.063 mmol, 16%). Run 2: (41.1 mg, 0.200 mmol, 50%), (17.6 mg rsm, 0.085 mmol, 21%). Run 3: (45.2 mg, 0.220 mmol, 55%), (13.8 mg rsm, 0.067 mmol, 17%). Average: 52% yield±2.4, 18% rsm±2.2.

$^1$H-NMR (500 MHz, CDCl$_3$) δ 4.64 (t, J=5.5 Hz, 2H), 4.26 (s, 1H), 2.01 (d, J=13.0 Hz, 2H), 1.75 (t, J=5.5 Hz, 2H), 1.69-1.59 (m, 3H), 1.49-1.42 (m, 4H), 1.33-1.24 (m, 1H); $^{13}$C-NMR (125 MHz, CDCl$_3$) δ 68.7, 58.6, 36.3, 34.9, 25.7, 20.9; IR (ATR, cm$^{-1}$) 3247, 2930, 2860, 1466, 1445, 1417, 1357, 1341, 1279, 1186, 1153, 1111, 1023, 996, 945, 933, 926, 900, 871, 849, 739; HRMS (ESI) m/z calculated for C$_8$H$_{16}$NO$_3$S [M+H]$^+$: 206.0851, found 206.0850.

(+)-(4R,7S,8S)-4,4,7-trimethyloctahydrobenzo[e][1,2,3]oxathiazine 2,2-dioxide [14]

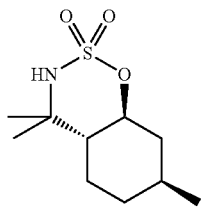

(−)-(1R,2S,5R)-menthyl sulfamate S8 (94.1 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used. Product was purified via flash column chromatography on silica (35 mm fritted glass column, 150 mm SiO$_2$) using 4:1 hexanes/EtOAc. Pure product was isolated as a white solid.

Run 1: (81.9 mg, 0.351 mmol, 88%), 0% rsm. Run 2: (79.9 mg, 0.342 mmol, 86%), 0% rsm. Run 3: (79.0 mg, 0.339 mmol, 85%), 0% rsm. Average: 86% yield±1.2, 0% rsm.

$^1$H-NMR (500 MHz, CDCl$_3$) δ 4.58 (dt, J=10.5, 4.5 Hz, 1H), 4.54 (br. s, 1H), 2.10-2.07 (m, 1H), 1.79-1.73 (m, 2H), 1.59-1.51 (m, 1H), 1.47 (dt, J=11.3, 3.0 Hz, 1H), 1.36 (s, 3H), 1.24 (s, 3H), 1.08-1.00 (m, 1H), 0.96 (d, J=6.0 Hz, 3H); $^{13}$C-NMR (125 MHz, CDCl$_3$) δ 82.4, 59.1, 48.7, 40.4, 34.1, 31.4, 29.4, 25.2, 21.9, 21.2; IR (film, cm$^{-1}$) 3280, 2958, 2922, 2862, 1460, 1410, 1389, 1373, 1336, 1225, 1200, 1184, 1161, 1137, 1086, 1012, 991, 920, 903, 885, 860, 818; [α]$^{25}$$_D$=+23.5° (c=1.0, CHCl$_3$); HRMS (ESI) m/z calculated for C$_{10}$H$_{20}$NO$_3$S [M+H]$^+$: 234.1164, found 234.1164.

(±)-methyl 3-(2,2-dioxido-1,2,3-oxathiazinan-4-yl)propanoate [15]

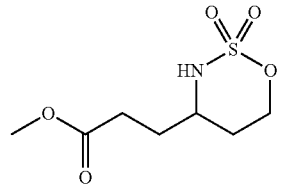

Methyl 6-(sulfamoyloxy)hexanoate S9 (90.1 mg, 0.400 mmol, 1.0 equiv), [Mn($^t$BuPc)]Cl (33.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used. Reaction stirred at rt for 17 h. Material was purified via flash column chromatography on silica (35 mm fritted glass column, 150 mm SiO$_2$) using 2:1 hexanes/EtOAc. Starting material and product were isolated as a mixture; yields were determined based on $^1$H NMR ratios. Pure product could be isolated by eluting with 5% Et$_2$O/CH$_2$Cl$_2$→10% Et$_2$O/CH$_2$Cl$_2$. Pure product was isolated as a white solid.

Run 1: (26.0 mg, 0.116 mmol, 29%), (37.1 mg rsm, 0.165 mmol, 41%). Run 2: (24.6 mg, 0.110 mmol, 28%), (42.2 mg rsm, 0.187 mmol, 47%). Run 3: (26.3 mg, 0.118 mmol, 30%), (32.0 mg rsm, 0.142 mmol, 36%). Average: 29% yield±0.8, 41% rsm±4.1.

$^1$H-NMR (500 MHz, CDCl$_3$) δ 4.74-4.68 (m, 1H), 4.54 (dt, J=11.0, 3.0 Hz, 1H), 4.22 (d, J=10.7 Hz, 1H), 3.78-3.71 (m, 1H), 3.69 (s, 3H), 2.49 (td, J=7.1, 1.5 Hz, 2H), 1.94 (dtd, J=14.5, 7.2, 4.5 Hz, 1H), 1.86-1.73 (m, 3H); $^{13}$C-NMR (125 MHz, CDCl$_3$) δ 173.6, 71.8, 55.9, 52.1, 30.2, 29.8, 29.7; IR (ATR, cm$^{-1}$) 3273, 2960, 2942, 1735, 1433, 1386, 1355, 1337, 1319, 1269, 1252, 1228, 1203, 1170, 1104, 1081, 1056, 1009, 982, 937, 906, 895, 856, 775; HRMS (ESI) m/z calculated for C$_7$H$_{14}$NO$_5$S [M+H]$^+$: 224.0593, found 224.0592.

(±)-methyl 4-(2,2-dioxido-1,2,3-oxathiazinan-4-yl)butanoate [16]

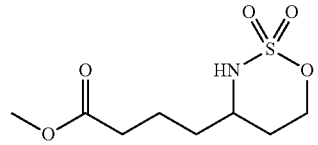

Methyl 7-(sulfamoyloxy)heptanoate S10 (95.7 mg, 0.400 mmol, 1.0 equiv), [Mn($^t$BuPc)]Cl (33.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used. Reaction stirred at rt for 17 h. Product was purified via flash column chromatography on silica (35 mm fritted glass column, 150 mm SiO$_2$) using 5% Et$_2$O/CH$_2$Cl$_2$→10% Et$_2$O/CH$_2$Cl$_2$. Pure product was isolated as a colorless oil with a minor amount (~6%) of an unidentified product-like impurity; reported yields are corrected to reflect amount of desired product isolated.

Run 1: (53.9 mg, 0.227 mmol, 57%), (20.4 mg rsm, 0.085 mmol, 21%). Run 2: (54.2 mg, 0.228 mmol, 57%), (17.1 mg rsm, 0.071 mmol, 18%). Run 3: (53.9 mg, 0.227 mmol, 57%), (17.9 mg rsm, 0.075 mmol, 19%). Average: 57% yield±0.0, 19% rsm±1.2.

$^1$H-NMR (500 MHz, CDCl$_3$) δ 4.74-4.69 (m, 1H), 4.54 (ddd, J=11.5, 4.5, 2.0 Hz, 1H), 4.08 (br. d, J=10.5 Hz, 1H), 3.76-3.69 (m, 1H), 3.68 (s, 3H), 2.35 (dt, J=7.3, 2.0 Hz, 2H), 1.84-1.51 (m, 6H); $^{13}$C-NMR (125 MHz, CDCl$_3$) δ 173.8, 72.1, 55.9, 51.8, 34.3, 33.3, 29.9, 20.6; IR (ATR, cm$^{-1}$) 3249, 2956, 1718, 1422, 1357, 1237, 1084, 1012, 987, 938, 917, 890, 862, 774, 731; HRMS (ESI) m/z calculated for C$_8$H$_{16}$NO$_5$S [M+H]$^+$: 238.0749, found 238.0750.

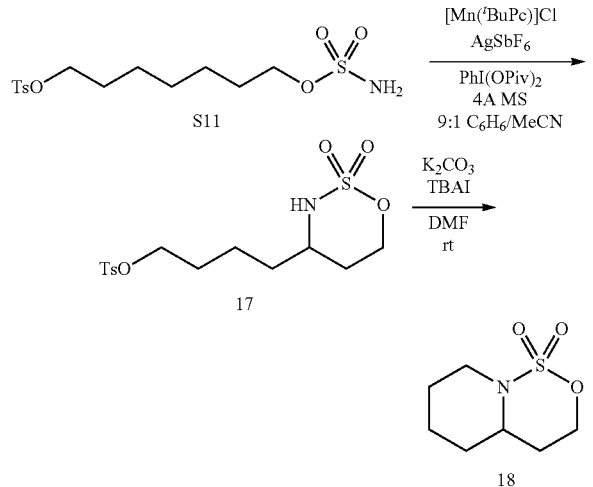

(±)-4-(2,2-dioxido-1,2,3-oxathiazinan-4-yl)butyl 4-methylbenzenesulfonate [17]

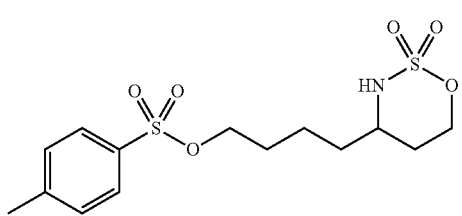 [SMILES: Cc1ccc(S(=O)(=O)OCCCCC2CCOS(=O)(=O)N2)cc1]

7-(tosyloxy)heptyl sulfamate S11 (146 mg, 0.400 mmol, 1.0 equiv), [Mn($^t$BuPc)]Cl (33.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used. Reaction stirred for 17 h. Product was purified via flash column chromatography on silica (35 mm fritted glass column, 150 mm SiO$_2$) using 5% Et$_2$O/CH$_2$Cl$_2$→10% Et$_2$O/CH$_2$Cl$_2$. Pure product was isolated as a colorless oil.

Run 1: (78.1 mg, 0.215 mmol, 54%), <10% rsm. Run 2: (79.2 mg, 0.218 mmol, 54%), <10% rsm. Run 3: (77.9 mg, 0.214 mmol, 54%), <10% rsm. Ave: 54% yield±0.0, <10% rsm.

$^1$H-NMR (500 MHz, CDCl$_3$) δ 7.79 (d, J=6.5 Hz, 2H), 7.36 (d, J=6.0 Hz, 2H), 4.70 (dt, J=12.0, 3.5 Hz, 1H), 4.53 (ddd, J=11.5, 4.5, 2.0 Hz, 1H), 4.04 (t, J=6.0 Hz, 2H), 3.87 (br. d, J=10.5 Hz, 1H), 3.70-3.62 (m, 1H), 2.46 (s, 3H), 1.73-1.63 (m, 4H), 1.54-1.40 (m, 4H); $^{13}$C-NMR (125 MHz, CDCl$_3$) δ 145.1, 133.0, 130.1, 128.0, 71.9, 70.0, 56.0, 34.5, 30.2, 28.4, 21.8, 21.3; HRMS (ESI) m/z calculated for C$_{14}$H$_{22}$NO$_6$S2 [M+H]$^+$: 364.0889, found 364.0887.

(±)-hexahydro-3H-pyrido[1,2-c][1,2,3]oxathiazine 1,1-dioxide [18]

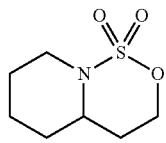 [SMILES: O=S1(=O)OCCC2CCCCN21]

Cyclization procedure was modified from a similar procedure reported in the literature (Kang, S.; Lee, H-K. *J. Org. Chem.* 2010, 75, 237). 17 (50.0 mg, 0.138 mmol, 1.0 equiv) was taken up in DMF (2.76 mL, 0.05M) in a 2 dram vial. K$_2$CO$_3$ (28.6 mg, 0.207 mmol, 1.5 equiv) and n-Bu$_4$NI (5.2 mg, 0.014 mmol, 0.10 equiv) were added, and then vial was capped and reaction stirred vigorously at rt for 15 h (no precautions were taken to remove oxygen or water). Upon completion, reaction was quenched with H$_2$O (1 mL), then diluted with EtOAc (15 mL) and H$_2$O (5 mL). After separating, the aqueous layer was extracted twice more with EtOAc (2×10 mL). Organic layers were combined and washed with H$_2$O (10 mL) and brine (2×10 mL), then dried over MgSO$_4$ and filtered. Flash column chromatography on silica (35 mm fritted glass column, 70 mm SiO$_2$) using 3:1 hexanes/EtOAc as eluent gave 21.1 mg (0.110 mmol) of pure product as a colorless oil (80% yield).

$^1$H-NMR (500 MHz, CDCl$_3$) δ 4.71 (ddd, J=13.5, 11.0, 2.5 Hz, 1H), 4.46 (ddd, J=11.5, 5.5, 1.5 Hz, 1H), 3.58 (ddt, J=11.5, 7.0, 3.0 Hz, 1H), 3.47-3.42 (m, 1H), 2.95 (ddd, J=11.5, 9.0, 4.0 Hz, 1H), 2.19 (dddd, J=14.5, 13.5, 12.0, 5.5 Hz, 1H), 1.85-1.80 (m, 1H), 1.75-1.64 (m, 3H), 1.58-1.44 (m, 3H); $^{13}$C-NMR (125 MHz, CDCl$_3$) δ 71.9, 57.4, 44.6, 31.2, 28.1, 24.6, 21.5; IR (ATR, cm$^{-1}$) 2974, 2957, 2939, 2867, 1468, 1445, 1427, 1360, 1343, 1300, 1282, 1254, 1208, 1107, 1089, 1047, 1030, 1011, 985, 959, 900, 872, 862, 799, 704; HRMS (ESI) m/z calculated for C$_7$H$_{14}$NO$_3$S [M+H]$^+$: 192.0694, found 192.0699.

(±)-6-(tert-butyl)-2-oxa-3-thia-4-azabicyclo[3.3.1] nonane 3,3-dioxide [19]

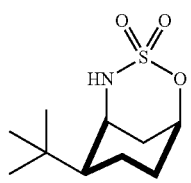

(±)-cis-4-(tert-butyl)cyclohexyl sulfamate S12 (94.1 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used. Product was purified via flash column chromatography on silica (35 mm fritted glass column, 150 mm SiO$_2$) using 2:1 hexanes/EtOAc. Pure product was isolated as a white solid.

Run 1: (83.0 mg, 0.356 mmol, 89%), 0% rsm. Run 2: (83.6 mg, 0.358 mmol, 90%), 0% rsm. Run 3: (84.9 mg, 0.364 mmol, 91%), 0% rsm. Average: 90% yield±0.8, 0% rsm.

$^1$H-NMR (500 MHz, CDCl$_3$) δ 4.93-4.92 (m, 1H), 4.56 (br. s, 1H), 3.71-3.67 (m, 1H), 2.43-2.39 (m, 1H), 2.03 (ddd, J=12.5, 6.0, 3.0 Hz, 1H), 1.71-1.64 (m, 2H), 1.59 (app. q, J=12.5 Hz, 1H), 1.33-1.25 (m, 1H), 1.03-0.98 (m, 1H), 0.89 (s, 9H); $^{13}$C-NMR (125 MHz, CDCl$_3$) δ 84.0, 58.5, 45.1, 32.5, 29.9, 27.8, 27.4, 20.3; IR (ATR, cm$^{-1}$) 3227, 2955, 2871, 1393, 1376, 1358, 1340, 1315, 1229, 1181, 1093, 996, 976, 952, 884, 870, 792, 760, 707, 692; HRMS (ESI) m/z calculated for C$_{10}$H$_{20}$NO$_3$S [M+H]$^+$: 234.1164, found 234.1168.

(±)-4-cyclopropyl-1,2,3-oxathiazolidine 2,2-dioxide [20]

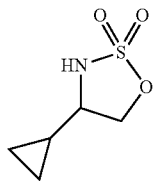

2-cyclopropylethyl sulfamate S13 (66.1 mg, 0.400 mmol, 1.0 equiv), [Mn($^t$BuPc)]Cl (33.2 mg, 0.040 mmol, 0.10 equiv), AgSbF$_6$ (13.7 mg, 0.040 mmol, 0.10 equiv), crushed 4 Å MS (100 mg), PhI(OPiv)$_2$ (325 mg, 0.800 mmol, 2.0 equiv) and 9:1 C$_6$H$_6$/MeCN (800 μL, 0.5M) were used. The reaction was stirred for 24 h at rt (~20° C.). Flash column chromatography on silica (35 mm fritted glass column, 150 mL SiO$_2$) using 20% EtOAc/hexanes→30% EtOAc/hexanes with 0.5% AcOH as eluent gave product as colorless oil.

Run 1: (33.1 mg, 0.203 mmol, 51%), (7.4 mg rsm, 0.045 mmol, 11%). Run 2: (34.1 mg, 0.209 mmol, 52%), (11.1 mg rsm, 0.067 mmol, 17%). Run 3: (32.9 mg, 0.202 mmol, 50%), (10.0 mg rsm, 0.060 mmol, 15%). Average: 51% yield±1.0, 14% rsm±3.1.

$^1$H-NMR (500 MHz, CDCl$_3$) δ 4.83 (br. d, J=8.0 Hz, 1H), 4.64 (dd, J=8.5, 6.4 Hz, 1H), 4.34 (t, J=8.2 Hz, 1H), 3.32 (app. p, J=7.4 Hz, 1H), 1.04 (qt, J=8.5, 4.7 Hz, 1H), 0.71-0.61 (m, 2H), 0.44 (dq, J=9.7, 5.0 Hz, 1H), 0.31 (dq, J=10.1, 5.0 Hz, 1H); $^{13}$C-NMR (125 MHz, CDCl$_3$) δ 74.6, 61.5, 12.6, 3.3, 2.6; IR (thin film, cm$^{-1}$): 3267, 3011, 1391, 1339, 1189, 1054, 966, 832, 789; HRMS (ESI) m/z calculated for C$_5$H$_9$NO$_3$SNa [M+Na]$^+$: 186.0201, found 186.0208.

(+)-(7S,8αR)-9,9-dimethylhexahydro-5H-4α,7-methanobenzo[e][1,2,3]oxathiazine 2,2-dioxide [21]

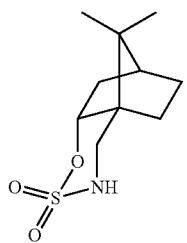

(−)-(1S,2R,4S)-borneyl sulfamate S14 (93.3 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used. Product was purified via flash column chromatography on silica (35 mm fritted glass column, 150 mm SiO$_2$) using 4:1 hexanes/EtOAc. Both 1° and 2° products were isolated separately as white solids.

Run 1: (47.3 mg 1°, 0.204 mmol, 51%), (25.4 mg 2°, 0.110 mmol, 27%), (15.4 mg rsm, 0.065 mmol, 17%). Run 2: (48.9 mg 1°, 0.211 mmol, 53%), (27.2 mg 2°, 0.118 mmol, 29%), (12.1 mg rsm, 0.052 mmol, 13%). Run 3: (49.5 mg 1°, 0.214 mmol, 54%), (24.4 mg 2°, 0.105 mmol, 26%), (12.6 mg rsm, 0.054 mmol, 14%). Average: 53% yield 1°+1.2, 27% yield 2°±1.2, 14% rsm±1.2.

$^1$H-NMR (500 MHz, CDCl$_3$) δ 5.13 (ddd, J=11.0, 5.0, 2.5 Hz, 1H), 4.41 (dd, J=10.5, 5.0 Hz, 1H), 3.58 (dd, J=14.0, 11.0 Hz, 1H), 3.08 (dd, J=14.0, 5.0 Hz, 1H), 2.34-2.27 (m, 2H), 1.86-1.80 (m, 2H), 1.51-1.45 (m, 1H), 1.41-1.36 (m, 1H), 1.26 (dd, J=14.0, 5.0 Hz, 1H), 0.97 (s, 3H), 0.95 (s, 3H); $^{13}$C-NMR (125 MHz, CDCl$_3$) δ 87.5, 47.6, 46.4, 45.8, 45.8, 32.6, 27.9, 24.0, 20.0, 18.9; IR (ATR, cm$^{-1}$) 3312, 2967, 2893, 1463, 1446, 1428, 1349, 1306, 1180, 1137, 1073, 1019, 989, 968, 922, 873, 840, 815, 797, 753; [α]$^{26}_D$=+37.9° (c=1.0, CHCl$_3$); HRMS (ESI) m/z calculated for C$_{10}$H$_{18}$NO$_3$S [M+H]$^+$: 232.1007, found 232.1008.

(−)-(3αR,4R,7R,7αS)-7,8,8-trimethylhexahydro-3H-4,7-methanobenzo[d][1,2,3]oxathiazole 2,2-dioxide [S36]

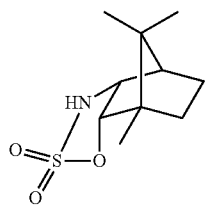

$^1$H-NMR (500 MHz, CDCl$_3$) δ 4.72 (dd, J=9.0, 2.0 Hz, 1H), 4.28 (br. s, 1H), 4.26-4.21 (m, 1H), 1.99 (dd, J=4.5, 4.0 Hz, 1H), 1.87 (ddd, J=14.0, 9.0, 5.0 Hz, 1H), 1.74-1.63 (m, 2H), 1.39 (dddd, J=13.5, 11.5, 6.0, 2.0 Hz, 1H), 1.01 (s, 3H), 1.00 (s, 3H), 0.96 (s, 3H); $^{13}$C-NMR (125 MHz, CDCl$_3$) δ 88.4, 56.4, 49.6, 48.5, 48.4, 26.5, 20.5, 19.4, 18.3, 14.3; IR (ATR, cm$^{-1}$) 3325, 2967, 2923, 1475, 1388, 1378, 1342, 1327, 1283, 1262, 1125, 1075, 1024, 1001, 982, 964, 906, 883, 853, 823, 759, 709; [α]$^{26}_D$=−38.7° (c=1.6, CHCl$_3$); HRMS (ESI) m/z calculated for C$_{10}$H$_{18}$NO$_3$S [M+H]$^+$: 232.1007, found 232.1007.

TABLE 3

Allylic C—H bond substrate scope.

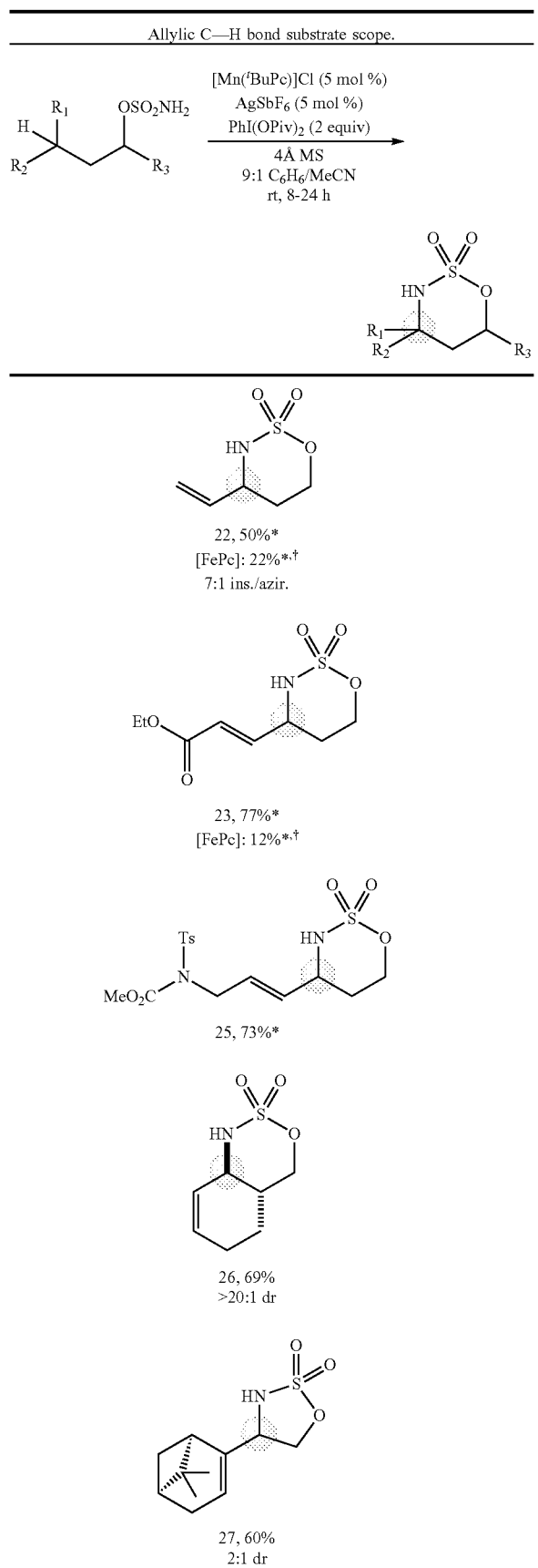

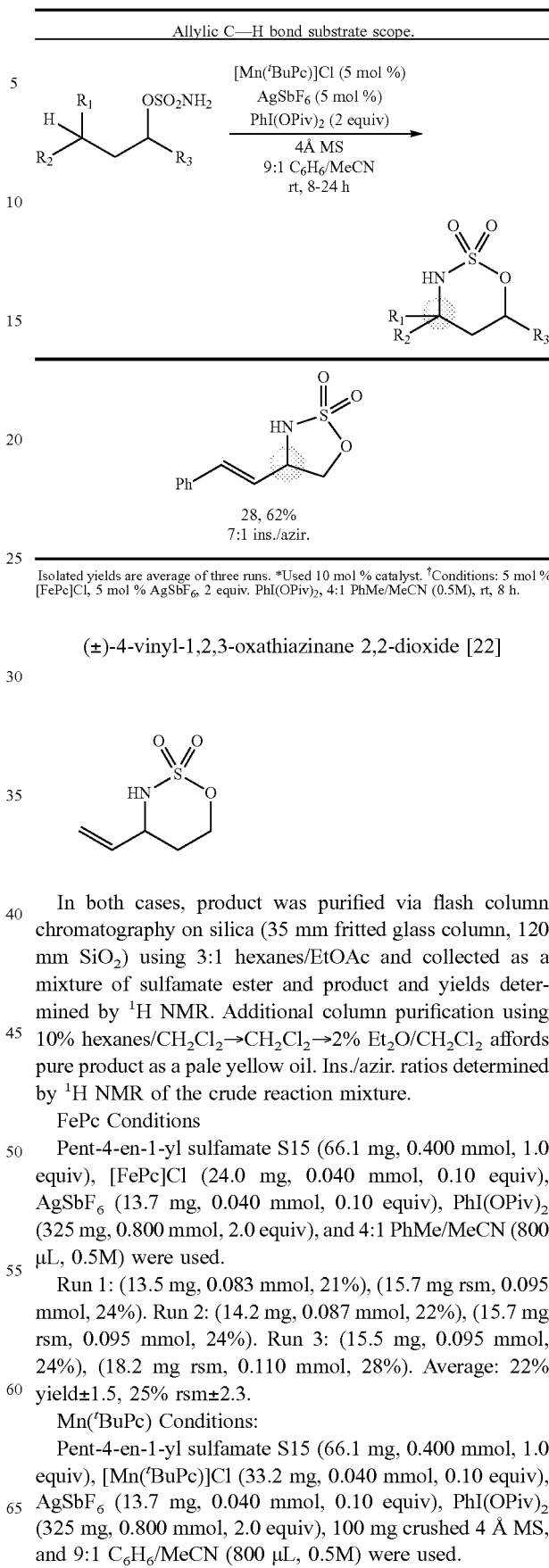

Isolated yields are average of three runs. *Used 10 mol % catalyst. †Conditions: 5 mol % [FePc]Cl, 5 mol % AgSbF$_6$, 2 equiv. PhI(OPiv)$_2$, 4:1 PhMe/MeCN (0.5M), rt, 8 h.

(±)-4-vinyl-1,2,3-oxathiazinane 2,2-dioxide [22]

In both cases, product was purified via flash column chromatography on silica (35 mm fritted glass column, 120 mm SiO$_2$) using 3:1 hexanes/EtOAc and collected as a mixture of sulfamate ester and product and yields determined by $^1$H NMR. Additional column purification using 10% hexanes/CH$_2$Cl$_2$→CH$_2$Cl$_2$→2% Et$_2$O/CH$_2$Cl$_2$ affords pure product as a pale yellow oil. Ins./azir. ratios determined by $^1$H NMR of the crude reaction mixture.

FePc Conditions

Pent-4-en-1-yl sulfamate S15 (66.1 mg, 0.400 mmol, 1.0 equiv), [FePc]Cl (24.0 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), and 4:1 PhMe/MeCN (800 μL, 0.5M) were used.

Run 1: (13.5 mg, 0.083 mmol, 21%), (15.7 mg rsm, 0.095 mmol, 24%). Run 2: (14.2 mg, 0.087 mmol, 22%), (15.7 mg rsm, 0.095 mmol, 24%). Run 3: (15.5 mg, 0.095 mmol, 24%), (18.2 mg rsm, 0.110 mmol, 28%). Average: 22% yield±1.5, 25% rsm±2.3.

Mn($^t$BuPc) Conditions:

Pent-4-en-1-yl sulfamate S15 (66.1 mg, 0.400 mmol, 1.0 equiv), [Mn($^t$BuPc)]Cl (33.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used.

Run 1: (33.7 mg, 0.207 mmol, 52%), (12.6 mg rsm, 0.076 mmol, 19%). Run 2: (32.0 mg, 0.196 mmol, 49%), (10.6 mg rsm, 0.064 mmol, 16%). Run 3: (31.2 mg, 0.191 mmol, 48%), (8.1 mg rsm, 0.050 mmol, 12%). Average: 50% yield±1.9, 16% rsm±3.5.

$^1$H-NMR (500 MHz, CDCl$_3$) δ 5.82 (ddd, J=17.1, 10.6, 4.9 Hz, 1H), 5.36-5.25 (m, 2H), 4.81-4.72 (m, 1H), 4.57 (ddd, J=11.9, 4.6, 2.2 Hz, 1H), 4.38-4.30 (m, 1H), 4.19 (d, J=8.7 Hz, 1H), 1.94-1.80 (m, 2H); $^{13}$C-NMR (125 MHz, CDCl$_3$) δ 135.0, 117.5, 71.8, 57.0, 29.2. These data are in agreement with that previously reported in the literature (Harvey et al., *J. Am. Chem. Soc.* 2011, 133, 17207).

(±)-ethyl (E)-3-(2,2-dioxido-1,2,3-oxathiazinan-4-yl)acrylate [23]

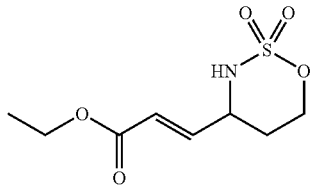

In both cases, reaction stirred at rt for 12 h. Product was purified via flash column chromatography on silica (35 mm fritted glass column, 120 mm SiO$_2$) using 20% acetone/hexanes→30% acetone/hexanes→40% acetone/hexanes.

FePc Conditions ethyl (E)-6-(sulfamoyloxy)hex-2-enoate S16 (94.9 mg, 0.400 mmol, 1.0 equiv), [FePc]Cl (24.0 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), and 4:1 PhMe/MeCN (800 μL, 0.5M) were used.

Run 1: (10.4 mg, 0.044 mmol, 11%), (55.1 mg rsm, 0.232 mmol, 58%). Run 2: (14.8 mg, 0.063 mmol, 16%), (48.4 mg rsm, 0.204 mmol, 51%). Run 3: (9.2 mg, 0.039 mmol, 10%), (66.4 mg rsm, 0.280 mmol, 70%). Average: 12% yield±2.6, 60% rsm±7.8.

Mn($^t$BuPc) Conditions:

Ethyl (E)-6-(sulfamoyloxy)hex-2-enoate S16 (94.9 mg, 0.400 mmol, 1.0 equiv), [Mn($^t$BuPc)]Cl (33.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used.

Run 1: (71.3 mg, 0.303 mmol, 76%), <10% rsm. Run 2: (71.6 mg, 0.305 mmol, 76%)<10% rsm. Run 3: (72.7 mg, 0.309 mmol, 77%)<10% rsm. Ave: 77% yield±0.5, <10% rsm.

Product was isolated as a yellow oil. $^1$H-NMR (500 MHz, CDCl$_3$) δ 6.84 (dd, J=15.9, 4.7 Hz, 1H), 6.04 (dd, J=15.6, 1.8 Hz, 1H), 4.82-4.77 (m, 1H), 4.61 (ddd, J=11.8, 3.4, 2.5 Hz, 1H), 4.56-4.50 (m, 1H), 4.23 (q, J=7.1 Hz, 2H), 4.15 (br. d, J=10.5 Hz, 1H), 1.94-1.89 (m, 2H), 1.30 (t, J=7.1 Hz, 3H); $^{13}$C-NMR (125 MHz, CDCl$_3$) δ 165.8, 143.1, 123.0, 71.6, 61.2, 55.8, 28.9, 14.3. These data are in agreement with that previously reported in the literature (Harvey et al., *J. Am. Chem. Soc.* 2011, 133, 17207).

(±)-Methyl (E)-(3-(2,2-dioxido-1,2,3-oxathiazinan-4-yl)allyl)(tosyl)carbamate [25]

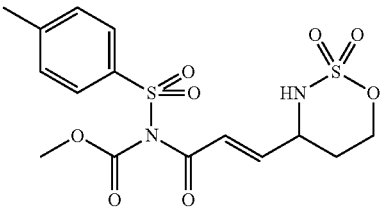 [SMILES: COC(=O)N(C(=O)/C=C/C1CCOS(=O)(=O)N1)S(=O)(=O)c1ccc(C)cc1]

(E)-6-((N-(methoxycarbonyl)-4-methylphenyl)sulfonamido)hex-4-en-1-yl sulfamate S17 (81.3 mg, 0.200 mmol, 1.0 equiv), [Mn($^t$BuPc)]Cl (16.6 mg, 0.020 mmol, 0.10 equiv), AgSbF$_6$ (6.9 mg, 0.020 mmol, 0.10 equiv), PhI(OPiv)$_2$ (325 mg, 0.800 mmol, 2.0 equiv), 100 mg crushed 4 Å MS, and 4:1 PhMe/MeCN (400 μL, 0.5M) were used. Reaction stirred at rt for 12 h. Product was purified via flash column chromatography on silica (35 mm fritted glass column, 120 mm SiO$_2$) using 2:1 hexane/EtOAc→1:1 hexanes/EtOAc. Pure product was isolated as a white solid.

Run 1: (58 mg, 0.144 mmol, 72%), <5% rsm. Run 2: (59 mg, 0.146 mmol, 73%), <5% rsm. Run 3: (60 mg, 0.149 mmol, 76%), <5% rsm. Average: 73% yield±1.5, <5% rsm.

$^1$H-NMR (500 MHz, CDCl$_3$) δ 7.81 (d, J=8.2 Hz, 2H), 7.33 (d, J=8.0 Hz, 2H), 5.86 (dt, J=15.6, 5.7 Hz, 1H), 5.76 (dd, J=15.6, 5.2 Hz, 1H), 4.76 (td, J=11.7, 11.0, 4.4 Hz, 1H), 4.60-4.56 (m, 1H), 4.46 (d, J=5.5 Hz, 2H), 4.38 (tt, J=10.2, 5.0 Hz, 1H), 3.96 (d, J=10.3 Hz, 1H), 3.71 (s, 3H), 2.45 (s, 3H), 1.95-1.82 (m, 2H); $^{13}$C-NMR (125 MHz, CDCl$_3$) δ 152.6, 145.1, 136.2, 130.9, 129.6, 128.5, 128.1, 71.8, 56.3, 54.2, 47.9, 29.4, 21.8; IR (film, cm$^{-1}$) 3255, 2960, 1736, 1596, 1443, 1359, 1242, 1170, 1089, 1011, 973, 937, 910, 866, 771, 736, 673, 579, 546; HRMS (ESI) m/z calculated for C$_{15}$H$_{21}$N$_2$O$_7$S2 [M+H]$^+$: 405.0790, found 405.0786.

(±)-hexahydrobenzo[d][1,2,3]oxathiazine 2,2-dioxide [26]

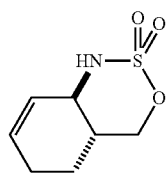

(±)-cyclohex-3-en-1-ylmethyl sulfamate S18 (76.5 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used. Product was purified via flash column chromatography on silica (35 mm fritted glass column, 120 mm SiO$_2$) using 5:1 hexanes/EtOAc. Pure product was isolated as a white solid.

Run 1: (50.8 mg, 0.268 mmol, 67%), <5% rsm. Run 2: (54.4 mg, 0.287 mmol, 72%), <5% rsm. Run 3: (51.5 mg, 0.272 mmol, 68%), <5% rsm. Average: 69% yield±2.2, <5% rsm.

$^1$H-NMR (500 MHz, CDCl$_3$) δ 6.06-6.02 (m, 1H), 5.75-5.72 (m, 1H), 4.96 (dd, J=11.8, 3.1 Hz, 1H), 4.35 (dd, J=11.8, 1.4 Hz, 1H), 4.32-4.28 (m, 1H), 4.05 (br. d, J=11.2 Hz, 1H), 2.31-2.12 (m, 2H), 1.92 (tdd, J=14.1, 11.2, 5.9 Hz, 1H), 1.72-1.67 (m, 2H); $^{13}$C-NMR (125 MHz, CDCl$_3$) δ 133.6, 123.7, 76.8, 52.4, 31.1, 25.0, 20.0. These data are in agreement with that previously reported in the literature (Harvey et al., J. Am. Chem. Soc. 2011, 133, 17207).

4-((1R,5S)-6,6-dimethylbicyclo[3.1.1]hept-2-en-2-yl)-1,2,3-oxathiazolidine 2,2-dioxide [27]

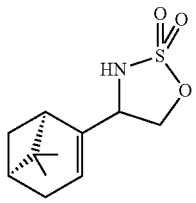 [SMILES: CC1(C)[C@H]2CC=C(C3COS(=O)(=O)N3)[C@@H]1C2]

(−)-2-((1R,5S)-6,6-dimethylbicyclo[3.1.1]hept-2-en-2-yl)ethyl sulfamate S19 (98.1 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used. Product was purified via flash column chromatography on silica (35 mm fritted glass column, 120 mm SiO$_2$) using 5:1 hexanes/EtOAc. Pure product was isolated as a white solid and a 2:1 mixture of inseparable diastereomers.

Run 1: (57.3 mg, 0.235 mmol, 59%), <5% rsm. Run 2: (59.7 mg, 0.245 mmol, 61%), <5% rsm. Run 3: (58.4 mg, 0.240 mmol, 60%), <5% rsm. Ave: 60% yield±1.3, <5% rsm.

$^1$H-NMR (500 MHz, CDCl$_3$) δ 5.72-5.70 (m, 1H-D$_{maj}$+1H-D$_{min}$), 4.58-4.46 (m, 2H-D$_{maj}$+2H-D$_{min}$), 4.32 (s, 1H-D$_{maj}$+1H-D$_{min}$), 4.20 (t, J=8.4 Hz, 1H-D$_{min}$), 4.16 (t, J=8.1 Hz, 1H-D$_{maj}$), 2.48 (dq, J=8.9, 5.7 Hz, 1H-D$_{maj}$+1H-D$_{min}$), 2.40-2.22 (m, 3H-D$_{maj}$+3H-D$_{min}$), 2.18-2.12 (m, 1H-D$_{maj}$+1H-D$_{min}$), 1.32 (s, 3H-D$_{maj}$+3H-D$_{min}$), 1.16 (d, J=8.9 Hz, 1H-D$_{maj}$), 1.13 (d, J=8.9 Hz, 1H-D$_{min}$), 0.83 (s, 3H-D$_{min}$), 0.79 (s, 3H-D$_{maj}$); $^{13}$C-NMR (125 MHz, CDCl$_3$) δ 141.2, 141.1, 124.7, 124.1, 72.5, 72.2, 60.1, 60.0, 41.6, 41.4, 40.6, 40.6, 38.1, 31.6, 31.4, 31.4, 26.0, 25.9, 21.3, 21.2; IR (film, cm$^{-1}$) 3281, 2918, 2832, 1721, 1469, 1384, 1347, 1287, 1064, 973, 922, 886, 796, 773, 658, 637, 513, 487; HRMS (ESI) m/z calculated for C$_{11}$H$_{17}$NO$_3$SNa [M+Na]$^+$: 266.0827, found 266.0827.

(±)-(E)-4-styryl-1,2,3-oxathiazolidine 2,2-dioxide [28]

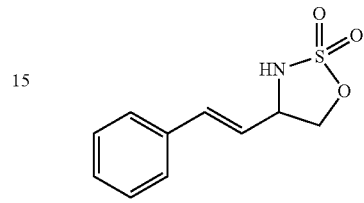

(E)-4-phenylbut-3-en-1-yl sulfamate S20 (90.0 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used. Product was purified via flash column chromatography on silica (35 mm fritted glass column, 150 mm SiO$_2$) using 3:1 hexanes/EtOAc. Pure product was isolated as a white solid. Insertion to aziridination ratio was determined from $^1$H NMR of the crude mixture.

Run 1: (57.7 mg, 0.256 mmol, 64%), <5% rsm. Run 2: (55.1 mg, 0.245 mmol, 61%), <5% rsm. Run 3: (54.6 mg, 0.242 mmol, 61%), <5% rsm. Ave: 62% yield±1.7, <5% rsm.

$^1$H-NMR (500 MHz, CDCl$_3$) δ 7.42-7.30 (m, 5H), 6.75 (d, J=15.8 Hz, 1H), 6.13 (dd, J=15.8, 7.8 Hz, 1H), 4.77-4.64 (m, 2H), 4.46 (br. d, J=6.6 Hz, 1H), 4.36 (t, J=8.0 Hz, 1H); $^{13}$C-NMR (125 MHz, CDCl$_3$) δ 136.7, 135.0, 129.2, 129.0, 127.0, 122.1, 74.0, 58.7. These data are in agreement with that previously reported in the literature (Zalatan D. N.; Du Bois, J. J. Am. Chem. Soc. 2008, 130, 9220).

TABLE 4

Propargylic and ethereal C—H bond substrate scope.

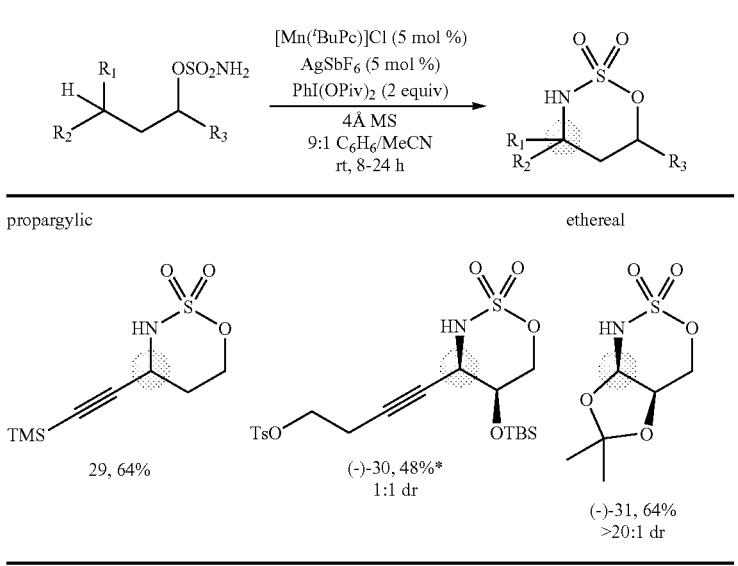

Isolated yields are average of three runs. *Used 10 mol % cat.

(±)-4-((trimethylsilyl)ethynyl)-1,2,3-oxathiazinane 2,2-dioxide [29]

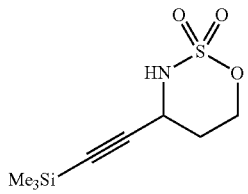 [SMILES: C[Si](C)(C)C#CC1CCOS(=O)(=O)N1]

5-(trimethylsilyl)pent-4-yn-1-yl sulfamate S21 (94.13 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used. Product was purified via flash column chromatography on silica (35 mm fritted glass column, 150 mm SiO$_2$) using 4:1 hexanes/EtOAc. Pure product was isolated as a white solid.

Run 1: (60.0 mg, 0.257 mmol, 64%), <5% rsm. Run 2: (58.2 mg, 0.249 mmol, 62%), <5% rsm. Run 3: (60.0 mg, 0.257 mmol, 64%), <5% rsm. Ave: 64% yield±1.1, <5% rsm.

$^1$H-NMR (500 MHz, CDCl$_3$) δ 4.70 (ddd, J=12.7, 11.8, 2.5 Hz, 1H), 4.58-4.51 (m, 2H), 4.30 (d, J=10.1 Hz, 1H), 2.10 (dddd, J=14.8, 12.6, 11.6, 4.9 Hz, 1H), 2.01-1.97 (m, 1H), 0.17 (s, 9H); $^{13}$C-NMR (125 MHz, CDCl$_3$) δ 100.1, 91.6, 71.4, 48.1, 30.9, −0.3; IR (film, cm$^{-1}$) 3233, 2962, 2901, 2193, 1717, 1463, 1430, 1358, 1254, 1190, 1170, 1077, 1061, 997, 941, 922, 876, 780, 757, 710, 665; HRMS (ESI) m/z calculated for C$_8$H$_{16}$NO$_3$SiS [M+H]$^+$: 234.0620, found 234.0623.

(−)-4-((4S,5S)-5-((tert-butyldimethylsilyl)oxy)-2,2-dioxido-1,2,3-oxathiazinan-4-yl)but-3-yn-1-yl 4-methylbenzenesulfonate [30]

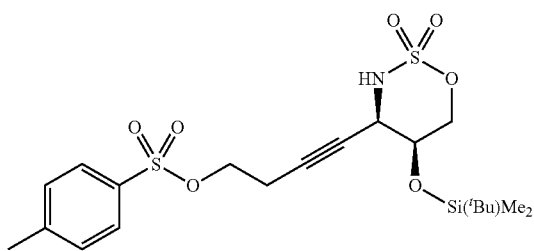

(S)-2-((tert-butyldimethylsilyl)oxy)-7-(tosyloxy)hept-4-yn-1-yl sulfamate S22 (98.3 mg, 0.200 mmol, 1.0 equiv), [Mn($^t$BuPc)]Cl (16.6 mg, 0.020 mmol, 0.10 equiv), AgSbF$_6$ (6.9 mg, 0.020 mmol, 0.10 equiv), PhI(OPiv)$_2$ (325 mg, 0.800 mmol, 2.0 equiv), 50 mg crushed 4 Å MS, and 9:1 C$_6$H$_6$/MeCN (800 μL, 0.5M) were used. Reaction stirred at rt for 12 hours. Product was purified via flash column chromatography on silica (75 mL SiO$_2$) using 5:1 hexanes/EtOAc→4:1 hexanes/EtOAc. Product was isolated as a clear oil as a mixture of diastereomers. Additional column purification using a gradient of 10% hexanes/CH$_2$Cl$_2$→CH$_2$Cl$_2$→1% Et$_2$O/CH$_2$Cl$_2$ allowed separation of diastereomers.

Run 1: (45.7 mg, 0.093 mmol, 47%), <5% rsm. Run 2: (47.9 mg, 0.098 mmol, 49%), <5% rsm. Run 3: (46.5 mg, 0.095 mmol, 48%), <5% rsm. Average: 48% yield±1, <5% rsm.

Syn Diastereomer:
$^1$H-NMR (500 MHz, CDCl$_3$) δ 7.80 (d, J=8.3 Hz, 2H), 7.38 (d, J=7.9 Hz, 2H), 4.65-4.54 (m, 3H), 4.28 (dd, J=12.3, 1.9 Hz, 1H), 4.07 (td, J=6.9, 1.0 Hz, 2H), 3.67 (dt, J=2.1, 1.0 Hz, 1H), 2.58 (td, J=6.8, 1.7 Hz, 2H), 2.47 (s, 3H), 0.92 (s, 9H), 0.14 (s, 3H), 0.12 (s, 3H); $^{13}$C-NMR (125 MHz, CDCl$_3$) δ 145.4, 132.8, 130.1, 128.1, 81.4, 76.9, 75.9, 67.1, 64.0, 53.4, 25.7, 21.8, 19.8, 18.2, −4.6, −4.7; IR (film, cm$^{-1}$) 3257, 2929, 2857, 1422, 1364, 1257, 1176, 1137, 1074, 1028, 986, 904, 864, 838, 776, 664, 553, 480, 459; [α]$_D^{25}$=−18.2° (c=1.28, CHCl$_3$); HRMS (ESI) m/z calculated for C$_{20}$H$_{32}$NO$_7$S$_2$Si [M+H]$^+$: 490.1389, found 490.1386.

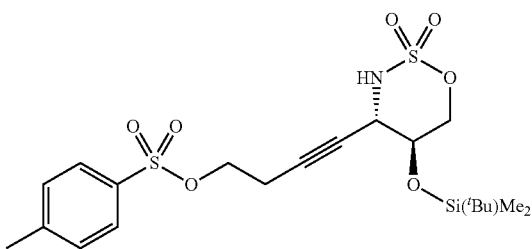

Anti Diastereomer:
$^1$H-NMR (500 MHz, CDCl$_3$) δ 7.80 (d, J=8.3 Hz, 2H), 7.37 (d, J=8.6 Hz, 2H), 4.55 (d, J=8.7 Hz, 1H), 4.45 (dd, J=11.7, 4.0 Hz, 1H), 4.31 (dd, J=11.6, 8.2 Hz, 1H), 4.22 (ddt, J=9.6, 7.8, 2.2 Hz, 1H), 4.11 (t, J=6.6 Hz, 2H), 3.79 (td, J=7.9, 4.0 Hz, 1H), 2.61 (td, J=6.7, 2.0 Hz, 2H), 2.47 (s, 3H), 0.89 (s, 9H), 0.12 (s, 3H), 0.12 (s, 3H); $^{13}$C-NMR (125 MHz, CDCl$_3$) δ 145.4, 132.9, 130.1, 128.0, 82.4, 77.3, 73.1, 67.3, 66.4, 53.3, 25.6, 21.8, 20.0, 18.1, −4.5, −4.6; IR (film, cm$^{-1}$) 3257, 2929, 2857, 1719, 1598, 1432, 1369, 1259, 1190, 1133, 1046, 904, 840, 782, 664, 618, 555, 492; [α]$_D^{25}$=−38.1° (c=0.54, CHCl$_3$); HRMS (ESI) m/z calculated for C$_{20}$H$_{32}$NO$_7$S2Si [M+H]$^+$: 490.1389, found 490.1388.

(−)-(4R,7R)-6,6-dimethyltetrahydro-[1,3]dioxolo[4,5-d][1,2,3]oxathiazine 2,2-dioxide [31]

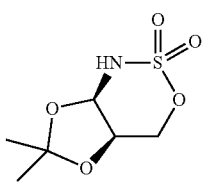

(−)-(S)-(2,2-dimethyl-1,3-dioxolan-4-yl)methyl sulfamate S23 (84.49 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used. Product was purified via flash column chromatography on silica (35 mm fritted glass column, 120 mm SiO$_2$) using 3:1 hexanes/EtOAc→2:1 hexanes/EtOAc. Pure product was isolated as a pale yellow solid.

Run 1: (55.5 mg, 0.265 mmol, 66%), <5% rsm. Run 2: (52.6 mg, 0.251 mmol, 63%), <5% rsm. Run 3: (52.9 mg, 0.253 mmol, 63%), <5% rsm. Ave: 64% yield±1.4, <5% rsm.
$^1$H-NMR (500 MHz, CD$_3$OD) δ 5.41 (d, J=5.1 Hz, 1H), 4.59-4.58 (m, 2H), 4.30 (dt, J=5.2, 1.6 Hz, 1H), 1.54 (s, 3H), 1.34 (s, 3H); $^{13}$C-NMR (125 MHz, CD$_3$OD) δ 111.5, 85.6, 71.7, 71.5, 26.9, 25.6. [α]$_D^{25}$=−36.7° (c=0.71, acetone). These data are in agreement with that previously reported in the literature (Fleming et al., *J. Am. Chem. Soc.* 2007, 129, 9964).
TABLE 5
Benzylic C—H bond substrate scope.
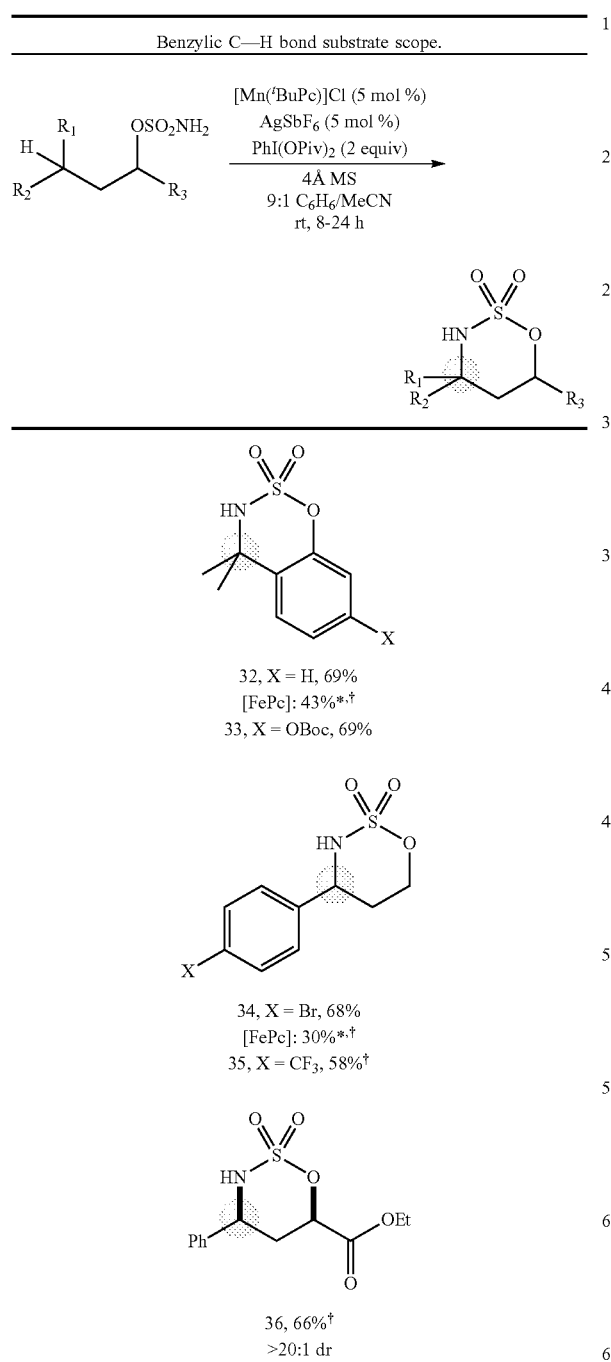
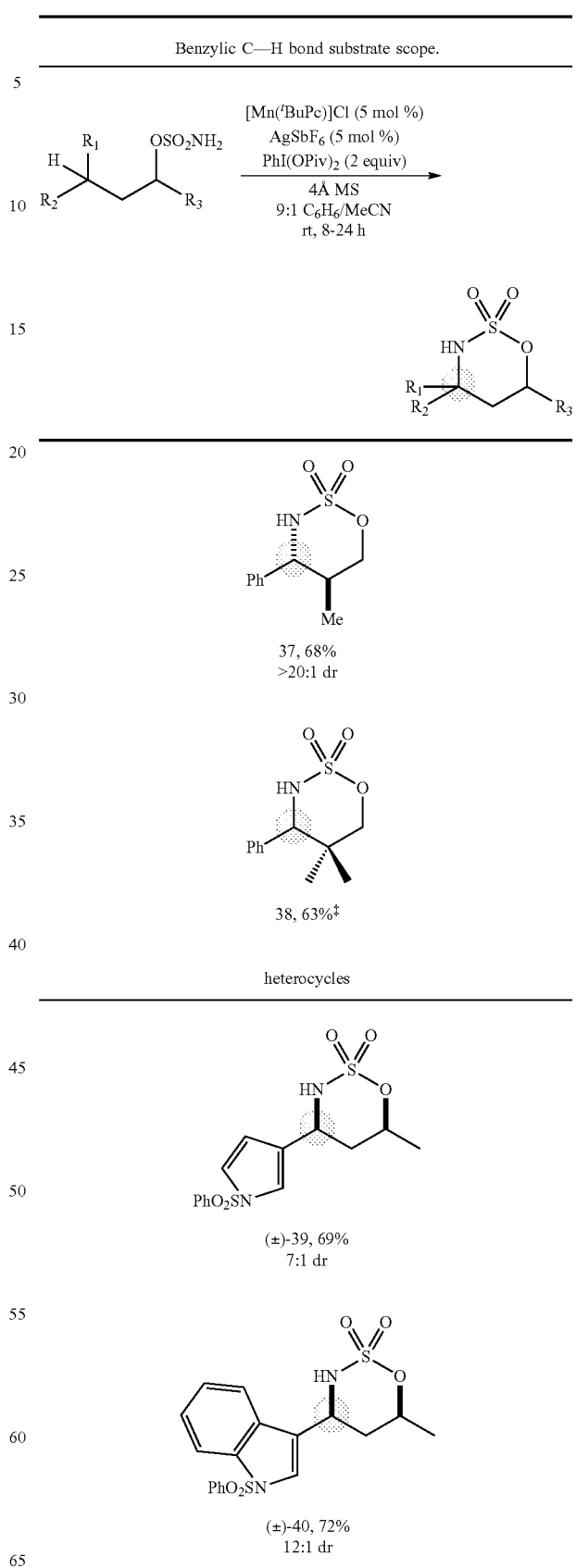

TABLE 5-continued

Benzylic C—H bond substrate scope.

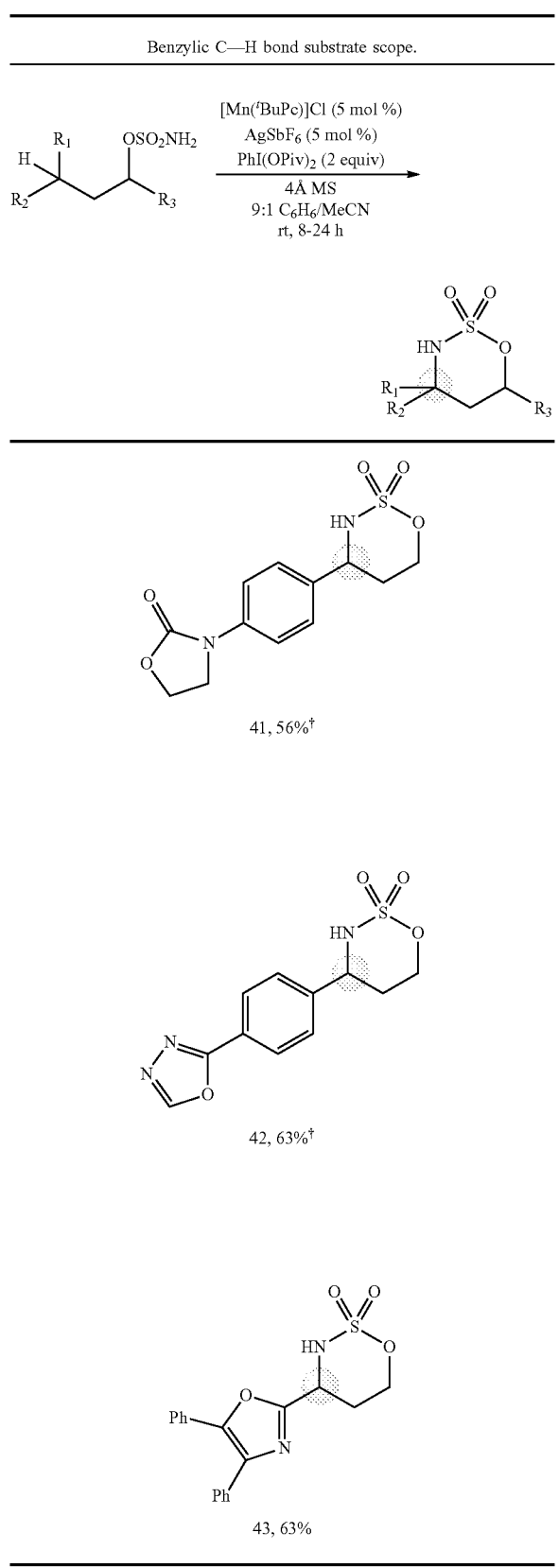

41, 56%†

42, 63%†

43, 63%

Isolated yields are average of three runs. *Conditions: 5 mol % [FePc]Cl, 5 mol % AgSbF₆, 2 equiv. PhI(OPiv)₂, 4:1 PhMe/MeCN (0.5M), rt, 8 h. †Used 10 mol % catalyst. ‡10% of 1° C—H amination also isolated.

4,4-dimethyl-3,4-dihydrobenzo[e][1,2,3]oxathiazine 2,2-dioxide [32]

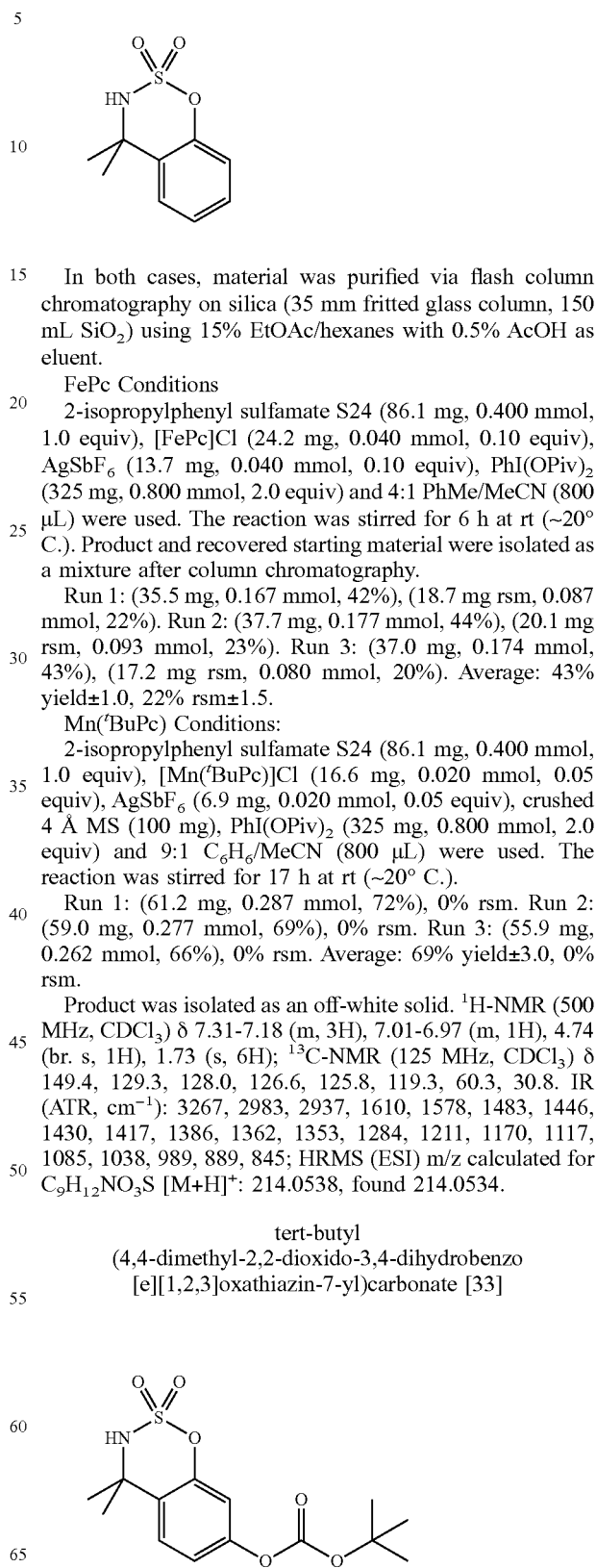

In both cases, material was purified via flash column chromatography on silica (35 mm fritted glass column, 150 mL $SiO_2$) using 15% EtOAc/hexanes with 0.5% AcOH as eluent.

FePc Conditions 2-isopropylphenyl sulfamate S24 (86.1 mg, 0.400 mmol, 1.0 equiv), [FePc]Cl (24.2 mg, 0.040 mmol, 0.10 equiv), AgSbF₆ (13.7 mg, 0.040 mmol, 0.10 equiv), PhI(OPiv)₂ (325 mg, 0.800 mmol, 2.0 equiv) and 4:1 PhMe/MeCN (800 µL) were used. The reaction was stirred for 6 h at rt (~20° C.). Product and recovered starting material were isolated as a mixture after column chromatography.

Run 1: (35.5 mg, 0.167 mmol, 42%), (18.7 mg rsm, 0.087 mmol, 22%). Run 2: (37.7 mg, 0.177 mmol, 44%), (20.1 mg rsm, 0.093 mmol, 23%). Run 3: (37.0 mg, 0.174 mmol, 43%), (17.2 mg rsm, 0.080 mmol, 20%). Average: 43% yield±1.0, 22% rsm±1.5.

Mn(ᵗBuPc) Conditions:

2-isopropylphenyl sulfamate S24 (86.1 mg, 0.400 mmol, 1.0 equiv), [Mn(ᵗBuPc)]Cl (16.6 mg, 0.020 mmol, 0.05 equiv), AgSbF₆ (6.9 mg, 0.020 mmol, 0.05 equiv), crushed 4 Å MS (100 mg), PhI(OPiv)₂ (325 mg, 0.800 mmol, 2.0 equiv) and 9:1 $C_6H_6$/MeCN (800 µL) were used. The reaction was stirred for 17 h at rt (~20° C.).

Run 1: (61.2 mg, 0.287 mmol, 72%), 0% rsm. Run 2: (59.0 mg, 0.277 mmol, 69%), 0% rsm. Run 3: (55.9 mg, 0.262 mmol, 66%), 0% rsm. Average: 69% yield±3.0, 0% rsm.

Product was isolated as an off-white solid. $^1$H-NMR (500 MHz, $CDCl_3$) δ 7.31-7.18 (m, 3H), 7.01-6.97 (m, 1H), 4.74 (br. s, 1H), 1.73 (s, 6H); $^{13}$C-NMR (125 MHz, $CDCl_3$) δ 149.4, 129.3, 128.0, 126.6, 125.8, 119.3, 60.3, 30.8. IR (ATR, $cm^{-1}$): 3267, 2983, 2937, 1610, 1578, 1483, 1446, 1430, 1417, 1386, 1362, 1353, 1284, 1211, 1170, 1117, 1085, 1038, 989, 889, 845; HRMS (ESI) m/z calculated for $C_9H_{12}NO_3S$ [M+H]⁺: 214.0538, found 214.0534.

tert-butyl (4,4-dimethyl-2,2-dioxido-3,4-dihydrobenzo[e][1,2,3]oxathiazin-7-yl)carbonate [33]

5-((tert-butoxycarbonyl)oxy)-2-isopropylphenyl sulfamate S25 (99.4 mg, 0.300 mmol, 1.0 equiv), [Mn(tBuPc)]Cl (12.4 mg, 0.015 mmol, 0.05 equiv), AgSbF$_6$ (5.2 mg, 0.015 mmol, 0.05 equiv), crushed 4 Å MS (75 mg), PhI(OPiv)$_2$ (244 mg, 0.600 mmol, 2.0 equiv) and 9:1 C$_6$H$_6$/MeCN (600 μL) were used. The reaction was stirred for 17 h at rt (~20° C.). Flash column chromatography on silica (35 mm fritted glass column, 150 mm SiO$_2$) using 15% EtOAc/hexanes→20% EtOAc/hexanes with 0.5% AcOH as eluent afforded product as white solid.

Run 1: (69.1 mg, 0.210 mmol, 70%), <5% rsm. Run 2: (68.7 mg, 0.209 mmol, 70%), <5% rsm. Run 3: (65.9 mg, 0.200 mmol, 67%), <5% rsm. Average: 69% yield±1.7, <5% rsm.

$^1$H-NMR (500 MHz, CDCl$_3$) δ 7.22 (d, J=8.5 Hz, 1H), 7.05 (dd, J=8.5, 2.5 Hz, 1H), 6.90 (t, J=1.8 Hz, 1H), 4.64 (br. s, 1H), 1.71 (s, 6H), 1.56 (s, 9H); $^{13}$C-NMR (125 MHz, CDCl$_3$) δ 151.3, 150.9, 149.6, 127.2, 125.4, 118.9, 112.4, 84.6, 60.1, 30.8, 27.7; IR (ATR, cm$^{-1}$): 3237, 2984, 1734, 1498, 1435, 1417, 1392, 1365, 1288, 1247, 1205, 1175, 1139, 1119, 1090, 961, 887, 856, 811; HRMS (ESI) m/z calculated for C$_{14}$H$_{19}$NO$_6$SNa [M+Na]$^+$: 352.0831, found 352.0831.

(±)-4-(4-bromophenyl)-1,2,3-oxathiazinane 2,2-dioxide [34]

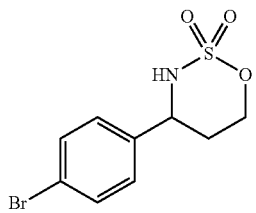 [SMILES: O=S1(=O)NC(c2ccc(Br)cc2)CCO1]

In both cases, the reaction was stirred for 12 h at rt (~20° C.). Crude material was purified via flash column chromatography on silica (35 mm fritted glass column, 150 mm SiO$_2$) using 25% EtOAc/hexanes→30% EtOAc/hexanes with 0.5% AcOH as eluent.

FePc Conditions:
2,3-(4-bromophenyl)propyl sulfamate S26 (118.0 mg, 0.400 mmol, 1.0 equiv), [FePc]Cl (12.1 mg, 0.02 mmol, 0.05 equiv), AgSbF$_6$ (6.9 mg, 0.020 mmol, 0.05 equiv), PhI(OPiv)$_2$ (325 mg, 0.800 mmol, 2.0 equiv) and 4:1 PhMe/MeCN (800 μL) were used. Product and recovered starting material were isolated as a mixture.

Run 1: (30.4 mg, 0.104 mmol, 26%), (48.7 mg rsm, 0.166 mmol, 41%). Run 2: (39.2 mg, 0.134 mmol, 34%), (51.9 mg rsm, 0.176 mmol, 44%). Run 3: (36.1 mg, 0.123 mmol, 31%), (50.5 mg rsm, 0.172 mmol, 43%). Average: 30% yield±4.0, 43% rsm±1.5.

Mn(tBuPc) Conditions:
3-(4-bromophenyl)propyl sulfamate S26 (118.0 mg, 0.400 mmol, 1.0 equiv), [Mn(tBuPc)]Cl (16.6 mg, 0.020 mmol, 0.05 equiv), AgSbF$_6$ (6.9 mg, 0.020 mmol, 0.05 equiv), crushed 4 Å MS (100 mg), PhI(OPiv)$_2$ (325 mg, 0.800 mmol, 2.0 equiv) and 9:1 C$_6$H$_6$/MeCN (800 μL) were used.

Run 1: (80.1 mg, 0.274 mmol, 69%), 0% rsm. Run 2: (77.2 mg, 0.264 mmol, 66%), 0% rsm. Run 3: (79.1 mg, 0.271 mmol, 68%), 0% rsm. Average: 68% yield±1.5, 0% rsm.

Product was isolated as a white solid. $^1$H-NMR (500 MHz, acetone-d$_6$) δ 7.59 (d, J=8.1 Hz, 2H), 7.47 (d, J=8.1 Hz, 2H), 6.40 (br. d, J=9.9 Hz, 1H), 4.92-4.83 (m, 1H), 4.79 (td, J=12.0, 2.5 Hz, 1H), 4.69 (ddd, J=12.0, 4.8, 1.8 Hz, 1H), 2.30-2.18 (m, 1H), 2.14 (m, 1H); $^{13}$C-NMR (500 MHz, acetone-d$_6$) δ 139.5, 132.6, 129.6, 122.4, 72.7, 59.3, 30.8; IR (ATR, cm$^{-1}$): 3258, 2961, 1490, 1406, 1434, 1420, 1297, 1235, 1193, 1184, 1174, 1063, 1018, 1007, 937, 904, 868, 833, 806; HRMS (ESI) m/z calculated for C$_9$H$_9$NO$_3$SBr [M−H]$^-$: 289.9487, found 289.9489.

(±)-4-(4-(trifluoromethyl)phenyl)-1,2,3-oxathiazinane 2,2-dioxide [35]

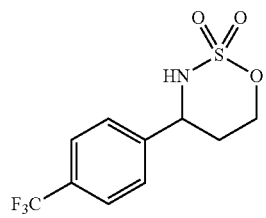 [SMILES: O=S1(=O)NC(c2ccc(C(F)(F)F)cc2)CCO1]

3-(4-trifluoromethyl)propyl sulfamate S27 (113.3 mg, 0.400 mmol, 1.0 equiv), [Mn(tBuPc)]Cl (33.1 mg, 0.040 mmol, 0.10 equiv), AgSbF$_6$ (13.7 mg, 0.040 mmol, 0.10 equiv), crushed 4 Å MS (100 mg), PhI(OPiv)$_2$ (325 mg, 0.800 mmol, 2.0 equiv) and 9:1 C$_6$H$_6$/MeCN (800 μL) were used. The reaction was stirred for 12 h at rt (~20° C.). Flash column chromatography on silica (35 mm fritted glass column, 150 mL SiO$_2$) using 25% EtOAc/hexanes→35% EtOAc/hexanes with 0.5% AcOH as eluent afforded product as white solid.

Run 1: (67.3 mg, 0.239 mmol, 60%), <5% rsm. Run 2: (64.2 mg, 0.228 mmol, 57%), <5% rsm. Run 3: (65.4 mg, 0.233 mmol, 58%), <5% rsm. Average: 58% yield±1.5, <5% rsm.

$^1$H-NMR (500 MHz, Acetonitrile-d$_3$) δ 7.73 (d, J=8.2 Hz, 2H), 7.60 (d, J=8.1 Hz, 2H), 5.60 (br. d, J=10.0 Hz, 1H), 4.91 (ddd, J=12.6, 10.1, 3.0 Hz, 1H), 4.77 (td, J=12.1, 2.5 Hz, 1H), 4.67 (ddd, J=11.6, 5.0, 1.8 Hz, 1H), 2.21-2.14 (m, 1H), 2.09-2.05 (m, 1H); $^{13}$C-NMR (125 MHz, Acetonitrile-d$_3$) δ 144.0, 130.6 (q, J=32.3 Hz), 128.3, 126.5 (q, J=3.9 Hz), 125.2 (q, J=271.3 Hz), 73.3, 59.3, 30.3; $^{19}$F-NMR (470 MHz, Acetonitrile-d$_3$) δ −62.82; IR (ATR, cm$^{-1}$): 3232, 1623, 1444, 1412, 1364, 1350, 1326, 1249, 1187, 1159, 1115, 1067, 1018, 946, 915, 870, 845, 816; HRMS (EI) m/z calculated for C$_{10}$H$_{10}$NO$_3$SF$_3$ [M+]: 281.03335, found 281.03377.

(±)-ethyl-4-phenyl-1,2,3-oxathiazinane-6-carboxylate 2,2-dioxide [36]

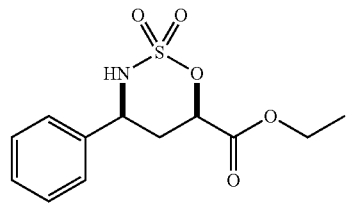 [SMILES: CCOC(=O)[C@H]1C[C@@H](c2ccccc2)NS(=O)(=O)O1]

(±)-ethyl 4-phenyl-2-(sulfamoyloxy)butanoate S28 (114.9 mg, 0.400 mmol, 1.0 equiv), [Mn($^t$BuPc)]Cl (33.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used. Product was purified via flash column chromatography on silica (35 mm fritted glass column, 150 mm SiO$_2$) using 4:1 hexanes/EtOAc. Pure product was isolated as a white solid.

Run 1: (74.9 mg, 0.263 mmol, 66%), <5% rsm. Run 2: (74.0 mg, 0.259 mmol, 65%), <5% rsm. Run 3: (70.1 mg, 0.246 mmol, 61%), <5% rsm. Ave: 64% yield±2.2, <5% rsm.

$^1$H-NMR (500 MHz, CDCl$_3$) δ 7.44-7.37 (m, 5H), 5.33 (dd, J=12.5, 2.5 Hz, 1H), 4.88 (ddd, J=12.5, 10.0, 3.0 Hz, 1H), 4.69 (br. d, J=9.5 Hz, 1H), 4.29 (q, J=7.0 Hz, 2H), 2.41 (dt, J=14.0, 3.0 Hz, 1H), 2.29 (dt, J=14.5, 12.0 Hz, 1H), 1.31 (t, J=7.0 Hz, 3H); $^{13}$C-NMR (125 MHz, CDCl$_3$) δ 167.4, 137.5, 129.3, 129.2, 126.7, 78.8, 62.9, 58.5, 32.4, 14.1. These data are in agreement with that previously reported in the literature (Espino et al., *J. Am. Chem. Soc.* 2001, 123, 6935).

(±)-trans-5-methyl-4-phenyl-1,2,3-oxathiazinane 2,2-dioxide [37]

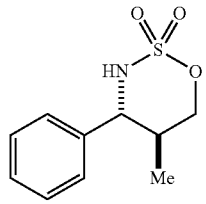 [SMILES: C[C@@H]1COS(=O)(=O)N[C@H]1c1ccccc1]

(±)-2-methyl-3-phenylpropyl sulfamate S29 (91.7 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), crushed 4 Å MS (100 mg), PhI(OPiv)$_2$ (325 mg, 0.800 mmol, 2.0 equiv) and 9:1 C$_6$H$_6$/MeCN (800 μL) were used. The reaction was stirred for 8 h at rt (~20° C.). Flash column chromatography on silica (35 mm fritted glass column, 150 mm SiO$_2$) using 20% EtOAc/hexanes→30% EtOAc/hexanes with 0.5% AcOH as eluent gave product as white solid as a single diastereomer.

Run 1: (64.8 mg, 0.285 mmol, 71%), 0% rsm. Run 2: (59.1 mg, 0.260 mmol, 65%), 0% rsm. Run 3: (61.5 mg, 0.271 mmol, 68%), 0% rsm. Average: 68% yield±3.0, 0% rsm.

$^1$H-NMR (500 MHz, CDCl$_3$) δ 7.43-7.34 (m, 3H), 7.34-7.29 (m, 2H), 4.70 (d, J=8.9 Hz, 1H), 4.52-4.44 (m, 2H), 4.34 (dd, J=11.0, 9.0 Hz, 1H), 2.42-2.31 (m, 1H), 0.69 (d, J=6.7 Hz, 3H); $^{13}$C-NMR (125 MHz, CDCl$_3$) δ 137.1, 129.3, 129.2, 127.4, 76.7, 65.6, 34.0, 12.0; IR (ATR, cm$^{-1}$): 3260, 2983, 2940, 1459, 1424, 1354, 1193, 1175, 1088, 1072, 1016, 968, 923, 887; HRMS (ESI) m/z calculated for C$_{10}$H$_{14}$NO$_3$S [M+H]$^+$: 228.0694, found 228.0691.

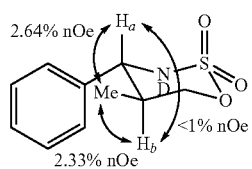

Stereochemistry Assignment: To avoid potential proton peak overlap with the exchangeable NH proton, D$_2$O was added into NMR sample to saturate the NH peak. $^1$H-NMR (500 MHz, CDCl$_3$, D$_2$O) δ 7.43-7.34 (m, 3H), 7.34-7.29 (m, 2H), 4.52-4.44 (m, 2H), 4.34 (d, J=11.0 Hz, 1H), 2.42-2.31 (m, 1H), 0.69 (dd, J=6.9, 1.3 Hz, 3H). Notably the coupling pattern of benzylic proton H$_a$ (4.34 ppm) changed from dd (J=11.0, 9.0 Hz) to d (J=11.0 Hz).

A series of 1D nOe difference experiments were conducted to assign the relative stereochemistry of the structure. When H$_a$ was irradiated, 2.64% nOe was observed on corresponding methyl peak while only 0.94% nOe was observed on H$_b$ peak. Similarly, when H$_b$ was irradiated, 2.33% nOe of methyl was observed while H$_a$ only gave 0.09% nOe. These results indicate H$_a$ and H$_b$ are in an anti-configuration.

(±)-5,5-dimethyl-4-phenyl-1,2,3-oxathiazinane 2,2-dioxide [38]

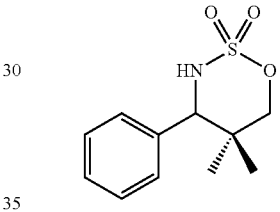

2,2-dimethyl-3-phenylpropyl sulfamate S30 (97.3 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), crushed 4 Å MS (100 mg), PhI(OPiv)$_2$ (325 mg, 0.800 mmol, 2.0 equiv) and 9:1 C$_6$H$_6$/MeCN (800 μL, 0.5M) were used. The reaction was stirred for 17 h at rt (~20° C.). Flash column chromatography on silica (35 mm fritted glass column, 150 mL SiO$_2$) using 15% EtOAc/hexanes→20% EtOAc/hexanes with 0.5% AcOH as eluent gave product as white solid. Minor 1° C—H amination product S37 was also isolated separately as white solid.

Run 1: (59.7 mg benzylic, 0.247 mmol, 62%), (8.8 mg 1°, 0.036 mmol, 9%), 0% rsm.

Run 2: (58.8 mg benzylic, 0244 mmol, 61%), (9.3 mg 1°, 0.039 mmol, 10%), 0% rsm. Run 3: (63.3 mg benzylic, 0.262 mmol, 66%), (10.7 mg 1°, 0.045 mmol, 11%), 0% rsm. Average: 63% benzylic±2.6, 10% 1°±1.0, 0% rsm.

$^1$H-NMR (500 MHz, CDCl$_3$) δ 7.41-7.33 (m, 3H), 7.24-7.17 (m, 2H), 5.11 (d, J=7.9 Hz, 1H), 4.62 (d, J=7.4 Hz, 1H), 4.60 (d, J=3.9 Hz, 1H), 4.10 (d, J=11.4 Hz, 1H), 1.09 (s, 3H), 0.80 (s, 3H); $^{13}$C-NMR (125 MHz, CDCl$_3$) δ 135.1, 128.8, 128.5, 128.0, 82.5, 67.3, 34.0, 21.5, 17.4; IR (ATR, cm$^{-1}$): 3272, 2974, 1711, 1469, 1459, 1428, 1365, 1349, 1188, 1047, 1013. 960, 908, 851, 803; HRMS (ESI) m/z calculated for C$_{11}$H$_{16}$NO$_3$S [M+H]$^+$: 242.0851, found 242.0847.

(±)-5-benzyl-5-methyl-1,2,3-oxathiazinane 2,2-dioxide [S37]

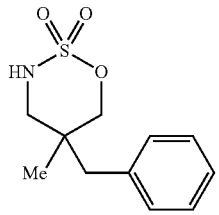 [SMILES: CC1(Cc2ccccc2)CNS(=O)(=O)OC1]

¹H-NMR (500 MHz, CDCl₃) δ 7.36-7.27 (m, 3H), 7.17-7.11 (m, 2H), 4.76 (t, J=7.5 Hz, 1H), 4.35 (d, J=11.8 Hz, 1H), 4.23 (d, J=11.6 Hz, 1H), 3.39-3.28 (m, 2H), 2.82 (d, J=13.4 Hz, 1H), 2.60 (d, J=13.4 Hz, 1H), 0.94 (s, 3H); ¹³C-NMR (125 MHz, CDCl₃) δ 135.4, 130.5, 128.7, 127.2, 79.7, 54.1, 40.6, 32.5, 19.1; IR (ATR, cm⁻¹): 3280, 2925, 1496, 1446, 1418, 1391, 1356, 1337, 1174, 1155, 1028, 951, 931, 854; HRMS (ESI) m/z calculated for $C_{11}H_{16}NO_3S$ [M+H]⁺: 242.0851, found 242.0845.

(±)-6-methyl-4-(1-(phenylsulfonyl)-1H-pyrrol-3-yl)-1,2,3-oxathiazinane 2,2-dioxide [39]

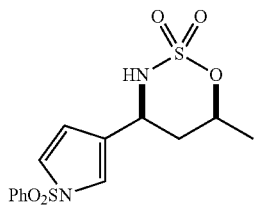

4-(1-(phenylsulfonyl)-1H-pyrrole-3-yl)butan-2-yl sulfamate S31 (143 mg, 0.400 mmol, 1.0 equiv), [Mn(ᵗBuPc)]Cl (16.6 mg, 0.020 mmol, 0.05 equiv), AgSbF₆ (6.9 mg, 0.020 mmol, 0.05 equiv), PhI(OPiv)₂ (325 mg, 0.800 mmol, 2.0 equiv), 100 mg crushed 4 Å MS, and 9:1 C₆H₆/MeCN (800 μL, 0.5M) were used. By ¹H NMR analysis of the crude mixture, the d.r. was determined to be 7:1 syn:anti. Flash column chromatography on silica (35 mm fritted glass column, 150 mm SiO₂) using 10% EtOAc/hexanes→60% EtOAc/hexanes as eluent gave oxathiazinane product as a ~7:1 syn:anti mixture of diastereomers. Pure syn diastereomer can be isolated using flash column chromatography on silica (35 mm fritted glass column, 150 mm SiO₂) using 9:1 hexanes/EtOAc→1:1 hexanes/EtOAc. Anti diastereomer always eluted with syn diastereomer and trace rsm.

Run 1: (96.3 mg (6.8:1 syn:anti), 0.270 mmol, 68%), <5% rsm. Run 2: (101.1 mg (6.9:1 syn:anti), 0.284 mmol, 71%), <5% rsm. Run 3: (99.8 mg (7.1:1 syn:anti), 0.280 mmol, 70%), <5% rsm. Average: 69% yield±1.7 (7:1 syn:anti), <5% rsm.

Syn Diastereomer:
Pure product was isolated as a white solid. ¹H NMR (500 MHz, CDCl₃) δ 7.92 (dd, J=7.6, 1.8, Hz, 2H), 7.64-7.60 (m, 1H), 7.53 (t, J=7.7 Hz, 2H), 7.42-7.41 (m, 1H), 6.31-6.30 (m, 1H), 6.27 (t, J=3.4 Hz, 1H), 5.44 (ddd, J=12.5, 10.2, 2.6 Hz, 1H), 4.95 (dqd, J=12.5, 6.3, 1.9 Hz, 1H), 3.69-3.67 (m, 1H), 2.08 (dt, J=14.2, 2.4 Hz, 1H), 1.84 (dt, J=14.4, 11.9 Hz, 1H), 1.45 (d, J=6.3 Hz, 3H); ¹³C NMR (125 MHz, CDCl₃) δ 138.3, 134.5, 131.3, 129.5, 127.8, 124.3, 113.5, 111.4, 80.5, 50.5, 37.0, 21.2; HRMS (ESI) m/z calculated for $C_{14}H_{17}N_2O_5S$ [M+H]⁺: 357.0579, found 357.0576.

(±)-6-methyl-4-(1-(phenylsulfonyl)-1H-indol-3-yl)-1,2,3-oxathiazinane2,2-dioxide [40]

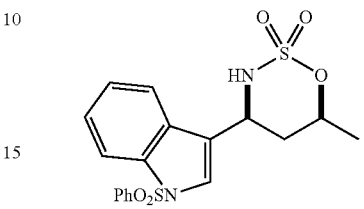

4-(1-(phenylsulfonyl)-1H-indol-3-yl)butan-2-yl sulfamate S32 (164 mg, 0.400 mmol, 1.0 equiv), [Mn(ᵗBuPc)]Cl (16.6 mg, 0.020 mmol, 0.05 equiv), AgSbF₆ (6.9 mg, 0.020 mmol, 0.05 equiv), PhI(OPiv)₂ (325 mg, 0.800 mmol, 2.0 equiv), 100 mg crushed 4 Å MS, and 9:1 C₆H₆/MeCN (800 μL) were used. By ¹H NMR analysis of the crude mixture, the d.r. was determined to be 12:1 syn:anti. Flash column chromatography on silica (25 mm fritted glass column, 150 mm SiO₂) using 9:1 hexanes/EtOAc→3:2 hexanes/EtOAc as eluent gave oxathiazinane product as a ~12:1 syn:anti mixture of diastereomers. Pure syn diastereomer can be isolated using flash column chromatography on silica (35 mm fritted glass column, 150 mm SiO₂) using 4:1 hexanes/EtOAc as eluent.

Run 1: (115.8 mg, 0.285 mmol, 71%), <5% rsm. Run 2: (112.9 mg, 0.278 mmol, 70%), <5% rsm. Run 3: (119.3 mg, 0.294 mmol, 73%), <5% rsm. Ave: 71% yield±1.2, <5% rsm.

Syn Diastereomer:
Pure product was isolated as a white solid. ¹H NMR (500 MHz, CDCl₃) δ 7.97 (d, J=8.3 Hz, 1H), 7.90-7.88 (m, 2H), 7.71 (d, J=7.9 Hz, 1H), 7.58-7.53 (m, 2H), 7.47 (t, J=7.7 Hz, 2H), 7.38-7.35 (m, 1H), 7.29-7.26 (m, 1H), 5.08-5.03 (m 2H), 4.14 (d, J=10.3 Hz, 1H), 2.23 (dt, J=14.1, 2.5 Hz, 1H), 2.02 (dt, J=14.2, 11.9 Hz, 1H), 1.52 (d, J=6.2 Hz, 3H); ¹³C NMR (126 MHz, CDCl₃) δ 137.9, 135.3, 134.4, 129.6, 128.4, 127.0, 125.9, 123.9, 123.2, 120.6, 120.1, 113.8, 80.6, 51.5, 36.0, 21.3; HRMS (ESI) m/z calculated for $C_{18}H_{19}N_2O_5S_2$ [M+H]⁺: 407.0735, found 407.0731.

(±)-3-(4-(2,2-dioxido-1,2,3-oxathiazinan-4-yl)phenyl)oxazolidin-2-one [41]

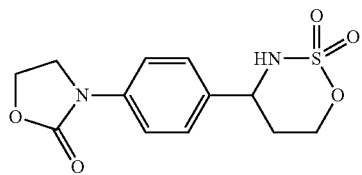 [SMILES: O=C1OCCN1c1ccc(C2CCOS(=O)(=O)N2)cc1]

3-(4-(2-oxooxazolidin-3-yl)phenyl)propyl sulfamate S33 (60.0 mg, 0.200 mmol, 1.0 equiv), [Mn(ᵗBuPc)]Cl (16.6 mg, 0.020 mmol, 0.10 equiv), AgSbF₆ (6.9 mg, 0.020 mmol, 0.10 equiv), PhI(OPiv)₂ (163 mg, 0.400 mmol, 2.0 equiv) and 2:1:1 C₆H₆/Acetone/MeCN (600 μL, 0.33M) were used. Reaction stirred at 45° C. for 18 h. Flash column chromatography on silica (35 mm fritted glass column, 75 mm SiO$_2$) using 30% EtOAc/hexanes→75% EtOAc/hexanes as eluent gave oxathiazinane product as a white solid.

Run 1: (33.5 mg, 0.112 mmol, 56%), <5% rsm. Run 2: (32.1 mg, 0.108 mmol, 54%), <5% rsm. Run 3: (35.3 mg, 0.118 mmol, 59%), <5% rsm. Average: 56% yield±2.1, <5% rsm.

$^1$H NMR (500 MHz, Acetone-d$_6$) δ 7.67-7.64 (m, 2H), 7.52-7.50 (m, 2H), 6.32 (d, J=10.1 Hz, 1H), 4.87-4.76 (m, 2H), 4.69 (ddd, J=11.5, 5.0, 1.7 Hz, 1H), 4.52-4.48 (m, 2H), 4.17-4.14 (m, 2H), 2.30-2.21 (m, 1H), 2.12-2.08 (m, 1H); $^{13}$C NMR (125 MHz, Acetone-d$_6$) δ 155.9, 139.9, 135.0, 128.0, 118.8, 72.7, 62.3, 59.4, 45.7, 31.0; HRMS (ESI) m/z calculated for C$_{12}$H$_{15}$N$_2$O$_5$S [M+H]$^+$: 299.0702, found 299.0702.

(±)-4-(4-(1,3,4-oxadiazol-2-yl)phenyl)-1,2,3-oxathiazinane 2,2-dioxide [42]

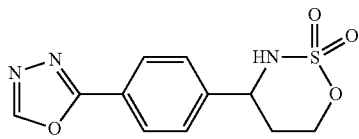 [SMILES: O=S1(=O)NC(c2ccc(-c3nnco3)cc2)CCO1]

(4-(1,3,4-oxadiazol-2-yl)phenyl)propyl sulfamate S34 (113 mg, 0.400 mmol, 1.0 equiv), [Mn($^t$BuPc)]Cl (33.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv) and 4:1 CH$_2$Cl$_2$/MeCN (1.2 mL, 0.33M) were used. The reaction stirred at rt for 18 h. Flash column chromatography on silica (35 mm fritted glass column, 150 mm SiO$_2$) using 30% EtOAc/hexanes→90% EtOAc/hexanes as eluent gave oxathiazinane product.

Run 1: (72.9 mg, 0.259 mmol, 65%), <5% rsm. Run 2: (70.1 mg, 0.249 mmol, 62%), <5% rsm. Run 3: (71.2 mg, 0.253 mmol, 63%), <5% rsm. Average: 63% yield±1.3, <5% rsm.

$^1$H NMR (500 MHz, CD$_3$OD) δ 9.04 (s, 1H), 8.12 (d, J=8.0 Hz, 2H), 7.66 (d, J=8.5 Hz, 2H), 4.93 (dd, J=11.9, 3.1 Hz, 1H), 4.81 (td, J=12.0, 2.6 Hz, 1H), 4.68 (ddd, J=11.5, 4.8, 1.8 Hz, 1H), 2.24-2.10 (m, 2H); $^{13}$C-NMR (125 MHz, CD$_3$OD) δ165.8, 155.5, 144.9, 128.6, 124.3, 73.1, 59.7, 31.0; HRMS (ESI) m/z calculated for C$_{11}$H$_{12}$N$_3$O$_4$S [M+H]$^+$: 282.0549, found 282.0541.

(±)-4-(4,5-diphenyloxazol-2-yl)-1,2,3-oxathiazinane 2,2-dioxide [43]

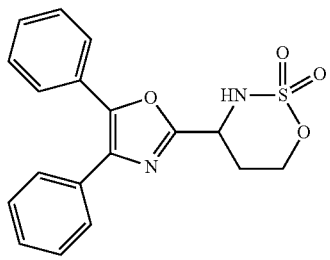 [SMILES: O=S1(=O)NC(c2nc(-c3ccccc3)c(-c3ccccc3)o2)CCO1]

3-(4,5-diphenyloxazol-2-yl) propyl sulfamate S35 (143 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv) and 9:1 C$_6$H$_6$/MeCN (800 µL, 0.5M) were used. The reaction stirred at rt for 12 h. Flash column chromatography on silica (35 mm fritted glass column, 150 mm SiO$_2$) using 30% EtOAc/hexanes→80% EtOAc/hexanes gave oxathiazinane product. Significant EtOAc remains on the product after prolonged vacuum; the peaks corresponding to EtOAc are labeled in the provided spectrum and yields reported account for this by integration in $^1$H NMR.

Run 1: (87.4 mg, 0.245 mmol, 61%), <5% rsm. Run 2: (89.8 mg, 0.252 mmol, 63%), <5% rsm. Run 3: (90.2 mg, 0.253 mmol, 63%), <5% rsm. Average: 63% yield±1.1, <5% rsm.

$^1$H NMR (500 MHz, CDCl$_3$) δ 7.65-7.63 (m, 2H), 7.61-7.58 (m, 2H), 7.43-7.36 (m, 6H), 5.15 (ddd, J=11.9, 10.3, 3.2 Hz, 1H), 4.98-4.90 (m, 2H), 4.70 (ddd, J=11.8, 5.0, 2.0 Hz, 1H), 2.38 (dddd, J=14.8, 12.6, 11.8, 4.9 Hz, 1H), 2.25-2.20 (m, 1H); $^{13}$C NMR (126 MHz, CDCl$_3$) δ 158.5, 146.7, 135.6, 131.6, 129.4, 129.0, 128.9, 128.8, 128.2, 128.0, 71.4, 53.1, 28.9; HRMS (ESI) m/z calculated for C$_{18}$H$_{17}$N$_2$O$_4$S [M+H]$^+$: 357.0909, found 357.0910.

Example 5. Effect of Silver Salt Additive on Reactivity

Control experiments have demonstrated that AgSbF$_6$ itself is not a catalyst for the reaction, with only starting material recovered when the phthalocyanine catalyst is not present in the reaction. However, inclusion of AgSbF$_6$ is important for optimal reactivity, likely via an in situ metathesis that generates a cationic metal phthalocyanine complex. The magnitude to which AgSbF$_6$ impacts the overall reactivity increases as the substrate becomes more challenging (e.g. aliphatic C—H bonds, substrates without biasing groups). Below are reactivity comparisons under the optimized reaction conditions with and without AgSbF$_6$.

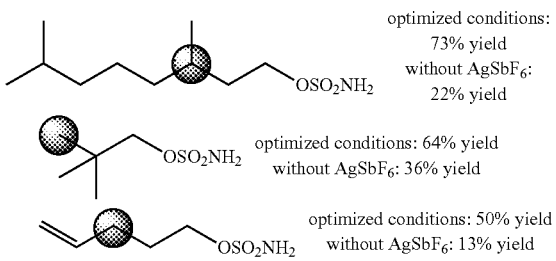

Hammett Study.

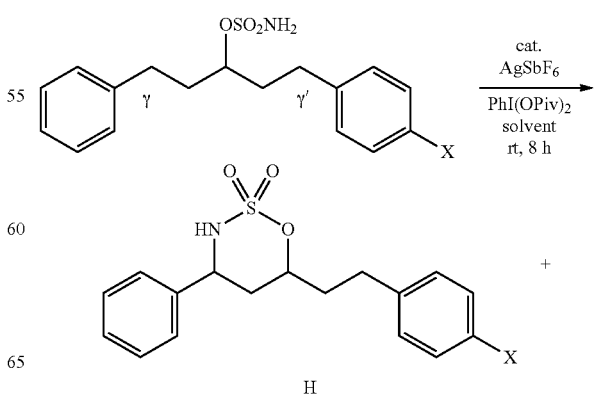

-continued

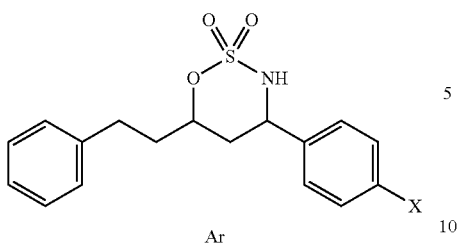

Ar

Figure 2:
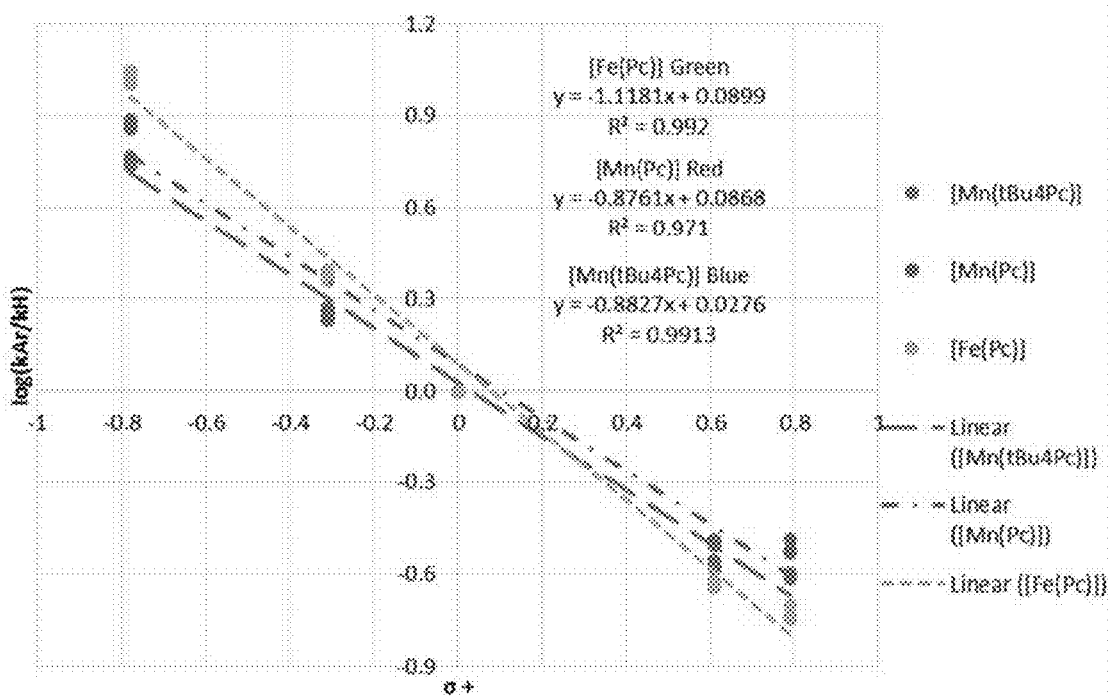
FIG. 2. Graph for Hammett analysis as described in Example 5. Least Squared (LS) Regression was performed on each catalyst with 13 data point sets (3 runs for each of the 4 substrates and (0,0)).

See FIG. 2—S1 for Hammett analysis. Least Squared (LS) Regression was performed on each catalyst with 13 data point sets (3 runs for each of the 4 substrates and (0,0)). Analysis of the Hammett ρ values are listed in the following table. These data were obtained in Excel with LINEST function.

| Catalyst | ρ from LS | SD (ρ) | ρ Value |
|---|---|---|---|
| [Mn($^t$BuPc)] | −0.883 | 0.025 | −0.883 ± 0.025 |
| [MnPc] | −0.876 | 0.046 | −0.876 ± 0.046 |
| [FePc] | −1.118 | 0.030 | −1.118 ± 0.030 |

TABLE 6

Raw data for [FePc]Cl.

| Substrate | σ+ | γ:γ' | $k_{Ar}/k_H$ | $\log(k_{Ar}/k_H)$ |
|---|---|---|---|---|
| NO$_2$ | 0.79 | 5.02:1 | 0.1992 | −0.7007 |
| NO$_2$ | 0.79 | 5.58:1 | 0.1792 | −0.7466 |
| NO$_2$ | 0.79 | 5.41:1 | 0.1848 | −0.7332 |
| CF$_3$ | 0.61 | 4.4:1 | 0.2273 | −0.6435 |
| CF$_3$ | 0.61 | 4.2:1 | 0.2381 | −0.6232 |
| CF$_3$ | 0.61 | 4.2:1 | 0.2381 | −0.6232 |
| Me | −0.31 | 1:2.30 | 2.3000 | 0.3617 |
| Me | −0.31 | 1:2.37 | 2.3700 | 0.3747 |
| Me | −0.31 | 1:2.47 | 2.4700 | 0.3927 |
| OMe | −0.78 | 1:11.1 | 11.1000 | 1.0453 |
| OMe | −0.78 | 1:10.5 | 10.5000 | 1.0212 |
| OMe | −0.78 | 1:10.1 | 10.1000 | 1.0043 |
| H | 0 | 1.00:1 | 1.0000 | 0.0000 |

TABLE 7

Raw data for [MnPc]Cl.

| Substrate | σ+ | γ:γ' | $k_{Ar}/k_H$ | $\log(k_{Ar}/k_H)$ |
|---|---|---|---|---|
| NO$_2$ | 0.79 | 3.07:1 | 0.3257 | −0.4871 |
| NO$_2$ | 0.79 | 3.4:1 | 0.2941 | −0.5315 |
| NO$_2$ | 0.79 | 3.31:1 | 0.3021 | −0.5198 |
| CF$_3$ | 0.61 | 3.1:1 | 0.3226 | −0.4914 |
| CF$_3$ | 0.61 | 3.2:1 | 0.3125 | −0.5051 |
| CF$_3$ | 0.61 | 3.1:1 | 0.3226 | −0.4914 |
| Me | −0.31 | 1:1.7 | 1.7000 | 0.2304 |
| Me | −0.31 | 1:1.72 | 1.7200 | 0.2355 |
| Me | −0.31 | 1:1.8 | 1.8000 | 0.2553 |
| OMe | −0.78 | 1:7.2 | 7.2000 | 0.8573 |
| OMe | −0.78 | 1:7.5 | 7.5000 | 0.8751 |
| OMe | −0.78 | 1:7.7 | 7.7000 | 0.8865 |
| H | 0 | 1.00:1 | 1.0000 | 0.0000 |

TABLE 8

Raw data for [Mn($^t$BuPc)]Cl.

| Substrate | σ+ | γ:γ' | $k_{Ar}/k_H$ | $\log(k_{Ar}/k_H)$ |
|---|---|---|---|---|
| NO$_2$ | 0.79 | 3.93:1 | 0.2545 | −0.5944 |
| NO$_2$ | 0.79 | 3.97:1 | 0.2519 | −0.5988 |
| NO$_2$ | 0.79 | 4.11:1 | 0.2433 | −0.6138 |
| CF$_3$ | 0.61 | 3.80:1 | 0.2632 | −0.5798 |
| CF$_3$ | 0.61 | 3.75:1 | 0.2667 | −0.5740 |
| CF$_3$ | 0.61 | 3.57:1 | 0.2801 | −0.5527 |
| Me | −0.31 | 1:1.79 | 1.7900 | 0.2529 |
| Me | −0.31 | 1:1.83 | 1.8300 | 0.2625 |
| Me | −0.31 | 1:1.88 | 1.8800 | 0.2742 |
| OMe | −0.78 | 1:5.74 | 5.7400 | 0.7589 |
| OMe | −0.78 | 1:5.86 | 5.8600 | 0.7679 |
| OMe | −0.78 | 1:5.44 | 5.4400 | 0.7356 |
| H | 0 | 1.00:1 | 1.0000 | 0.0000 |

(±)-1-(4-nitrophenyl)-5-phenylpentan-3-yl sulfamate [S38]

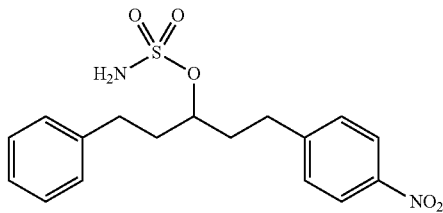 [SMILES: NS(=O)(=O)OC(CCc1ccccc1)CCc1ccc([N+](=O)[O-])cc1]

Prepared according to method B. 1.997 g (7.00 mmol) (±)-1-(4-nitrophenyl)-5-phenylpentan-3-ol were used, along with Et$_3$N (1.9 mL, 14.0 mmol, 2.0 equiv), CH$_2$Cl$_2$ (7 mL+14 mL), ClSO$_2$NCO (1.22 mL, 14.0 mmol, 2.0 equiv), formic acid (530 μL, 14.0 mmol, 2.0 equiv). Flash column chromatography on silica (45 mm fritted glass column, 200 mm SiO$_2$) using 4:1 hexanes/EtOAc→3:2 hexanes/EtOAc as eluent gave 1.79 g (4.92 mmol) of pure product as a yellow solid (70% yield).

$^1$H NMR (500 MHz, CDCl$_3$) δ 8.14 (d, J=9.0 Hz, 2H), 7.34-7.28 (m, 4H), 7.23-7.18 (m, 3H), 4.73-4.65 (m, 3H), 2.90-2.81 (m, 2H), 2.80-2.72 (m, 2H), 2.19-2.03 (m, 4H); $^{13}$C NMR (125 MHz, CDCl$_3$) δ 148.6, 146.4, 140.5, 129.1, 128.5, 128.2, 126.2, 123.7, 83.0, 35.4, 35.2, 31.1, 30.8; HRMS (ESI) m/z calculated for C$_{17}$H$_{20}$N$_2$O$_5$SNa [M+Na]$^+$: 387.0991, found 387.0986. These data agree with that previously reported in the literature (Harvey et al., J. Am. Chem. Soc. 2011, 133, 17207).

(±)-1-phenyl-5-(4-(trifluoromethyl)phenyl)pentan-3-yl sulfamate [S39]

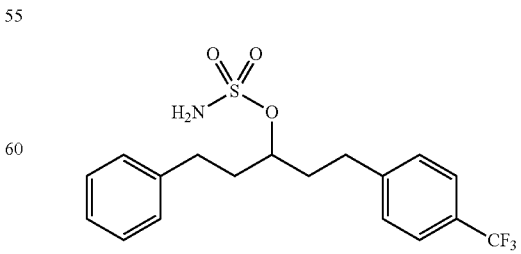

Prepared according to method A. 1.634 g (5.30 mmol) of (±)-1-phenyl-5-(4-(trifluoromethyl)phenyl)pentan-3-ol were used, along with NaH (148 mg, 5.84 mmol, 1.1 equiv), DMF (5 mL+4 mL), ClSO$_2$NCO (696 µL, 7.95 mmol, 1.5 equiv), formic acid (300 µL, 9.75 mmol, 1.5 equiv) and MeCN (4 mL). Flash column chromatography on silica (45 mm fritted glass column, 175 mm SiO$_2$) using 3:1 hexanes/EtOAc as eluent gave 1.250 g (3.23 mmol) of pure product as a white solid (61% yield).

$^1$H-NMR (500 MHz, CDCl$_3$) δ 7.54 (d, J=8.0 Hz, 2H), 7.31-7.28 (m, 4H), 7.23-7.17 (m, 3H), 4.70-4.64 (m, 3H), 2.83-2.73 (m, 4H), 2.17-2.03 (m, 4H); $^{13}$C-NMR (125 MHz, CDCl$_3$) δ 145.2, 140.8, 128.8, 128.7, 128.5, 126.4, 125.6 (q, J$_{C-F}$=3.9 Hz), 83.6, 35.7, 35.6, 31.3, 31.0. These data agree with that previously reported in the literature (Harvey et al., *J. Am. Chem. Soc.* 2011, 133, 17207).

(±)-1-phenyl-5-(p-tolyl)pentan-3-yl sulfamate [S40]

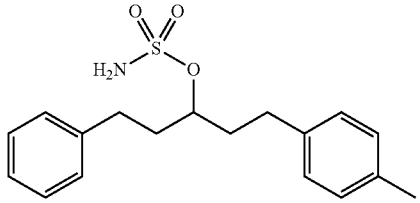 [SMILES: Cc1ccc(CCC(CCc2ccccc2)OS(N)(=O)=O)cc1]

Prepared according to method A. 3.200 g (12.6 mmol) of (±)-1-phenyl-5-(p-tolyl)pentan-3-ol were used, along with NaH (350 mg, 13.9 mmol, 1.1 equiv), DMF (13+10 mL), ClSO$_2$NCO (1.7 mL, 19.1 mmol, 1.5 equiv), formic acid (712 µL, 19.1 mmol, 1.5 equiv) and MeCN (10.4 mL). Flash column chromatography on silica (35 mm fritted glass column, 150 mm SiO$_2$) using 3:1 hexanes/EtOAc→2:1 hexanes/EtOAc as eluent gave 2.01 g (6.03 mmol) of pure product as a white solid (48% yield).

$^1$H-NMR (500 MHz, CDCl$_3$) δ 7.31-7.28 (m, 2H), 7.22-7.18 (m, 3H), 7.11-7.06 (m, 4H), 4.68 (app. p, J=6.5 Hz, 1H), 4.54 (br. s, 2H), 2.79-2.66 (m, 4H), 2.32 (s, 3H), 2.15-2.01 (m, 4H); $^{13}$C-NMR (125 MHz, CDCl$_3$) δ 141.1, 137.9, 135.8, 129.4, 128.7, 128.5, 128.4, 126.3, 84.8, 35.9, 35.8, 31.2, 30.8, 21.1. These data agree with that previously reported in the literature (Harvey et al., *J. Am. Chem. Soc.* 2011, 133, 17207).

(±)-1-(4-methoxyphenyl)-5-phenylpentan-3-yl sulfamate [S41]

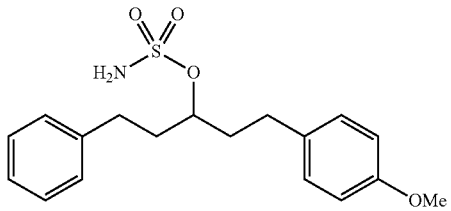 [SMILES: COc1ccc(CCC(CCc2ccccc2)OS(N)(=O)=O)cc1]

Prepared according to method A. 1.351 g (5.00 mmol) (±)-1-(4-methoxyphenyl)-5-phenylpentan-3-ol were used, along with NaH (140 mg, 5.50 mmol, 1.1 equiv), MeCN (5 mL), ClSO$_2$NCO (870 µL, 10.0 mmol, 2 equiv), formic acid (380 µL, 10.0 mmol, 2 equiv) and DMF (10 mL). Flash column chromatography on silica (45 mm fritted glass column, 200 mm SiO$_2$) using 4:1 hexanes/EtOAc→3:2 hexanes/EtOAc as eluent gave 1.290 g (3.69 mmol) of pure product as a pale yellow oil (74% yield).

$^1$H NMR (500 MHz, CDCl$_3$) δ 7.35 (t, J=7.4 Hz, 2H), 7.28-7.23 (m, 3H), 7.15 (d, J=8.3 Hz, 2H), 6.89 (d, J=8.2 Hz, 2H), 5.19 (br. s, 2H), 4.72 (p, J=5.9 Hz, 1H), 3.82 (s, 3H), 2.83-2.69 (m, 4H), 2.15-2.04 (m, 4H); $^{13}$C NMR (125 MHz, CDCl$_3$) δ 157.8, 141.1, 133.1, 129.3, 128.5, 128.4, 126.1, 113.9, 83.8, 55.2, 35.9, 35.6, 31.0, 30.1. These data agree with that previously reported in the literature (Harvey et al., *J. Am. Chem. Soc.* 2011, 133, 17207).

Para-nitrophenyl Versus Phenyl.

In all cases, the product ratio was established by HPLC analysis of the crude reaction mixture (reaction aliquots were filtered through a short silica plug with $^i$PrOH into a HPLC vial. Flash column chromatography on silica (35 mm fritted glass column, 150 mm SiO$_2$) using 9:1 hexanes/EtOAc→3:2 hexanes/EtOAc as eluent gave oxathiazinane product as a mixture of constitutional isomers. Each pure constitutional isomer can be isolated using flash column chromatography on silica (35 mm fritted glass column, 150 mm SiO$_2$) using 9:1 hexanes/EtOAc→2:1 hexanes/EtOAc. Products retained EtOAc after prolonged drying in vacuo; this mass was accounted for when calculating yields. Additionally, free Pc ligand co-elutes with the minor products and its peaks are labeled and its mass accounted for in yields.

FePc Conditions:

1-(4-nitrophenyl)-5-phenylpentan-3-yl sulfamate S38 (73.0 mg, 0.200 mmol, 1.0 equiv), [FePc]Cl (12.0 mg, 0.020 mmol, 0.10 equiv), AgSbF$_6$ (6.9 mg, 0.020 mmol, 0.10 equiv), PhI(OPiv)$_2$ (163 mg, 0.400 mmol, 2.0 equiv) and 4:1 PhMe/MeCN (400 µL, 0.5M) were used. By HPLC analysis of the crude product, γ:γ' was 5.34±0.29:1.

Run 1: (39.1 mg, 0.108 mmol, 54%), (12.3 mg rsm, 0.034 mmol, 17%), γ:γ'=5.02:1. Run 2: (38.4 mg, 0.106 mmol, 53%), (11.6 mg rsm, 0.032 mmol, 16%), γ:γ'=5.58:1. Run 3: (37.0 mg, 0.102 mmol, 51%), (10.1 mg rsm, 0.028 mmol, 14%), γ:γ'=5.41:1. Average: 53% yield±1.5, 16% rsm±1.5.

MnPc Conditions:

1-(4-nitrophenyl)-5-phenylpentan-3-yl sulfamate S38 (73.0 mg, 0.200 mmol, 1.0 equiv), [MnPc]Cl (12.0 mg, 0.020 mmol, 0.10 equiv), AgSbF$_6$ (6.9 mg, 0.020 mmol, 0.10 equiv), PhI(OPiv)$_2$ (163 mg, 0.400 mmol, 2.0 equiv) and 4:1 PhMe/MeCN (400 µL, 0.5M) were used. By HPLC analysis of the crude product, γ:γ' was 3.26±0.17:1.

Run 1: (48.5 mg, 0.134 mmol, 67%), <5% rsm, γ:γ'=3.07:1. Run 2: (46.4 mg, 0.128 mmol, 64%), <5% rsm, γ:γ'=3.40:1. Run 3: (45.7 mg, 0.126 mmol, 63%), <5% rsm, γ:γ'=3.31:1. Average: 65% yield±2.1, <5% rsm.

Mn($^t$BuPc) Conditions:

1-(4-nitrophenyl)-5-phenylpentan-3-yl sulfamate S38 (73.0 mg, 0.200 mmol, 1.0 equiv), [Mn($^t$BuPc)]Cl (16.6 mg, 0.020 mmol, 0.10 equiv), AgSbF$_6$ (6.9 mg, 0.020 mmol, 0.10 equiv), PhI(OPiv)$_2$ (163 mg, 0.400 mmol, 2.0 equiv) and 9:1 C$_6$H$_6$/MeCN (400 µL, 0.5M) were used. By HPLC analysis of the crude product, γ:γ' was 4.05+0.09:1.

Run 1: (59.4 mg, 0.164 mmol, 82%), <5% rsm, γ:γ'=4.11:1. Run 2: (61.6 mg, 0.170 mmol, 85%), <5% rsm, γ:γ'=3.97:

1. Run 3: (63.4 mg, 0.175 mmol, 88%), <5% rsm, γ:γ'=3.93:1. Average: 85% yield±3.0, <5% rsm.

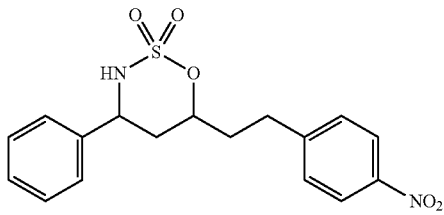 [SMILES: O=[N+]([O-])c1ccc(CCC2CC(c3ccccc3)NS(=O)(=O)O2)cc1]

(±)-4-(4-nitrophenyl)-6-phenethyl-1,2,3-oxathiazinane 2,2-dioxide [S42]

Product was isolated as a white solid. $^1$H NMR (500 MHz, CDCl$_3$) δ 8.18 (d, J=9.0 Hz, 2H), 7.43-7.36 (m, 5H), 7.34-7.32 (m, 2H), 4.85-4.76 (m, 2H), 4.21 (d, J=9.1 Hz, 1H), 3.01 (ddd, J=14.1, 9.3, 4.9 Hz, 1H), 2.91 (dt, J=14.0, 8.3 Hz, 1H), 2.19-2.14 (m, 1H), 2.08-1.93 (m, 3H); $^{13}$C NMR (125 MHz, CDCl$_3$) δ 148.1, 146.9, 137.8, 129.6, 129.4, 129.2, 126.4, 124.1, 82.6, 58.3, 36.5, 36.4, 30.7. These data agree with that previously reported in the literature (Harvey et al., *J. Am. Chem. Soc.* 2011, 133, 17207).

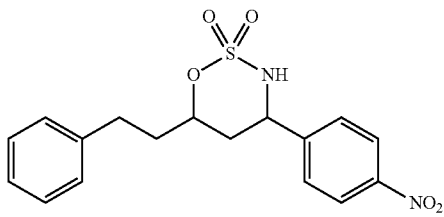 [SMILES: O=[N+]([O-])c1ccc(C2CC(CCc3ccccc3)OS(=O)(=O)N2)cc1]

(±)-6-(4-nitrophenethyl)-4-phenyl-1,2,3-oxathiazinane 2,2-dioxide [S43]

Product was isolated as a white solid. $^1$H NMR (500 MHz, CDCl$_3$) δ 8.27 (d, J=7.0 Hz, 2H), 7.54 (d, J=8.5 Hz, 2H), 7.34-7.31 (m, 2H), 7.26-7.20 (m, 3H), 4.90 (dtt, J=11.7, 5.9, 3.4 Hz, 2H), 4.18 (d, J=9.2 Hz, 1H), 2.89 (ddd, J=14.0, 8.9, 5.2 Hz, 1H), 2.80 (dt, J=13.9, 8.2 Hz, 1H), 2.21-2.09 (m, 2H), 2.02-1.89 (m, 2H); $^{13}$C NMR (125 MHz, CDCl$_3$) δ 144.7, 140.1, 134.5, 128.9, 128.7, 127.5, 126.6, 124.5, 83.1, 57.6, 37.1, 36.1, 30.7; HRMS (ESI) m/z calculated for $C_{17}H_{18}N_2O_5SNa$ [M+Na]$^+$: 385.0834, found 385.0830.

Para-(trifluoromethyl)Phenyl Versus Phenyl.

In all cases, the product ratio was established by HPLC analysis of the crude reaction mixture (reaction aliquots were filtered through a short silica plug with $^i$PrOH into a HPLC vial. Flash column chromatography on silica (35 mm fritted glass column, 150 mm SiO$_2$) using 4:1 hexanes/EtOAc as eluent gave oxathiazinane product as a mixture of constitutional isomers. Each pure constitutional isomer can be isolated using flash column chromatography on silica (35 mm fritted glass column, 150 mm SiO$_2$) using 9:1 hexanes/EtOAc→4:1 hexanes/EtOAc.

FePc Conditions:
(±)-1-phenyl-5-(4-(trifluoromethyl)phenyl)pentan-3-yl sulfamate S39 (77.5 mg, 0.200 mmol, 1.0 equiv), [FePc]Cl (12.0 mg, 0.020 mmol, 0.10 equiv), AgSbF$_6$ (6.9 mg, 0.020 mmol, 0.10 equiv), PhI(OPiv)$_2$ (163 mg, 0.400 mmol, 2.0 equiv) and 4:1 PhMe/MeCN (400 μL, 0.5M) were used. By HPLC analysis of the crude product, γ:γ' was 4.27±0.12:1.
Run 1: (88.1 mg, 0.229 mmol, 57%), (>5% rsm), γ:γ'=4.4:1. Run 2: (84.8 mg, 0.220 mmol, 55%), (>5% rsm), γ:γ'=4.2:1. Run 3 (80.7 mg, 0.209 mmol, 52%), (>5% rsm), γ:γ'=4.2:1. Average: 55% yield±2.4, <5% rsm.

MnPc Conditions:
(±)-1-phenyl-5-(4-(trifluoromethyl)phenyl)pentan-3-yl sulfamate S39 (77.5 mg, 0.200 mmol, 1.0 equiv), [MnPc]Cl (12.0 mg, 0.020 mmol, 0.10 equiv), AgSbF$_6$ (6.9 mg, 0.020 mmol, 0.10 equiv), PhI(OPiv)$_2$ (163 mg, 0.400 mmol, 2.0 equiv) and 4:1 PhMe/MeCN (400 μL, 0.5M) were used. By HPLC analysis of the crude product, γ:γ' was 3.13±0.06:1.
Run 1: (108.3 mg, 0.281 mmol, 70%), (>5% rsm), γ:γ'=3.1:1. Run 2: (102.4 mg, 0.266 mmol, 66%), (>5% rsm), γ:γ'=3.2:1. Run 3: (106.2 mg, 0.276 mmol, 69%), (>5% rsm), γ:γ'=3.1. Average: 69% yield±1.9, <5% rsm.

Mn($^t$BuPc) Conditions:
(±)-1-phenyl-5-(4-(trifluoromethyl)phenyl)pentan-3-yl sulfamate S39 (77.5 mg, 0.200 mmol, 1.0 equiv), [Mn($^t$BuPc)]Cl (16.6 mg, 0.020 mmol, 0.10 equiv), AgSbF$_6$ (6.9 mg, 0.020 mmol, 0.10 equiv), PhI(OPiv)$_2$ (163 mg, 0.400 mmol, 2.0 equiv) and 9:1 C$_6$H$_6$/MeCN (400 μL, 0.5M) were used. By HPLC analysis of the crude product, γ:γ' was 3.71-0.12:1.
Run 1: (56.7 mg, 0.147 mmol, 73%), <5% rsm, γ:γ'=3.75:1. Run 2: (52.4 mg, 0.136 mmol, 68%), <5% rsm, γ:γ'=3.57:1. Run 3: (55.1 mg, 0.143 mmol, 72%), <5% rsm, γ:γ'=3.80:1. Average: 71% yield±2.6, <5% rsm.

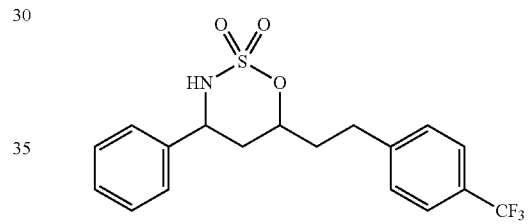

4-phenyl-6-(4-(trifluoromethyl)phenethyl)-1,2,3-oxathiazinane 2,2-dioxide [S44]

$^1$H-NMR (500 MHz, CDCl$_3$) δ 7.57 (d, J=8.0 Hz, 2H), 7.40-7.30 (m, 7H), 4.86-4.76 (m, 2H), 4.42-4.37 (m, 1H), 2.95-2.80 (m, 2H), 2.16-2.12 (m, 1H), 2.04-1.93 (m, 3H); $^{13}$C-NMR (125 MHz, CDCl$_3$) δ 144.6, 138.0, 129.2, 129.0, 126.4, 125.6 (q, J$_{C-F}$=3.8 Hz), 83.0, 58.4, 36.6, 36.2, 30.5. These data agree with that previously reported in the literature (Harvey et al., *J. Am. Chem. Soc.* 2011, 133, 17207).

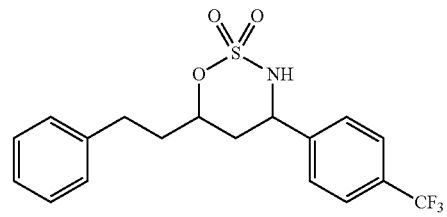 [SMILES: O=S1(=O)NC(c2ccc(C(F)(F)F)cc2)CC(CCc2ccccc2)O1]

6-phenethyl-4-(4-(trifluoromethyl)phenyl)-1,2,3-oxathiazinane 2,2-dioxide [S45]

$^1$H-NMR (500 MHz, CDCl$_3$) δ 7.67 (d, J=8.0 Hz, 2H), 7.47 (d, J=8.0 Hz, 2H), 7.31 (dd, J=8.0, 7.0 Hz, 2H), 7.25-7.19 (m, 3H), 4.90-4.81 (m, 2H), 4.45 (d, J=9.0 Hz, 1H), 2.89-2.74 (m, 2H), 2.19-2.11 (m, 1H), 2.07-1.91 (m, 3H); $^{13}$C-NMR (125 MHz, CDCl$_3$) δ 141.8, 140.2, 128.8, 128.6, 126.3 (q, $J_{C-F}$=3.8 Hz), 83.3, 57.9, 37.0, 36.2, 30.7; IR (thin film, cm$^{-1}$): 3262, 3029, 2931, 1623, 1497, 1437, 1419, 1365, 1327, 1191, 1127, 1070, 1018, 918, 879, 756; HRMS (ESI) m/z calculated for C$_{18}$H$_{19}$F3NO$_3$S [M+H]$^+$: 386.1038, found 386.1039.

Para-methylphenyl Versus Phenyl.

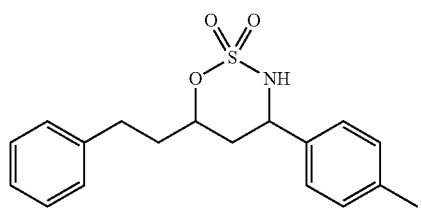 [SMILES: Cc1ccc(C2CC(CCc3ccccc3)OS(=O)(=O)N2)cc1]

In all cases, the product ratio was determined by $^1$H NMR analysis of the crude product mixture after reaction work-up. Flash column chromatography on silica (35 mm fritted glass column, 75 mm SiO$_2$) using 3:1 hexanes/EtOAc as eluent gave oxathiazinane product as a mixture of constitutional isomers. Pure constitutional isomers cannot be isolated and as such the $^1$H NMR spectrum of the mixture is provided but not tabulated.

FePc Conditions:

1-phenyl-5-(p-tolyl)pentan-3-yl sulfamate S40 (67 mg, 0.200 mmol, 1.0 equiv), [FePc]Cl (12.0 mg, 0.020 mmol, 0.10 equiv), AgSbF$_6$ (6.9 mg, 0.020 mmol, 0.10 equiv), PhI(OPiv)$_2$ (163 mg, 0.400 mmol, 2.0 equiv) and 4:1 PhMe/MeCN (400 μL, 0.5M) were used. By $^1$H NMR analysis of the crude product, γ:γ' was 1:2.38+0.09.

Run 1: (38.0 mg, 0.115 mmol, 57%), <5% rsm, γ:γ'=1:2.30. Run 2: (39.7 mg 0.120 mmol, 60%), <5% rsm, γ:γ'=1:2.37. Run 3: (40.7 mg 0.123 mmol, 61%), <5% rsm, γ:γ'=1:2.47. Average: 59% yield±2.0, <5% rsm.

MnPc Conditions:

1-phenyl-5-(p-tolyl)pentan-3-yl sulfamate S40 (67 mg, 0.200 mmol, 1.0 equiv), [MnPc]Cl (12.0 mg, 0.020 mmol, 0.1 equiv), AgSbF$_6$ (6.9 mg, 0.020 mmol, 0.1 equiv), PhI(OPiv)$_2$ (163 mg, 0.400 mmol, 2.0 equiv) and 4:1 PhMe/MeCN (400 μL, 0.5M) were used. By $^1$H NMR analysis of the crude product, γ:γ' was 1:1.74±0.05.

Run 1: (41.0 mg, 0.124 mmol, 62%), <5% rsm, γ:γ'=1:1.7. Run 2: (43.3 mg 0.131 mmol, 65%), <5% rsm, γ:γ'=1:1.72. Run 3: (43.9 mg 0.132 mmol, 66%), <5% rsm, γ:γ'=1:1.8. Average: 64% yield±2.0, <5% rsm.

Mn($^t$BuPc) Conditions:

1-phenyl-5-(p-tolyl)pentan-3-yl sulfamate S40 (67 mg, 0.200 mmol, 1.0 equiv), Mn($^t$BuPc)Cl (16.6 mg, 0.020 mmol, 0.10 equiv), AgSbF$_6$ (6.9 mg, 0.020 mmol, 0.10 equiv), PhI(OPiv)$_2$ (163 mg, 0.400 mmol, 2.0 equiv) and 9:1 C$_6$H$_6$/MeCN (400 μL, 0.5M) were used. By $^1$H NMR analysis of the product mixture, γ:γ' was 1:1.83±0.05.

Run 1: (45.5 mg, 0.137 mmol, 69%), <5% rsm, γ:γ'=1:1.88. Run 2: (44.2 mg, 0.133 mmol, 67%), <5% rsm, γ:γ'=1:1.83. Run 3: (50.0 mg, 0.151 mmol, 76%), <5% rsm, γ:γ'=1:1.79. Average: 70% yield±4.6, <5% rsm.

Para-methoxyphenyl Versus Phenyl.

In all cases, the product ratio was established by HPLC analysis of the crude reaction mixture (reaction aliquots were filtered through a short silica plug with $^i$PrOH into a HPLC vial). Flash column chromatography on silica (35 mm fritted glass column, 75 mm SiO$_2$) using 30% EtOAc/hexanes as eluent gave oxathiazinane product as a mixture of constitutional isomers. Pure major constitutional isomer can be isolated as a white solid using flash column chromatography on silica (35 mm fritted glass column, 75 mm SiO$_2$) using 9:1 hexanes/EtOAc→3:1 hexanes/EtOAc as eluent. The minor constitutional isomer was always isolated as a mixture with the major product.

FePc Conditions:

1-(4-methoxyphenyl)-5-phenylpentan-3-yl sulfamate S41 (70.0 mg, 0.200 mmol, 1.0 equiv), [FePc]Cl (12.0 mg, 0.020 mmol, 0.10 equiv), AgSbF$_6$ (6.9 mg, 0.020 mmol, 0.10 equiv), PhI(OPiv)$_2$ (163 mg, 0.400 mmol, 2.0 equiv), and 4:1 PhMe/MeCN (400 μL, 0.5M) were used. By HPLC analysis of the crude product, γ:γ' was 1:10.57+0.50.

Run 1: (38.4 mg, 0.111 mmol, 55%), <5% rsm, γ:γ'=1:11.1. Run 2: (39.2 mg, 0.113 mmol, 56%), <5% rsm, γ:γ'=1:10.5. Run 3: (40.2 mg, 0.116 mmol, 58%), <5% rsm, γ:γ'=1:10.1. Average: 56% yield±1.2, <5% rsm.

MnPc Conditions:

1-(4-methoxyphenyl)-5-phenylpentan-3-yl sulfamate S41 (70.0 mg, 0.200 mmol, 1.0 equiv), [MnPc]Cl (12.0 mg, 0.020 mmol, 0.10 equiv), AgSbF$_6$ (6.9 mg, 0.020 mmol, 0.10 equiv), PhI(OPiv)$_2$ (163 mg, 0.400 mmol, 2.0 equiv), and 9:1 C$_6$H$_6$/MeCN (400 μL, 0.5M) were used. By HPLC analysis of the crude product, γ:γ' was 1:7.47+0.25.

Run 1: (41.1 mg, 0.118 mmol, 59%), <5% rsm, γ:γ'=1:7.2. Run 2: (42.9 mg, 0.123 mmol, 62%), <5% rsm, γ:γ'=1:7.7. Run 3: (44.8 mg, 0.129 mmol, 64%), <5% rsm, γ:γ'=1:7.5. Average: 62% yield±2.5, <5% rsm.

Mn($^t$BuPc) Conditions:

1-(4-methoxyphenyl)-5-phenylpentan-3-yl sulfamate S41 (70.0 mg, 0.200 mmol, 1.0 equiv), [Mn($^t$BuPc)]Cl (16.6 mg, 0.020 mmol, 0.10 equiv), AgSbF$_6$ (6.9 mg, 0.020 mmol, 0.10 equiv), PhI(OPiv)$_2$ (163 mg, 0.400 mmol, 2.0 equiv) and 9:1 C$_6$H$_6$/MeCN (400 μL, 0.5M) were used. By HPLC analysis of the crude product, γ:γ' was 1:5.68+0.22.

Run 1: (57.7 mg, 0.166 mmol, 83%), <5% rsm, γ:γ'=1:5.44. Run 2: (56.6 mg, 0.163 mmol, 82%), <5% rsm, γ:γ'=1:5.86. Run 3: (52.5 mg, 0.151 mmol, 75%), <5% rsm, γ:γ'=1:5.74. Average: 80% yield±4.0, <5% rsm.

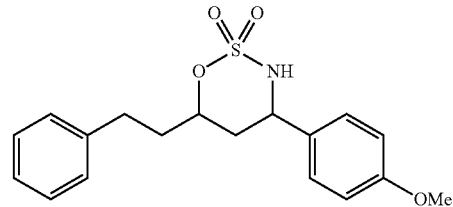 [SMILES: COc1ccc(C2CC(CCc3ccccc3)OS(=O)(=O)N2)cc1]

(±)-6-(4-methoxyphenethyl)-4-phenyl-1,2,3-oxathiazinane 2,2-dioxide [S46]

Product was isolated as a white solid. $^1$H NMR (500 MHz, CDCl$_3$) δ 7.33-7.30 (m, 2H), 7.26-7.20 (m, 5H), 6.92-6.90 (m, 2H), 4.87-4.82 (m, 1H), 4.72 (ddd, J=12.0, 8.7, 2.8 Hz, 1H), 4.13 (d, J=9.2 Hz, 1H), 3.81 (s, 3H), 2.87 (ddd, J=14.1, 9.1, 5.2 Hz, 1H), 2.77 (ddd, J=13.9, 8.9, 7.6 Hz, 1H), 2.18-2.10 (m, 1H), 2.02-1.91 (m, 3H). $^{13}$C NMR (125 MHz, CDCl$_3$) δ 160.0, 140.4, 130.2, 128.8, 128.7, 127.7, 126.5, 114.6, 83.2, 57.8, 55.5, 37.2, 36.4, 30.8. These data agree with that previously reported in the literature (Harvey et al., J. Am. Chem. Soc. 2011, 133, 17207).

Example 6. C—H Bond Reactivity Trends

TABLE 9

C—H bond reactivity trends for Fe and Mn catalysts.

(±)-5-methyl-1-phenylhexan-3-yl sulfamate [45]

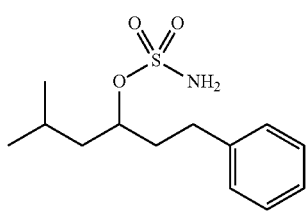 [SMILES: CC(C)CC(CCc1ccccc1)OS(N)(=O)=O]

Prepared according to method A. 1.600 g (8.56 mmol) of (±)-5-methyl-1-phenylhexan-3-ol were used, along with NaH (237 mg, 9.4 mmol, 1.1 equiv), DMF (8.5 mL+6.8 mL), ClSO$_2$NCO (1.11 mL, 12.8 mmol, 1.5 equiv), formic acid (483 µL, 12.8 mmol, 1.5 equiv) and MeCN (6.5 mL). Flash column chromatography on silica (35 mm fritted glass column, 150 mm SiO$_2$) using 9:1 hexanes/EtOAc→4:1 hexanes/EtOAc as eluent gave 1.720 g (6.34 mmol) of pure product as a white solid (74% yield).

$^1$H-NMR (500 MHz, CDCl$_3$) δ 7.31-7.28 (m, 2H), 7.22-7.19 (m, 3H), 4.76-4.69 (m, 3H), 2.75 (td, J=8.5, 3.0 Hz, 2H), 2.11-2.00 (m, 2H), 1.79-1.72 (m, 2H), 1.51 (ddd, J=16.0, 10.0, 5.5 Hz, 1H), 0.95 (d, J=6.0 Hz, 3H), 0.93 (d, J=6.5 Hz, 3H); $^{13}$C-NMR (125 MHz, CDCl$_3$) δ 141.3, 128.6, 128.5, 126.2, 83.5, 43.3, 36.2, 31.1, 24.6, 22.9, 22.6. These data are in agreement with that previously reported in the literature (Fiori et al., *Tetrahedron* 2009, 65, 3042).

(±)-2-methyl-8-(trimethylsilyl)oct-7-yn-4-yl sulfamate [46]

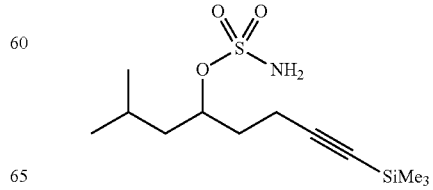

Prepared according to method B. 2.655 g (12.5 mmol) of (±)-2-methyl-8-(trimethylsilyl)oct-7-yn-4-ol were used, along with Et$_3$N (3.5 mL, 25 mmol, 2.0 equiv), CH$_2$Cl$_2$ (13 mL+36 mL), ClSO$_2$NCO (2.18 mL, 25 mmol, 2.0 equiv), formic acid (943 μL, 25 mmol, 2.0 equiv). Flash column chromatography on silica (35 mm fritted glass column, 150 mm SiO$_2$) using 9:1 hexanes/EtOAc→4:1 hexanes/EtOAc as eluent gave 2.290 g (7.85 mmol) of pure product as a white solid (63% yield).

$^1$H-NMR (500 MHz, CDCl$_3$) δ 4.84-4.80 (m, 2H), 2.40 (t, J=6.8 Hz, 2H), 1.92-1.88 (m, 2H), 1.77-1.71 (m, 2H), 1.53-1.47 (m, 1H), 0.96 (d, J=6.0 Hz, 3H), 0.94 (d, J=6.5 Hz, 3H), 0.16 (s, 9H); $^{13}$C-NMR (125 MHz, CDCl$_3$) δ 106.0, 86.7, 82.5, 43.6, 33.0, 24.6, 22.7, 22.6, 16.9, 0.2; IR (ATR, cm$^{-1}$) 3370, 3284, 2960, 2873, 2175, 1559, 1470, 1359, 1250, 1183, 923, 844, 761; HRMS (ESI) m/z calculated for C$_{12}$H$_{26}$NO$_3$SSi [M+H]$^+$: 292.1403, found 292.1406.

(±)-2-methyloctan-4-yl sulfamate [47]

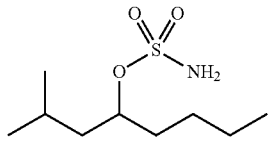

Prepared according to method A. 1.863 g (12.9 mmol) of (±)-2-methyloctan-4-ol were used, along with NaH (359 mg, 14.2 mmol, 1.1 equiv), DMF (13 mL+10 mL), ClSO$_2$NCO (1.69 mL, 19.4 mmol, 1.5 equiv), formic acid (731 μL, 19.4 mmol, 1.5 equiv) and MeCN (10 mL). Flash column chromatography on silica (45 mm fritted glass column, 170 mm SiO$_2$) using 9:1 hexanes/EtOAc→4:1 hexanes/EtOAc as eluent gave 2.017 g (9.03 mmol) of pure product as a colorless oil (70% yield). This sulfamate ester generated precipitate rapidly and was repurified if not used within a week.

$^1$H-NMR (500 MHz, CDCl$_3$) δ 4.75 (br. s, 2H), 4.67 (app. dq, J=7.5, 5.5 Hz, 1H), 1.79-1.66 (m, 4H), 1.47-1.29 (m, 5H), 0.95 (d, J=7.0 Hz, 3H), 0.93 (d, J=6.5 Hz, 3H), 0.91 (t, J=7.0 Hz, 3H); $^{13}$C-NMR (125 MHz, CDCl$_3$) δ 84.3, 43.3, 34.3, 26.9, 24.5, 23.0, 22.7, 22.5, 14.1; HRMS (ESI) m/z calculated for C$_9$H$_{21}$NO$_3$SNa [M+Na]$^+$: 246.1140, found 246.1139.

Tertiary C—H Versus Allylic C—H.

In all cases, flash column chromatography on silica (35 mm fritted glass column, 150 mm SiO$_2$) using 6:1 hexanes:EtOAc+1% AcOH as eluent gave pure syn and anti oxathiazinanes separately; the olefin maintained a >20:1 E/Z geometry in each case. Data for [FePc]Cl has been obtained previously by our group, including complete characterization of the sulfamate ester, syn and anti allylic oxathiazinanes, 3° oxathiazinane, and aziridine (Paradine, S. M.; White, M. C. J. Am. Chem. Soc. 2012, 134, 2036).

MnPc Conditions:

(±)-(E)-2-methylnon-7-en-4-yl sulfamate 44 (94.0 mg, 0.400 mmol, 1.0 equiv), [MnPc]Cl (24.0 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used. By $^1$H-NMR analysis of the crude product, γ:γ' was <1:20, ins./azir. was >20:1, and d.r. was 3:1 syn:anti.

Run 1: (54.6 mg syn+12.1 mg anti (4.5:1 d.r.), 0.286 mmol, 72%), <5% rsm. Run 2: (56.0 mg syn+11.1 mg anti (5:1 d.r.), 0.288 mmol, 72%), <5% rsm. Run 3: (56.3 mg syn+11.2 mg anti (5:1 d.r.), 0.290 mmol, 73%), <5% rsm. Average: 72% yield allylic±0.5 (γ:γ' crude=<1:20), <5% rsm.

Mn($^t$BuPc) Conditions:

(±)-(E)-2-methylnon-7-en-4-yl sulfamate 44 (94.0 mg, 0.400 mmol, 1.0 equiv), Mn($^t$BuPc)Cl (16.6 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used. By $^1$H-NMR analysis of the crude product, γ:γ' was <1:20, ins./azir. was >20:1, and d.r. was 4:1 syn:anti.

Run 1: (55.0 mg syn+13.8 mg anti (4:1 d.r.), 0.296 mmol, 74%), 0% rsm. Run 2: (51.9 mg syn+14.0 mg anti (3.7:1 d.r.), 0.284 mmol, 71%), 0% rsm. Run 3: (55.6 mg syn+15.9 mg anti (3.5:1 d.r.), 0.308 mmol, 77%), 0% rsm. Average: 74% yield allylic±2.4 (γ:γ' crude=<1:20), 0% rsm.

Tertiary C—H Versus Benzylic C—H.

In all cases, material was purified via flash column chromatography on silica (35 mm fritted glass column, 150 mm SiO$_2$) using 10% EtOAc/hexanes→15% EtOAc/hexanes→20% EtOAc/hexanes, isolating the 3° and benzylic products and starting material separately.

FePc Conditions:

5-methyl-1-phenylhexan-3-yl sulfamate 45 (109 mg, 0.400 mmol, 1.0 equiv), [FePc]Cl (24.0 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), and 4:1 PhMe/MeCN (800 μL, 0.5M) were used. By $^1$H-NMR analysis of the crude product, γ:γ' was 1:14.

Run 1: (56.2 mg benzylic, 0.208 mmol, 52%), (5.5 mg 3° (10:1 benzylic/3°), 0.020 mmol, 5%), (14.5 mg rsm, 0.053 mmol, 13% rsm). Run 2: (53.9 mg benzylic, 0.200 mmol, 50%), (5.7 mg 3° (10:1 benzylic/3°), 0.021 mmol, 5%), (12.4 mg rsm, 0.046 mmol, 11%). Run 3: (55.5 mg benzylic, 0.206 mmol, 51%), (5.8 mg 3° (10:1 benzylic/3°), 0.021 mmol, 5%), (13.4 mg rsm, 0.049 mmol, 12%). Ave: 51% yield benzylic±0.8 (γ:γ' crude=1:14), 12% rsm±0.8.

MnPc Conditions:

5-methyl-1-phenylhexan-3-yl sulfamate 45 (109 mg, 0.400 mmol, 1.0 equiv), [MnPc]Cl (24.0 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used. By $^1$H-NMR analysis of the crude product, γ:γ' was 1:3.

Run 1: (66.8 mg benzylic, 0.247 mmol, 62%), (23.0 mg 3° (2.9:1 benzylic/3°), 0.085 mmol, 21%), 0% rsm. Run 2: (65.6 mg benzylic, 0.242 mmol, 61%), (19.9 mg 3° (2.8:1 benzylic/3°), 0.073 mmol, 18%), 0% rsm. Run 3: (64.7 mg benzylic, 0.240 mmol, 60%), (20.5 mg 3° (2.8:1 benzylic/3°), 0.076 mmol, 19%), 0% rsm. Average: 61% yield benzylic±0.8 (γ:γ' crude=1:3), 0% rsm.

Mn($^t$BuPc) Conditions:

5-methyl-1-phenylhexan-3-yl sulfamate 45 (109 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used. By $^1$H-NMR analysis of the crude pdt, γ:γ' was 1:3.

Run 1: (66.0 mg benzylic, 0.244 mmol, 61%), (22.8 mg 3° (2.9:1 benzylic/3°), 0.084 mmol, 21%), 0% rsm. Run 2: (62.6 mg benzylic, 0.232 mmol, 58%), (18.0 mg 3° (2.7:1 benzylic/3°), 0.067 mmol, 17%), 0% rsm. Run 3: (63.0 mg benzylic, 0.233 mmol, 58%), (20.7 mg 3° (2.8:1 benzylic/

3°), 0.077 mmol, 19%), 0% rsm. Average: 59% yield benzylic±1.4 (γ:γ' crude=1:3), 0% rsm.

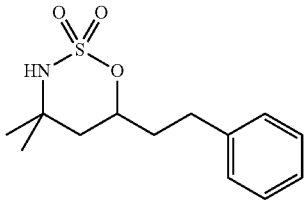 [SMILES: CC1(C)CC(CCc2ccccc2)OS(=O)(=O)N1]

4,4-dimethyl-6-phenethyl-1,2,3-oxathiazinane 2,2-dioxide [S47]

$^1$H-NMR (500 MHz, CDCl$_3$) δ 7.31 (dd, J=12.5, 7.5 Hz, 2H), 7.23-7.19 (m, 3H), 4.84-4.82 (m, 1H), 4.34 (br. s, 1H), 2.84 (ddd, J=15.5, 9.5, 5.0 Hz, 1H), 2.78-2.72 (m, 1H), 2.06 (dtd, J=14.5, 9.0, 5.5 Hz, 1H), 1.89 (dddd, J=13.5, 9.5, 7.5, 4.0 Hz, 1H), 1.68-1.60 (m, 2H), 1.47 (s, 3H), 1.30 (s, 3H); $^{13}$C-NMR (125 MHz, CDCl$_3$) δ 140.6, 128.7, 128.6, 126.4, 80.4, 56.0, 41.5, 37.2, 31.9, 30.9, 25.2. These data agree with that previously reported in the literature (Fiori et al., *Tetrahedron* 2009, 65, 3042).

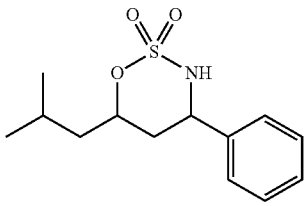 [SMILES: CC(C)CC1CC(c2ccccc2)NS(=O)(=O)O1]

6-isobutyl-4-phenyl-1,2,3-oxathiazinane 2,2-dioxide [S48]

$^1$H-NMR (500 MHz, CDCl$_3$) δ 7.42-7.33 (m, 5H), 4.95 (dddd, J=11.5, 9.0, 4.5, 2.0 Hz, 1H), 4.81 (ddd, J=12.0, 9.0, 3.0 Hz, 1H), 4.21 (br. d, J=9.0 Hz, 1H), 2.04 (dt, J=14.5, 3.0 Hz, 1H), 1.94-1.86 (m, 2H), 1.79 (ddd, J=9.0, 6.0 Hz, 1H), 1.44 (ddd, J=12.5, 8.5, 4.0 Hz, 1H), 0.97 (d, J=6.5 Hz, 3H), 0.95 (d, J=6.5 Hz, 3H); $^{13}$C-NMR (125 MHz, CDCl$_3$) δ 138.2, 129.3, 129.0, 126.4, 83.9, 58.4, 44.3, 36.8, 23.9, 23.0, 22.0. These data agree with that previously reported in the literature (Fiori et al., *Tetrahedron* 2009, 65, 3042).

Tertiary C—H Versus Propargylic C—H.

In all cases, material was purified via flash column chromatography on silica (35 mm fritted glass column, 150 mm SiO$_2$) using 10% EtOAc/hexanes→15% EtOAc/hexanes, isolating product and starting material separately.

FePc Conditions:

2-methyl-8-(trimethylsilyl)oct-7-yn-4-yl sulfamate 46 (116.6 mg, 0.400 mmol, 1.0 equiv), [FePc]Cl (24.0 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), and 4:1 PhMe/MeCN (800 μL, 0.5M) were used. By $^1$H-NMR analysis of the crude product, γ:γ' was 1:3.

Run 1: (61.1 mg propargylic, 0.211 mmol, 53%), (21.7 mg 3°, 0.075 mmol, 19%), 0% rsm. Run 2: (64.7 mg propargylic, 0.223 mmol, 56%), (23.6 mg 3°, 0.081 mmol, 20%), 0% rsm. Run 3: (61.7 mg propargylic, 0.213 mmol, 53%), (26.1 mg 3°, 0.090 mmol, 23%), 0% rsm. Average: 54% yield±1.7 propargylic (γ:γ' crude=1:2.6), 0% rsm.

MnPc Conditions:

2-methyl-8-(trimethylsilyl)oct-7-yn-4-yl sulfamate 46 (116.6 mg, 0.400 mmol, 1.0 equiv), [MnPc]Cl (24.0 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used. By $^1$H-NMR analysis of the crude product, γ:γ' was 1:2.

Run 1: (61.0 mg propargylic, 0.210 mmol, 53%), (34.8 mg tertiary, 0.120 mmol, 30%). Run 2: (69.9 mg propargylic, 0.241 mmol, 60%), (36.4 mg tertiary, 0.126 mmol, 31%). Run 3: (65.1 mg propargylic, 0.225 mmol, 56%), (37.9 mg tertiary, 0.131 mmol, 33%). Average: 56% yield±3.5 propargylic (γ:γ' crude=1:2), 0% rsm.

Mn($^t$BuPc) Conditions:

2-methyl-8-(trimethylsilyl)oct-7-yn-4-yl sulfamate 46 (116.6 mg, 0.400 mmol, 1.0 equiv), [Mn($^t$BuPc)]Cl (16.6 mg, 0.020 mmol, 0.05 equiv), AgSbF$_6$ (6.9 mg, 0.020 mmol, 0.05 equiv), PhI(OPiv)$_2$ (325 mg, 0.800 mmol, 2.0 equiv), 100 mg crushed 4 Å MS, and 9:1 C$_6$H$_6$/MeCN (800 μL, 0.5M) were used. By $^1$H-NMR analysis of the crude product, γ:γ' was 1:2.

Run 1: (81.6 mg propargylic, 0.282 mmol, 70%), (30.8 mg tertiary, 0.106 mmol, 27%). Run 2: (78.4 mg propargylic, 0.271 mmol, 68%), (28.7 mg tertiary, 0.099 mmol, 25%). Run 3: (80.0 mg propargylic, 0.276 mmol, 69%), (32.5 mg tertiary, 0.112 mmol, 28%). Average: 69% yield±0.8 propargylic (γ:γ' crude=1:2), 0% rsm.

4,4-dimethyl-6-(4-(trimethylsilyl)but-3-yn-1-yl)-1,2,3-oxathiazinane 2,2-dioxide [S49]

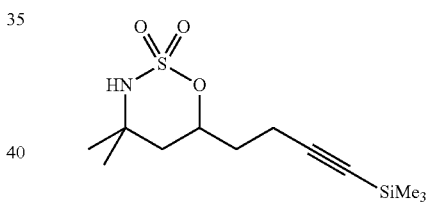

$^1$H-NMR (500 MHz, CDCl$_3$) δ 5.00-4.96 (m, 1H), 4.28 (br. s, 1H), 2.40 (t, J=7.0 Hz, 2H), 1.99-1.92 (m, 1H), 1.84-1.77 (m, 1H), 1.70-1.59 (m, 2H), 1.50 (s, 3H), 1.30 (s, 3H), 0.14 (s, 9H); $^{13}$C-NMR (125 MHz, CDCl$_3$) δ 134.5, 123.7, 104.9, 86.3, 79.8, 56.0, 41.2, 33.9, 31.9, 25.2, 15.6, 0.1; (ATR, cm$^{-1}$) 3269, 2960, 1730, 1423, 1389, 1374, 1354, 1250, 1194, 1164, 944, 908, 844, 873, 760; HRMS (ESI) m/z calculated for C$_{12}$H$_{24}$NO$_3$SSi [M+H]$^+$: 290.1246, found 290.1238.

6-isobutyl-4-((trimethylsilyl)ethynyl)-1,2,3-oxathiazinane 2,2-dioxide [S50]

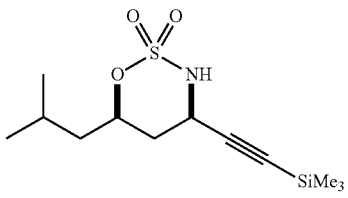

Syn Diastereomer:
¹H-NMR (500 MHz, CDCl₃) δ 4.77 (dddd, J=11.6, 9.0, 4.3, 2.1 Hz, 1H), 4.50 (ddd, J=12.0, 10.4, 3.0 Hz, 1H), 4.12 (d, J=10.4 Hz, 1H), 2.02 (dt, J=14.6, 2.6 Hz, 1H), 1.90-1.81 (m, 1H), 1.82-1.66 (m, 2H), 1.38 (ddd, J=14.2, 8.5, 4.4 Hz, 1H), 0.94 (d, J=4.5 Hz, 3H), 0.93 (d, J=4.8 Hz, 3H), 0.17 (s, 9H); ¹³C-NMR (125 MHz, CDCl₃) δ 100.4, 91.5, 82.4, 47.6, 44.1, 37.2, 23.9, 23.0, 22.1, −0.2; (ESI) m/z calculated for $C_{12}H_{24}NO_3SSi$ [M+H]⁺: 290.1246, found 290.1244.

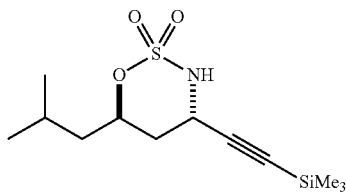

Anti Diastereomer:
¹H-NMR (500 MHz, CDCl₃) δ 5.19-5.14 (m, 1H), 4.67 (d, J=6.0 Hz, 1H), 4.49-4.46 (m, 1H), 2.02-1.77 (m, 4H), 1.44-1.39 (m, 1H), 0.97 (d, J=6.4 Hz, 3H), 0.95 (d, J=6.5 Hz, 3H), 0.18 (s, 9H); ¹³C-NMR (125 MHz, CDCl₃) δ 101.1, 91.6, 81.4, 46.1, 43.3, 35.2, 24.1, 22.7, 22.0, 0.0; (ATR, cm⁻¹) 3278, 2960, 2874, 1470, 1422, 1371, 1251, 1189, 1097, 1015, 867, 845, 791, 761; (ESI) m/z calc' for $C_{12}H_{24}NO_3SSi$ [M+H]⁺: 290.1246, found 290.1252.

Tertiary C—H Versus Secondary C—H.

In all cases, material was purified via flash column chromatography on silica (35 mm fritted glass column, 150 mm SiO₂) using 4:1 hexanes/EtOAc, isolating product and starting material separately. The 3°+2° products could not be separated by any column conditions and were thus isolated as a mixture.

FePc Conditions:
(±)-2-methyloctan-4-yl sulfamate 47 (89.3 mg, 0.400 mmol, 1.0 equiv), [FePc]Cl (24.0 mg, 0.040 mmol, 0.10 equiv), AgSbF₆ (13.7 mg, 0.040 mmol, 0.10 equiv), PhI(OPiv)₂ (325 mg, 0.800 mmol, 2.0 equiv), and 4:1 PhMe/MeCN (800 μL, 0.5M) were used. By ¹H-NMR analysis of the crude product, γ:γ' was >20:1.
Run 1: (26.5 mg 3°, 0.120 mmol, 30%), (27.5 mg rsm, 0.123 mmol, 31%). Run 2: (28.3 mg 3°, 0.128 mmol, 32%), (33.6 mg rsm, 0.151 mmol, 38%). Run 3: (27.1 mg 3°, 0.122 mmol, 31%), (33.4 mg rsm, 0.150 mmol, 37%). Average: 31% yield 3°±0.8, 35% rsm±3.1.

MnPc Conditions:
(±)-2-methyloctan-4-yl sulfamate 47 (89.3 mg, 0.400 mmol, 1.0 equiv), [MnPc]Cl (24.0 mg, 0.040 mmol, 0.10 equiv), AgSbF₆ (13.7 mg, 0.040 mmol, 0.10 equiv), PhI(OPiv)₂ (325 mg, 0.800 mmol, 2.0 equiv), 100 mg crushed 4 Å MS, and 9:1 C₆H₆/MeCN (800 μL, 0.5M) were used. By ¹H-NMR analysis of the crude pdt, γ:γ' was 5:1.
Run 1: (55.8 mg 3°, 0.252 mmol, 63%), 0% rsm. Run 2: (57.2 mg 3°, 0.259 mmol, 65%), 0% rsm. Run 3: (59.0 mg 3°, 0.267 mmol, 67%), 0% rsm. Ave: 65% yield 3°+1.6, 0% rsm.

Mn(ᵗBuPc) Conditions:
(±)-2-methyloctan-4-yl sulfamate 47 (89.3 mg, 0.400 mmol, 1.0 equiv), [Mn(ᵗBuPc)]Cl (16.6 mg, 0.020 mmol, 0.05 equiv), AgSbF₆ (6.9 mg, 0.020 mmol, 0.05 equiv), PhI(OPiv)₂ (325 mg, 0.800 mmol, 2.0 equiv), 100 mg crushed 4 Å MS, and 9:1 C₆H₆/MeCN (800 μL, 0.5M) were used. By ¹H-NMR analysis of the isolated pdt, γ:γ' was 5:1.
Run 1: (70.6 mg 3°, 0.319 mmol, 80%), 0% rsm. Run 2: (71.1 mg 3°, 0.321 mmol, 80%), 0% rsm. Run 3: (74.3 mg 3°, 0.336 mmol, 84%), 0% rsm. Ave: 81% yield 3°±1.9, 0% rsm.

6-butyl-4,4-dimethyl-1,2,3-oxathiazinane 2,2-dioxide [S51]

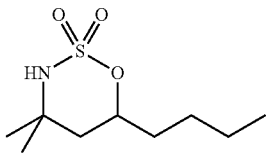

Product was isolated as a white solid. ¹H-NMR (500 MHz, CDCl₃) δ 4.84-4.79 (m, 1H), 4.06 (s, 1H), 1.77-1.71 (m, 1H), 1.66-1.56 (m, 3H), 1.51-1.31 (m, 4H), 1.48 (s, 3H), 1.30 (s, 3H), 0.91 (t, J=7.0 Hz, 3H); ¹³C-NMR (125 MHz, CDCl₃) δ 81.4, 56.0, 41.7, 35.1, 32.1, 26.8, 25.3, 22.4, 14.0; IR (ATR, cm⁻¹) 3264, 2974, 2953, 2931, 2874, 1472, 1456, 1429, 1418, 1388, 1374, 1345, 1271, 1190, 1179, 1152, 1043, 1008, 988, 952, 890, 822, 766, 728; HRMS (ESI) m/z calculated for $C_9H_{19}NO_3SNa$ [M+Na]⁺: 244.0983, found 244.0982.

Example 7. Intramolecular Kinetic Isotope Effect Study

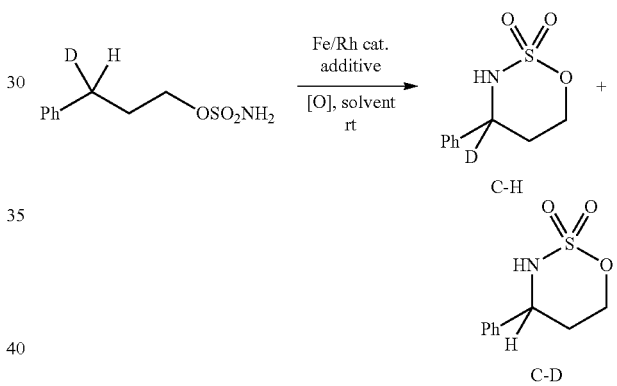

Method for KIE Determination:

The column-purified product mixture S52 (ca. 30 mg in 700 μL CDCl₃) was analyzed by ¹³C-NMR (600 MHz instrument) (see Fiori et al., Tetrahedron 2009, 65, 3042; Wang, P.; Adams, J. J. Am. Chem. Soc. 1994, 116, 3296; Paradine, S. M.; White, M. C. J. Am. Chem. Soc. 2012, 134, 2036). Cr(acac)₃ (15 mg) was added directly to the solution in the NMR tube immediately prior to running the NMR study; this helps to significantly reduce delay times needed to obtain accurate integrations. The experiment was run under inverse-gated decoupling conditions without sample spinning. The following parameters were used for the experiment, listed as Varian commands:

| | |
|---|---|
| temp = 23 | dm = 'nny' (inverse-gated decoupling) |
| d1 = 5 (initial delay) | at = 0.5 (acquisition time) |
| setsw(180, 0) (spectral width, in ppm) | bs = 64 (block size for FID) |
| nt = 2944 (number of scans) | pw = pw90 = 7.0 (pulse width, 90° pulse width) |

The KIE was reported as the area of the deuterated peak over that of the protonated peak. Three identical NMR experiments were run and an average value was calculated with error reported as a standard deviation.

[FePc]Cl: C—H/C-D=4.79±0.13 (4.95, 4.63, 4.78).
[MnPc]Cl: C—H/C-D=4.46±0.08 (4.57, 4.44, 4.38).
[Mn(tBuPc)]Cl: C—H/C-D=4.23±0.10 (4.20, 4.13, 4.36).
Rh$_2$(OAc)$_4$: C—H/C-D=3.83±0.10 (3.82, 3.96, 3.71).

(±)-4-deuterio-4-phenyl-tetrahydro-1,2,3-oxathiazine-2,2-dioxide [S52]

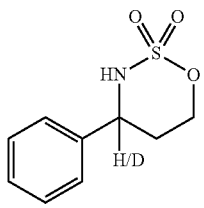

(±)-3-deuterio-3-phenylprop-1-yl sulfamate 48 (86.5 mg, 0.400 mmol, 1.0 equiv), [MnPc]Cl (24.0 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv) and 9:1 C$_6$H$_6$:MeCN (800 µL) were used. Flash column chromatography on silica (35 mm fritted glass column, 150 mm SiO$_2$) using 3:1 hexanes/EtOAc as eluent gave the deuterated and protonated oxathiazinanes as a mixture.

Run 1: (58.4 mg, 0.1273 mmol, 68%), <5% rsm. Run 2: (55.7 mg, 0.260 mmol, 65%), <5% rsm. Run 3: (55.1 mg, 0.257 mmol, 64%), <5% rsm. Average: 66% yield±1.7, <5% rsm.

This compound has been reported and fully characterized previously by our group (Paradine, S. M.; White, M. C. *J. Am. Chem. Soc.* 2012, 134, 2036).

Example 8. Olefin Isomerization Study

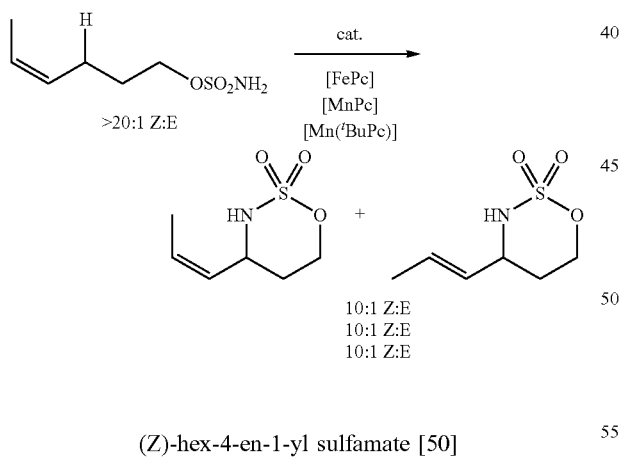

(Z)-hex-4-en-1-yl sulfamate [50]

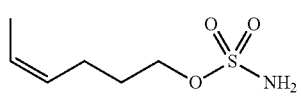

Prepared according to method A. 500 mg (584 µL, 5.0 mmol) of cis-4-hexene-1-ol were used, along with NaH (138 mg, 5.5 mmol, 1.1 equiv), DMF (8.9 mL), ClSO$_2$NCO (651 µL, 7.5 mmol, 1.5 equiv), formic acid (283 µL, 7.5 mmol, 1.5 equiv) and MeCN (3.8 mL). Flash column chromatography on silica (100 mL SiO$_2$) using 4:1 hexanes/EtOAc→3:1 hexanes/EtOAc as eluent gave 756 mg (4.2 mmol) of pure product as a colorless oil (84% yield).

$^1$H-NMR (500 MHz, CDCl$_3$) δ 5.56-5.49 (m, 1H), 5.38-5.32 (m, 1H), 4.79 (br. s, 2H), 4.22 (t, J=6.5 Hz, 2H), 2.18 (q, J=7.3 Hz, 2H), 1.82 (tt, J=7.3, 6.6 Hz, 2H), 1.62 (ddd, J=6.8, 1.7, 0.9 Hz, 3H); $^{13}$C-NMR (125 MHz, CDCl$_3$) δ 128.6, 125.9, 71.2, 28.8, 22.9, 13.0. These data are in agreement with that previously reported in the literature (Fiori et al., *Tetrahedron* 2009, 65, 3042).

Procedure for Olefin Isomerization Experiments.

In all cases, crude material was purified via flash column chromatography on silica (35 mm fritted glass column, 120 mm SiO$_2$) using 9:1 CH$_2$Cl$_2$/hexanes→19:1 CH$_2$Cl$_2$/hexanes as eluent, affording pure oxathiazinane as a white solid.

[FePc] Conditions:

(Z)-hex-4-en-1-yl sulfamate 50 (71.7 mg, 0.400 mmol, 1.0 equiv), [FePc]Cl (24.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), and 4:1 PhMe/MeCN (800 µL, 0.5M) were used. By $^1$H-NMR analysis of the crude product, Z/E was 10:1 (this ratio was confirmed by subjecting column-purified Z/E mixtures of products to $^1$H-NMR analysis).

[MnPc] Conditions:

(Z)-hex-4-en-1-yl sulfamate 50 (71.7 mg, 0.400 mmol, 1.0 equiv), [MnPcCl (24.1 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used. By $^1$H-NMR analysis of the crude product, Z/E was 10:1 (this ratio was confirmed by subjecting column-purified Z/E mixtures of products to $^1$H-NMR analysis).

[Mn(tBuPc)] Conditions:

(Z)-hex-4-en-1-yl sulfamate 50 (71.7 mg, 0.400 mmol, 1.0 equiv), [Mn(tBuPc)]Cl (33.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used. By $^1$H-NMR analysis of the crude product, Z/E was 10:1 (this ratio was confirmed by subjecting column-purified Z/E mixtures of products to $^1$H-NMR analysis).

(Z)-4-(prop-1-en-1-yl)-1,2,3-oxathiazinane 2,2-dioxide [Z-7]

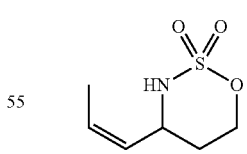

$^1$H-NMR (500 MHz, CDCl$_3$) δ 5.77 (dqd, J=10.8, 7.0, 1.2 Hz, 1H), 5.27 (ddq, J=10.1, 8.1, 1.9 Hz, 1H), 4.81 (ddd, J=12.8, 11.7, 2.4 Hz, 1H), 4.66-4.60 (m, 1H), 4.57 (ddd, J=11.7, 5.0, 1.7 Hz, 1H), 4.01 (br. d, J=9.3 Hz, 1H), 1.90 (dddd, J=14.6, 12.8, 11.7, 5.0 Hz, 1H), 1.80-1.71 (m, 4H); $^{13}$C-NMR (125 MHz, CDCl$_3$) δ 130.8, 127.1, 71.9, 52.8, 30.1, 13.8. These data are in agreement with that previously reported in the literature (Fiori et al., *Tetrahedron* 2009, 65, 3042).

Example 9. Stereoretention Study

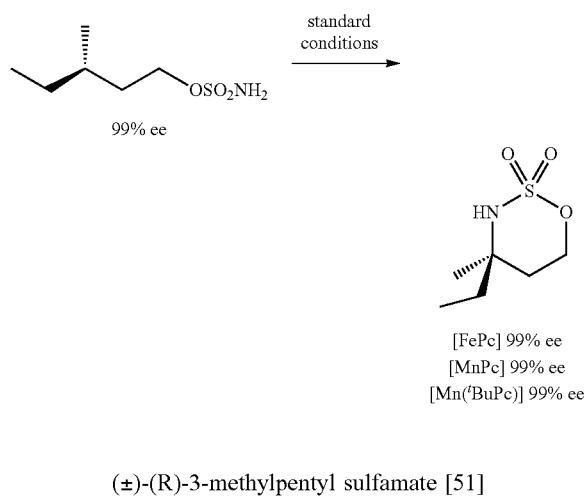

(±)-(R)-3-methylpentyl sulfamate [51]

Prepared according to method A. 1.00 mL (8.12 mmol) of (±)-(R)-3-methyl-1-pentanol were used, along with NaH (226 mg, 8.93 mmol, 1.1 equiv), DMF (8 mL+6 mL), ClSO$_2$NCO (1.06 mL, 12.2 mmol, 1.5 equiv), formic acid (460 µL, 12.2 mmol, 1.5 equiv) and MeCN (6 mL). Flash column chromatography on silica (35 mm fritted glass column, 150 mm SiO$_2$) using 3:1 hexanes/EtOAc as eluent gave 1.385 g (7.64 mmol) of pure product as a colorless oil (94% yield).

$^1$H-NMR (500 MHz, CDCl$_3$) δ 4.96 (br. s, 2H), 4.28-4.21 (m, 2H), 1.83-1.74 (m, 1H), 1.57-1.49 (m, 2H), 1.41-1.33 (m, 1H), 1.20 (dp, J=14.0, 7.0 Hz, 1H), 0.91 (d, J=6.5 Hz, 3H), 0.88 (t, J=7.5 Hz, 3H); $^{13}$C-NMR (125 MHz, CDCl$_3$) δ 70.3, 35.3, 31.0, 29.4, 18.9, 11.3; [α]$^{25}_D$=+5.8° (c=2.0, CHCl$_3$). These data agree with that previously reported in the literature (Espino et al., *J. Am. Chem. Soc.* 2001, 123, 6935).

(+)-(R)-4-ethyl-4-methyl-1,2,3-oxathiazinane 2,2-dioxide [52]

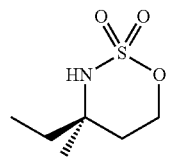

In all cases, material was purified via flash column chromatography on silica (35 mm fritted glass column, 150 mm SiO$_2$) using CH$_2$Cl$_2$→2% Et$_2$O/CH$_2$Cl$_2$, affording pure product (starting material was not collected). Enantiopurity was established by chiral GC analysis using a CycloSil-B column with an isocratic method at 160° C. Racemic product: t$_r$ (R)=22.51 min, t$_r$ (S)=24.35 min; Enantioenriched product: t$_r$ (R)=22.51 min.

FePc Conditions:
(+)-(R)-3-methylpentyl sulfamate 51 (72.5 mg, 0.400 mmol, 1.0 equiv), [FePc]Cl (24.0 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), and 4:1 PhMe/MeCN (800 µL, 0.5M) were used. By chiral GC analysis, product was 99% ee.

Run 1: (14.2 mg product, 0.079 mmol, 20%). Run 2: (13.7 mg product, 0.076 mmol, 19%). Run 3: (13.6 mg product, 0.076 mmol, 19%). Average: 19% yield±0.5.

MnPc Conditions:
(+)-(R)-3-methylpentyl sulfamate 51 (72.5 mg, 0.400 mmol, 1.0 equiv), [MnPc]Cl (24.0 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used. By chiral GC analysis, product was 99% ee.

Run 1: (33.3 mg product, 0.186 mmol, 46%). Run 2: (36.4 mg product, 0.203 mmol, 51%). Run 3: (34.4 mg product, 0.192 mmol, 48%). Average: 48% yield±2.1.

Mn($^t$BuPc) Conditions:
(+)-(R)-3-methylpentyl sulfamate 51 (72.5 mg, 0.400 mmol, 1.0 equiv), [Mn($^t$BuPc)]Cl (33.2 mg, 0.040 mmol, 0.10 equiv), AgSbF$_6$ (13.7 mg, 0.040 mmol, 0.10 equiv), PhI(OPiv)$_2$ (325 mg, 0.800 mmol, 2.0 equiv), 100 mg crushed 4 Å MS, and 9:1 C$_6$H$_6$/MeCN (800 µL, 0.5M) were used. By chiral GC analysis, product was 99% ee.

Run 1: (44.3 mg product, 0.247 mmol, 62%). Run 2: (43.2 mg product, 0.241 mmol, 60%). Run 3: (40.4 mg product, 0.225 mmol, 56%). Average: 59% yield±2.5.

Pure product is isolated as a white solid. $^1$H-NMR (500 MHz, CDCl$_3$) δ 4.77-4.63 (m, 2H), 4.10 (br. s, 1H), 1.86 (dq, J=14.5, 7.5 Hz, 1H), 1.79 (ddd, J=14.5, 8.0, 4.0 Hz, 1H), 1.71 (ddd, J=15.0, 6.5, 4.0 Hz, 1H), 1.52 (dq, J=14.0, 7.3 Hz, 1H), 1.37 (s, 3H), 0.97 (t, J=7.3 Hz, 3H); $^{13}$C-NMR (125 MHz, CDCl$_3$) δ 69.1, 59.2, 34.4, 33.7, 24.3, 7.6; [α]$^{26}_D$=+7.6° (c=1.8, CHCl$_3$). These data agree with that previously reported in the literature (Espino et al., *J. Am. Chem. Soc.* 2001, 123, 6935).

Example 10. Kinetic Analysis of C—H Amination Reactions

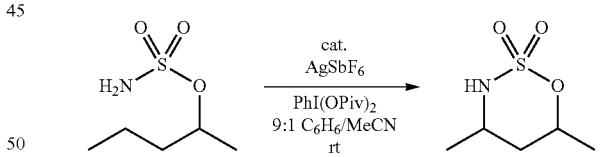

(±)-pentan-2-yl sulfamate [S53]

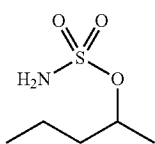

Prepared according to method A. 1.30 g (1.63 mL, 15.0 mmol) of pentan-2-ol were used, along with NaH (417 mg, 16.5 mmol, 1.1 equiv), DMF (27 mL), ClSO$_2$NCO (1.95 mL, 22.5 mmol, 1.5 equiv), formic acid (850 µL, 22.5 mmol, 1.5 equiv) and MeCN (11.3 mL). Flash column chromatography on silica (100 mL SiO$_2$) using 4:1 hexanes:EtOAc as eluent gave 2.00 g (11.7 mmol) of pure product as a colorless oil (80% yield).

$^1$H-NMR (500 MHz, CDCl$_3$) δ 4.76-4.70 (m, 3H), 1.79-1.71 (m, 1H), 1.60 (ddt, J=13.9, 9.7, 5.8 Hz, 1H), 1.51-1.38 (m, 2H), 1.44 (d, J=6.2 Hz, 3H), 0.97 (t, J=7.4 Hz, 3H); $^{13}$C NMR (125 MHz, CDCl$_3$) δ 81.7, 38.7, 20.7, 18.5, 13.9. These data are in agreement with that previously reported in the literature (Wehn et al., *J. Org. Lett.* 2003, 5, 4823).

(±)-4,6-dimethyl-1,2,3-oxathiazinane 2,2-dioxide [S54]

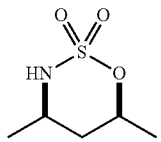

Syn Diastereomer:

Isolated as a white sold. $^1$H-NMR (500 MHz, CDCl$_3$) δ 4.89 (dqd, J=12.5, 6.3, 2.2 Hz, 1H), 3.87-3.78 (m, 1H), 3.65 (br. d, J=10.6 Hz, 1H), 1.84 (dt, J=14.3, 2.5 Hz, 1H), 1.44 (d, J=6.2 Hz, 3H), 1.38 (dt, J=14.4, 11.8 Hz, 1H), 1.29 (d, J=6.4 Hz, 3H); $^{13}$C NMR (125 MHz, CDCl$_3$) δ 81.0, 51.2, 38.8, 21.1, 20.7. These data are in agreement with that previously reported in the literature (When et al., *Org. Lett.* 2003, 5, 4823).

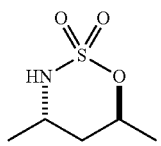

Anti Diastereomer:

Isolated as a white solid with ~20% of syn diastereomer. $^1$H-NMR (500 MHz, CDCl$_3$) δ 5.04 (dqd, J=9.8, 6.4, 3.3 Hz, 1H), 4.37 (d, J=7.8 Hz, 1H), 3.84 (dtd, J=14.5, 7.3, 4.7 Hz, 1H), 1.87-1.78 (m, 1H), 1.71-1.66 (m, 1H), 1.50 (d, J=6.5 Hz, 3H), 1.46 (d, J=7.1 Hz, 3H); $^{13}$C NMR (125 MHz, CDCl$_3$) δ 78.8, 77.4, 77.2, 76.9, 49.4, 36.0, 20.8, 19.7. These data are in agreement with that previously reported in the literature (When et al., *Org. Lett.* 2003, 5, 4823).

General Procedure for Reaction Profile Studies:

Into a 1 dram vial was added AgSbF$_6$ (6.9 mg, 0.020 mmol, 0.10 equiv), catalyst (0.020 mmol, 0.10 equiv), and a stir bar in a glovebox. The vial was then sealed with a septum-lined cap, covered in aluminum foil, taken out of the box, and topped with a balloon of argon. Pentan-2-yl sulfamate S53 (33.4 mg, 0.200 mmol, 1.0 equiv) was taken up in 9:1 C$_6$H$_6$/MeCN (400 μL, 0.5M) and added via syringe, followed by internal standard (decane, 19.5 μL, 0.500 equiv). After stirring for 10-15 min, a 10 μL aliquot was removed (as a t$_0$ timepoint), then PhI(OPiv)$_2$ (325 mg, 0.800 mmol, 2.0 equiv) was added under an inert atmosphere and reaction stirred at room temp (~23° C.) for 8 h. 10 μL aliquots were removed by syringe at 15 min, 30 min, 1 h, 1.5 h, 2 h, 3 h, 4 h, 6 h, and 8 h; aliquots were filtered through a short plug of silica (glass wool lined pipette, 1-2 mm SiO$_2$) with 1 mL Et$_2$O directly into a GC vial. Yields of S54 were established by GC analysis based on a standard curve. Each catalyst was run in triplicate; reported values are averages of three runs with error bars denoting standard deviation.

Figure 3:
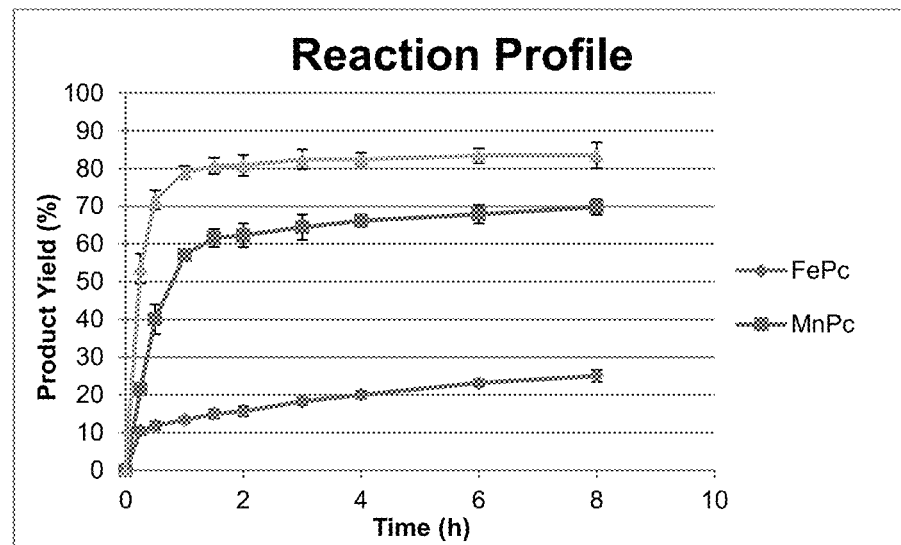
FIG. 3. Reaction profile with catalysts 1, 2, and 3.

See FIG. 3 for the reaction profile with catalysts 1, 2, and 3.

General Procedure for Initial Rate Analysis 5 mol % Conditions.

In order to obtain accurate initial rate data, all reactions for rate analysis were run at room temperature and at 0.25 M concentration. Into a flame-dried 1 dram vial was added AgSbF$_6$ (3.4 mg, 0.010 mmol, 0.05 equiv), [Mn($^t$BuPc)]Cl (8.3 mg, 0.010 mmol, 0.05 equiv), and a stir bar in a glovebox. The vial was then sealed with a septum-lined cap, covered in aluminum foil, taken out of the box, and topped with a balloon of argon. Pentan-2-yl sulfamate S53 (33.4 mg, 0.2 mmol, 1.0 equiv) and internal standard decane (0.08 mmol, 40 mol %), were dissolved in 9:1 C$_6$H$_6$/MeCN (400 μL, 0.5M) and added to the 1 dram vial. PhI(OPiv)$_2$ (163 mg, 0.400 mmol, 2.0 equiv) was dissolved in 9:1 C$_6$H$_6$/MeCN (400 μL, 0.5M), and added directly to the reaction. The vial was then sealed and placed to stir at rt. Aliquots (10 μL) were taken at the corresponding times from the reaction flask, and filtered through a silica pad with 600 μL of diethyl ether for GC analysis. The yield was determined by integration of the product peaks relative to the decane internal standard. Yields of S54 are reported as the average of three runs with error bars denoting standard deviation.

Figure 4:
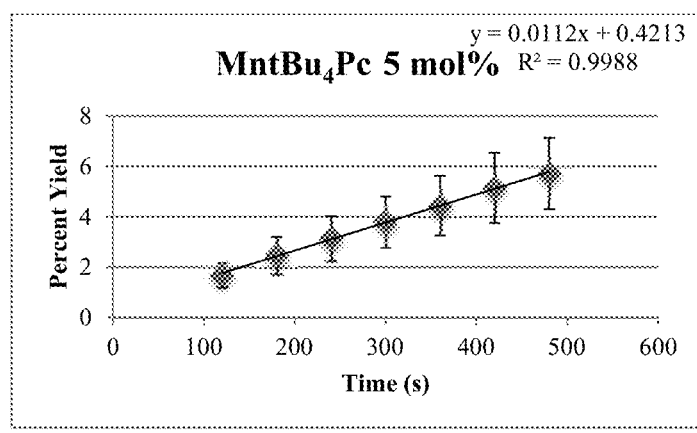
FIG. 4. Initial rates with 5 mol % catalyst 3.

See FIG. 4 for initial rates with 5 mol % catalyst 3.

10 mol % Conditions.

In order to obtain accurate initial rate data, all reactions for rate analysis were run at room temperature and 0.25 M concentration. Into a flame-dried 1 dram vial was added AgSbF$_6$ (6.8 mg, 0.020 mmol, 0.10 equiv), [Mn($^t$BuPc)]Cl (16.6 mg, 0.020 mmol, 0.10 equiv), and a stir bar in a glovebox. The vial was then sealed with a septum-lined cap, covered in aluminum foil, taken out of the box, and topped with a balloon of argon. Pentan-2-yl sulfamate S53 (33.4 mg, 0.2 mmol, 1.0 equiv) and internal standard decane (0.08 mmol, 40 mol %.), were dissolved in 9:1 C$_6$H$_6$:MeCN (400 μL, 0.5M) and added to the 1 dram vial. PhI(OPiv)$_2$ (163 mg, 0.400 mmol, 2.0 equiv) was dissolved in 9:1 C$_6$H$_6$/MeCN (400 μL, 0.5M), and added directly to the reaction. The vial was then sealed and placed to stir at room temperature. Aliquots (10 μL) were taken at the corresponding times from the reaction flask, and filtered through a silica pad with 600 μL of diethyl ether for GC analysis. The yield was determined by integration of the product peaks relative to the decane internal standard. Yields of S54 are reported as the average of three runs with error bars denoting standard deviation.

Figure 5:
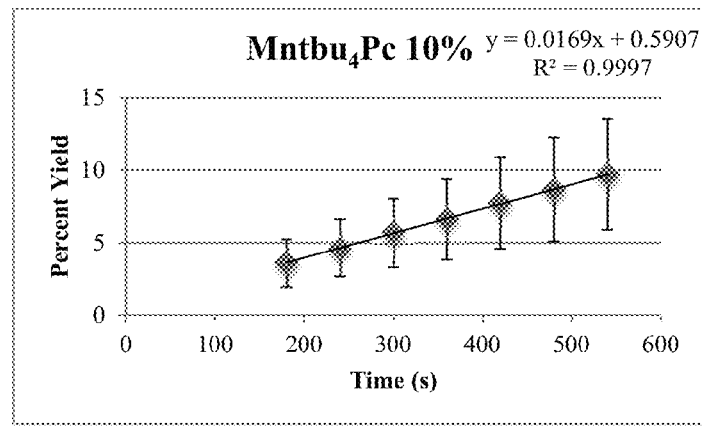
FIG. 5. Initial rates with 10 mol % catalyst 3.

See FIG. 5 for initial rates with 10 mol % catalyst 3.

Example 11. Determination of Kinetic Isotope Effect Via Initial Rates

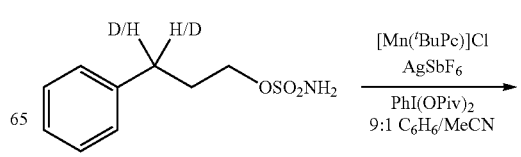

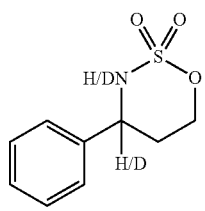

Figure 6:
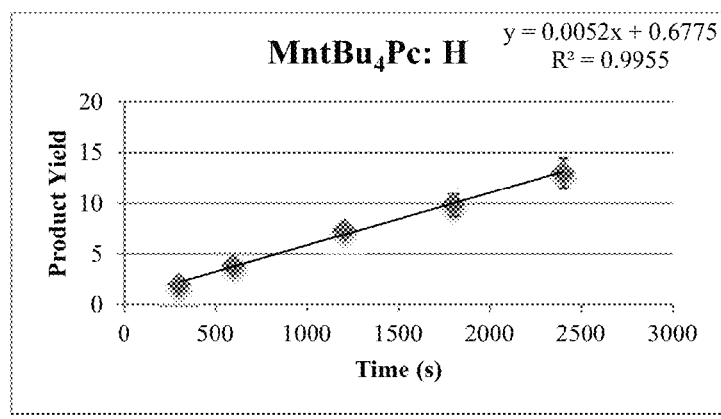
FIG. 6. Initial rates with 49 and 5 mol % catalyst 3.
Figure 7:
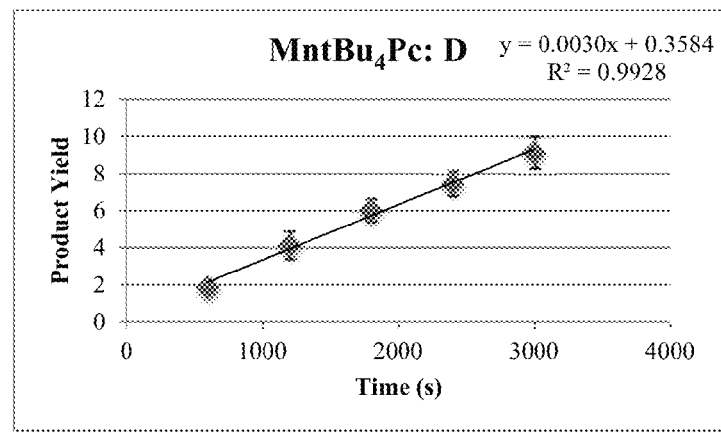
FIG. 7. Initial rates with 49-d$_2$ and 5 mol % catalyst 3.

General Procedure for Initial Rate Analysis at 5 Mol %:

In order to obtain accurate initial rate data, all reactions for rate analysis were run at room temperature and at 0.25 M concentration. To a 1 dram flame-dried borosilicate vial containing a Teflon stir bar was added [Mn($^t$BuPc)]Cl (0.010 mmol, 0.05 equiv) and AgSbF$_6$ (3.4 mg, 0.010 mmol, 0.05 equiv). 3-phenylpropyl sulfamate 49 or 3-phenylpropyl-3,3-d$_2$ sulfamate 49-d$_2$ (33.4 mg, 0.2 mmol, 1.0 equiv) and internal standard 1-fluoro-2-nitrobenzene (0.08 mmol, 40 mol %), were dissolved in 9:1 C$_6$H$_6$/MeCN (400 μL, 0.5M) and added to the 1 dram vial. PhI(OPiv)$_2$ (163 mg, 0.400 mmol, 2.0 equiv) was dissolved in 9:1 C$_6$H$_6$/MeCN (400 μL, 0.5M), and added directly to the reaction. The vial was then sealed and placed to stir at rt. Aliquots (10 μL) were taken at the corresponding times from the reaction flask, and filtered through a silica pad with 600 μL of isopropanol for HPLC (Zorbax CN, 4.6×250 nm) analysis. The yield was determined by integration of the product peaks relative to the 1-fluoro-2-nitrobenzene internal standard and comparison to a standard curve. Yields are reported as the average of three runs with error bars denoting standard deviation. Initial rates were determined for formation of 7 (FIGS. 6 and 7). Error for kinetic isotopes was calculated via propagation of the standard error of the mean for each set of rates.

(±)-3-phenylpropyl-3,3-d$_2$ sulfamate [49-d$_2$]

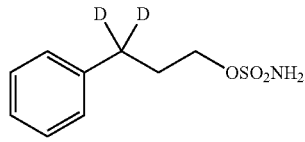

$^1$H-NMR (500 MHz, CDCl$_3$) δ 7.30 (t, J=7.5 Hz, 2H), 7.23-7.19 (m, 3H), 4.75 (br s, 2H), 4.22 (t, J=6.5 Hz, 2H), 2.08 (dt, J=7.5, 7.0 Hz, 2H).

$k_H/k_D$=0.0052/0.0030=1.7±0.1. See FIG. 6 for initial rates with 49 and 5 mol % catalyst 3. See FIG. 7 for initial rates with 49-d$_2$ and 5 mol % catalyst 3.

General Procedure for Initial Rate Analysis at 10 Mol %:

In order to obtain accurate initial rate data, all reactions for rate analysis were run at room temperature and at 0.25 M concentration. Into a flame-dried 1 dram vial was added AgSbF$_6$ (6.7 mg, 0.02 mmol, 0.10 equiv), [Mn($^t$BuPc)]Cl (16.6 mg, 0.02 mmol, 0.10 equiv), and a stir bar in a glovebox. The vial was then sealed with a septum-lined cap, covered in aluminum foil, taken out of the box, and topped with a balloon of argon. 3-phenylpropyl sulfamate 49 (43.1 mg, 0.2 mmol, 1.0 equiv) and internal standard 1-fluoro-2-nitrobenzene (0.08 mmol, 40 mol %), were dissolved in 9:1 C$_6$H$_6$/MeCN (400 μL, 0.5M) and added to the 1 dram vial. PhI(OPiv)$_2$ (163 mg, 0.400 mmol, 2.0 equiv) was dissolved in 9:1 C$_6$H$_6$/MeCN (400 μL, 0.5M), and added directly to the reaction. The vial was then sealed and placed to stir at rt. Aliquots (10 μL) were taken at the corresponding times from the reaction flask, and filtered through a silica pad with 600 μL of isopropanol for HPLC (Zorbax CN, 4.6×250 nm) analysis. The yield was determined by integration of the product peaks relative to the 1-fluoro-2-nitrobenzene internal standard and comparison to a standard curve. Yields are reported as the average of three runs with error bars denoting standard deviation.

Figure 8:
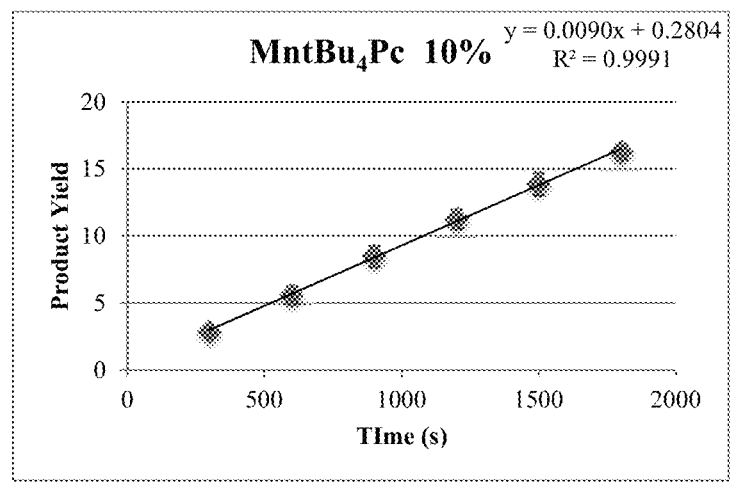
FIG. 8. Initial rates with 49 and 10 mol % catalyst 3.

See FIG. 8—S7 and initial rates with 49 and 10 mol % catalyst 3.

Example 12. Intermolecular Kinetic Isotope Effect Study

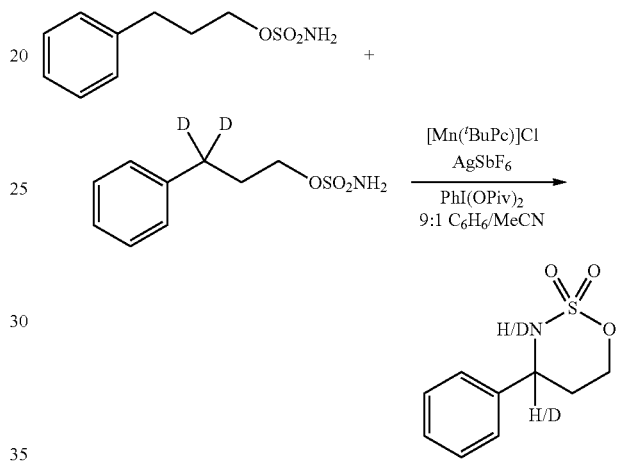

Method for KIE Determination:

The column-purified product mixture S52 (ca. 30 mg in 700 μL CDCl$_3$) was analyzed by $^{13}$C-NMR (600 MHz instrument) (Fiori et al., *Tetrahedron* 2009, 65, 3042). Cr(acac)$_3$ (15 mg) was added directly to the solution in the NMR tube immediately prior to running the NMR study; this helps to significantly reduce delay times needed to obtain accurate integrations. The experiment was run under inverse-gated decoupling conditions without sample spinning. The following parameters were used for the experiment, listed as Varian commands:

| | |
|---|---|
| temp = 23 | dm = 'nny' (inverse-gated decoupling) |
| d1 = 5 (initial delay) | at = 0.5 (acquisition time) |
| setsw(180, 0) (spectral width, in ppm) | bs = 64 (block size for FID) |
| nt = 4416 (number of scans) | |
| pw = 7.0 (pulse width) | pw90 = 7.0 (90° pulse width) |

The KIE was reported as the area of the protonated peak over that of the deuterated peak. The experiment was run in triplicate and each was analyzed by NMR. An average value was calculated with error reported as a standard deviation.

[Mn($^t$BuPc)]Cl: $k_H/k_D$=1.62+0.06 (1.56, 1.67, 1.64)

(±)-4-deuterio-4-phenyl-tetrahydro-1,2,3-oxathiazine-2,2-dioxide [S52]

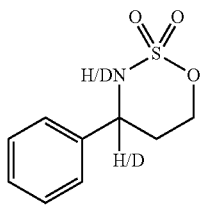

3-Phenylpropyl sulfamate 49 (43.1 mg, 0.200 mmol, 1.0 equiv), 3-phenylpropyl-3,3-$d_2$ sulfamate 49-$d_2$ (43.5 mg, 0.200 mmol, 1.0 equiv), [Mn($^t$BuPc)]Cl (16.6 mg, 0.020 mmol, 0.10 equiv), AgSbF$_6$ (6.9 mg, 0.020 mmol, 0.10 equiv), PhI(OPiv)$_2$ (162.5 mg, 0.400 mmol, 2.0 equiv) and 9:1 C$_6$H$_6$/MeCN (400 μL, 0.5M) were used. Flash column chromatography on silica (35 mm fritted glass column, 150 mm SiO$_2$) using 3:1 hexanes/EtOAc as eluent gave the deuterated and protonated oxathiazinanes as a mixture. This compound has been reported and fully characterized previously by our group (Paradine, S. M.; White, M. C. *J. Am. Chem. Soc.* 2012, 134, 2036).

Example 13. Diversification of Complex Molecules

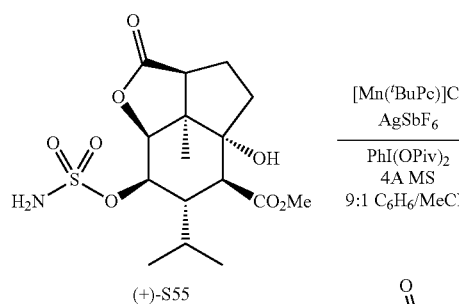

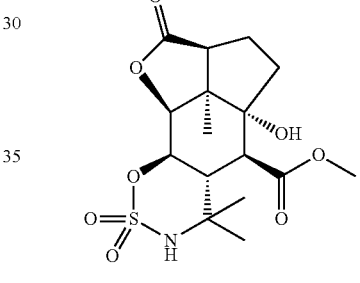

(+)-tetrahydropicrotoxin-(3-sulfamoyloxy)-15-methyl ester [S55]

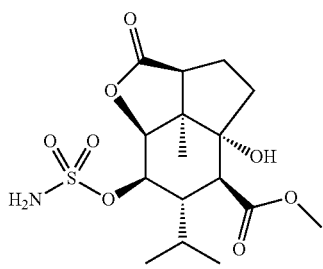

Prepared according to method B. 1.328 g (4.25 mmol) of (+)-tetrahydropicrotoxin-(3-hydroxy)-15-methyl ester (Bigi, M. A.; Reed, S. A.; White, M. C. *Nat. Chem.* 2011, 3, 216) were used, along with Et$_3$N (1.48 mL, 10.6 mmol, 2.5 equiv), ClSO$_2$NCO (923 μL, 10.6 mmol, 2.5 equiv), formic acid (400 μL, 10.6 mmol, 2.5 equiv) and CH$_2$Cl$_2$ (6 mL+6 mL). Flash column chromatography on silica (35 mm fritted glass column, 150 mm SiO$_2$) using 30% acetone/hexanes→40% acetone/hexanes as eluent gave 590 mg (1.50 mmol) of pure product as a white solid (35% yield).

$^1$H-NMR (500 MHz, CDCl$_3$) δ 4.95 (br. s, 2H), 4.80 (d, J=3.5 Hz, 1H), 4.71 (dd, J=10.0, 4.0 Hz, 1H), 3.75 (s, 3H), 2.79 (d, J=7.5 Hz, 1H), 2.65 (d, J=12.5 Hz, 1H), 2.36 (ddd, J=12.5, 11.0, 2.0 Hz, 1H), 2.22-2.07 (m, 3H), 1.95 (td, J=14.0, 6.5 Hz, 1H), 1.86-1.80 (m, 1H), 1.58 (dd, J=14.0, 5.5 Hz, 1H), 1.34 (s, 3H), 1.10 (d, J=7.0 Hz, 3H), 1.00 (d, J=7.0 Hz, 3H); $^{13}$C-NMR (125 MHz, CDCl$_3$) δ 179.5, 172.3, 83.2, 81.3, 78.7, 54.9, 53.1, 52.3, 52.1, 39.3, 37.7, 29.1, 27.6, 21.3, 19.7, 16.8; IR (ATR, cm$^{-1}$) 3254, 2960, 1760, 1720, 1566, 1438, 1371, 1236, 1015, 965, 931, 825, 796; [α]$^{25}_D$=+78.1° (c=1.0, CHCl$_3$); HRMS (ESI) m/z calculated for C$_{16}$H$_{26}$NO$_8$S [M+H]$^+$: 392.1379, found 392.1383.

(+)-tetrahydropicrotoxin-3-(2,2-dioxido-1,2,3-oxathiazinan-3-yl)-15-methyl ester [53]

(+)-tetrahydropicrotoxin-(3-sulfamoyloxy)-15-methyl ester S55 (78.3 mg, 0.200 mmol, 1.0 equiv), [Mn($^t$BuPc)]Cl (16.6 mg, 0.020 mmol, 0.10 equiv), AgSbF$_6$ (6.9 mg, 0.020 mmol, 0.10 equiv), PhI(OPiv)$_2$ (163 mg, 0.400 mmol, 2.0 equiv), 50 mg crushed 4 Å MS, and 9:1 C$_6$H$_6$/MeCN (800 μL, 0.5M) were used. Reaction stirred at rt for 17 h. Product was purified via flash column chromatography on silica (35 mm fritted glass column, 150 mm SiO$_2$) using 35% acetone/hexanes. Pure product was isolated as a white solid.

Run 1: (47.6 mg, 0.122 mmol, 61%), <10% rsm. Run 2: (44.6 mg, 0.115 mmol, 57%), <10% rsm. Run 3: (42.9 mg, 0.110 mmol, 55%), <10% rsm. Ave: 57% yield±2.1, <10% rsm.

$^1$H-NMR (500 MHz, acetone-d$_6$) δ 6.28 (s, 1H), 4.96 (dd, J=11.5, 3.5 Hz, 1H), 4.69 (d, J=3.5 Hz, 1H), 4.15 (br. s, 1H), 3.71 (s, 3H), 2.86 (d, J=7.5 Hz, 1H), 2.76 (d, J=12.0 Hz, 1H), 2.31 (t, J=12.0 Hz, 1H), 2.21-2.13 (m, 1H), 1.92-1.81 (m, 3H), 1.51 (s, 3H), 1.46 (s, 3H), 1.24 (s, 3H); $^{13}$C-NMR (125 MHz, acetone-d$_6$) δ 179.2, 173.0, 83.8, 82.9, 79.0, 59.5, 55.3, 52.4, 52.2, 51.6, 40.5, 38.3, 30.9, 27.8, 21.3, 19.2; IR (ATR, cm$^{-1}$) 3582, 3190, 2954, 1777, 1711, 1443, 1397, 1363, 1289, 1224, 1196, 1154, 1092, 1049, 993, 975, 938, 920, 903, 865, 839, 732, 707; [α]$^{23}$D=+66.7° (c=0.5, acetone); HRMS (ESI) m/z calculated for C$_{16}$H$_{24}$NO$_8$S [M+H]$^+$: 390.1223, found 390.1218.

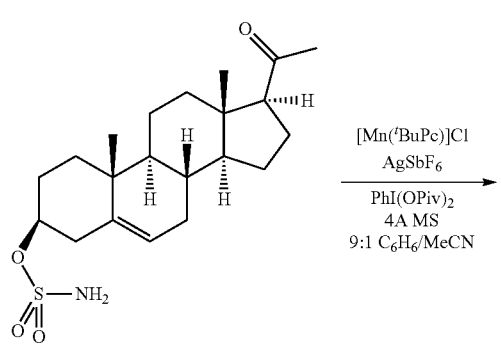

(+)-S56

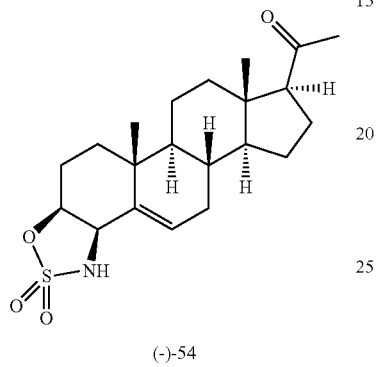

(−)-54

(+)-Pregenolyl Sulfamate [S56]

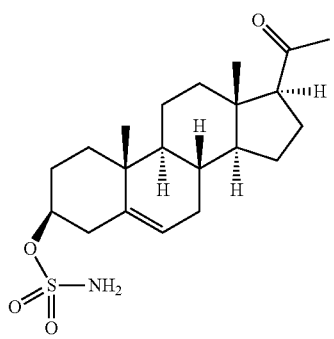

Prepared according to method B. 1.58 g (5.00 mmol) of (±)-pregnenolone were used, along with Et₃N (1.05 mL, 7.50 mmol, 1.5 equiv), ClSO₂NCO (653 μL, 7.50 mmol, 1.5 equiv), formic acid (283 μL, 7.50 mmol, 1.5 equiv) and CH₂Cl₂ (3.8 mL+7.1 mL). Flash column chromatography on silica (45 mm fritted glass column, 170 mm SiO₂) using 3:1 hexanes/EtOAc as eluent gave 967 mg (2.44 mmol) of pure product as a white solid (49% yield).

$^1$H-NMR (500 MHz, CDCl₃) δ 5.42 (dt, J=5.0, 2.0 Hz, 1H), 4.72 (br. s, 2H), 4.44 (tt, J 11.2, 5.3 Hz, 1H), 2.57-2.45 (m, 3H), 2.22-1.99 (m, 7H), 1.92 (dt, J=13.6, 3.7 Hz, 1H), 1.80-1.44 (m, 8H), 1.26-1.12 (m, 3H), 1.02 (s, 3H), 0.98 (dd, J=11.3, 4.9 Hz, 1H), 0.63 (s, 3H); $^{13}$C-NMR (125 MHz, CDCl₃) δ 209.9, 139.0, 123.5, 83.1, 63.8, 56.9, 49.9, 44.1, 38.8, 38.8, 37.0, 36.5, 31.9, 31.7, 28.6, 24.6, 22.9, 21.2, 19.3, 13.4; IR (film, cm$^{-1}$) 3421, 3239, 3102, 2937, 1683, 1580, 1470, 1451, 1376, 1352, 1174, 978, 937, 857, 820, 729; [α]$_D^{25}$=+19.4° (c=0.62, CHCl₃); HRMS (ESI) m/z calculated for C₂₁H₃₄NO₄S [M+H]⁺: 396.2209, found 396.2208.

(−)-3,4-(2,2-dioxido-1,2,3-oxathiazinan-3-yl)-pregnenolone [54]

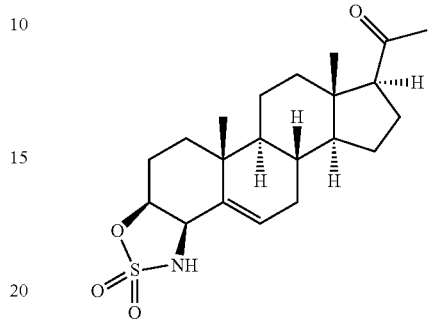

Pregenolyl sulfamate S56 (79.1 mg, 0.200 mmol, 1.0 equiv), [Mn($^t$BuPc)]Cl (16.6 mg, 0.020 mmol, 0.10 equiv), AgSbF₆ (6.9 mg, 0.020 mmol, 0.10 equiv), PhI(OPiv)₂ (325 mg, 0.800 mmol, 2.0 equiv), 100 mg crushed 4 Å MS, and 4:1 C₆H₆/MeCN (400 μL, 0.5M) were used. Reaction stirred at rt for 12 h. Product was purified via flash column chromatography on silica (35 mm fritted glass column, 120 mm SiO₂) using 20% EtOAc/hexanes→30% EtOAc/hexanes→40% EtOAc/hexanes. Pure product was isolated as a white solid.

Run 1: (41.9 mg, 0.106 mmol, 53%), <5% rsm. Run 2: (45.5 mg, 0.116 mmol, 58%), <5% rsm. Run 3: (42.3 mg, 0.107 mmol, 54%), <5% rsm. Ave: 55% yield±2.2, <5% rsm.

$^1$H-NMR (500 MHz, CDCl₃) δ 5.82 (dd, J=4.8, 2.3 Hz, 1H), 4.75 (dt, J=11.5, 6.0 Hz, 1H), 4.54 (t, J=5.5 Hz, 1H), 4.38 (d, J=5.0 Hz, 1H), 2.53 (t, J=8.8 Hz, 1H), 2.33-2.14 (m, 3H), 2.13 (s, 3H), 2.11-2.04 (m, 2H), 1.92 (dt, J=14.0, 4.0 Hz, 1H), 1.71-1.57 (m, 5H), 1.49-1.41 (m, 2H), 1.28-1.22 (m, 2H), 1.21 (s, 3H), 1.20-1.09 (m, 2H), 1.02-0.96 (m, 1H), 0.64 (s, 3H); $^{13}$C-NMR (125 MHz, CDCl₃) δ 209.5, 135.9, 133.3, 84.0, 63.6, 62.1, 56.9, 49.2, 44.0, 38.6, 36.2, 33.6, 32.1, 31.6, 31.5, 24.5, 23.8, 22.9, 21.2, 20.7, 13.4; IR (film, cm$^{-1}$) 3252, 2944, 1698, 1454, 1339, 1291, 1174, 966, 941, 754, 667, 587, 479; [α]$_D^{25}$=−23.6° (c=0.68, CHCl₃); HRMS (ESI) m/z calculated for C₂₁H₃₂NO₄S [M+H]⁺: 394.2052, found 394.2053.

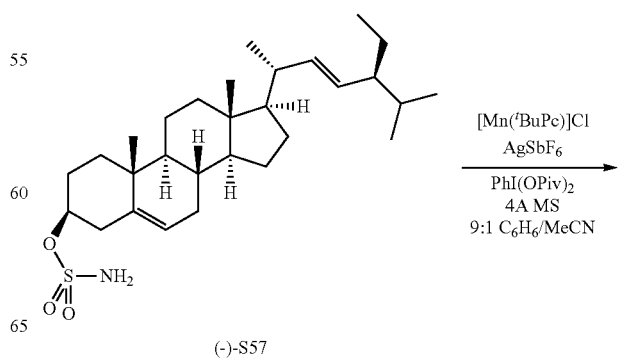

(−)-S57

(−)-3,4-(2,2-dioxido-1,2,3-oxathiazinan-3-yl)-stigmasterol [55]

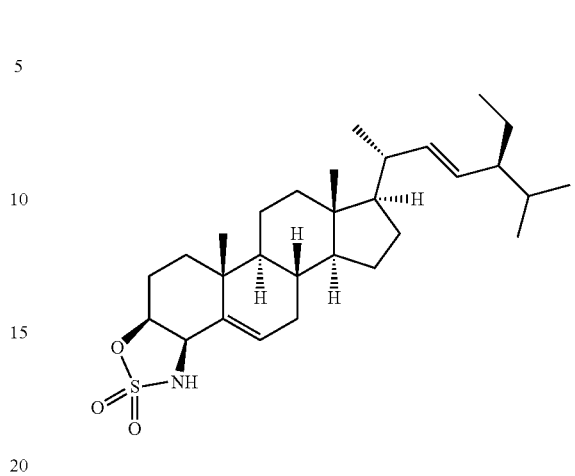

Stigmasteryl sulfamate S57 (98.4 mg, 0.200 mmol, 1.0 equiv), Mn(tBuPc)]Cl (16.6 mg, 0.020 mmol, 0.10 equiv), AgSbF$_6$ (6.9 mg, 0.020 mmol, 0.10 equiv), PhI(OPiv)$_2$ (325 mg, 0.800 mmol, 2.0 equiv), 100 mg crushed 4 Å MS, and 4:1 C$_6$H$_6$/MeCN (400 μL, 0.5M) were used. Reaction stirred for 12 h. Product was purified via flash column chromatography on silica (35 mm fritted glass column, 120 mm SiO$_2$) using 10% acetone/hexanes→15% acetone/hexanes. Pure product was isolated as a white solid.

Run 1: (61 mg, 0.125 mmol, 63%), <5% rsm. Run 2: (64 mg, 0.131 mmol, 66%), <5% rsm. Run 3: (67 mg, 0.137 mmol, 69%), <5% rsm. Average: 66% yield±2.1, <5% rsm.

$^1$H-NMR (500 MHz, CDCl$_3$) δ 5.82 (dd, J=4.7, 2.2 Hz, 1H), 5.15 (dd, J=15.1, 8.6 Hz, 1H), 5.02 (dd, J=15.1, 8.6 Hz, 1H), 4.74 (dt, J=10.7, 6.0 Hz, 1H), 4.53 (t, J=5.6 Hz, 1H), 4.29 (d, J=5.3 Hz, 1H), 2.27 (tdd, J=13.9, 10.8, 3.5 Hz, 1H), 2.14 (dt, J=17.2, 4.5 Hz, 1H), 2.08-1.99 (m, 3H), 1.91 (dt, J=14.0, 4.0, 1H), 1.72 (dtd, J=13.6, 9.4, 5.9 Hz, 1H), 1.63-1.39 (m, 10H), 1.28-1.25 (m, 2H), 1.23-0.99 (m, 10H), 0.93-0.90 (m, 2H), 0.88-0.75 (m, 9H), 0.71 (s, 3H); $^{13}$C-NMR (125 MHz, CDCl$_3$) δ 138.3, 135.9, 133.9, 129.7, 84.4, 62.4, 57.1, 56.1, 51.5, 49.5, 42.4, 40.7, 39.6, 36.3, 33.7, 32.3, 32.1, 31.7, 29.1, 27.3, 25.6, 24.5, 23.9, 21.4, 21.3, 20.8, 19.2, 12.5, 12.3; IR (film, cm$^{-1}$) 3326, 2955, 2867, 1456, 1369, 1321, 1190, 1173, 1021, 987, 940, 925, 820, 790, 752, 688; $[α]_D^{25}$=−60.1° (c=0.62, CHCl$_3$); HRMS (ESI) m/z calculated for C$_{29}$H$_{48}$NO$_3$S [M+H]$^+$: 490.3355, found 490.3362.

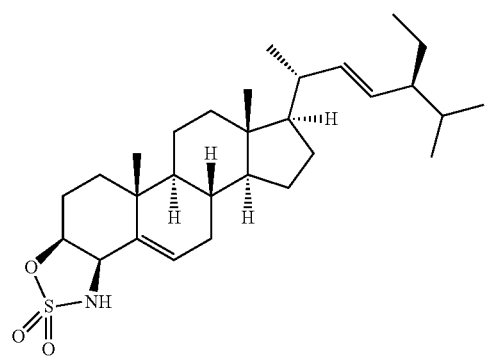

(−)-stigmasteryl sulfamate [S57]

Prepared according to method B. 2.06 g (5.00 mmol) of (−)-stigmasterol were used, along with Et$_3$N (1.38 mL, 10.0 mmol, 2.0 equiv), ClSO$_2$NCO (870 μL, 10.0 mmol, 2.0 equiv), formic acid (377 μL, 10.0 mmol, 2.0 equiv) and CH$_2$Cl$_2$ (5.0 mL+7.1 mL). Flash column chromatography on silica (45 mm fritted glass column, 170 mm SiO$_2$) using 4:1 hexanes/acetone as eluent gave 1.40 g (2.85 mmol) of pure product as a white solid (57% yield).

$^1$H-NMR (500 MHz, CDCl$_3$) δ 5.42-5.40 (m, 1H), 5.15 (dd, J=15.2, 8.6 Hz, 1H), 5.02 (dd, J=15.2, 8.5 Hz, 1H), 4.83 (br. s, 2H), 4.43 (tt, J=11.0, 5.3 Hz, 1H), 2.56-2.46 (m, 2H), 2.11-1.95 (m, 4H), 1.91 (dt, J=13.5, 3.7 Hz, 1H), 1.81-1.67 (m, 2H), 1.56-1.40 (m, 9H), 1.28-0.91 (m, 13H), 0.85-0.79 (m, 9H), 0.70 (s, 3H); $^{13}$C-NMR (125 MHz, CDCl$_3$) δ 138.9, 138.4, 129.5, 123.8, 83.5, 56.9, 56.1, 51.4, 50.1, 42.3, 40.7, 39.7, 38.9, 37.1, 36.6, 32.0, 31.9, 29.1, 28.7, 25.6, 24.5, 21.4, 21.3, 21.2, 19.4, 19.1, 12.4, 12.2; IR (film, cm$^{-1}$) 3323, 3262, 2962, 2937, 2893, 2866, 1569, 1458, 1381, 1328, 1189, 968, 869, 807, 737; $[α]_D^{25}$=−50.8° (c=0.5, CHCl$_3$); HRMS (ESI) m/z calculated for C$_{29}$H$_{49}$NO$_3$SNa [M+Na]$^+$: 514.3331, found 514.3333.

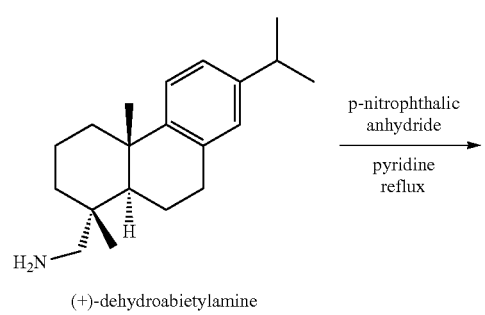

(+)-dehydroabietylamine p-nitrophthalic anhydride
→
pyridine reflux

115

-continued

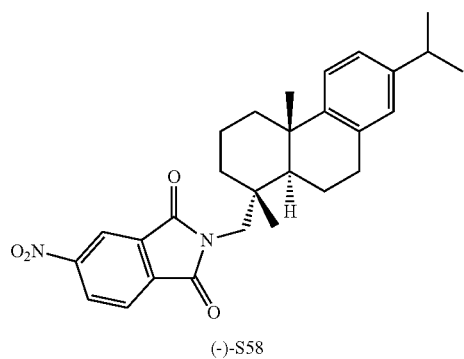
(−)-S58

AcCl
AlCl₃
⟶
DCE
0° C.→rt

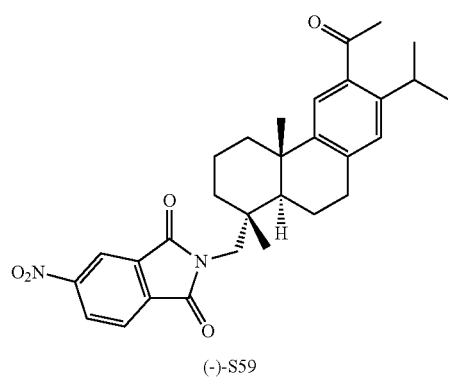
(−)-S59 mCPBA
⟶
CF₃CO₂H

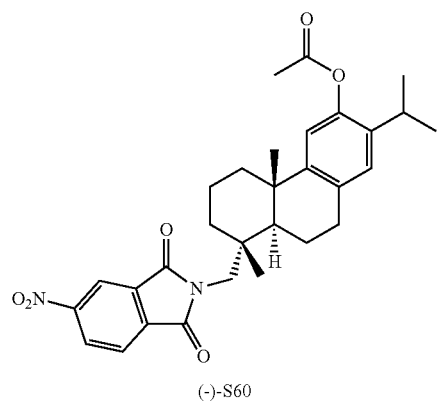
(−)-S60

NaHCO₃
⟶
H₂O, MeOH

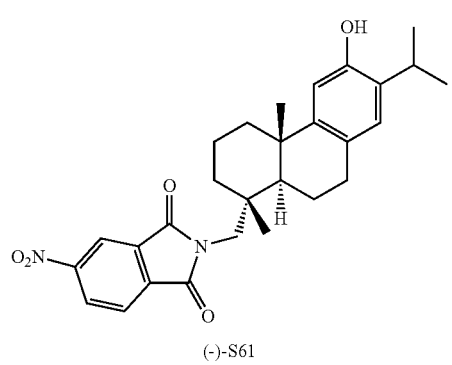
(−)-S61

ClSO₂NH₂
⟶
DMA

116

-continued

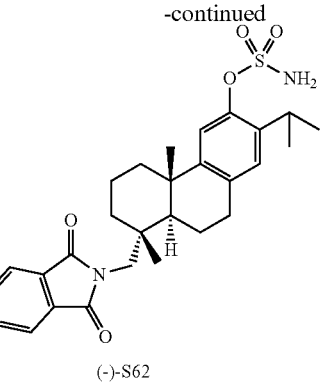
(−)-S62

[Mn(ᵗBuPc)]Cl
AgSbF₆
⟶
PhI(OPiv)₂
4Å MS
9:1 C₆H₆/MeCN

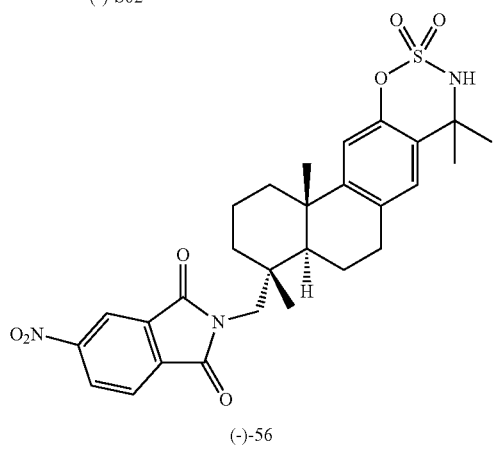
(−)-56

(−)-(N-nitroisoindolyl)dihydroabietylamine [S58]

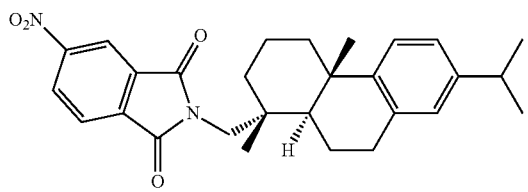 [SMILES: CC(C)c1ccc2c(c1)CC[C@H]1[C@](C)(CN3C(=O)c4ccc([N+](=O)[O-])cc4C3=O)CCC[C@]21C]

(+)-Dehydroabietylamine (2.89 g, 90% purity) was dissolved in 21 mL pyridine. 4-nitrophthalic anhydride (2.145 g, 11.1 mmol) was added and the reaction was allowed to stir under reflux overnight. Upon completion, the reaction was poured into 80 mL ice and extracted with Et₂O (3×50 mL). The combined organic layer was washed with 2M HCl (2×30 mL), H₂O (2×30 mL) and brine (30 mL), then dried over MgSO₄. The product was loaded on celite and was purified via MPLC separation (Silica 40 g Gold column, 40 mL/min, hexanes→5% EtOAc/hexanes) to give 2.301 g (5.0 mmol) S58.

$^1$H NMR (500 MHz, CDCl₃) δ 8.63 (d, J=1.9 Hz, 1H), 8.59 (dd, J=8.1, 2.0 Hz, 1H), 8.01 (d, J=8.1 Hz, 1H), 7.13 (d, J=8.1 Hz, 1H), 6.97 (dd, J=7.9, 2.1 Hz, 1H), 6.94-6.92 (s, 1H), 3.76 (d, J=13.8 Hz, 1H), 3.56 (d, J=13.8 Hz, 1H), 3.06-2.96 (m, 2H), 2.82 (hept, J=6.9 Hz, 1H), 2.25 (ddt, J=12.0, 8.2, 3.2 Hz, 2H), 1.84 (m, 1H), 1.68 (m, 2H), 1.52 (dt, J=13.4, 3.5 Hz, 1H), 1.44-1.38 (m, 1H), 1.36-1.25 (m, 2H), 1.24 (s, 3H), 1.22 (d, J=7.0 Hz, 6H), 1.08 (s, 3H); $^{13}$C-NMR (125 MHz, CDCl₃) δ 167.2, 166.9, 151.7, 147.1, 145.7, 136.4, 134.9, 133.4, 129.2, 127.1, 124.5, 123.8 (2 peaks), 118.7, 49.5, 45.1, 39.7, 38.1, 37.6, 37.0, 33.4, 30.0, 25.9, 24.1, 24.0, 19.5, 19.2, 18.5; IR (film, cm$^{-1}$): 2958, 2955, 2872, 1780, 1722, 1543, 1496, 1437, 1383, 1344, 1092, 910; [α]$^{27}_D$=−66.3° (c=0.63, CHCl$_3$); HRMS (ESI) m/z calculated for C$_{28}$H$_{33}$N$_2$O$_4$ [M+H]$^+$: 461.2440, found 461.2452.

(−)-12-acetyl-(N-nitroisoindolyl)dihydroabietylamine [S59]

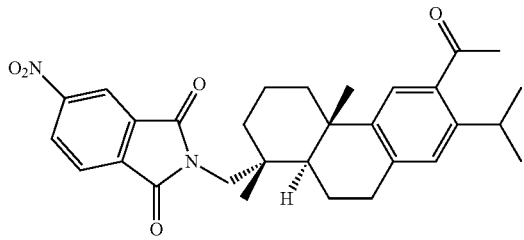 [SMILES: CC(=O)c1cc2c(cc1C(C)C)CC[C@H]1[C@](C)(CN3C(=O)c4ccc([N+](=O)[O-])cc4C3=O)CCC[C@]21C]

S58 (1.842 g, 4.00 mmol, 1.0 equiv) was dissolved in 25 mL (CHCl)$_2$ in a flame dried 100 mL recovery flask. Acetyl chloride (1.099 g, 14.0 mmol, 3.5 equiv) and AlCl$_3$ (1.600 g, 12.0 mmol, 3.0 equiv) was added at 0° C. The reaction was allowed to warm up slowly to rt and stirred for 22 h. The reaction mixture was poured into 30 mL cold 6M HCl and extracted with Et$_2$O (3×50 mL). The combined organic layers were washed by brine and dried over CaCl$_2$. Flash column chromatography on silica (50 mm fritted glass column, 200 mL SiO$_2$) using 10% EtOAc/hexanes→15% EtOAc/hexanes as eluent gave 1.889 g (3.76 mmol) product as a pale yellow solid (94% yield).

$^1$H NMR (500 MHz, CDCl$_3$) δ 8.63 (d, J=2.0 Hz, 1H), 8.59 (dd, J=8.1, 2.0 Hz, 1H), 8.01 (d, J=8.1 Hz, 1H), 7.35 (s, 1H), 7.08 (s, 1H), 3.76 (d, J=13.9 Hz, 1H), 3.56 (d, J=13.9 Hz, 1H), 3.44 (hept, J=6.8 Hz, 1H), 3.02 (dd, J=9.0, 4.5 Hz, 2H), 2.51 (s, 3H), 2.29-2.25 (m, 2H), 1.89-1.80 (m, 1H), 1.78-1.64 (m, 2H), 1.55-1.51 (m, 1H), 1.43-1.26 (m, 3H), 1.24 (s, 3H), 1.22 (d, J=6.9 Hz, 3H), 1.18 (d, J=6.9 Hz, 3H), 1.08 (s, 3H); $^{13}$C-NMR (125 MHz, CDCl$_3$) δ 203.3, 167.3, 167.0, 151.8, 146.8, 145.0, 139.1, 136.4, 136.3, 133.4, 129.3, 127.3, 124.6, 124.1, 118.8, 49.5, 45.1, 39.7, 38.1, 37.6, 37.0, 30.6, 30.1, 28.8, 26.0, 24.3, 24.2, 19.4, 19.3, 18.5; IR (ATR, cm$^{-1}$): 2929, 1781, 1719, 1678, 1539, 1435, 1384, 1338, 1262, 1232, 1194, 1088; [α]$^{26}_D$=−23.8° (c=1.0, CHCl$_3$); HRMS (ESI) m/z calculated for C$_{30}$H$_{35}$N$_2$O$_5$ [M+H]$^+$: 503.2546, found 503.2527.

(−)-12-acetoxy-(N-nitroisoindolyl)dihydroabietylamine [S60]

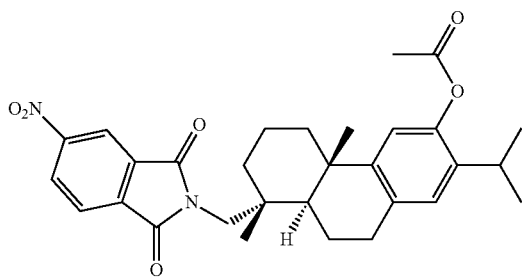 [SMILES: CC(=O)Oc1cc2c(cc1C(C)C)CC[C@H]1[C@](C)(CN3C(=O)c4ccc([N+](=O)[O-])cc4C3=O)CCC[C@]21C]

S59 (1.898 g, 3.76 mmol, 1.0 equiv.) was dissolved in 10 mL anhydrous CH$_2$Cl$_2$. mCPBA (2.292 g, 9.30 mmol, 2.5 equiv, 70% in H$_2$O) was added at 0° C. followed by dropwise addition of CF$_3$CO$_2$H (429 mg, 3.76 mmol, 1.0 equiv.). The reaction was allowed to warm up to rt and stir for 24 h. The reaction was sequentially washed by 10% Na$_2$SO$_3$ (10 mL), H$_2$O (10 mL), saturated aq. NaHCO$_3$ (10 mL), H$_2$O (10 mL), then organic layer was dried over CaCl$_2$. Flash column chromatography on silica (50 mm fritted glass column, 300 mL SiO$_2$) using 10% EtOAc/hexanes→15% EtOAc/hexanes as eluent gave 1.622 g (3.13 mmol) product as white solid (83% yield).

$^1$H NMR (500 MHz, CDCl$_3$) δ 8.64-8.63 (m, 1H), 8.59 (dd, J=8.2, 1.8 Hz, 1H), 8.01 (dd, J=8.1, 1.6 Hz, 1H), 6.97 (s, 1H), 6.76 (s, 1H), 3.78 (d, J=13.9, 1H), 3.51 (d, J=13.8, 1H), 3.0-2.97 (m, 2H), 2.89 (hept, J=6.8 Hz, 1H), 2.30-2.23 (m, 1H), 2.28 (s, 3H), 2.15-2.12 (m, 1H), 1.85-1.80 (m, 1H), 1.71-1.59 (m, 2H), 1.51 (dq, J=13.5, 2.7 Hz, 1H), 1.37 (dd, J=12.2, 2.0 Hz, 1H), 1.30 (ddd, J=21.0, 12.8, 4.1 Hz, 2H), 1.22 (s, 3H), 1.19 (d, J=6.8 Hz, 3H), 1.15 (d, J=7.0 Hz, 3H), 1.07 (s, 3H); $^{13}$C-NMR (125 MHz, CDCl$_3$) δ 170.1, 167.3, 167.0, 151.8, 148.4, 146.1, 137.0, 136.5, 133.5, 133.2, 129.3, 127.3, 124.6, 118.9, 117.6, 49.4, 44.5, 39.8, 38.1, 37.7, 37.1, 29.5, 27.2, 25.9, 23.1 (2 peaks), 21.1, 19.5, 19.3, 18.5; IR (ATR, cm$^{-1}$): 2931, 1756, 1719, 1622, 1540, 1497, 1435, 1397, 1383, 1339, 1205, 1164, 1087, 1060, 1041, 1017, 941, 911; [α]$^{26}_D$=−23.7° (c=0.94, CHCl$_3$); HRMS (ESI) m/z calculated for C$_{30}$H$_{35}$N$_2$O$_6$ [M+H]$^+$: 519.2495, found 519.2488.

(−)-12-hydroxy-(N-nitroisoindolyl)dihydroabietylamine [S61]

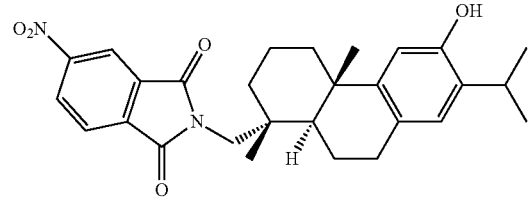 [SMILES: CC(C)c1cc2c(cc1O)[C@@]1(C)CCC[C@@](C)(CN3C(=O)c4ccc([N+](=O)[O-])cc4C3=O)[C@@H]1CC2]

S60 (1.540 g, 2.97 mmol, 1.0 equiv) was taken up in 8 mL MeOH. NaHCO$_3$ (1.072 g, 12.8 mmol, 4.3 equiv) was added into the mixture followed by 1 drop of H$_2$O. The reaction was stirred at rt for 24 h then 40° C. for 72 h. Upon completion as determined by TLC, CH$_2$Cl$_2$ (20 mL) and H$_2$O (20 mL) were added and the mixture was acidified with 3M H$_2$SO$_4$ to pH-5. The aqueous layer was extracted with TBME (3×30 mL). The combined organic layers were washed with brine and dried over MgSO$_4$. Flash column chromatography on silica (50 mm fritted glass column, 200 mL SiO$_2$) using 20% EtOAc/hexanes as eluent gave 896 mg (1.88 mmol) product as an orange solid (63% yield).

$^1$H NMR (500 MHz, CDCl$_3$) δ 8.63 (d, J=1.8 Hz, 1H), 8.58 (dd, J=8.2, 1.8 Hz, 1H), 8.01 (dd, J=8.1, 1.6 Hz, 1H), 6.87 (s, 1H), 6.59 (s, 1H), 4.63 (br. s, 1H), 3.75 (dd, J=13.9, 1.6 Hz, 1H), 3.57 (dd, J=13.8, 1.6 Hz, 1H), 3.10 (hept, J=6.8 Hz, 1H), 2.99-2.88 (m, 2H), 2.24-2.19 (m, 1H), 2.17-2.13 (m, 1H), 1.85-1.76 (m, 1H), 1.75-1.60 (m, 2H), 1.51 (dq, J=13.5, 2.7 Hz, 1H), 1.38 (dd, J=12.2, 2.0 Hz, 1H), 1.30 (ddd, J=21.0, 12.8, 4.1 Hz, 2H), 1.25-1.19 (m, 9H), 1.07 (s, 3H); $^{13}$C-NMR (125 MHz, CDCl$_3$) δ 167.3, 167.0, 151.9, 150.8, 148.2, 136.5, 133.5, 131.8, 129.3, 127.2, 127.0, 124.6, 118.8, 110.7, 49.7, 45.3, 39.8, 38.2, 37.7, 37.2, 29.4, 26.9, 25.8, 22.8, 22.7, 19.7, 19.3, 18.6; IR (thin film, cm$^{-1}$): 2960, 2935, 2892, 1780, 1720, 1620, 1543, 1466, 1437, 1416, 1398, 1385, 1344, 1165, 1090, 910; $[\alpha]^{26}_D = -41.6°$ (c=0.93, CHCl$_3$); HRMS (ESI) m/z calculated for C$_{28}$H$_{33}$N$_2$O$_5$ [M+H]$^+$: 477.2389, found 477.2388.

(−)-12-sulfamoyloxy-(N-nitroisoindolyl)dihydroabietylamine [S62]

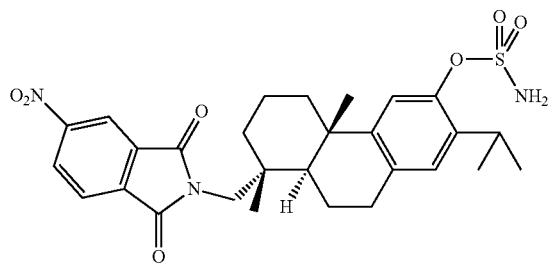 [SMILES: CC(C)c1cc2c(cc1OS(N)(=O)=O)[C@@]1(C)CCC[C@@](C)(CN3C(=O)c4ccc([N+](=O)[O-])cc4C3=O)[C@@H]1CC2]

Prepared according to method C. S61 (238 mg, 0.50 mmol, 1.0 equiv), ClSO$_2$NCO (65 µL, 0.75 mmol, 1.5 equiv), formic acid (28 µL, 0.75 mmol, 1.5 equiv), MeCN (1 mL) and DMA (1 mL) were used. Flash column chromatography on silica (35 mm fritted glass column, 150 mm SiO$_2$) using 20% EtOAc/hexanes as eluent gave 189 mg (0.34 mmol) of pure product as a white solid (68% yield).

$^1$H NMR (500 MHz, CDCl$_3$) δ 8.64 (s, 1H), 8.59 (dd, J=8.2, 1.9 Hz, 1H), 8.02 (d, J=8.2 Hz, 1H), 7.16 (s, 1H), 7.00 (s, 1H), 4.85 (br. s, 2H), 3.75 (d, J=13.8 Hz, 1H), 3.55 (d, J=13.8 Hz, 1H), 3.26 (hept, J=7.5, 7.0 Hz, 1H), 2.98 (dd, J=8.9, 4.5 Hz, 2H), 2.28-2.17 (m, 2H), 1.82 (ddd, J=18.0, 12.8, 9.0 Hz, 1H), 1.67 (dtd, J=18.4, 10.3, 4.0 Hz, 2H), 1.56-1.50 (m, 1H), 1.36-1.14 (m, 12H), 1.07 (s, 3H); $^{13}$C-NMR (125 MHz, CDCl$_3$) δ 167.4, 167.0, 151.8, 148.7, 145.7, 138.2, 136.4, 134.6, 133.4, 129.4, 127.7, 124.7, 118.9, 117.2, 49.5, 44.8, 39.7, 38.0, 37.8, 36.9, 29.5, 26.6, 25.8, 23.5, 23.4, 19.4, 19.3, 18.4; IR (thin film, cm$^{-1}$): 3402, 3383, 3296, 3107, 2964, 2937, 2870, 1780, 1722, 1624, 1543, 1495, 1464, 1437, 1385, 1344, 1248, 1190, 1153, 1088, 933; $[\alpha]^{25}_D = -23.1°$ (c=0.86, CHCl$_3$); HRMS (ESI) m/z calculated for C$_{28}$H$_{34}$N$_3$O$_7$S [M+H]$^+$: 556.2117, found 556.2128.

(−)-12,15-(2,2-dioxido-1,2,3-oxathiazinan-3-yl)-(N-nitroisoindolyl)dihydroabietylamine [56]

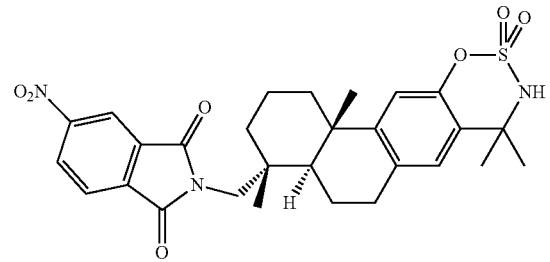 [SMILES: CC1(C)NS(=O)(=O)Oc2cc3c(cc21)CC[C@H]1[C@](C)(CN2C(=O)c4ccc([N+](=O)[O-])cc4C2=O)CCC[C@]31C]

S62 (111.1 mg, 0.200 mmol, 1.0 equiv), [Mn($^t$BuPc)]Cl (16.6 mg, 0.020 mmol, 0.10 equiv), AgSbF$_6$ (6.9 mg, 0.020 mmol, 0.10 equiv), crushed 4 Å MS (50 mg), PhI(OPiv)$_2$ (163 mg, 0.400 mmol, 2.0 equiv) and 9:1 C$_6$H$_6$/MeCN (400 µL) were used. The reaction was stirred for 24 h at rt (~20° C.). Flash column chromatography on silica (35 mm fritted glass column, 150 mm SiO$_2$) using 20% EtOAc/hexanes→30% EtOAc/hexanes with 0.5% AcOH as eluent gave product as slightly yellow solid.

Run 1: (77.7 mg, 0.140 mmol, 70%), 0% rsm. Run 2: (75.8 mg, 0.137 mmol, 68%), 0% rsm. Run 3: (79.1 mg, 0.143 mmol, 72%), 0% rsm. Average: 70% yield±2.0, 0% rsm.

$^1$H NMR (500 MHz, CDCl$_3$) δ 8.64 (d, J=2.0 Hz, 1H), 8.59 (dd, J=8.1, 2.0 Hz, 1H), 8.02 (d, J=8.1 Hz, 1H), 6.88 (s, 1H), 6.80 (s, 1H), 4.50 (d, J=4.2 Hz, 1H), 3.75 (d, J=13.8 Hz, 1H), 3.54 (d, J=13.9 Hz, 1H), 2.97 (dd, J=9.1, 4.6 Hz, 2H), 2.27 (dtd, J=11.5, 4.7, 2.4 Hz, 1H), 2.16-2.13 (m, 1H), 1.82 (tt, J=13.0, 9.1 Hz, 1H), 1.73-1.63 (m, 1H), 1.69 (s, 3H), 1.67 (s, 3H), 1.54-1.51 (m, 1H), 1.34-1.24 (m, 4H), 1.21 (s, 3H), 1.07 (s, 3H); $^{13}$C-NMR (125 MHz, CDCl$_3$) δ 167.3, 167.0, 151.9, 151.5, 147.4, 136.4, 133.4, 132.9, 129.4, 126.8, 125.0, 124.7, 118.9, 114.4, 60.1, 49.4, 44.6, 39.7, 38.0, 37.9, 36.9, 31.0, 30.9, 29.3, 25.7, 19.4, 19.3, 18.4; IR (thin film, cm$^{-1}$): 3267, 2933, 2870, 1780, 1720, 1624, 1541, 1493, 1429, 1400, 1387, 1344, 1207, 1173, 1155, 1092, 910; $[\alpha]^{25}_D = -43.6°$ (c=0.66, CHCl$_3$); HRMS (ESI) m/z calculated for C$_{28}$H$_{32}$N$_3$O$_7$S [M+H]$^+$: 554.1961, found 554.1968.

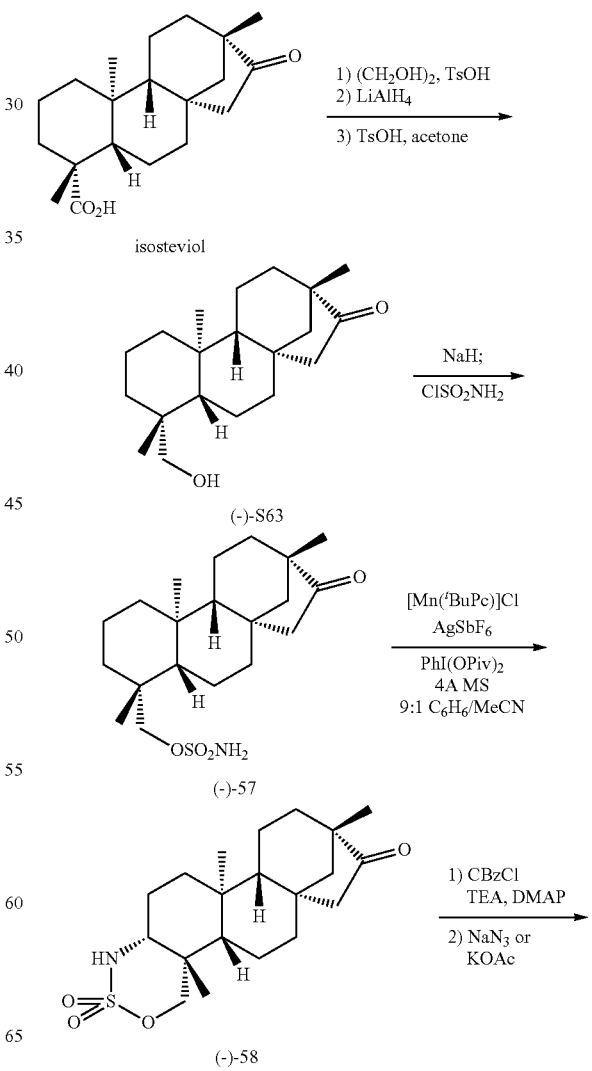

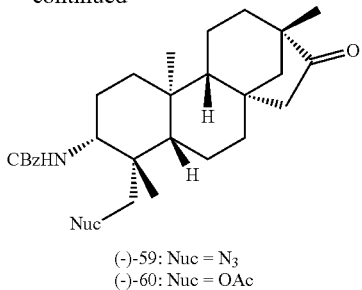

(−)-59: Nuc = N₃
(−)-60: Nuc = OAc (−)-18-hydroxy-13-methyl-17-norkauran-16-one
[S63]

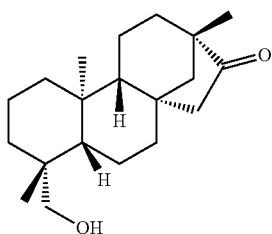

(−)-Isosteviol (2.229 g, 7.00 mmol, 1.0 equiv) was suspended in benzene (6 mL, ~1.2M) in a 25 mL round-bottom flask equipped with stir bar. Ethylene glycol (429 uL, 7.70 mmol, 1.1 equiv) and p-TSA (6.1 mg, 0.035 mmol, 0.005 equiv) were added, then flask was fitted with a Dean-Stark trap and condenser. Reaction stirred under reflux for 48 h. Upon completion, reaction was cooled to rt, diluted with CH₂Cl₂, and washed with H₂O (5 times). The organic layer was dried over MgSO₄ and concentrated in vacuo. Crude material was carried forward without additional purification.

LiAlH₄ (531 mg, 14.0 mmol, 2.0 equiv) was suspended in THF (35 mL) in a 250 mL multineck flask equipped with stir bar and reflux condenser. Isosteviol ketal from previous step was dissolved in remaining THF (35 mL) and added dropwise. Reaction was then heated to reflux and stirred 48 h. Upon completion, reaction was cooled to rt, diluted with Et₂O (100 mL), carefully quenched with dropwise addition of H₂O, then poured into a 500 mL Erylenmeyer flask containing sat. aq. Rochelle salt solution (150 mL). Once layers became clear, material was extracted with Et₂O (3×50 mL), then organic layer was dried over MgSO₄ and concentrated in vacuo. The resulting residue was suspended in acetone (14 mL, 0.5M) in a 50 mL round-bottom flask. p-TSA (12.1 mg, 0.070 mmol, 0.01 equiv) was added, then reaction stirred for 48 h at room temp. Upon completion, reaction was diluted with Et₂O (50 mL) and washed with H₂O (4×15 mL). Organic layer was dried over MgSO₄ and concentrated in vacuo. Flash column chromatography on silica (35 mm fritted glass column, 150 mm SiO₂) using 2:1 hexanes/EtOAc as eluent gave 1.037 g (3.41 mmol) of pure S63 as a white solid (49% yield over three steps).

$^1$H-NMR (500 MHz, CDCl₃) δ 3.74 (d, J=11.0 Hz, 1H), 3.44 (d, J=10.5 Hz, 1H), 2.64 (dd, J=18.5, 3.8 Hz, 1H), 1.82-1.73 (m, 2H), 1.71-1.61 (m, 5H), 1.57-1.48 (m, 3H), 1.43-1.20 (m, 7H), 1.07-1.05 (m, 2H), 0.99 (s, 3H), 0.97 (s, 3H), 0.96-0.88 (m, 1H), 0.86 (s, 3H); $^{13}$C-NMR (125 MHz, CDCl₃) δ 222.9, 65.6, 57.0, 55.6, 54.6, 48.8 (2 peaks), 41.8, 39.6, 39.5, 38.6, 37.7, 37.5, 35.6, 27.2, 20.4, 20.3, 20.0, 18.1, 15.6; IR (ATR, cm⁻¹) 3536, 2927, 2843, 1737, 1715, 1454, 1400, 1253, 1115, 1090, 1070, 1033, 975, 852; [α]$^{25}_D$=−40.7° (c=1.0, CHCl₃); HRMS (ESI) m/z calculated for C₂₀H₃₃O₂ [M+H]⁺: 305.2481, found 305.2479.

(−)-18-sulfamoyloxy-13-methyl-17-norkauran-16-one [57]

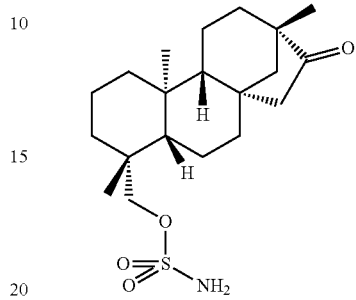

Prepared according to method A. 1.037 g (3.41 mmol) of S63 were used, along with NaH (94.6 mg, 3.75 mmol, 1.1 equiv), DMF (3 mL+2 mL), ClSO₂NCO (445 µL, 5.11 mmol, 1.5 equiv), formic acid (193 µL, 5.11 mmol, 1.5 equiv) and MeCN (2.5 mL). Flash column chromatography on silica (35 mm fritted glass column, 150 mm SiO₂) using 2:1 hexanes/EtOAc as eluent, followed by recrystallization from EtOAc layered with hexanes, gave 685 mg (1.79 mmol) of pure product as a white solid (52% yield).

$^1$H-NMR (500 MHz, CDCl₃) δ 4.67 (br. s, 2H), 4.35 (d, J=9.5 Hz, 1H), 3.97 (d, J=9.5 Hz, 1H), 2.63 (dd, J=18.5, 4.0 Hz, 1H), 1.83-1.62 (m, 7H), 1.59-1.36 (m, 6H), 1.30 (dq, J=13.0, 3.5 Hz, 1H), 1.27-1.18 (m, 2H), 1.12 (dd, J=12.5, 1.5 Hz, 1H), 1.09-1.02 (m, 1H), 1.04 (s, 3H), 0.98 (s, 3H), 0.94-0.88 (m, 1H), 0.88 (s, 3H); $^{13}$C-NMR (125 MHz, CDCl₃) δ 223.0, 74.3, 56.8, 55.5, 54.4, 48.9, 48.7, 41.5, 39.5, 39.2, 37.6, 37.4, 37.3, 35.7, 27.4, 20.3 (2 peaks), 20.0, 17.9, 15.7; IR (film, cm⁻¹) 3363, 3228, 2927, 2873, 2846, 1728, 1568, 1454, 1377, 1367, 1169, 1092, 962, 914, 837; [α]$^{25}_D$=−40.9° (c=1.0, CHCl₃); HRMS (ESI) m/z calculated for C₂₀H₃₄NO₄S [M+H]⁺: 384.2209, found 384.2208.

(−)-3,18-(2,2-dioxido-1,2,3-oxathiazinan-3-yl)-13-methyl-17-norkauran-16-one [58]

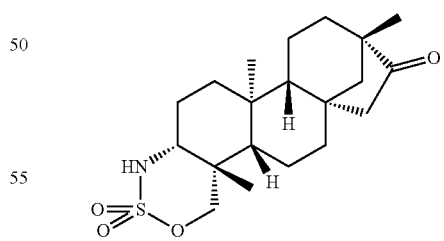

Preparative-Scale C—H Amination:

(−)-18-sulfamoyloxy-13-methyl-17-norkauran-16-one 57 (76.7 mg, 0.200 mmol, 1.0 equiv), [Mn($^t$BuPc)]Cl (8.3 mg, 0.010 mmol, 0.05 equiv), AgSbF₆ (3.4 mg, 0.010 mmol, 0.05 equiv), PhI(OPiv)₂ (325 mg, 0.800 mmol, 2.0 equiv), 100 mg crushed 4 Å MS, and 9:1 C₆H₆/MeCN (800 µL, 0.5M) were used. Product was purified via flash column chromatography on silica (35 mm fritted glass column, 150 mm SiO₂) using 2:1 hexanes/EtOAc. Pure product was isolated as a white solid. X-ray quality crystals were obtained via diffusion crystallization from EtOAc with pentane.

Run 1: (71.2 mg, 0.187 mmol, 93%), 0% rsm. Run 2: (70.4 mg, 0.185 mmol, 92%), 0% rsm. Run 3: (70.1 mg, 0.184 mmol, 92%), 0% rsm. Average: 92% yield±0.5, 0% rsm.

Reduced Catalyst and Oxidant Loadings:
(−)-18-sulfamoyloxy-13-methyl-17-norkauran-16-one 57 (147 mg, 0.400 mmol, 1.0 equiv), [Mn($^t$BuPc)]Cl (8.3 mg, 0.010 mmol, 0.025 equiv), AgSbF$_6$ (3.4 mg, 0.010 mmol, 0.025 equiv), PhI(OPiv)$_2$ (244 mg, 0.600 mmol, 1.5 equiv), 100 mg crushed 4 Å MS, and 9:1 C$_6$H$_6$/MeCN (800 µL, 0.5M) were used. Flash column chromatography on silica (35 mm fritted glass column, 150 mm SiO$_2$) using 2% Et$_2$O/CH$_2$Cl$_2$-5% Et$_2$O/CH$_2$Cl$_2$→Et$_2$O gave 116.0 mg (0.304 mmol) of pure product as a white solid (76% yield). This yield is identical to that obtained when the reaction is run on a larger scale.

Gram-Scale C—H Amination:
(−)-18-sulfamoyloxy-13-methyl-17-norkauran-16-one 57 (1.00 g, 2.61 mmol, 1.0 equiv), [Mn($^t$BuPc)]Cl (54.0 mg, 0.065 mmol, 0.025 equiv), AgSbF$_6$ (22.1 mg, 0.065 mmol, 0.025 equiv), PhI(OPiv)$_2$ (1.590 mg, 3.92 mmol, 1.5 equiv), 650 mg crushed 4 Å MS, and 9:1 C$_6$H$_6$/MeCN (5.2 mL, 0.5M) were used. Product was purified via flash column chromatography on silica (45 mm fritted glass column, 200 mm SiO$_2$) using 5% Et$_2$O/CH$_2$Cl$_2$→Et$_2$O. Pure product was isolated as a white solid.

Run 1: (768 mg, 2.01 mmol, 77%), (155 mg rsm, 0.404 mmol, 16%). Run 2: (730 mg, 1.91 mmol, 73%), (145 mg rsm, 0.378 mmol, 15%). Run 3: (738 mg, 1.93 mmol, 74%), (130 mg rsm, 0.339 mmol, 13%). Average: 75% yield±1.7, 15% rsm±0.9.

$^1$H-NMR (500 MHz, CDCl$_3$) δ 5.31 (d, J=3.5 Hz, 1H), 5.02 (d, J=11.5 Hz, 1H), 3.95 (d, J=12.0 Hz, 1H), 2.96 (d, J=12.0 Hz, 1H), 2.60 (dd, J=19.0, 3.5 Hz, 1H), 2.53 (app. q, J=12.8 Hz, 1H), 1.79-1.50 (m, 9H), 1.41-1.33 (m, 2H), 1.33 (s, 3H), 1.27-1.12 (m, 5H), 0.96 (s, 3H), 0.94 (s, 3H); $^{13}$C-NMR (125 MHz, CDCl$_3$) δ 222.2, 75.4, 63.7, 55.2, 54.9, 54.2, 48.8, 48.6, 41.1, 39.2, 37.5, 37.1 (2 peaks), 35.8, 24.5, 23.6, 20.2, 19.9, 19.8, 15.5; IR (film, cm$^{-1}$) 3242, 2949, 2929, 2850, 1726, 1454, 1437, 1371, 1360, 1180, 947, 785, 773; [α]$^{25}_D$=−4.5° (c=1.0, CHCl$_3$); HRMS (ESI) m/z calculated for C$_{20}$H$_{32}$NO$_4$S [M+H]$^+$: 382.2052, found 382.2055.

Figure 9:
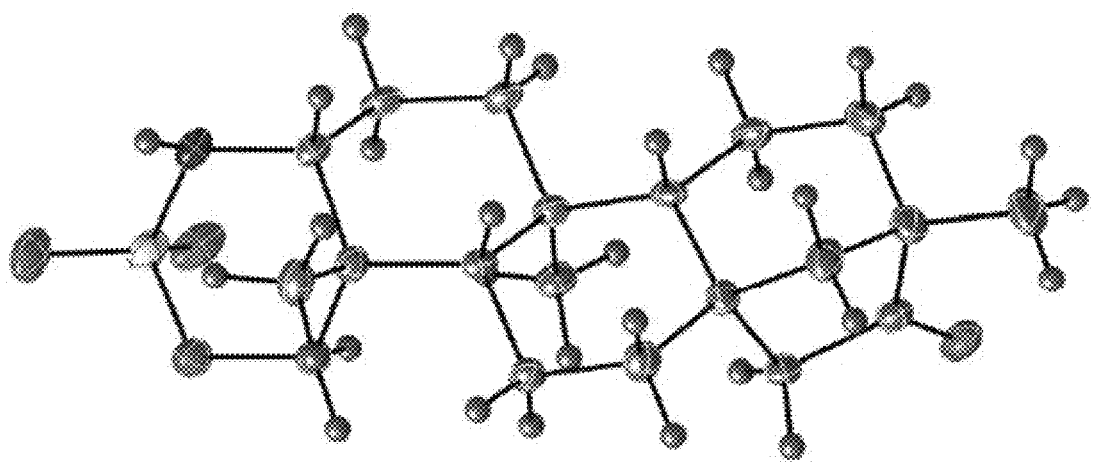
FIG. 9. Crystal structure of (−)-(18,18-dioxido-1,2,3-oxathiazinan-3-yl)-13-methyl-17-norkauran-16-one (58).

See FIG. 9—Scheme S1 for the crystal structure of (−)-(18,18-dioxido-1,2,3-oxathiazinan-3-yl)-13-methyl-17-norkauran-16-one (58). Crystal data and structure refinement for 58 were obtained and recorded.

(−)-N-benzylcarbamoyl-3,18-(2,2-dioxido-1,2,3-oxathiazinan-3-yl)-13-methyl-17-norkauran-16-one [S64]

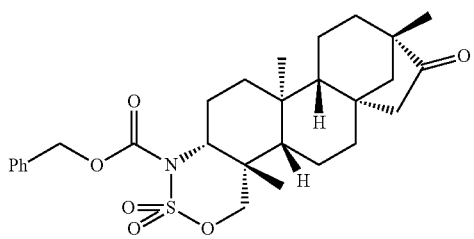

(−)-3,18-(2,2-dioxido-1,2,3-oxathiazinan-3-yl)-13-methyl-17-norkauran-16-one 58 (76.2 mg, 0.200 mmol, 1.0 equiv) was taken up in THF (870 µL). 4-dimethylaminopyridine (24.0 mg, 0.200 mmol, 1.0 equiv), Et$_3$N (557 µL, 4.00 mmol, 20 equiv), and benzyl chloroformate (275 µL, 1.90 mmol, 9.5 equiv) were added and reaction was stirred for 2 h. Flash column chromatography on silica (35 mm fritted glass column, 150 mm SiO$_2$) using 4:1 hexanes/EtOAc→2:1 hexanes/EtOAc as eluent gave 85.3 mg (0.170 mmol) of pure product as a white solid (83% yield).

$^1$H-NMR (500 MHz, CDCl$_3$) δ 7.44-7.42 (m, 2H), 7.37 (t, J=7.3 Hz, 2H), 7.34-7.32 (m, 1H), 5.33 (dd, J=12.5, 17.5 Hz, 2H), 4.85 (d, J=12.0 Hz, 1H), 4.13 (d, J=11.9 Hz, 2H), 2.64 (dd, J=18.5, 3.8 Hz, 1H), 2.24 (qd, J=13.6, 13.1, 3.2 Hz, 1H), 1.83-1.54 (m, 9H), 1.404-1.39 (m, 2H), 1.31 (s, 3H), 1.29-1.17 (m, 4H), 1.03 (dd, J=13.9, 3.9 Hz, 1H), 0.99 (s, 3H), 0.97 (s, 3H); $^{13}$C-NMR (125 MHz, CDCl$_3$) δ 221.6, 152.4, 134.9, 128.8, 128.5, 127.7, 75.9, 69.5, 67.2, 55.2, 54.6, 54.2, 48.8, 48.7, 40.9, 39.2, 38.1, 37.2, 37.1 (2 peaks), 26.9, 23.7, 20.3, 20.2, 19.9, 14.3; IR (thin film, cm$^{-1}$) 2935, 2852, 1736, 1456, 1392, 1290, 1174, 976, 813, 751; [α]$^{25}_D$=−50.7° (c=1.2, CHCl$_3$); HRMS (ESI) m/z calculated for C$_{28}$H$_{38}$NO$_6$S [M+H]$^+$: 516.2420, found 516.2421.

(−)-3-(benzylcarbamoyl)-18-azido-13-methyl-17-norkauran-16-one [59]

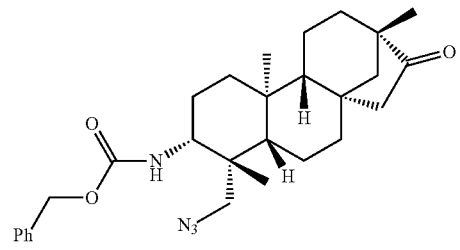

CBz-protected (−)-3,18-(2,2-dioxido-1,2,3-oxathiazinan-3-yl)-13-methyl-17-norkauran-16-one S64 (103 mg, 0.200 mmol, 1.0 equiv) was taken up in DMF (500 µL) in a 1-dram vial. Sodium azide (26.0 mg, 0.400 mmol, 2.0 equiv) was added, then vial was sealed with a Teflon-lined cap and reaction stirred at 40° C. for 48 h. After cooling to rt, reaction was diluted with 1.5 mL Et$_2$O and 0.5 mL 10% aq. HCl, then stirred for 30 min. This mixture was poured into 15 mL brine, then extracted with Et$_2$O (3×15 mL). The combined organic layers were washed with brine and dried over MgSO$_4$. Flash column chromatography on silica (35 mm fritted glass column, 120 mm SiO$_2$) using 4:1 hexanes/EtOAc as eluent gave 53.3 mg (0.111 mmol) of product as a white solid (56% yield).

$^1$H-NMR (500 MHz, CDCl$_3$) δ 7.36-7.29 (m, 5H), 5.68 (d, J=9.0 Hz, 1H), 5.12 (d, J=12.5 Hz, 1H), 5.05 (d, J=12.5 Hz, 1H), 3.71 (d, J=13.0 Hz, 1H), 3.36 (ddd, J=12.5, 8.5, 4.0 Hz, 1H), 3.22 (d, J=13.0 Hz, 1H), 2.59 (dd, J=18.8, 3.8 Hz, 1H), 1.80-1.06 (m, 17H), 1.14 (s, 3H), 0.97 (s, 3H), 0.83 (s, 3H); $^{13}$C-NMR (125 MHz, CDCl$_3$) δ 222.2, 156.3, 136.8, 128.6, 128.2, 128.1, 66.6, 59.6, 57.2, 55.4, 54.4, 54.0, 48.8, 48.5, 41.8, 41.3, 39.3, 38.3, 37.3 (2 peaks), 37.2, 25.3, 23.6, 20.5, 20.2, 19.9, 15.8; IR (thin film, cm$^{-1}$) 3408, 2935, 2850, 2101, 1733, 1512, 1455, 1246, 1072, 1047, 1016, 755; [α]$^{25}_D$=−28.0° (c=2.3, CHCl$_3$); HRMS (ESI) m/z calculated for C$_{28}$H$_{39}$N$_4$O$_3$ [M+H]$^+$: 479.3026, found 479.3022.

125

(−)-3-(benzylcarbamoyl)-18-acetoxy-13-methyl-17-norkauran-16-one [60]

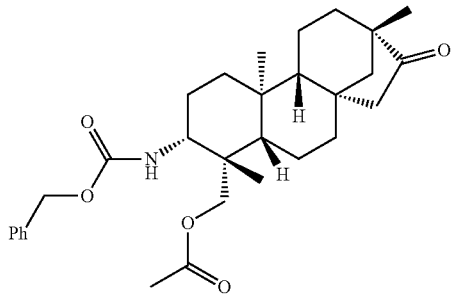

CBz-protected (−)-3,18-(2,2-dioxido-1,2,3-oxathiazinan-3-yl)-13-methyl-17-norkauran-16-one S64 (103 mg, 0.200 mmol, 1.0 equiv) was taken up in DMF (500 μL) in a 1-dram vial. Potassium acetate (58.9 mg, 0.600 mmol, 3.0 equiv) was added and reaction was stirred at 80° C. for 48 h. Additional KOAc (9.8 mg, 0.100 mmol, 0.5 equiv) was added at this point, then reaction continued to stir at 80° C. for 24 h more. After cooling to rt, reaction was diluted with Et$_2$O (1.5 mL) and 10% aq. HCl (0.5 mL), then stirred for 30 min. This mixture was poured into brine (15 mL), then extracted with Et$_2$O (3×15 mL). The combined organic layers were washed with brine and dried over MgSO$_4$. Flash column chromatography on silica (35 mm fritted glass column, 150 mm SiO$_2$) using 5% Et$_2$O in DCM as eluent gave 74.9 mg (0.15 mmol) of pure product as a white solid (76% yield).

$^1$H NMR (500 MHz, CDCl$_3$) δ 7.35-7.28 (m, 5H), 5.33 (d, J=9.3 Hz, 1H), 5.09 (s, 2H), 4.21-4.09 (m, 2H), 3.39 (ddd, J=13.0, 9.3, 4.1 Hz, 1H), 2.59 (dd, J=18.5, 3.7 Hz, 1H), 2.01 (s, 3H), 1.77-1.49 (m, 10H), 1.42-1.31 (m, 3H), 1.25-1.08 (m, 4H), 1.05 (s, 3H), 0.96 (s, 3H), 0.82 (s, 3H); $^{13}$C NMR (126 MHz, CDCl$_3$) δ 222.2, 170.8, 156.3, 136.9, 128.5, 128.1, 127.9, 66.5, 65.2, 59.0, 57.2, 55.2, 54.2, 48.8, 48.5, 41.5, 41.3, 39.3, 38.4, 37.2, 37.2, 25.5, 22.7, 21.1, 20.5, 20.3, 19.9, 15.5; IR (thin film, cm$^{-1}$): 3445, 3349, 2936, 2850, 1737, 1520, 1455, 1399, 1375, 1317, 1246, 1126, 1072, 1047, 1017, 754; [α]$^{25}_D$=−25.5° (c=1.6, CHCl$_3$); HRMS (ESI) m/z calculated for C$_{30}$H$_{42}$NO$_5$ [M+H]$^+$: 496.3063, found 496.3070.

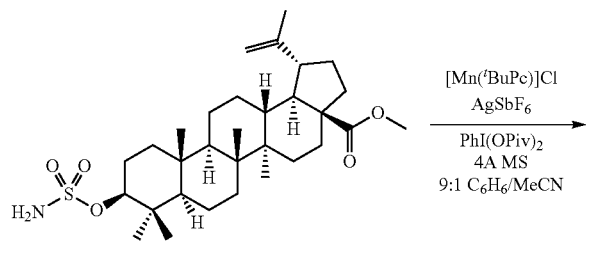

126

(+)-3-(Sulfamoyloxy) Betulinic Acid Methyl Ester [61]

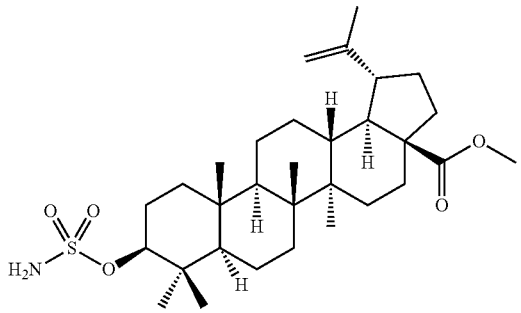

Prepared according to method B. Betulinic acid methyl ester (Santos et al., *Bioorg. Med. Chem.*, 2009, 17, 6241) (304 mg, 0.645 mmol, 1.0 equiv) was used, along with ClSO$_2$NCO (169 μL, 1.94 mmol, 3.0 equiv), formic acid (73 μL, 1.94 mmol, 3.0 equiv), Et$_3$N (273 μL, 1.94 mmol, 3.0 equiv) and CH$_2$Cl$_2$ (1.0 mL+2.0 mL). Flash column chromatography on silica (35 mm fritted glass column, 150 mm SiO$_2$) using 20% acetone/hexanes as eluent afforded 196 mg (0.357 mmol) of pure product as a white solid (55% yield). NOTE: the product should be stored and transferred under an Ar atmosphere.

$^1$H NMR (500 MHz, CDCl$_3$) δ 5.00 (br. d, J=8.7 Hz, 2H), 4.72 (d, J=2.5 Hz, 1H), 4.62-4.55 (br. s, 1H), 4.18 (dd, J=12.1, 4.6 Hz, 1H), 3.65 (s, 3H), 2.97 (td, J=10.9, 4.5 Hz, 1H), 2.26-2.13 (m, 2H), 2.05-1.97 (m, 1H), 1.93-1.78 (m, 3H), 1.75-1.64 (m, 2H), 1.67 (s, 3H), 1.56 (t, J=11.4 Hz, 1H), 1.52-1.46 (m, 1H), 1.45-1.30 (m, 8H), 1.30-1.18 (m, 2H), 1.16-1.10 (m, 1H), 1.06-0.79 (m, 2H), 1.00 (s, 3H), 0.94 (s, 3H), 0.89 (s, 3H), 0.83 (s, 3H), 0.82 (s, 3H), 0.79-0.73 (m, 1H); $^{13}$C-NMR (125 MHz, CDCl$_3$) δ 176.8, 150.6, 109.8, 91.9, 56.6, 55.7, 51.4, 50.5, 49.5, 47.1, 42.5, 40.7, 38.8, 38.6, 38.3, 37.1, 37.1, 34.3, 32.2, 30.7, 29.7, 28.1, 25.5, 24.5, 21.0, 19.5, 18.4, 16.3, 16.2, 16.0, 14.8; IR (ATR, cm$^{-1}$): 3269, 2947, 2868, 1728, 1642, 1449, 1328, 1186, 1136, 929, 903, 874, 846; [α]$^{27}$D=+14.2° (c=1.1, CHCl$_3$); HRMS (ESI) m/z calculated for C$_{31}$H$_{52}$NO$_5$S [M+H]$^+$: 550.3566, found 550.3571.

(−)-3,23-(2,2-dioxido-1,2,3-oxathiazinan-3-yl)-24-methyl betulinic acid methyl ester [62]

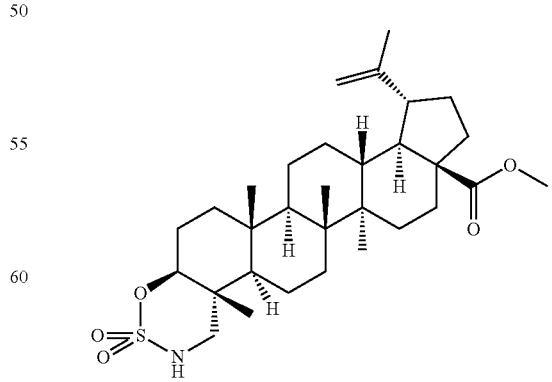

61 (110.0 mg, 0.200 mmol, 1.0 equiv), [Mn($^t$BuPc)]Cl (16.6 mg, 0.020 mmol, 0.10 equiv), AgSbF$_6$ (6.9 mg, 0.020 mmol, 0.10 equiv), 50 mg crushed 4 Å MS, PhI(OPiv)$_2$ (163 mg, 0.400 mmol, 2.0 equiv) and 9:1 C$_6$H$_6$/MeCN (600 μL, 0.33 M) were used. The reaction was stirred for 24 h at rt (~20° C.). Flash column chromatography on silica (35 mm fritted glass column, 150 mm SiO$_2$) using 10% acetone/hexanes→15% acetone/hexanes with 0.5% AcOH as eluent afforded product as white solid. We observed a minor product resulting from epoxidation of the aminated product (confirmed by $^1$H NMR and HRMS), likely due to the presence of exogenous water or oxygen. This normally accounted for an additional ~5% of the total C—H amination, although in some cases accounted for 10-15% yield if special precautions were not taken.

Run 1: (78.9 mg, 0.144 mmol, 72%), 0% rsm. Run 2: (83.5 mg, 0.152 mmol, 76%), 0% rsm. Run 3: (86.6 mg, 0.158 mmol, 79%), 0% rsm. Average: 76% yield±3.5, 0% rsm.

$^1$H NMR (500 MHz, acetone-d$_6$) δ 6.53 (dd, J=9.8, 5.0 Hz, 1H), 4.73 (d, J=2.4 Hz, 1H), 4.60 (d, J=2.3 Hz, 1H), 4.50 (dd, J=12.2, 4.1 Hz, 1H), 3.65 (s, 3H), 3.25 (dd, J=13.8, 5.0 Hz, 1H), 3.15 (dd, J=13.8, 9.5 Hz, 1H), 3.02 (td, J=11.0, 5.0 Hz, 1H), 2.28 (ddd, J=12.9, 11.4, 3.6 Hz, 1H), 2.23-2.18 (m, 1H), 1.92-1.76 (m, 4H), 1.76-1.57 (m, 3H), 1.70 (s, 3H), 1.55-1.10 (m, 14H), 1.09 (s, 3H), 1.05-1.00 (m, 1H), 1.04 (s, 3H), 0.96 (s, 3H), 0.95 (s, 3H); $^{13}$C-NMR (125 MHz, Acetone-d$_6$) δ 176.8, 151.5, 110.3, 91.0, 57.3, 56.6, 52.6, 51.7, 51.2, 50.2, 48.1, 43.4, 41.8, 39.6, 39.1, 38.5, 37.5, 37.0, 34.7, 32.8, 31.4, 30.6, 26.3, 24.5, 21.7, 19.6, 18.8, 17.7, 16.5, 15.2, 11.5; IR (ATR, cm$^{-1}$): 3285, 2946, 2870, 1723, 1642, 1450, 1432, 1359, 1184, 1153, 1134, 1044, 938, 881, 843, 825; [α]$^{26}_D$=−12.4° (c=1.05, CHCl$_3$); HRMS (ESI) m/z calculated for C$_{31}$H$_{50}$NO$_5$S [M+H]$^+$: 548.3410, found 548.3414.

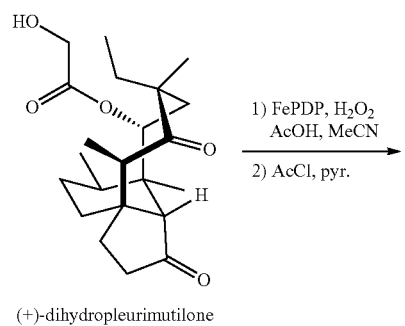

(+)-dihydropleurimutilone

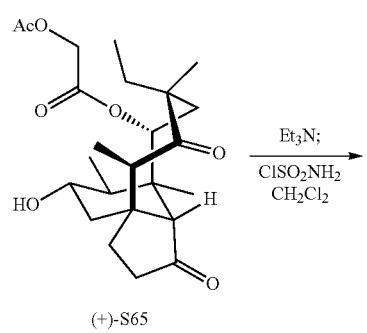

(+)-S65

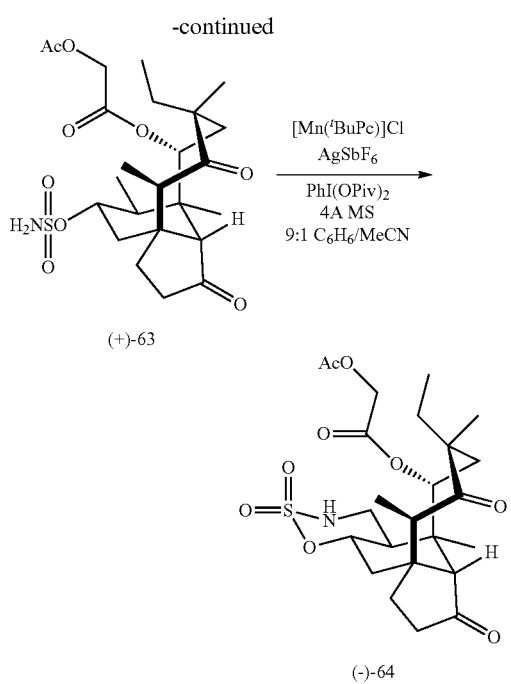

(+)-(7S)-hydroxy-dihydropleuromutilone-acetate [S65]

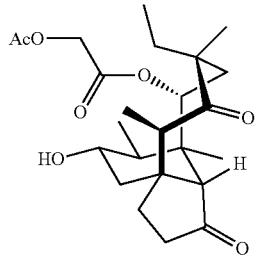 [SMILES: CC[C@]1(C)C[C@@H](OC(=O)COC(C)=O)C2(C)C(C)C(O)C[C@]3(CCC(=O)C23)[C@@H](C)C1=O]

(−)-(7S)-hydroxy-dihydropleuromutilone (Chen, M. S.; White, M. C. 2010, 327, 566) (25.0 mg, 0.063 mmol, 1.0 equiv.) was dissolved in 0.2 mL pyridine. Acetyl chloride (45.0 mg, 0.063 mmol, 1.0 equiv.) was added at 0° C. The reaction was allowed to stir at 0° C. for 3 h. The reaction was diluted with 10 mL CH$_2$Cl$_2$, washed with 1M HCl (2×5 mL), H$_2$O (5 mL) and dried over Na$_2$SO$_4$. Flash column chromatography on silica (35 mm fritted glass column, 30 mL SiO$_2$) using 30% EtOAc/hexanes→50% EtOAc/hexanes as eluent gave 19.9 mg (0.0456 mmol) product as white solid (72% yield).

$^1$H NMR (500 MHz, CDCl$_3$) δ 5.91 (d, J=8.8 Hz, 1H), 4.61-4.51 (ab q., 2H), 3.86 (td, J=11.0, 4.6 Hz, 1H), 3.41 (q, J=6.6 Hz, 1H), 2.31-2.16 (m, 4H), 2.18 (s, 3H), 2.10-2.03 (m, 1H), 1.99 (dd, J=15.8, 8.8 Hz, 1H), 1.64-1.63 (m, 1H), 1.57-1.46 (m, 4H), 1.49 (s, 3H), 1.35 (d, J=15.8 Hz, 1H), 1.14 (d, J=6.4 Hz, 3H), 1.11-1.03 (m, 1H), 0.98 (s, 3H), 0.95 (d, J=7.2 Hz, 3H), 0.79 (t, J=7.5 Hz, 3H); $^{13}$C-NMR (125 MHz, CDCl$_3$) δ 217.4, 216.1, 170.4, 167.1, 70.7, 69.3, 61.5, 58.5, 51.6, 45.8, 44.5, 43.7, 43.4, 43.2, 39.2, 34.5, 29.9, 24.4, 22.1, 20.6, 15.1, 13.0, 12.1, 9.2; IR (ATR, cm$^{-1}$): 3497, 2972, 2942, 1735, 1693, 1454, 1421, 1377, 1282, 1242, 1199, 1080, 1029, 972, 958, 916; [α]$^{25}_D$=+9.9° (c=1.11, CHCl$_3$); HRMS (ESI) m/z calculated for C$_{24}$H$_{37}$O$_7$ [M+H]$^+$: 437.2539, found 437.2540.

(+)-(7S)-sulfamoyloxy-dihydropleuromutilone-acetate [63]

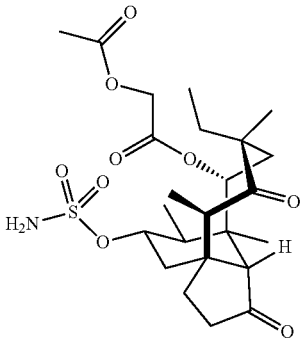 [SMILES: CC[C@]1(C)C[C@@H](OC(=O)COC(C)=O)C2(C)C(C)C(OS(N)(=O)=O)C[C@]3(CCC(=O)C23)[C@@H](C)C1=O]

Prepared according to method B. S65 (258.9 mg, 0.59 mmol) was used, along with ClSO$_2$NCO (154 μL, 1.77 mmol, 3.0 equiv), formic acid (69 μL, 1.77 mmol, 3.0 equiv), Et$_3$N (247 μL, 1.77 mmol, 3.0 equiv) and CH$_2$Cl$_2$ (1.0 mL+1.0 mL). Flash column chromatography on silica (50 mm fritted glass column, 300 mL SiO$_2$) using 30% EtOAc/hexanes→50% EtOAc/hexanes as eluent gave 145.3 mg (0.28 mmol) of pure product as a white solid (48% yield).

$^1$H NMR (500 MHz, CDCl$_3$) δ 6.07 (d, J=8.4 Hz, 1H), 4.82 (br. s, 2H), 4.68-4.62 (m, 2H), 4.44 (d, J=16.2 Hz, 1H), 3.44 (q, J=6.6 Hz, 1H), 2.47 (ddd, J=14.1, 4.6, 2.3 Hz, 1H), 2.30-2.18 (m, 3H), 2.17 (s, 3H), 2.00 (dd, J=15.9, 8.5 Hz, 1H), 1.82 (dq, J=11.4, 7.1 Hz, 1H), 1.64 (d, J=2.5 Hz, 1H), 1.60-1.45 (m, 3H), 1.50 (s, 3H), 1.42-1.32 (m, 2H), 1.16 (d, J=6.5 Hz, 3H), 1.03 (d, J=7.1 Hz, 3H), 0.99 (s, 3H), 0.81 (t, J=7.4 Hz, 3H); $^{13}$C-NMR (125 MHz, CDCl$_3$) δ 216.9, 215.5, 171.0, 167.6, 81.2, 70.5, 61.6, 58.4, 51.5, 46.0, 44.1, 43.6, 43.1, 42.1, 37.0, 34.4, 29.8, 24.5, 22.0, 20.6, 15.2, 13.0, 12.0, 9.2; IR (ATR, cm$^{-1}$): 3273, 2973, 1735, 1694, 1563, 1455, 1376, 1284, 1199, 1182, 1080, 973, 956 m 918, 863; $[\alpha]^{25}_D$=+34.4° (c=0.95, CHCl$_3$); HRMS (ESI) m/z calculated for C$_{24}$H$_{37}$NO$_9$SNa [M+Na]$^+$: 538.2087, found 538.2083.

(−)-7,16-(2,2-dioxido-1,2,3-oxathiazinan-3-yl)-dihydropleuromutilone-acetate [64]

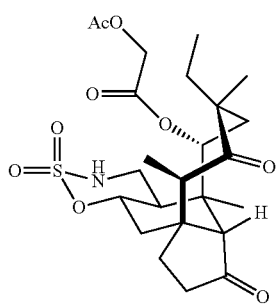 [SMILES: CC[C@]1(C)C[C@@H](OC(=O)COC(C)=O)C2(C)C3CNS(=O)(=O)OC3C[C@]3(CCC(=O)C23)[C@@H](C)C1=O]

63 (103.1 mg, 0.200 mmol, 1.0 equiv), [Mn($^t$BuPc)]Cl (16.6 mg, 0.020 mmol, 0.10 equiv), AgSbF$_6$ (6.9 mg, 0.020 mmol, 0.10 equiv), crushed 4 Å MS (50 mg), PhI(OPiv)$_2$ (163 mg, 0.400 mmol, 2.0 equiv) and 9:1 C$_6$H$_6$/MeCN (400 μL, 0.5M) were used. The reaction was stirred for 24 h at rt (~20° C.). Flash column chromatography on silica (35 mm fritted glass column, 150 mm SiO$_2$) using 20% EtOAc/hexanes→30% EtOAc/hexanes with 0.5% AcOH as eluent gave product as colorless oil.

Run 1: (82.2 mg, 0.160 mmol, 80%), <5% rsm. Run 2: (88.6 mg, 0.172 mmol, 86%), <5% rsm. Run 3: (89.0 mg, 0.173 mmol, 87%), <5% rsm. Average: 84% yield±3.8, <5% rsm.

$^1$H NMR (500 MHz, CDCl$_3$) δ 5.72 (d, J=8.7 Hz, 1H), 5.05 (td, J=11.4, 4.9 Hz, 1H), 4.76 (dd, J=10.6, 4.2 Hz, 1H), 4.59 (s, 2H), 3.45 (dt, J=14.0, 3.3 Hz, 1H), 3.37 (q, J=6.5 Hz, 1H), 3.28 (dt, J=14.3, 11.2 Hz, 1H), 2.37-2.12 (m, 5H), 2.16 (s, 3H), 1.93-1.84 (m, 2H), 1.75 (d, J=2.5 Hz, 1H), 1.57-1.49 (m, 2H), 1.51 (s, 3H), 1.39 (d, J=15.9 Hz, 1H), 1.30-1.23 (m, 1H), 1.13 (d, J=6.5 Hz, 3H), 0.96 (s, 3H), 0.77 (t, J=7.4 Hz, 3H). $^{13}$C-NMR (125 MHz, CDCl$_3$) δ 216.6, 215.5, 170.5, 166.7, 81.4, 70.4, 61.4, 58.1, 51.5, 45.6, 45.2, 44.6, 43.3, 42.8, 42.4, 35.4, 34.2, 29.7, 23.9, 22.0, 20.5, 14.1, 13.0, 9.2. IR (ATR, cm$^{-1}$): 3262, 2969, 1736, 1693, 1420, 1368, 1283, 1183, 1072, 1038, 978, 960, 921, 865, 824; $[\alpha]^{25}_D$=−7.8° (c=0.83, CHCl$_3$); HRMS (ESI) m/z calculated for C$_{24}$H$_{36}$NO$_9$S [M+H]$^+$: 514.2111, found 514.2109.

$^1$H and $^{13}$C-NMR spectra of all reported compounds, as well as labeled, integrated $^{13}$C-NMR spectra of purified H/D mixtures for the KIE study, GC traces of standards and enriched substrates for the stereoretention experiments, and nOE and 2D NMR spectra for the betulinic acid and pleuromutilone substrates have been recorded.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method to carry out a C—H amination comprising contacting a substrate and an effective amount of a compound of Formula I:

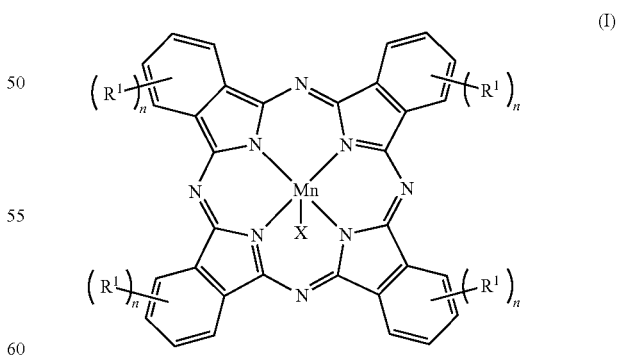

wherein
X is an anion;
each R$^1$ is independently (C$_1$-C$_{16}$)alkyl, (C$_1$-C$_{16}$)cycloalkyl, or (C$_1$-C$_8$)alkyl(C$_1$-C$_{16}$)cycloalkyl; and
each n is independently 1, 2, 3, or 4;
in a suitable solvent system;

wherein the substrate comprises at least three carbon atoms, a sulfonamide moiety, and at least one sp³ C—H bond;

thereby effecting C—H amination of the substrate wherein the amination forms a 1,3-amino alcohol motif comprising a cyclic sulfamate ester.

2. The method of claim 1 wherein the contacting is carried out in the presence of an oxidant.

3. The method of claim 2 wherein the oxidant is PhI(OPiv)₂.

4. The method of claim 1 wherein the contacting is carried out in the presence of a drying agent.

5. The method of claim 1 wherein the contacting is carried out at about 20° C. to about 30° C.

6. The method of claim 1 wherein the contacting is carried out in the presence of AgSbF₆.

7. The method of claim 1 wherein the substrate comprises benzylic, ethereal, 3°, 2°, or 1° aliphatic C—H bonds, or a combination thereof.

8. The method of claim 1 wherein the amination forms a six-membered ring.

9. The method of claim 1 wherein the amination forms a five-membered ring.

10. The method of claim 1 wherein the C—H amination occurs at a strong 1° sp³ C—H bond in the presence of weaker 2° and/or 3° C—H bonds.

11. The method of claim 1 wherein the substrate comprises one or more alkene or alkyne moieties.

12. The method of claim 1 wherein X is halo or SbF₆.

13. The method of claim 12 wherein X is chloro.

14. The method of claim 1 wherein R¹ is (C₃-C₅)alkyl.

15. The method of claim 14 wherein R¹ is tert-butyl.

16. The method of claim 1 wherein R¹ is (C₃-C₁₀)cycloalkyl.

17. The method of claim 16 wherein R¹ is adamantyl.

18. The method of claim 1 wherein each R¹ is the same.

19. The method of claim 1 wherein at least one R¹ is different than another R¹.

20. The method of claim 1 wherein the compound of Formula I is compound 3:

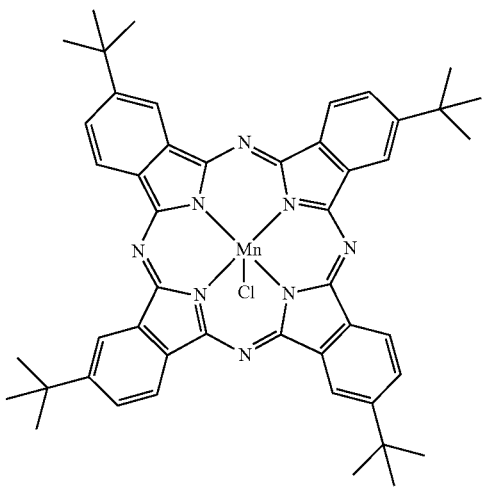

(3)

* * * * *